US009102711B2

(12) United States Patent
Takeuchi

(10) Patent No.: US 9,102,711 B2
(45) Date of Patent: Aug. 11, 2015

(54) METHODS AND MATERIALS FOR TARGETED MUTAGENESIS

(75) Inventor: Toshihiko Takeuchi, Oakland, CA (US)

(73) Assignee: XOMA TECHNOLOGY LTD., Berkeley, CA (US)

( * ) Notice: Subject to any disclaimer, the term of this patent is extended or adjusted under 35 U.S.C. 154(b) by 0 days.

(21) Appl. No.: 12/811,331

(22) PCT Filed: Dec. 31, 2008

(86) PCT No.: PCT/US2008/088651
§ 371 (c)(1), (2), (4) Date: Nov. 4, 2010

(87) PCT Pub. No.: WO2009/088933
PCT Pub. Date: Jul. 16, 2009

(65) Prior Publication Data

US 2011/0118131 A1 May 19, 2011

Related U.S. Application Data

(60) Provisional application No. 61/018,101, filed on Dec. 31, 2007, provisional application No. 61/018,105, filed on Dec. 31, 2007, provisional application No. 61/018,113, filed on Dec. 31, 2007.

(51) Int. Cl.

| | |
|---|---|
| ***C12N 15/10*** | (2006.01) |
| ***C07K 16/00*** | (2006.01) |
| ***C07K 16/30*** | (2006.01) |
| ***C07K 16/46*** | (2006.01) |

(52) U.S. Cl.
CPC ................. *C07K 16/00* (2013.01); *C07K 16/30* (2013.01); *C07K 16/465* (2013.01); *C12N 15/102* (2013.01); *C12N 15/1034* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,725,677 | A | 2/1988 | Koster et al. |
| 5,576,184 | A | 11/1996 | Better et al. |
| 5,723,323 | A | 3/1998 | Kauffman et al. |
| 5,766,886 | A | 6/1998 | Studnicka et al. |
| 6,171,820 | B1 | 1/2001 | Short |
| 6,358,709 | B1 | 3/2002 | Short et al. |
| 6,479,258 | B1 | 11/2002 | Short |
| 6,537,776 | B1 | 3/2003 | Short |
| 6,849,425 | B1 | 2/2005 | Huse et al. |
| 7,117,096 | B2 | 10/2006 | Luo et al. |
| 2003/0044772 | A1 | 3/2003 | Watkins et al. |
| 2006/0024308 | A1 | 2/2006 | Crea et al. |
| 2007/0020267 | A1 | 1/2007 | Fuh et al. |

FOREIGN PATENT DOCUMENTS

| | | |
|---|---|---|
| WO | 98/17792 | 4/1998 |
| WO | 00/53744 | 9/2000 |
| WO | 2007/094842 | 8/2007 |

OTHER PUBLICATIONS

Akunuma et al., Combinatorial Mutagenesis to restrict amino acid usage in an enzyme to a reduced set; PNAS, vol. 99, No. 21, pp. 12549-13553, 2002.*

Knappik et al. Fully Synthetic Human Combinatorial Antibody Libraries (HuCAL) Based on Modular Consensus Frameworks and CDRs Randomized with Trinucleotides; J Mol Biol, vol. 296, pp. 57-86, 2000.*

Knappik et al. Fully Synthetic Human Combinatorial Antibody Libraries (HuCAL) Based on Modular Consensus Frameworks and CDRs Randomized with Trinucleotides; Supplemental Table 3, J Mol Biol, vol. 296, pp. 57-86, 2000.*

Mena and Daugherty, Automated design of degenerate codon libraries; PEDS, vol. 18, No. 12, pp. 559-561, 2005), Borrebaeck (Borrebaeck and Ohlin, Antibody evolution beyond Nature; Nature Biotechnology, vol. 20, pp. 1189-1190, 2002.*

Gilardi et al., Engineering the Maltose Binding Protein for Reagentless Fluorescence Sensing; Analytical Chemistry, vol. 66, pp. 3840-3847, 1994.*

Borrebaeck and Ohlin, Antibody evolution beyond Nature; Nature Biotechnology, vol. 20, pp. 1189-1190, 2002.*

Wark et al., "Latest technologies for the enhancement of antibody affinity," Advanced Drug Delivery Reviews 58 (2006) 657-670.

Wu et al., "Ultra-potent Antibodies Against Respiratory Syncytial Virus: Effects of Binding Kinetics and Binding Valence on Viral Neutralization," J. Mol. Biol. (2005) 350, 126-144.

Arkin, A.P. et al., "Optimizing nucleotide mixtures to encode specific subsets of amino acids for semi-random mutagenesis" Nature Biotechnology, Nature Publishing Group, New York, NY, vol. 10, No. 3, Mar. 1, 1999, pp. 297-300.

Akanuma, S., et al. "Combinational mutagenesis to restrict amino acid usage in an enzyme to a reduced set" Proceedings of the National Academy of the Sciences of USA, National Academy of Science, Washington, DC; US, vol. 99, No. 21, Oct. 15, 2002, pp. 13549-13553.

Boder, E.T. et al., "Yeast surface display for screening combinatorial polypeptide libraries" Nat. Biotech. 1997, 15 (6):553-7.

Chames, P., et al., "Selection of antibodies against biotinylated antigens" Methods Mol. Bio. 2002, 178:147-57.

Chothia, C., et al., "Canonical structures for the hypervariable regions of immunoglobulins," Journal of Molecular Biology, London GB, vol. 196, No. 4 Aug. 20, 1987, pp. 901-917 [retrieved on Aug. 20, 1987].

(Continued)

*Primary Examiner* — Jennifer Dunston
*Assistant Examiner* — Addison D Ault
(74) *Attorney, Agent, or Firm* — Jones Day

(57) ABSTRACT

The present disclosure relates to methods and materials for mutagenesis, including for the generation of novel or improved proteins and libraries or arrays of mutant proteins or nucleic acids encoding such mutant proteins.

8 Claims, 30 Drawing Sheets

(56) References Cited

OTHER PUBLICATIONS

Clark, M.A., "Standard protocols for the construction of Fab libraries" Methods Mol. Bio. 2002, 178:39-58.
Coomber, D.W.,"Panning of antibody phage-display libraries. Standard protocols" Methods Mol. Bio. 2002, 178:133-45.
Crameri, et al., "Display of expression products of cDNA libraries on phage surfaces; A versatile screening system for selective isolation of genes by specific gene-product/ligand interaction" Eur. J. Biochem. 1994, 226:53-58.
Cwirla, et al., "Peptides on phage: A vast library of peptides for identifying ligands" Proc. Nati. Acad. Sci. 1990, 87:6378-6382.
De Kruif, et al., "Rapid selection of cell subpopulation-specific human monoclonal antibodies from a synthetic phage antibody library" Proc. Natl. Acad. Sci. 1995, 92:3938-3942.
Fack, et al., "Epitope mapping by phage display: random versus gene-fragment libraries" Jrnl Immunological Methods 1997, 206: 43-52.
Felici, F., et al., "Selection of antibody ligands from a large library of oligopeptides expressed on a multivalent exposition vector" J Mol. Biol. 1991, 222(2):301-10.
Gram, H., et al., "Phage display as a rapid gene expression system: production of bioactive cytokine-phage and generation of neutralizing monoclonal antibodies" Jrnl. Immuno. Methods 1993, 161(2):169-76.
Griffiths, A., et al., "Analytical Biotechnology; Strategies for selection of antibodies by phage display" Current Opinion Biotech. 1998, 102-108.
Hoogenboom, H.R., "Overview of antibody phage-display technology and its applications" Methods Mol. Bio. 2002, 178:1-37.
Hughes, M. D. et al. "Removing the redundancy from randomized gene libraries" Journal of Molecular Biology, vol. 331, No. 5, Aug. 29, 2003, pp. 973-979, ISSN: 0022-2836.
Hutchison III, Clyde A., "Mutagenesis at a Specific Position in a DNA Sequence" Jrnl Biological Chemistry 1978, 253(18):6551-6560.
Jacobsson, K et al. "Phage display shot-gun cloning of ligand-binding domains of prokaryotic receptors approaches 100% correct clones" Biotechniques 1996 20(6):1070-6.
Jacobsson, K., et al., "Shot-gun phage display mapping of two streptococcal cell-surface proteins" Microbio. Res. 1997, 152(2):121-8.
Jespers, L,S., et al "hZLG6: a phage lambda vector for high-efficiency cloning and surface expression of cDNA libraries on filamentous phage" Gene 1996, 173: 179-181.
Katz, B.A. "Structural and mechanistic determinants of affinity and specificity of ligands discovered or engineered by phage display" Ann. Rev. Biophys. Biomol. Struct. 1997, 26:27-45.
Kay, B.K., et al., "An M13 phage library displaying random 38-amino-acid peptides as a source of novel sequences with affinity to selected targets" Gene 1993, 128(1):59-65.
Labean, T.H., et al. "Design of synthetic gene libraries encoding random sequence proteins with desired ensemble characteristics" Protein Science, vol. 2, No. 8, 1993, pp. 1249-1254.
Larsson, O., et al. "Quantitative codon optimisation of DNA libraries encoding sub-random peptides: design and characterisation of novel library encoding transmembrane domain peptides" Nucleic Acids Research Dec. 1, 2002, vol. 30, No. 23, p. e133.
Lee, C.V. et al., "High-Affinity human antibodies from phage-displayed synthetic fab libraries with a single framework scaffold" Journal of Molecular Biology, London, GB, vol. 340, No. 5, Jul. 23, 2004, pp. 1073-1093.
MacCallum et al., "Antibody-antigen interactions: Contact analysis and binding site topography" Journal of Molecular Biology, London, GB, vol. 262, No. 5, pp. 732-745, Jan. 1, 1996.
Magliery, T. "Mixed Codons Worksheet" [Online] Jul. 23, 2003, Retrieved from the Internet: <URL: http://www.chemistry.ohio-state.edu/~magliery/mixedcodons/mixed_codons_worksheet_v1.zip> [retrieved on Mar. 23, 2009].
McGregor, D., "Selection of proteins and peptides from libraries displayed on filamentous bacteriophage" Mol. Biotech. 1996, 6(2):155-62.
Mena, M. et al. "Automated dsigned of degenerate condon libraries" Protein Engineering Design & Selection, vol. 18, No. 12, Dec. 2005, pp. 559-561.
Mendez, M.J., et al., "Functional transplant of megabase human immunoglobulin loci recapitulates human antibody response in mice" Nat Genet. 1997, 15(2):146-56. Erratum in: Nat Genet 1997, 16(4):410.
Petersen, G., et al., "Mapping of linear epitopes recognized by monoclonal antibodies with gene-fragment phage display libraries" Mol. Gen. Genet. 1995, 249(4):425-31.
Rader, C. et al. "Phage display of combinatorial antibody libraries" Current Opinion Biotech 1997, 8:503-508.
Rajpal, A. et al. "A general method for greatly improving the affinity of antibodies by using combinatorial libraries" Proceedings of the National Academy of the Sciences of USA, National Academy of Science, Washington, DC; US, vol. 102, No. 24, Jun. 1, 2005, pp. 8466-8471.
Razin, A. et al., "Efficient correction of a mutation by use of chemically synthesized DNA" Proc. Nati. Acad. Scs. 1978, 75 (9):4268-4270.
Rossenu, S., et al., "A phage display technique for a fast, sensitive, and systematic investigation of protein-protein interactions" J Protein Chem. 1997, 16(5):499-503.
Smith, George P., "Filamentous Fusion Phage: Novel Expression Vectors That Display Cloned Antigens on the Virion Surface" Science Mag 1985, 228:1315-1317.
Studnicka, et al., "Human-engineered monoclonal antibodies retain full specific binding activity by preserving non-CDR complementarity-modulating residues" Protein Eng. 1994 7(6):805-14.
Tomandl, D. et al. "Computer-assisted Design of Doped Libraries in Evolutionary methods in biotechnology" 2004, Wiley-VCH Verlag, Weinheim.
Wolf, E., et al. "Combinatiorial codons: A computer program to approximate amino acid probabilities with biased nucleotide usage" Protein Science, vol. 8, No. 3, Mar. 1999, pp. 680-688.
Wu, et al, "Stepwise in vitro affinity maturation of Vitaxin, an avb3-specific humanized mAb" Proc. Natl. Acad. Sci. 1998, 95: 6037-6042.
PCT International Search Report and Written Opinion of the ISA; PCT/US2008/088631, dated Jul. 7, 2009.
PCT International Preliminary Reporton Patentability; PCT/US2008/088631, dated Jul. 20, 2009.
PCT International Search Report and Written Opinion of the ISA; PCT/US2008/088651, dated Apr. 17, 2009.
PCT International Preliminary Report on Patentability; PCT/US2008/088651, dated Jul. 6, 2010.
PCT International Search Report and Written Opinion of the ISA; PCT/US2008/088639, dated Jul. 20, 2009.
PCT International Preliminary Report on Patentability; PCT/US2008/088639, dated Jul. 6, 2010.
Main et al., "A potent human anti-cotaxin 1 antibody, CAT-213. Isolation by phage display, in vitro and in vivo efficacy," JPET Fast Forward. Published on Sep. 14, 2006 as DOI:10.1124/jpet.106.110734.
Fellouse et al., "High-throughput Generation of Synthetic Antibodies from Highly Functional Minimalist Phage-displayed Libraries," J. Mol. Biol. (2007) 373, 924-940.
Kretz et al., "Gene Site Saturation Mutagenesis: A Comprehensive Mutagenesis Approach," Methods in Enzymology, vol. 388:3-11 (2004).
Sammond et al., "Structure-based Protocol for Identifying Mutations that Enhance Protein-Protein Binding Affinities," J. Mol. biol. (2007) 371, 1392-1404.

* cited by examiner

Figure 2A

```
pos               10        20       abcdef 30        40        50
prox      .S.S..::.....:.......:.SPCCCCCCCCSCCCSISI.I.:...:.ISSCCCC
murING1   DIVMTQAAFSNPVTLGTSGSISCRSSKSLLHS-NGITYLYWYLQKPGQSPQLLIYQMS
cspc       1    222 2  1  321       3  1     2   4          3    31
mK2       DVVMTQTPLSLPVSLGDQASISCRSSQSLvHS-NGNTYLeWYLQKPGQSPKLLIYkVS
humING1         S L       E
disc      +-+o+++o++++++o+++++++-+-o-------------o-o+++o+++o+-oo----
expo      +-+-+-+o++o+-+++++-+-+-+-+++++++++-+++-=-=o=++++o=o=--o+++
risk      LHLHLHLMLLMLHLMLLLHLHLHLHMHHHHHHHHHHHHHHHHMHLMLLMHMHHHHHHH
pos               10        20       abcdef 30        40        50

pos             60        70        80        90     abcdef  100      a
prox      C.PP..:....S.S.S..S...............I:ISICCCCCCCCCCISI............
murING1   NLASGVPDRFSSSGSGTDFTLRISRVEAEDVGVYYCAQNLELPR------TFGGGTKLEI-K  (SEQ ID NO: 815)
cspc       43        2         1        1     3 3241 4     4
mK2       NRFSGVPDRFSGSGSGTDFTLKISRVEAEDLGVYYCfQgtHVPP-----yTFGGGTKLEI-KRA (SEQ ID NO: 816)
humING1    R                   K                               Q
disc      -+oo++o++++-+-+o++-+++++++++++++++-o-------------oo+++++++++++
expo      ++o++-o+o-+-+-+-++-+-+-++-+++-+---=-=-=+++oooooo=-=-+--+-++++++
risk      HLMMLHMLMHLHLHLHLLHLHLHLLHLLLHLHHHHHHHHHHHHHHHHHHHHHLHHLHLLLLLL
pos             60        70        80        90     abcdef  100      a
```

Figure 2B

```
pos             10        20        30     ab   40        50  abc
prox    PS.S....:....:.......:.SPSSCSCCCCSISSSI.I.:...I.ISSCSCCCCCCCCC
murING1 QIQLVQSGPELKKPGETVKISCKASGYTFTKYGMN--WVKQAPGKGLKWMGWINTY--TEEP
cspc    31  2      3   41             4 4  3     2   2 4 1 5  24 21442
mH2a    EVQLQQSGPELVKPGASVKiSCKASGYTFTdYyMnN-WVKQspGKsLEWIGdInP--gnGgT
humING1           V     S                           Q
disc    o-+o++++o++++o+++++++-+oo---------ooo-o+++o+++o+-oo-----------
expo    +-+-+-+-o++o+++++-+-+-+-+--+-++o+-=---=o=++++o=o=--o-o+++++o++
risk    MHLHLHLHMLLMLMLLLHLHLHLHMHHHHHHHHHHHHHHMHLMLLMHMHHHHHHHHHHHHHH
pos             10        20        30     ab   40        50  abc

pos      60       70        80  abc      90       100abcdefghijk      110
prox    CPSPP.P....S.S.P..P.S...............I:ISICCCCCCCCCCCCCCCICCI..........
murING1 TYGDDFKGRFAFSLETSASTANLQINNLKSEDTATYFCARFGSA------------VDYWGQGTSVTVSS (SEQ ID NO: 817)
cspc    1 334    13221113 2  21 111  3   1 2 2  33342222322224422       1
mH2a    sYNQKFKGKATLTvDKSSSTAYMqLsSLTSEDSAVYYCARxxyysssxmxaxxYYaFDYWGQGTtVTVSS (SEQ ID NO: 818)
humING1           T T D  T   Y E SS R                                   L
disc    -oooo+o++++-+-+o++o+-+++++++++++++++++-o--------------------o+++++++++
expo    +o-+o-++o-+-+-+o++o+-+-+-++-+++-+-o-=-=-=oo+oooooooooooo=oo=-+--+-+-++
risk    HMHMMHMLMHLHLHLMLLMLHLHLHLLHLLLHLHMHHHHHHHHHHHHHHHHHHHHHHHHHHLHHLHLHLL
pos      60       70        80  abc      90       100abcdefghijk       110
```

Figure 2C

```
pos                 10        20      abcdef 30        40        50
bind/disc     +-+o+++o++++++o+++++++-+-o------------o-o+++o+++o+-oo----
bury/exp      +-+-+-+o++o+-+++++-+-+-+-+++++++++-+++-=-=o=++++o=o=--o+++
risk          LHLHLHLMLLMLHLMLLLHLHLHLHMHHHHHHHHHHHHHHHHMHLMLLMHMHHHHHHH
Prox          .S.S.S..::.......:.......:.SPCCCCCCCCSCCCSISI.I.:...:.ISSCCCC
cA5           DIQMTQOPSSVSASVGDRLTXICRASQ------DINRWLAWQQTPGNAPKLLIHSAT
Cspc                                        3 142                32 1
A8.2          DIQMTQSPSSVSASAGDRVTITCRASQ------GISTWLAWYQQKPGAPKLLIYAAS
Cspc                                         2 12
hK1 (TAE)     DIQMTQSPSSLSASVGDRVTITCRASQSLV---sIsnyLaWYQQKPGKAPKLLIYaAS
pos                10         20      abcdef  30       40        50

pos               60         70        80          90    abcdef  100     a
bind/disc     -+oo++o++++-+-+-+o++-+++++++++++++++-o-------------oo++++++++++++
bury/exp      ++o++-o+o-+-+-+-++-+-+-++-+++-+---=-=-=+++ooooooo=-=-+--+-++++++
risk          HLMMLHMLMHLHLHLHLLHHLHLHLLHLLLHLHHHHHHHHHHHHHHHHHHHHHLHHLHLLLLLL
Prox          C.PP..:....S.S.S..S..............I:ISICCCCCCCCCISI...........
cA5           SLQSGVPSRFSGSGSOTDFTLTINSLMDFATYYCQQADSFPL------TFGGGTKVEI-K     (SEQ ID NO: 946)
Cspc           3                                 43 2 3
A8.2          SLQSGVPSRFSGSGSGTDFTLTISSLQPEDFATYFCQQGYRFPF------TFGPGTKVEI-K   (SEQ ID NO: 947)
Cspc           3                               2   4342 3
hK1 (TAE)     sLeSGVPSRFSGSGSGTDFTLTISSLQPEDFATYYCQQyns1PE-----wTFGQGTKVEI-KRT (SEQ ID NO: 819)
pos               60        70        80         90    abcdef 100        a
```

Figure 2D

```
pos               10         20         30     ab   40         50  abc
bind/disc   o-+o++++o++++o+++++++-+oo---------ooo-o+++o+++o+-oo----------
bury/exp    +-+-+-+-o++o+++++-+-+-+-+--+-++o+-=---=o=++++o=o=--o-o+++++o++
risk        MHLHLHLHMLLMLMLLLHLHLHLHMHHHHHHHHHHHHHHMHLMLLMHMHHHHHHHHHHHHHH
Prox        PS.S....:....:.......SPSSCSCCCCSISSSI.I.:...I.ISSCSCCCCCCCCC E
cAS         EVQLLESGGGLVQPGGSLRLSCAASGFTFSKYFMF--WVRQAPGKGLEWVSVISP--SGGMT
Cspc                                      4 3 3                2   3  3  2
A8.2        EVQLLESGGGLVQPGGSLRLSCAASGFTFSMYDMH--WVRQAPGKGLEWVSYIYP-SGGIT
Cspc                                      2 4 4                2  33  3  2
hH3 (TAE)   EVQLVESGGGLVQPGGSLRLSCAASGFTFSsyaMs--WVRQAPGKGLEWVsvIsgKtdGgst

pos               10         20         30     ab   40         50  abc

Pos          60        70         80    abc   90      100abcdefghijk       110
bind/disc   -oooo+o++++-+-+o++o+-++++++++++++++-o------------------o+++++++++
bury/disc   +o-+o-++o-+-+-+o++o+-+-+-++-+++-+-o-=-=-=oo+ooooooooooo=oo=-+--+-+-++
risk        HMHMMHMLMHLHLHLMLLMLHLHLHLLHLLLHLHMHHHHHHHHHHHHHHHHHHHHHHHLHHLHLHLL
Prox        CPSPP.P....S.S.P..P.S..............I:ISICCCCCCCCCCCCCCICCI..........
cAS         RYADSVKGRPTISRDNSKNTLYLQMNSLRAEDTAVYYCARVGFGGNS----------DYWGQGTLVTVSS (SEQ ID NO: 948)
Cspc                                                 2323322
A8.2        WYADSVKGRFTISRDNSKNTLYLQMNSLRAEDTAVYYCARQGGPNWF----------DPWGQGTLVTVSS (SEQ ID NO: 949)
Cspc                                                 2331242          3
hH3 (TAE)   yYADSVKGRFTISRDnSKNTLYLQMNSLRaEDTAVYYCArxxxxxxlsgxyyyyhyFDyWGQGTLVTVSS (SEQ ID NO: 838)
Pos          60         70         80  abc    90      100abcdefghijk       110
```

Figure 3A

```
prox   .S.S..::.....:......:.SPCCCCCCCSCCCSISI.I.:...:.ISSCCCC
pos           10        20       abcdef 30        40        50
hK1    DIQMTQSPSSLSASVGDRVTITCRASQSLV---sIsnyLaWYQQKPGKAPKLLIYaAS
hK2    DIVMTQSPLSLPVTPGEPASISCRSSQSLLHS-DGnnYLnWYLQKPGQsPQLLIYlvS
hK3    EIVLTQSPGTLSLSPGERATLSCRASQS-----vSSSYLAWYQQKPGQAPRLLIYGAS
hK4    DIVMTQSPDSLAVSLGERATINCkSSQSVLYSSNNKNYLAWYQQKPGQPPKLLIYWAS
mK1    DIVMTQSPSSLaVsAGEKVTMSCKSSQSLLnSgnqKNYLAWYQQKPGQsPKLLIYwAS
mK2    DVVMTQTPLSLPVSLGDQASISCRSSQSLvHS-NGNTYLeWYLQKPGQSPKLLIYkVS
mK3    DIVLTQSPASLAVSLGQRATISCRASeSVds-yGnSfMHWYQQKPGQPPKLLIYaAS
mK4    EIVLTQSPAIMsASPGEKVTMTCSASSS-----VSSsYLHWYQQKpGxSPKLWIYrTS
mK5    DIqMTQSpsSLSASlGDRVTItCrASQD-----DIsnyLnWYQQKPggspKLLIYyaS
mK6    QIVLTQSPAIMSASPGEKVTMTCSASS-------SVSYMHWYQQKSGTSPKrWIYDTS
hL1    ZSVLTQPPS-vSgaPGQrVTISCSGSSSNi---IGnNyVsWYQQLPGTAPKLLIYdnN
hL2    ZSALTQPaS-VSGSPGQSiTISCTGTSsDV---ggynaVSWyQQhPGKAPKLlIydvt
hL3    SYeLTQPPS-VSVSPGQTArITCSGDn------LgdkyvhWYQQKPGQaPVLVIYdDx
hL4    -SELTQpPsxVSVAxGQTvrITCxGDS-N----LGxYdAsWYQQKPxQAPxLVIYGxN
hL5    XSALTQPPS-ASGSPGQSVTISCTGTSSDV---GgynYVSWYQQHaGkAPKviIyEVn
hL6    NFMLTQPHS-VSESPGKTVTISCTgSsGS----IASnYVQWYQQRPGSAPTTVIYEDN
mL     qAVVTQESA-LTTSPGETVTLTCRSSTGAV---TTSNYANWVQEKPDHLFTGLIGGTN
```

Figure 3B

```
prox   C.PP..:....S.S.S..S..............I:ISICCCCCCCCCCISI...........
pos          60        70        80        90     abcdef  100     a
hK1    sLeSGVPSRFSGSGSGTDFTLTISSLQPEDFATYYCQQynslPE-----wTFGQGTKVEI-KRT (SEQ ID NO: 819)
hK2    NRaSGVPDRFSGSGSGTDFTLKISRVEAEDVGVYYCMQalQ-PR------TFGQGTKVEI-KRT (SEQ ID NO: 820)
hK3    SRATGIPDRFSGSGSGTDFTLTISRLEPEDFAVYYCQQYGsSPP-----lTFGQGTKVEI-KRT (SEQ ID NO: 821)
hK4    TRESGVPDRFSGSGSGTDFTLTISSLQAEDVAVYYCQQYYStP-------TFGQGTKVEI-KRT (SEQ ID NO: 822)
mK1    TRESGVPDRFTGSGSGTDFTLTISSVQAEDLAVYYCQndYSYP------LTFGAGTKLEL-KRA (SEQ ID NO: 823)
mK2    NRFSGVPDRFSGSGSGTDFTLKISRVEAEDLGVYYCfQgtHVPP-----yTFGGGTKLEI-KRA (SEQ ID NO: 824)
mK3    NLESGVPARFSGSGSGTDFTLnIhPVEedDaATYYCQQSnEdPP-----wTFGGGTKLEI-KRA (SEQ ID NO: 825)
mK4    NLASGVPARFSGSGSGTSYSLTISSMEAEDAATYYCQQwSsyPxG----lTFGaGTKLEI-KRA (SEQ ID NO: 826)
mK5    rLhsGVPSRFSGSGSGTDYSLTISnLEqEDiAtYfCQQgntlPP-----rTFGGGTKLEI-KRA (SEQ ID NO: 827)
mK6    KLASGVPARFSGSGSGTSYSLTISSMEAEDAATYYCQQWSSNPPM---PlTFGAGTKLEL-KRA (SEQ ID NO: 828)
hL1    kRPSGvPDRFSGSKSGTSAsLAIxGLQseDEADYYCatWDdSLsaxNSApVFGGGTKLTVLGQP (SEQ ID NO: 829)
hL2    dRPSGvPdRFSGSKSGnTASLTISGLQaEDEADYYCsSYgggsxx----nVFGGGTKxTVLGQP (SEQ ID NO: 830)
hL3    kRPSGIPERFSGSnSGnTATLTISGvqAgDEADYYCQaWDSssdhPG—vVFGGGTKLTVLGQP  (SEQ ID NO: 831)
hL4    NRPSGIPDRFSGSSSGxTASLTITGAQAEDEADYYCNSRDSSGxx----xxFGGGTKLTVLGQP (SEQ ID NO: 832)
hL5    kRPSGVPDRFSGSKSgNTASLTVSGLqAEDEADYYCSSYegsdN-----FVFGtGTKvTVLgQP (SEQ ID NO: 833)
hL6    QRPSGVPDRFSGS-SSNSASLTISGLKTEDEADYYCQSYDsnNh-----wVFGGGTKLTVLGQP (SEQ ID NO: 834)
mL     NRAPGVPARFSGSLIGDKAALTITGAQTEDEAIYFCALWYSNHEQFV—WVFGGGTKLTVLGQP  (SEQ ID NO: 835)
```

Figure 3C

```
prox    PS.S....:....:......:.SPSSCSCCCCSISSSI.I.:...I.ISSCSCCCCCCCCC
pos              10        20        30    ab   40        50  abc
hH1     qVQLVQSGAEVKKPGaSVKVSCKASGYTFtSYaIs--WVRQAPGQGLEWMGwInPY-gnGdT
hH2     QVQLQESGPGLVKPSqTLSLTCtvSGgSvSsyxwswnWIRQPPGkGLEWIGrIyYRAysgst
hH3     EVQLVESGGGLVQPGGSLRLSCAASGFTFSsyaMs--WVRQAPGKGLEWVsvIsgKtdGgst
mH1a    eVQLQESGPsLVKPSQtLSLTCSVTGdSITSgYwnNSWIRxFPGNKLEwMGYIsx--YSGST
mH1b    QVQLKESGPGLVAPSQSLSITCTVSGFSLTSYGVHVSWVRQPPGKGLEWLGVIW---aGGST
mH2a    EVQLQQSGPELVKPGASVKiSCKASGYTFTdYyMnN-WVKQspGKsLEWIGdInP--gnGgT
mH2b    QVQLQQPGAELVKPGASVKLSCKASGYTFTSYWMH--WVKQRPGQGLEWIGrIdP--nsGgT
mH2c    EVQLQQSGAELVKPGASVKLSCTASGFNIKDTYMH--WVKQRPEQGLEWIGRIDP--ANGNT
mH3a    EVKLVESGGGLVQPGGSLRLSCATSGFTFSDFYME--WVRQPPGKaLEWiAasRNKANdYTT
mH3b    EVKLLESGGGLVQPGGSLKLSCAASGFDFSRYWMS--WVRQAPGKGLEWIGEINPKADSSTI
mH3c    EVKLEESGGGLVQPGGSMKLSCVASGFTFSNYWMnxxWVRQSPEKGLEWVAeIRLKSdNYAT
mH3d    EVqLVESGGGLVKPGGSLKLSCAASGFTFSsYaMS--WVRQTPEKRLEWVAtISsKSgGgyT
mH5a    EVQLQQSGAELVRAGSSVKMSCKASGYTFTSYGIN--WVKQRPGQGLEWIGYINP--GNGYT
mH5b    EVQLQQSGAELVKAGSSVKMSCSATGYTFSSYGLY--WVRQAPGQGLExxGYISS--SSAYP
mHms    xVQLveSGggLVkPGgSvKlSCkASGfTFssfgMsNFWVRQaPgKgLEWvgwINsKLgggai
```

Figure 3D

```
prox    CPSPP.P....S.S.P..P.S..............I:ISICCCCCCCCCCCCCCICCI..........
pos      60        70        80  abc      90       100abcdefghijk      110
hH1     nYAQkFQGRVTiTaDtStSTAYMELSSLRSeDTAVYYCARapgygsgggcyrgdyxFDyWGQGTLVTVSS (SEQ ID NO: 836)
hH2     xYnpSLKSRvTIsvDTSKNQFSLkLsSVTaaDTAVYYCARexxxgxxgddyyyxxgfDvWGQGTlVTVSS (SEQ ID NO: 837)
hH3     yYADSVKGRFTISRDnSKNTLYLQMNSLRaEDTAVYYCArxxxxxxlsgxyyyyhyFDyWGQGTLVTVSS (SEQ ID NO: 838)
mH1a    yYNPSLKSRISITRDTSKNQyfLQLNSVTTEDTATYYCARxxygyxxyxydxYYyYFDYWGQGTtvtVSS (SEQ ID NO: 839)
mH1b    NYNSALmSRLSISKDNSKSQVFLKMNSLQTDDTAMYYCARDrGxyyyxsgxxxYYAmDYWGQGTsVTVSS (SEQ ID NO: 840)
mH2a    sYNQKFKGKATLTvDKSSSTAYMqLsSLTSEDSAVYYCARxxyysssxmxaxxYYaFDYWGQGTtVTVSS (SEQ ID NO: 841)
mH2b    nYNEKFKsKATLTVDKSSSTAYMQLSSLTSEDSAVYYCARyyyggssxxvYx-YwyFDYWGQGTtvTVSS (SEQ ID NO: 842)
mH2c    KYDPKFQGKATITADTSSNTAYLQLSSLTSEDTAVYYCARgyyyydsxVG---YyAMDYWGQGTxVTVSS (SEQ ID NO: 843)
mH3a    EYSASVKGRFtvSRDtSQSILYLQMNALRAEDtAiYYCARdyyygssyyeGPVYWYFDVWGaGTTVTVSS (SEQ ID NO: 844)
mH3b    NYTPSLKDKFIISRDNAKNTLYLQMSKVRSEDTALYYCARlggygyfgSS---YYamdYWGQGTtvTVSS (SEQ ID NO: 845)
mH3c    HYAESVKGRFTISRDDSKSSVYLQMNNLRAEDTGIYYCTtggyggxRRS-----xWFaYWGQGTlVTVSs (SEQ ID NO: 846)
mH3d    YYPDSVKGRFTISRDNAKNTLYLQMSSLrSEDTAmYYCARgxyyyxxgsaPF-DYAmDYWGQGTsVTVSS (SEQ ID NO: 847)
mH5a    kYNEKFKGKTTLTVDKSSSTAYMQLRSLTSEDSAVYFCARSxYYGGSYyyxFAYYyFDYWGQGTTLTVSS (SEQ ID NO: 848)
mH5b    NYAQKFQGRVTITADESTNTAYMELSSLRSEDTAVYFCAVRVISRYF---------DGWGQGTLV---- (SEQ ID NO: 849)
mHms    yYAdtxKGRFTISRDNsKsTLYLQMssLrSEDTAtYyCARxgyyggrrsxxxSYwyFDYWGQGTtVTVSS (SEQ ID NO: 850)
```

Figure 4

Physical Size

(DIVIDE SIZE DIFFERENCES BY THREE AND DROP THE FRACTION AFTER THE DECIMAL)

| Nonpolar Size | Polar | Negative | Positive | | Special Size | |
|---|---|---|---|---|---|---|
| 10 | W | | | | 10 | |
| 9 | | | | | 9 | |
| 8 | | Y | | | 8 | |
| 7 | F | | | R | 7 | |
| 6 | | | | H | 6 | |
| 5 | | Q | E | K | 5 | |
| 4 | L I M | N | D | | 4 | x |
| 3 | V | T | | | 3 | p |
| 2 | | S | | | 2 | c |
| 1 | A | | | | 1 | |
| 0 | G | | | | 0 | - |

Chemical-Function Charge-and-Class

(1 POINT FOR CHANGE OF CLASS, PLUS 1 POINT FOR EACH UNIT OF CHARGE DIFFERENCE)

0 no change in class or charge
1 Nonpolar vs. Polar; Nonconserved vs. (Nonpolar or Polar)
2 (Positive or Negative) vs. (Nonpolar or Polar or Nonconserved)
3 Positive vs. Negative

Nonidentity

1 any change of sidechain, including insertions or deletions

Repeated Identical Mutation

2 each repeat

Figure 5

```
                                                                                                          AscI
                                                                                                       ~~~~~~~~~
2901                                                                                                   GG CGCGCCTAAC
                                                                                                       CC GCGCGGATTG
3001 CATCTATTTC AAGGAGACAG TCATAATGAA ATACCTATTG CCTACGGCAG CCGCTGGATT GTTATTACTC GCTGCCCAAC CAGCGATGGC GCAGATCCAG
     GTAGATAAAG TTCCTCTGTC AGTATTACTT TATGGATAAC GGATGCCGTC GGCGACCTAA CAATAATGAG CGACGGGTTG GTCGCTACCG CGTCTAGGTC
                                                                                             CDR1
                                                                                    ~~~~~~~~~~~~~~~~~~~~
3101 TTGGTGCAGT CTGGACCTGA GCTGAAGAAG CCTGGAGAGA CAGTCAAGAT CTCCTGCAAG GCTTCTGGAT ATACCTTCAC AAAATATGGA ATGAACTGGG
     AACCACGTCA GACCTGGACT CGACTTCTTC GGACCTCTCT GTCAGTTCTA GAGGACGTTC CGAAGACCTA TATGGAAGTG TTTTATACCT TACTTGACCC
                                                              CDR2
                                          ~~~~~~~~~~~~~~~~~~~~~~~~~~~~~~~~~
3201 TGAAGCAGGC TCCAGGAAAG GGTTTAAAGT GGATGGGCTG GATAAACACC TACACTGAAG AGCCTACATA TGGTGATGAC TTCAAGGGAC GGTTTGCCTT
     ACTTCGTCCG AGGTCCTTTC CCAAATTTCA CCTACCCGAC CTATTTGTGG ATGTGACTTC TCGGATGTAT ACCACTACTG AAGTTCCCTG CCAAACGGAA
                                                                                                       CDR3
                                                                                                  ~~~~~~~~~~~~~
3301 CTCTTTGGAA ACCTCTGCCA GCACTGCCAA TTTGCAGATC AACAACCTCA AAAGTGAGGA CACGGCTACA TATTTCTGTG CAAGATTTGG CTCTXXXGTG
     GAGAAACCTT TGGAGACGGT CGTGACGGTT AAACGTCTAG TTGTTGGAGT TTTCACTCCT GTGCCGATGT ATAAAGACAC GTTCTAAACC GAGACGACAC
      CDR3
     ~~~~~~
3401 GACTACTGGG GTCAAGGAAC CTCGGTCACC GTCTCCTCAG CCTCCACCAA GGGCCCATCG GTCTTCCCCC TGGCACCCTC CTCCAAGAGC ACCTCTGGGG
     CTGATGACCC CAGTTCCTTG GAGCCAGTGG CAGAGGAGTC GGAGGTGGTT CCCGGGTAGC CAGAAGGGGG ACCGTGGGAG GAGGTTCTCG TGGAGACCCC
3501 GCACAGCGGC CCTGGGCTGC CTGGTCAAGG ACTACTTCCC CGAACCGGTG ACGGTGTCGT GGAACTCAGG CGCCCTGACC AGCGGCGTTC ATACCTTCCC
     CGTGTCGCCG GGACCCGACG GACCAGTTCC TGATGAAGGG GCTTGGCCAC TGCCACAGCA CCTTGAGTCC GCGGGACTGG TCGCCGCAAG TATGGAAGGG
3601 GGCTGTCCTA CAGTCCTCAG GACTCTACTC CCTCAGCAGC GTGGTGACCG TGCCCTCCAG CAGCTTGGGC ACCCAGACCT ACATCTGCAA CGTGAATCAC
     CCGACAGGAT GTCAGGAGTC CTGAGATGAG GGAGTCGTCG CACCACTGGC ACGGGAGGTC GTCGAACCCG TGGGTCTGGA TGTAGACGTT GCACTTAGTG
                                                               NotI
                                                            ~~~~~~~~~
3701 AAGCCCAGCA ACACCAAGGT GGACAAGAGA GTTGAGCCCA AATCTTGTGC GGCCGC (SEQ ID NO: 950)
     TTCGGGTCGT TGTGGTTCCA CCTGTTCTCT CAACTCGGGT TTAGAACACG CCGGCG (SEQ ID NO: 951)
```

Combination of beneficial ING Vk TAE mutations

Combination of beneficial ING VH TAE mutations

Figure 9A

ING-1 KABAT HEAVY CHAIN (KABAT NUMBERING)

```
                                   CDR1                 CDR2
1        10        20    26        36                   50 52A
QIQLVQSGPELKKPGETVKISCKASGYTFTKYGMNWVKQAPGKGLKWMGWINTYTEEPT
                                              CDR3
       66              82  83          95      103
YGDDFKGRFAFSLETSASTANLQINNLKSEDTATYFCARFGSAVDYWGQGTSVTVSS (SEQ ID NO: 952)
```

ING-1 CHOTHIA HEAVY CHAIN

```
                           CDR1                        CDR2
QIQLVQSGPELKKPGETVKISCKASGYTFTKYGMNWVKQAPGKGLKWMGWINTYTEEPT
                                              CDR3
YGDDFKGRFAFSLETSASTANLQINNLKSEDTATYFCARFGSAVDYWGQGTSVTVSS (SEQ ID NO: 953)
```

ING-1 IMGT HEAVY CHAIN

```
                           CDR1                         CDR2
QIQLVQSGPELKKPGETVKISCKASGYTFTKYGMNWVKQAPGKGLKWMGWINTYTEEPT
                                           CDR3
YGDDFKGRFAFSLETSASTANLQINNLKSEDTATYFCARFGSAVDYWGQGTSVTVSS (SEQ ID NO: 954)
```

ING-1 KABAT LIGHT CHAIN (KABAT NUMBERING)

```
                           CDR1                        CDR2
1                       24 27   28     35               50
QIVMTQAAFSNPVTLGTSGSISCRSSKSLLHSNGITYLYWYLQKPGQSPQLLIYQMS
                                         CDR3
    57                                  89                 98
NLASGVPDRFSSSGSGTDFTLRISRVEAEDVGVYYCAQNLELPRTFGGGTKLEMKR (SEQ ID NO: 955)
```

ING-1 CHOTHIA LIGHT CHAIN

```
                           CDR1                         CDR2
QIVMTQAAFSNPVTLGTSGSISCRSSKSLLHSNGITYLYWYLQKPGQSPQLLIYQMS
                                         CDR3
NLASGVPDRFSSSGSGTDFTLRISRVEAEDVGVYYCAQNLELPRTFGGGTKLEMKR (SEQ ID NO: 956)
```

ING-1 IMGT LIGHT CHAIN

```
                             CDR1                       CDR2
QIVMTQAAFSNPVTLGTSGSISCRSSKSLLHSNGITYLYWYLQKPGQSPQLLIYQMS
                                         CDR3
NLASGVPDRFSSSGSGTDFTLRISRVEAEDVGVYYCAQNLELPRTFGGGTKLEMKR (SEQ ID NO: 957)
```

Figure 9B

XPA23 KABAT HEAVY CHAIN (KABAT NUMBERING)

1 10 26 36 50 52A
EVQLLESGGGLVQPGGSLRLSCAASGFTFSKYFMFWVRQAPGKGLEWVSVISPSGGMTR
66 82 83 95 103
YADSVKGRFTISRDNSKNTLYLQMNSLRAEDTAVYYCARVGYGGNSDYWGQGTLVTVSS (SEQ ID NO: 958)

XPA23 CHOTHIA HEAVY CHAIN

CDR1 CDR2
EVQLLESGGGLVQPGGSLRLSCAASGFTFSKYFMFWVRQAPGKGLEWVSVISPSGGMTR
CDR3
YADSVKGRFTISRDNSKNTLYLQMNSLRAEDTAVYYCARVGYGGNSDYWGQGTLVTVSS (SEQ ID NO: 959

XPA23 IMGT HEAVY CHAIN

CDR1 CDR2
EVQLLESGGGLVQPGGSLRLSCAASGFTFSKYFMFWVRQAPGKGLEWVSVISPSGGMTR
CDR3
YADSVKGRFTISRDNSKNTLYLQMNSLRAEDTAVYYCARVGYGGNSDYWGQGTLVTVSS (SEQ ID NO: 960)

XPA23 KABAT LIGHT CHAIN (KABAT NUMBERING)

CDR1 CDR2
1 24 35 50 57
DIQMTQSPSSVSASVGDRLTIICRASQDINRWLAWYQQTPGNAPKLLIHSATSLQSGVP
CDR3
89 98
SRFSGSGSGTDFTLTINSLQPEDFATYYCQQADSFPLTFGGGTKVEIKR (SEQ ID NO: 961)

XPA23 CHOTHIA LIGHT CHAIN

CDR1 CDR2
DIQMTQSPSSVSASVGDRLTIICRASQDINRWLAWYQQTPGNAPKLLIHSATSLQSGVP
CDR3
SRFSGSGSGTDFTLTINSLQPEDFATYYCQQADSFPLTFGGGTKVEIKR (SEQ ID NO: 962)

XPA23 IMGT LIGHT CHAIN

CDR1 CDR2
DIQMTQSPSSVSASVGDRLTIICRASQDINRWLAWYQQTPGNAPKLLIHSATSLQSGVP
CDR3
SRFSGSGSGTDFTLTINSLQPEDFATYYCQQADSFPLTFGGGTKVEIKR (SEQ ID NO: 963)

XPA23 VH (SEQ ID NO: 958)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|
| E | V | Q | L | L | E | S | G | G | G | L | V | Q | P | G | G | S | L | R | L | S | C | A | A |

H1-1 ─ H1-2 ─ H1-3

| 25 | 26 | 27 | 28 | 29 | 30 | 31 | 32 | 33 | 34 | 35 | 36 | 37 |
|----|----|----|----|----|----|----|----|----|----|----|----|----|
| S | G | F | T | F | S | K | Y | F | M | W | V | R |

H2-1 ─ H2-2 ─ H2-3 ─ H2-4 ─ H2-5

| 38 | 39 | 40 | 41 | 42 | 43 | 44 | 45 | 46 | 47 | 48 | 49 | 50 | 51 | 52 | 53 | 54 | 55 | 56 | 57 | 58 | 59 |
|----|----|----|----|----|----|----|----|----|----|----|----|----|----|----|----|----|----|----|----|----|----|
| S | R | D | N | S | P | G | G | M | T | R | Y | A | D | S | V | K | G | R | F | T | I |

| 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 |
|----|----|----|----|----|----|----|----|----|----|----|----|----|----|----|----|----|----|----|----|----|----|----|----|
| S | R | D | N | S | K | N | T | L | Y | L | Q | M | N | S | L | R | A | E | D | T | A | V | Y |

H3-1 ─ H3-2 ─ H3-3 ─ H3-4 ─ H3-5

| 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|----|----|----|----|----|----|----|----|----|----|----|----|----|----|----|----|-----|-----|-----|-----|-----|-----|-----|-----|
| Y | C | A | R | V | G | Y | G | N | S | D | Y | W | G | Q | G | T | L | V | T | V | S | S |

Figure 10B

XPA23 V-kappa

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|
| D | I | Q | M | T | Q | S | P | S | S | V | S | A | S | V | G | D | R | L | T | I | I | C | R |

| 25 | 26 | 27 | 28 | 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|
| A | S | Q | D | I | N | R | W | L | A | W | Y | Q | Q | T | P | G | N | A | P | K | L |

| 47 | 48 | 49 | 50 | 51 | 52 | 53 | 54 | 55 | 56 | 57 | 58 | 59 | 60 | 61 | 62 | 63 | 64 | 65 | 66 |
|---|---|---|---|---|---|---|---|---|---|---|---|---|---|---|---|---|---|---|---|
| L | I | H | S | A | T | S | L | Q | S | G | V | P | S | R | F | S | G | S | G |

| 67 | 68 | 69 | 70 | 71 | 72 | 73 | 74 | 75 | 76 | 77 | 78 | 79 | 80 | 81 | 82 | 83 | 84 | 85 | 86 |
|---|---|---|---|---|---|---|---|---|---|---|---|---|---|---|---|---|---|---|---|
| S | G | T | D | F | T | L | T | I | N | S | L | Q | P | E | D | F | A | T | Y |

| 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|
| Y | C | Q | Q | A | D | S | F | P | L | T | F | G | G | G | T | K | V | E | I | K | (SEQ ID NO: 987) |

FIGURE 10C

ING-1 VH

HC1

1 2 3 4 5 6 7 8 9 10 11 12 13 14 15 16 17 18 19 20 21 22 23 24 25 26 27 28 29 30 31 32 33 34 35 36 37 38 39 40 41 42 43 44 45

1 2 3 4 5

G Y T F T K Y G M N

Q I Q L V Q S G P E L K K P G E T V K I S C K A S W V K Q A P G K G L

HC2

50 51 52 53 54 55 56 57 58 59 60 61 62 63 64 65 66 67 68 69 70 71 72 73 74 75 76 77 78 79 80 81 82 83 84 85 86 87 88 89 90 91 92 93 94

1 2 3 4 1 2 3 4 5

W I N T Y T L E E T Y G D D F K G

R F A F S L E T S A S T A N L Q I N N L K S E D T A T Y

HC3

99 100 101 102 103 104 105 106 107 108 109 110 111 112 113 114 115 116 117 118 119 120 121 122 123 124 125 126 127 128 129 130 132 133 134 135 136 137 138 139 140 141 142 143 144

1 2 3 1 2

F G S A V D Y (SEQ ID NO: 988)

FIGURE 10D

ING-1 V-kappa

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | LC1 | | | | | | | | | | | | | | | |
| | | | | | | | | | | | | | | | | | | | | | | | | | | 1 | 2 | 3 | 4 | 1 | 2 | 3 | | 1 | 2 | 3 | | | | | | | | |
| | | | | | | | | | | | | | | | | | | | | | | | R | S | S | K | S | L | L | M | S | N | G | I | T | Y | L | Y | | | | | | |
| Q | I | V | M | T | Q | A | A | F | S | N | P | V | T | L | G | T | S | G | S | I | S | C | | | | | | | | | | | | | | | | | W | Y | L | Q | K | P |

| 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | LC2 | | | | | | | | | | | | | | | | | | | | | | | | | | | | | | | | | | | | |
| | | | 1 | 2 | 3 | 4 | 5 | | | | | | | | | | | | | | | | | | | | | | | | | | | | | | | | | | | | | |
| | | | Y | Q | M | S | N | L | A | S | | | | | | | | | | | | | | | | | | | | | | | | | | | | | | | | C | A | Q |
| L | L | I | | | | | | | | | G | V | P | D | R | F | S | S | S | G | S | G | T | D | F | T | L | R | I | S | R | V | E | A | E | D | V | G | V | Y | Y | | | |

(SEQ ID NO: 989)

Figure 11

ING-1 Heavy Chain $k_{off}$ Map

| HCDR1 | $k_{off}$ fold-improvement |
|---|---|
| T28V | 2.08 |
| T28I | 2.45 |
| T28P | 2.16 |
| T30Y | 2.00 |
| G33F | 7.19 |
| G33L | 2.27 |
| G33P | 6.31 |

| HCDR2 | $k_{off}$ fold-improvement |
|---|---|
| W50D | 3.27 |
| T53V | 2.44 |
| T53I | 11.40 |
| T53A | 9.03 |
| Y54R | 3.72 |
| Y54K | 3.62 |
| Y54N | 2.11 |
| Y54G | 3.72 |
| T59W | 2.24 |

| HCDR3 | $k_{off}$ fold-improvement |
|---|---|
| G100R | 7.51 |
| S101K | 2.20 |
| S101Q | 2.18 |
| S101V | 1.92 |
| S101I | 3.53 |
| S101G | 3.31 |
| A102R | 2.18 |
| A102H | 2.40 |
| A102Y | 3.01 |
| A102W | 3.13 |
| A102F | 2.97 |
| A102G | 3.58 |

Figure 12

ING-1 Light chain $k_{off}$ Map

| LCDR1 | $k_{off}$ fold-improvement |
|---|---|
| S28R | 2.78 |
| S28K | 2.32 |
| S28H | 1.90 |
| S28Y | 2.02 |
| S28F | 2.38 |
| S28Q | 1.99 |
| S28V | 2.15 |
| S28I | 2.35 |
| S28L | 2.60 |
| S28P | 2.42 |
| L29S | 2.03 |
| L29A | 1.97 |
| H31Y | 2.16 |
| H31T | 1.94 |
| Y37H | 4.07 |

| LCDR2 | $k_{off}$ fold-improvement |
|---|---|
| Y54K | 3.62 |
| Y54L | 3.44 |
| Q55R | 5.31 |
| Q55H | 3.82 |
| Q55W | 4.11 |
| S57W | 2.34 |
| N58W | 1.99 |
| N58V | 2.84 |
| N58I | 2.51 |
| N58P | 3.47 |

| LCDR3 | $k_{off}$ fold-improvement |
|---|---|
| L97I | 2.62 |
| E98R | 3.08 |
| E98K | 2.22 |
| E98T | 4.90 |
| E98S | 2.21 |
| E98L | 2.82 |
| L99I | 2.07 |
| P100Y | 1.94 |

Figure 13

XPA23 Heavy chain mutations with 2-fold koff improvement

| HCDR1 | $k_{off}$ fold-improvement |
|---|---|
| K31Y | 2.5 |
| K31W | 3.6 |
| K31L | 5.4 |
| K31P | 4.6 |
| K31H | 6.5 |

| HCDR2 | $k_{off}$ fold-improvement |
|---|---|
| S54K | 5.0 |
| G56L | 2.2 |
| G56Q | 3.2 |
| G56I | 4.4 |
| G56K | 4.8 |
| G56R | 4.8 |

| HCDR3 | $k_{off}$ fold-improvement |
|---|---|
| Y101L | 4.9 |
| G103V | 3.9 |
| N104A | 3.4 |
| N104V | 2.6 |
| S105E | 2.2 |
| S105P | 3.7 |

Figure 14

XPA23 Light chain mutations with >2-fold koff improvement

| LCDR1 | $k_{off}$ fold-improvement |
|---|---|
| Q27S | 3.3 |
| Q27F | 3.7 |
| Q27G | 4.2 |
| D28L | 7.8 |
| D28S | 5.2 |
| D28W | 3.8 |

| LCDR2 | $k_{off}$ fold-improvement |
|---|---|
| A51G | 3.8 |
| S53K | 4.1 |
| S53R | 3.3 |

| LCDR3 | $k_{off}$ fold-improvement |
|---|---|
| D92S | 6.6 |
| S93D | 4.6 |
| S93E | 3.7 |
| P95S | 4.0 |
| P95A | 3.9 |
| L96W | 5.5 |

Figure 15
A.
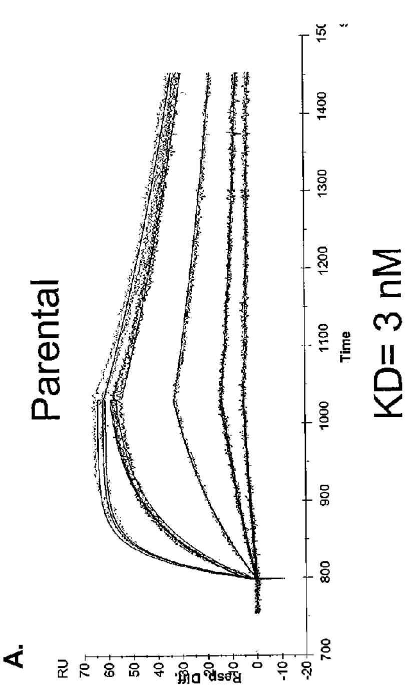
B.
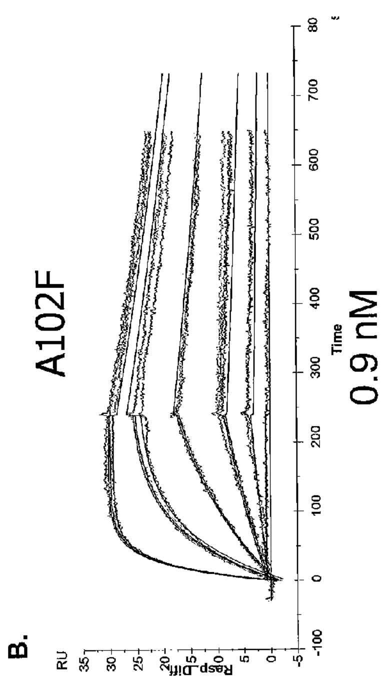
C.
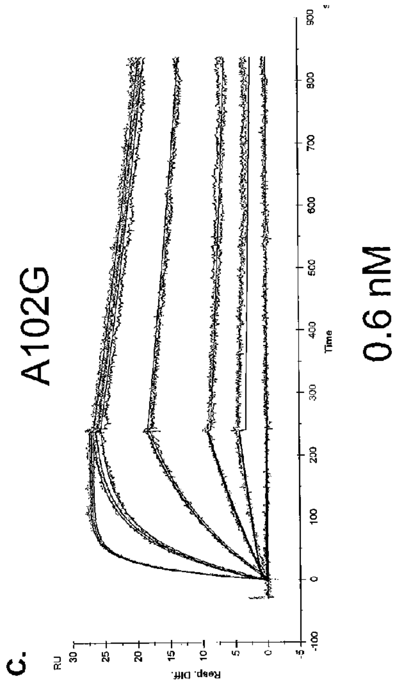
D.
| | K-on IgG | K-off IgG | KD IgG | Fold Improvement |
|---|---|---|---|---|
| Ch-ING-1 Fab/IgG (Parental) | 4.9e+5 | 2.0e-3 | 3.1e-9 | |
| A102F | 7.7e+5 | 7.6e-4 | 9.9e-10 | 3.1 |
| A102G | 8.8e+5 | 5.3e-4 | 6.0e-10 | 5.1 |

TAE (ING-1 LC)

METHODS AND MATERIALS FOR TARGETED MUTAGENESIS

CROSS-REFERENCE TO RELATED APPLICATIONS

This application claims the benefit of International Patent Application No. PCT/US2008/088651, filed on Dec. 31, 2008; U.S. Provisional Application No. 61/018,113, filed Dec. 31, 2007; U.S. Provisional Application No. 61/018,105, filed Dec. 31, 2007; and U.S. Provisional Application No. 61/018,101, filed Dec. 31, 2007, the disclosures of which are herein incorporated by reference in their entirety.

FIELD

The present disclosure relates to methods and materials for mutagenesis, including for the generation of novel or improved proteins and libraries or arrays of mutant proteins or nucleic acids encoding such mutant proteins.

BACKGROUND

Mutagenesis is a powerful research tool whereby genetic information is deliberately changed in a stable manner (see, e.g., Hutchinson et al. (1978) *J. Biol. Chem.* 253:6551; and Razin et al. (1978) *Proc. Natl. Acad. Sci. USA* 75:4268). Mutagenesis may be performed experimentally by employing the use of recombinant DNA technology and used to introduce specific mutations in a gene to study the effects on its encoded protein. By comparing the properties of a wild-type protein and the mutants generated, it may be possible to identify individual amino acids or domains of amino acids that may be important for the structural integrity and/or biochemical function of the protein (e.g., binding and/or catalytic activity).

Methods of mutagenesis may be random (e.g., error prone PCR) or deliberate (e.g., site directed mutagenesis). A common feature of many methods of mutagenesis is the use of synthetic primers (e.g., oligonucleotides) carrying desired changes in a nucleotide sequence at the site of mutagenesis. For example, saturation mutagenesis uses primers with one or more degenerate codons (e.g., a NNN, a NNK or a NNS codon) that codes for all possible amino acid substitutions at one or more sites in the parent nucleic sequence. Such degenerate codons may code for 32 to 64 unique codons which collectively may encode 20 amino acids in a redundant fashion (e.g., multiple codons for the same amino acid) and a stop codon. For example, given the degeneracy of the genetic code some amino acid residues may be overrepresented (e.g., Arg, Leu, and Ser). This technique depends on screening a large number of variants and may require multiple large libraries using phage or ribosomal display to explore the variants. Another technique, error prone PCR uses polymerase to introduce mutations at random positions in a parent nucleic acid sequence. This technique may introduce mutations outside of an area of interest (e.g., a binding pocket such as a CDR) and necessitate backmutation to identify a productive mutation. Accordingly, methods for mutagenesis are desired that produce manageable libraries comprising targeted mutations at one or more positions in a parent nucleic acid sequence.

SUMMARY

The present disclosure relates to methods and materials for mutagenesis, including for the generation of novel or improved proteins and libraries or arrays of mutant proteins or nucleic acids encoding such mutant proteins. The present disclosure provides methods and materials for targeted mutagenesis of proteins, including by mutating one or more selected positions in a parent nucleic acid sequence. The proteins targeted for mutagenesis can be natural, synthetic or engineered proteins or variants (e.g., mutants of such proteins). The proteins can include binding proteins such as antibodies or their binding fragments and ligands or receptors. The proteins can also include enzymes or catalytic molecules.

The present disclosure provides methods of mutagenesis of a parent nucleic acid sequence encoding a protein by obtaining one or more primers that each comprise at least one 2 to 12 fold degenerate codon, wherein the primers are complementary to a sequence in the parent nucleic acid sequence and wherein the primers code for amino acid mutations at each of one or more amino acid positions encoded by the parent nucleic acid sequence; and subjecting the parent nucleic acid sequence to replication or polymerase based amplification using the obtained primers, wherein replication or amplification of the parent nucleic acid sequence with the primers generates variant nucleic acid sequences and wherein the variant nucleic acid sequences comprise amino acid mutations at the one or more positions in the parent nucleic acid sequence with the exception of cysteine and methionine.

The present disclosure provides methods of mutagenesis of a parent nucleic acid encoding a protein to generate modified proteins by obtaining one or more primers that each comprise at least one 2 to 12 fold degenerate codon, wherein each primer comprises at least two oligonucleotide sequences that are complementary to a sequence in the parent nucleic acid and code for an amino acid mutation with the exception of cysteine or methionine at one amino acid position encoded by the parent nucleic acid; and mutating the parent nucleic acid by replication or polymerase based amplification using the one or more obtained primers, wherein replication or amplification of the parent nucleic acid with the one or more primers generates mutated nucleic acids that encode modified proteins.

The present disclosure also provides libraries/arrays of mutated nucleic acid sequences generated by the methods of the present disclosure.

The present disclosure also provides methods for mutagenesis of a protein to obtain modified proteins with mutated amino acid sequences by identifying one or more amino acid positions in the protein for mutagenesis; substituting one or more of the identified amino acid residues in the protein with other amino acid residues excluding cysteine and methionine to generate a library or an array of modified proteins with mutated amino acid sequences; screening the library or array of modified proteins in an assay for a biological activity of the protein; and obtaining modified proteins having the biological activity of the protein.

The present disclosure also provides methods for generating an array of nucleic acids encoding modified proteins by obtaining a collection of nucleic acids encoding modified proteins containing amino acid mutations other than cysteine and methionine at amino acid residues of a parent protein sequence by mutagenesis of a nucleic acid encoding the protein sequence using primers that each comprise at least one 2 to 12 fold degenerate codon; sequencing the collection of nucleic acids encoding the modified proteins; and arranging each sequenced nucleic acid encoding a modified protein to generate an array of nucleic acid sequences each encoding a modified protein.

The present disclosure also provides methods for generating an array of nucleic acid sequences encoding modified proteins by preparing a plurality of nucleic acid sequences by mutagenesis that encode a plurality of modified proteins that vary from a parent protein sequence at one or more amino acid positions and contain one of eighteen different amino acids excluding cysteine and methionine at each position mutated from the parent protein sequence; and arranging each prepared nucleic acid sequence to generate an array of nucleic acid sequences each encoding a modified protein.

The present disclosure also provides libraries/arrays of mutated nucleic acid sequences generated by the method of the present disclosure.

The present disclosure also provides methods for generating an array of clones comprising nucleic acids encoding modified proteins by preparing a plurality of nucleic acids by mutagenesis that encode a plurality of modified proteins that vary from a parent protein sequence at one or more amino acid positions and contain one of eighteen different amino acids excluding cysteine and methionine at each position varied from the parent protein sequence; transfecting the prepared nucleic acids prepared into host cells and selecting clones comprising the transfected nucleic acids; and arranging each selected clone to generate an array of clones with each arrayed clone capable of expressing a modified protein.

The present disclosure also provides methods of producing a nucleic acid library with an equal representation of non-redundant amino acid changes at an amino acid position encoded by a parent nucleic acids by providing a set of primers that each comprise at least one degenerate codon, wherein each primer comprises at least two oligonucleotide sequence that are complementary to a sequence in the parent nucleic acid and code for an amino acid mutation with the exception of cysteine and methionine at one amino acid position encoded by the parent nucleic acid, wherein the primers code for an equal representation of non-redundant amino acid changes at the one position; hybridizing a primer from the set to the parent nucleic acid; replicating or amplifying the parent nucleic acid molecule with the primer to generate nucleic acids that code for amino acid changes at the one position; repeating the hybridizing and replicating steps with each remaining primer from the set; pooling the nucleic acids produced with each primer; and obtaining a library of nucleic acids coding for an equal representation of amino acid changes at the one position.

The present disclosure also provides methods for obtaining a nucleic acid sequence with an improvement in comparison to a parent nucleic acid sequence with respect to at least one molecular or biological property of interest by obtaining a set of primers that each comprise at least one 2 to 12 fold degenerate codon that does not code for cysteine and methionine, wherein the primers are complementary to a sequence in the parent nucleic acid sequence and wherein the primers code for non-redundant amino acid mutations at one amino acid position encoded by the parent nucleic acid sequence; mutating the parent nucleic acid sequence by replication or polymerase based amplification using the obtained set of primers to generate variant nucleic acid sequences; producing a library or array of variant nucleic acid sequences from (b) coding for amino acid mutations at the one position in the parent nucleic acid sequence; and screening the library or array of variant nucleic acid sequences to identify nucleic acid sequences that have a desirable improvement in comparison with the parent nucleic acid sequence with respect to at least one molecular or biological property of interest.

The present disclosure also provides methods of making modified proteins with mutated amino acid sequences by modifying the amino acid sequence of a protein to produce amino acid mutations at an amino acid residue in the protein to generate a library or an array of modified proteins with mutated amino acid sequences, wherein the amino acid mutations exclude cysteine and methionine; and selecting modified proteins from the library or the array that have a biological activity of an unmodified protein.

The present disclosure also provides methods for selecting modified proteins with mutated amino acid sequences by obtaining a library or an array of modified proteins comprising amino acid mutations at one amino acid residues in an amino acid sequence of a protein, wherein the amino acid mutations exclude cysteine and methionine; assaying the modified proteins for a biological activity of an unmodified protein; and selecting the modified proteins that have a biological activity of the unmodified protein.

The present disclosure also provides a set of primers that each comprise at least one 2 to 12 fold degenerate codon, wherein each primer comprises at least two oligonucleotide sequences that are complementary to a sequence in a parent nucleic acid and code for an amino acid mutation with the exception of cysteine or methionine at one amino acid position encoded by the parent nucleic acid.

The present disclosure also provides a kit for mutagenesis of an amino acid residue encoded by a parent nucleic acid comprising a set of primers that each comprise at least one 2 to 12 fold degenerate codon, wherein each primer comprises at least two oligonucleotide sequences that are complementary to a sequence in a parent nucleic acid and code for an amino acid mutation with the exception of cysteine or methionine at one amino acid position encoded by the parent nucleic acid.

The present disclosure also provides libraries/arrays comprising variants of a protein sequence, wherein the variants each comprise an amino acid mutation at one amino acid position in the protein sequence of a parent protein and wherein the amino acid mutations are not cysteine or methionine.

The present disclosure also provides methods for obtaining a nucleic acid sequence with an improvement in comparison to a parent nucleic acid sequence with respect to at least one molecular or biological property of interest by mutating the parent nucleic acid by polymerase based amplification using one or more primers that each comprise at least one 2 to 12 fold degenerate codon to generate mutated nucleic acid sequences, wherein each primer comprises at least two oligonucleotide sequences that are complementary to a sequence in the parent nucleic acid and code for an amino acid mutation with the exception of cysteine or methionine at one amino acid position encoded by the parent nucleic acid; sequencing the mutated nucleic acid sequences; arranging each sequenced mutated nucleic acid sequence comprising one amino acid mutation to generate an array of mutated nucleic acid sequences; and screening the array of variant nucleic acid sequences to identify nucleic acid sequences that have a desirable improvement in comparison with the parent nucleic acid sequence with respect to at least one molecular or biological property of interest.

In some embodiments, the amino acid mutations are selected from the group consisting of: alanine, arginine, asparagine, aspartic acid, glutamine, glutamine acid, glycine, histidine, isoleucine, leucine, lysine, phenylalanine, proline, serine, threonine, tryptophan, tyrosine and valine at each position.

In some embodiments, the primers code for eighteen amino acid mutations at the one amino acid position encoded by the parent nucleic acid.

In some embodiments, three primers that each comprise at least one 2 to 12 fold degenerate codon are obtained. In some embodiments, seven primers that each comprise at least one 2 to 12 fold degenerate codon are obtained. In some embodiments, the degenerate codons are selected from the group consisting of: NHT or NHC (where N=A/G/C/T, H=A/C/T), VAG or VAA (where V=A/C/G) and BGG or DGG (where B=C/G/T, D=A/G/T). In some embodiments, the degenerate codons are selected from the group consisting of: ARG (where R=A/G), WMC (where W=A/T and M=A/C), CAS (where S=C/G), GAS (where S=C/G), NTC (where N=A/G/C/T), KGG (where K=G/T) and SCG (where S=C/G).

In some embodiments, the primers code for basic amino acid mutations at the one amino acid position encoded by the parent nucleic acid. In some embodiments, one primer that comprises at least one 2 to 12 fold degenerate codon is obtained. In some embodiments, the one primer comprises a degenerate codon which codes for arginine and lysine. In some embodiments, the degenerate codon is represented by ARG (where, R=A/G).

In some embodiments, the primers code for polar amino acid mutations at the one amino acid position encoded by the parent nucleic acid. In some embodiments, two primers that comprise at least one 2 to 12 fold degenerate codon is obtained. In some embodiments, the two primers comprise degenerate codons that collectively code for serine, threonine, asparagine and tyrosine. In some embodiments, the degenerate codons are represented by WMC (where, W=A/T; M=A/C) and CAS (where S=C/G).

In some embodiments, the primers code for acidic amino acid mutations at the one amino acid position encoded by the parent nucleic acid. In some embodiments, one primer that comprises at least one 2 to 12 fold degenerate codon is obtained. In some embodiments, the one primer comprises a degenerate codon that codes for glutamic acid and aspartic acid. In some embodiments, the degenerate codon is represented by GAS (where S=C/G).

In some embodiments, the primers code for non-polar amino acid mutations at the one amino acid position encoded by the parent nucleic acid. In some embodiments, three primers that comprise at least one 2 to 12 fold degenerate codon are obtained. In some embodiments, the three primers comprise degenerate codons that collectively code for glutamic acid and aspartic acid. In some embodiments, the degenerate codons are represented by NTC (where, N=A/G/C/T), KGG (where, K=G/T), and SCG (where S=C/G).

In some embodiments, the parent nucleic acid encodes a binding molecule. In some embodiments, the binding molecule is an antibody or fragment thereof.

In some embodiments the methods may further comprise selecting the one or more positions in the parent nucleic acid sequence for mutation. In some embodiments the methods may further comprise transforming the mutated nucleic acid sequences into competent cells.

In some embodiments, the step of substituting is performed with one or more primers that each comprise at least one 2 to 12 fold degenerate codon, wherein each primer comprises at least two oligonucleotide sequences that are complementary to a sequence in a parent nucleic acid and code for an amino acid substitution with the exception of cysteine and methionine at one amino acid position encoded by the parent nucleic acid. In some embodiments, the step of modifying is performed with one or more primers that each comprise at least one 2 to 12 fold degenerate codon, wherein each primer comprises at least two oligonucleotide sequences that are complementary to a sequence in a parent nucleic acid and code for an amino acid substitution with the exception of cysteine and methionine at one amino acid position encoded by the parent nucleic acid.

In some embodiments, the biological property of interest is binding.

In some embodiments, modified proteins are selected that have increased activity as compared to the unmodified protein. In some embodiments, modified proteins are selected that have decreased activity as compared to the unmodified protein. In some embodiments, modified proteins are selected that have equal activity as compared to the unmodified protein.

Additional features and advantages are described herein, and will be apparent from, the following Detailed Description and the Figures.

BRIEF DESCRIPTION OF THE FIGURES

The Figures relate to exemplary proteins, including those useful for mutagenesis according to methods and materials disclosed herein.

FIGS. 2A-2D: Alignments of sequences in the light chain and heavy chain, with lines (e.g., prox, cspc) relating to affinity enhancement and lines relating to human engineering (e.g., risk) are shown. In each set of lines, the top ones apply the present disclosure to the murine ING1 antibody (2A-2B), and the bottom ones relate the present disclosure to the general principles of human engineering (Studnicka et al., Protein Engineering, 7(6):805-814 (1994); U.S. Pat. No. 5,766,886). Each set of lines shows the Kabat position numbers (pos), the general classification of proximity groups for each position of every antibody (prox), the murine ING1 monoclonal antibody sequence to be affinity-enhanced (murINGI), the conspicuousness value as described herein of each position for affinity-enhancement when the murine ING1 antibody is compared to murine consensus sequences (cspc), several murine consensus sequences to which ING1 is compared (mK2 or mH2a), the human ING1 residues which are introduced during the HUMAN ENGINEERING™ process (humING1), the degree of disconnection of the sidechain from the antibody's combining site (disc) as described herein, the degree of outward-orientation of the sidechain on the antibody's surface (outw) as described herein, the degree of risk for human engineering (risk), and the Kabat position numbers (pos) (2A-2B). Similarly, FIGS. 2C and 2D are alignments of sequences in the light chain and heavy chain of IL-1 antibody (also referred to as cA5 and/or XPA23), with lines (e.g., prox, cspc) relating to affinity enhancement and lines relating to human engineering (e.g., risk).

FIGS. 3A-3D are mutual alignments of consensus sequences (Kabat et al. (1991) (eds), Sequences of Proteins of Immunological Interest, 5th ed.) for major murine and human subgroups of the light chain and heavy chain. Each alignment relates them to the proximity groups as described herein for each position (prox), and the Kabat position numbers (pos).

FIG. 4 shows a chart of the numerical components which can be added together to calculate each amino acid's affinity-enhancement conspicuousness value, including the components for changes in class-and-charge, for changes in physical size due to somatic mutation, and for repeated identical mutations at the same position in multiple homologous antibodies.

FIG. 5 shows PCR mutagenesis of CDR3 utilizing the CDR-H3 oligonucleotide H3-3NP2 (SEQ ID NO: 267): 5'-GCTACATATTTCTGTGCAAGATTTG GCTCT-KGGGTGGACTACTGGGGTCAAGG-3', which introduces an amino acid substitution into CDR3, and the reverse primer NotI-R (SEQ ID NO: 285): 5'-AGCGGCCGCACAA-GATTTGGGCTCAACTCTC-3', which incorporates the NotI restriction site into the PCR product.

FIG. 9A-9B shows CDR1, CDR2 and CDR3 as identified by the Kabat, Chothia and IMGT numbering scheme for ING-1 (9A) and XPA23 (9B).

FIG. 10A-10D depict a continuous numbering scheme for the heavy and light chain of XPA23 (10A and 10B, respectively). Consecutive numbering from position 1 in the light chain continues in the heavy chain such that position 1 in the heavy chain is also assigned number 108 since the light chain sequence ends at number 107. Boxed residues indicate CDRs identified by the IMGT method. FIGS. 10C and 10D show a continuous numbering scheme for the heavy and light chain of ING-1 (10C and 10D, respectively).

FIG. 11: Periplasmic extracts of clones containing one of the eighteen preferred amino acid mutations at Heavy Chain contacting positions in ING-1 were tested on Biacore for improved off-rate (see example 7). Clones with greater than 1.9-fold decrease in off-rate are listed.

FIG. 12: Periplasmic extracts of clones containing one of the eighteen preferred amino acid mutations at Light Chain contacting positions in ING-1 were tested on Biacore for improved off-rate (see example 7). Clones with greater than 1.9-fold decrease in off-rate are listed.

FIG. 13: Periplasmic extracts of clones containing one of the eighteen preferred amino acid mutations at Heavy Chain contacting positions in XPA23 were tested on Biacore for improved off-rate (see example 7). Clones with greater than 1.9-fold decrease in off-rate are listed.

FIG. 14: Periplasmic extracts of clones containing one of the eighteen preferred amino acid mutations at Light Chain contacting positions in XPA23 were tested on Biacore for improved off-rate (see example 7). Clones with greater than 1.9-fold decrease in off-rate are listed.

FIG. 15A-15D depicts two modified IgGs with an A102F or 102G substitution that were prepared and evaluated by Biacore with improved affinity (15B-15C, respectively) as compared to the parental (15A) ING-1 antibody. 15D shows the affinity determination kinetics for both the modified and parental ING-1 antibodies.

DETAILED DESCRIPTION

Figure 1:
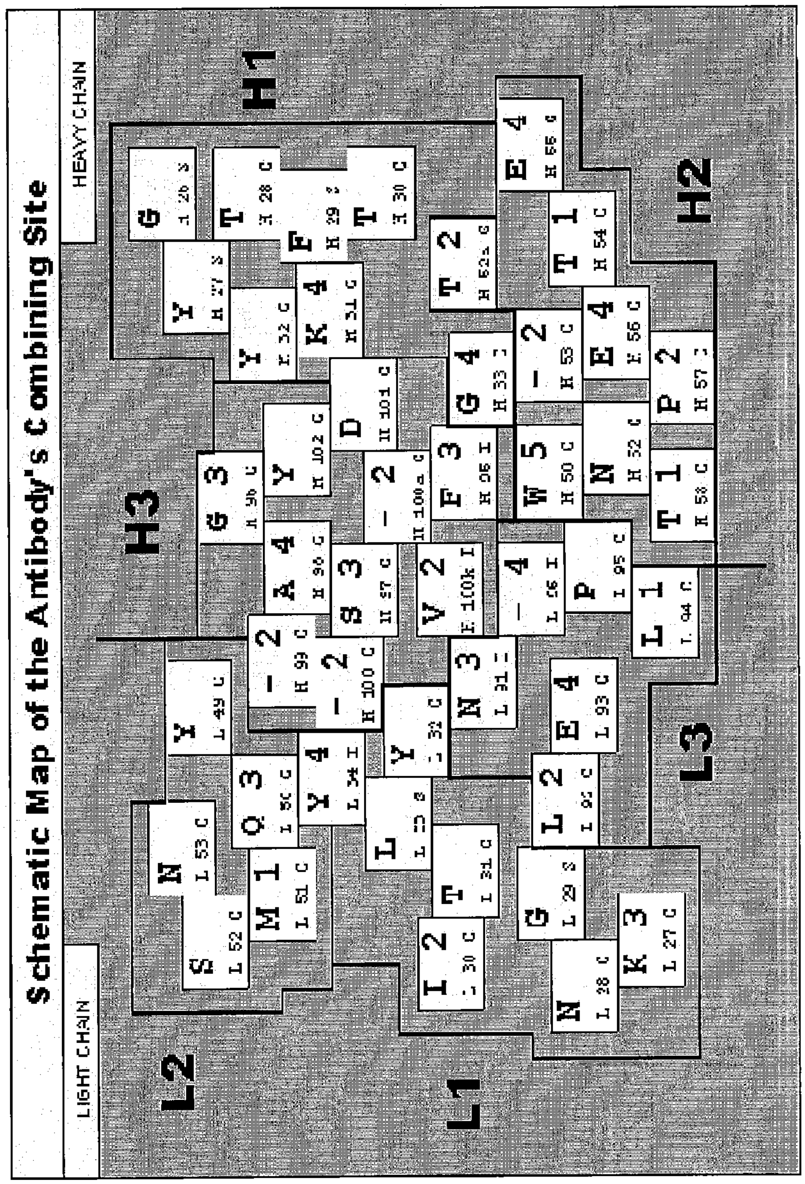
FIG. 1 is a generalized schematic map of an exemplary antibody combining site as described herein, looking downward onto the "top" surface of a variable domain comprising a light chain variable region and a heavy chain variable region. It shows the six CDR loops (L1, L2, L3, H1, H2, H3) which are spatially located directly above the three-dimensional structure of the evolutionarily-conserved framework underneath. As shown and discussed herein, this map provides roughly approximate higher-order structural information, which is not available from the linear primary sequence alone, such as the identity of potential nearest neighbors in the space-filling model of a generic variable domain. Specific features of the murine ING1 monoclonal antibody have been added to this map, so that it can also call attention to localized domains of the antibody's combining site containing clusters of high-conspicuousness positions as described herein, which are likely to be in contact with sidechains on the antigen. In particular, each amino-acid position in the murine ING1 antibody is represented on this map by a white rectangle containing a group of symbols. The letter and number at the bottom-left of each rectangle (e.g., "H 98" in CDR-loop H3) is the Kabat-position number of the amino-acid residue on the antibody molecule within either chain (L=light, H=heavy). The small upper-case letter (e.g., "B") at the bottom-right is a designation for the residue's proximity as described herein (C=Contacting, P=Peripheral, S=Supporting, I=Interfacial) relative to the antibody's binding site (shown on the "prox" line in FIGS. 2A-2D). The large upper-case letter (e.g., "A") at the upper-left is the amino-acid code for the residue's sidechain (line "murING1" in FIGS. 2A-2D). The large single digit at the upper right (e.g., "3") in some rectangles is the non-zero conspicuousness-value as described herein of affinity enhancement for the sidechain (line "cspc" in FIGS. 2A-2D), calculated in reference to the appropriate human consensus sequence for light chain (hK2) or heavy chain (hH 1). Rectangles with no such value reflect a conspicuousness of zero.

The present disclosure provides methods and materials for targeted mutagenesis of one or more selected positions in a parent nucleic acid sequence (e.g., a nucleotide sequence coding for an antibody or binding fragment thereof such as an IgG, Fab or ScFv). When the parent nucleic acid sequence encodes an antibody variable region, preferred positions for selection and mutagenesis are those encoding one of more CDR amino acid residues. Particularly preferred is mutation of each of the CDR residues in a heavy and/or light chain variable region. Techniques for site-directed mutagenesis of a nucleotide sequence rely on using degenerate codons including, for example, NNK or NNS. However, these degenerate codons may code for an overrepresentation of one or more amino acid residues which may result in the production of a large nucleotide library that does not contain all possible amino acid substitutions at a position of interest. The present disclosure provides novel degenerate codons that encode for an equal representation of eighteen amino acid residues including a stop codon. Notably, the degenerate codons may not code for cysteine and/or methionine. Additionally, the novel degenerate codons each collectively code for eighteen amino acid residues eliminating any redundancy which may result in an over-representation of one or more amino acid residues. As a result, the degenerate codons of the present disclosure allow for the generation of smaller, focused libraries that contain eighteen amino acid substitutions at a position of interest.

The present disclosure provides methods of mutagenesis of a parent nucleic acid sequence encoding a protein (e.g., an antibody or binding fragment thereof such as an IgG, Fab or scFv) by obtaining one or more primers that each comprise at least one 2 to 12 fold degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)), wherein the primers are complementary to a sequence in the parent nucleic acid sequence and wherein the primers code for amino acid mutations at each of one or more amino acid positions encoded by the parent nucleic acid sequence; and subjecting the parent nucleic acid sequence to replication or polymerase based amplification using the obtained primers, wherein replication or amplification of the parent nucleic acid sequence with the primers generates variant nucleic acid sequences and wherein the variant nucleic acid sequences comprise amino acid mutations at the one or more positions in the parent nucleic acid sequence with the exception of cysteine and methionine. Optionally, two or more mutations may be combined by recombinant DNA techniques into a single mutated protein.

The present disclosure provides methods of mutagenesis of a parent nucleic acid encoding a protein (e.g., an antibody or binding fragment thereof such as an IgG, Fab or scFv) to generate modified proteins by obtaining one or more primers that each comprise at least one 2 to 12 fold degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)), wherein each primer comprises at least two oligonucleotide sequences that are complementary to a sequence in the parent nucleic acid and code for an amino acid mutation with the exception of cysteine or methionine at one amino acid position encoded by the parent nucleic acid; and mutating the parent nucleic acid by replication or polymerase based amplification using the one or more obtained primers, wherein replication or amplification of the parent nucleic acid with the one or more primers generates mutated nucleic acids that encode modified proteins.

The present disclosure also provides libraries/arrays of mutated nucleic acid sequences generated by the methods of the present disclosure.

The present disclosure also provides methods for mutagenesis of a protein (e.g., an antibody or binding fragment thereof such as an IgG, Fab or scFv) to obtain modified proteins with mutated amino acid sequences by identifying one or more amino acid positions in the protein for mutagenesis; substituting one or more of the identified amino acid residues in the protein with other amino acid residues excluding cysteine and methionine to generate a library or an array of modified proteins with mutated amino acid sequences; screening the library or array of modified proteins in an assay for a biological activity of the protein; and obtaining modified proteins having the biological activity of the protein.

The present disclosure also provides methods for generating an array of nucleic acids encoding modified proteins (e.g., an antibody or binding fragment thereof such as an IgG, Fab or scFv) by obtaining a collection of nucleic acids encoding modified proteins containing amino acid mutations other than cysteine and methionine at amino acid residues of a parent protein sequence by mutagenesis of a nucleic acid encoding the protein sequence using primers that each comprise at least one 2 to 12 fold degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)); sequencing the collection of nucleic acids encoding the modified proteins; and arranging each sequenced nucleic acid encoding a modified protein to generate an array of nucleic acid sequences each encoding a modified protein.

The present disclosure also provides methods for generating an array of nucleic acid sequences encoding modified proteins (e.g., an antibody or binding fragment thereof such as an IgG, Fab or scFv) by preparing a plurality of nucleic acid sequences by mutagenesis that encode a plurality of modified proteins that vary from a parent protein sequence at one or more amino acid positions and contain one of eighteen different amino acids excluding cysteine and methionine at each position mutated from the parent protein sequence; and arranging each prepared nucleic acid sequence to generate an array of nucleic acid sequences each encoding a modified protein.

The present disclosure also provides libraries/arrays of mutated nucleic acid sequences generated by the method of the present disclosure.

The present disclosure also provides methods for generating an array of clones comprising nucleic acids encoding modified proteins (e.g., an antibody or binding fragment thereof such as an IgG, Fab or scFv) by preparing a plurality of nucleic acids by mutagenesis that encode a plurality of modified proteins that vary from a parent protein sequence at one or more amino acid positions and contain one of eighteen different amino acids excluding cysteine and methionine at each position varied from the parent protein sequence; transfecting the prepared nucleic acids prepared into host cells and selecting clones comprising the transfected nucleic acids; and arranging each selected clone to generate an array of clones with each arrayed clone capable of expressing a modified protein.

The present disclosure also provides methods of producing a nucleic acid library with an equal representation of non-redundant amino acid changes at an amino acid position encoded by a parent nucleic acids by providing a set of primers that each comprise at least one degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)), wherein each primer comprises at least two oligonucleotide sequence that are complementary to a sequence in the parent nucleic acid and code for an amino acid mutation with the exception of cysteine and methionine at one amino acid position encoded by the parent nucleic acid, wherein the primers code for an equal representation of non-redundant amino acid changes at the one position; hybridizing a primer from the set to the parent nucleic acid; replicating or amplifying the parent nucleic acid molecule with the primer to generate nucleic acids that code for amino acid changes at the one position; repeating the hybridizing and replicating steps with each remaining primer from the set; pooling the nucleic acids produced with each primer; and obtaining a library of nucleic acids coding for an equal representation of amino acid changes at the one position.

The present disclosure also provides methods for obtaining a nucleic acid sequence with an improvement in comparison to a parent nucleic acid sequence with respect to at least one molecular or biological property of interest by obtaining a set of primers that each comprise at least one 2 to 12 fold degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)) that does not code for cysteine and methionine, wherein the primers are complementary to a sequence in the parent nucleic acid sequence and wherein the primers code for non-redundant amino acid mutations at one amino acid position encoded by the parent nucleic acid sequence; mutating the parent nucleic acid sequence by replication or polymerase based amplification using the obtained set of primers to generate variant nucleic acid sequences; producing a library or array of variant nucleic acid sequences from (b) coding for amino acid mutations at the one position in the parent nucleic acid sequence; and screening the library or array of variant nucleic acid sequences to identify nucleic acid sequences that have a desirable improvement in comparison with the parent nucleic acid sequence with respect to at least one molecular or biological property of interest.

The present disclosure also provides methods of making modified proteins (e.g., an antibody or binding fragment thereof such as an IgG, Fab or scFv) with mutated amino acid sequences by modifying the amino acid sequence of a protein to produce amino acid mutations at an amino acid residue in the protein to generate a library or an array of modified proteins with mutated amino acid sequences, wherein the amino acid mutations exclude cysteine and methionine; and selecting modified proteins from the library or the array that have a biological activity of an unmodified protein.

The present disclosure also provides methods for selecting modified proteins (e.g., an antibody or binding fragment thereof such as an IgG, Fab or scFv) with mutated amino acid sequences by obtaining a library or an array of modified proteins comprising amino acid mutations at one amino acid residues in an amino acid sequence of a protein, wherein the amino acid mutations exclude cysteine and methionine; assaying the modified proteins for a biological activity of an unmodified protein; and selecting the modified proteins that have a biological activity of the unmodified protein.

The present disclosure also provides a set of primers that each comprise at least one 2 to 12 fold degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)), wherein each primer comprises at least two oligonucleotide sequences that are complementary to a sequence in a parent nucleic acid and code for an amino acid mutation with the exception of cysteine or methionine at one amino acid position encoded by the parent nucleic acid.

The present disclosure also provides a kit for mutagenesis of an amino acid residue encoded by a parent nucleic acid comprising a set of primers that each comprise at least one 2 to 12 fold degenerate codon (e.g., NHT or NHC (where N=A/G/C/T, H=A/C/T), VAG or VAA (where V=A/C/G) and BGG or DGG (where B=C/G/T, D=A/G/T), ARG (where R=A/G), WMC (where W=A/T and M=A/C), CAS (where S=C/G), GAS (where S=C/G), NTC (where N=A/G/C/T), KGG (where K=G/T) and SCG (where S=C/G)), wherein each primer comprises at least two oligonucleotide sequences that are complementary to a sequence in a parent nucleic acid and code for an amino acid mutation with the exception of cysteine or methionine at one amino acid position encoded by the parent nucleic acid.

The present disclosure also provides libraries/arrays comprising variants of a protein sequence, wherein the variants each comprise an amino acid mutation at one amino acid position in the protein sequence of a parent protein and wherein the amino acid mutations are not cysteine or methionine.

Selection of a Defined Region or Amino Acid Residue for Mutagenesis

A region(s) or a specific amino acid residue(s) in a protein may be subjected to the methods of mutagenesis as described herein. A region of a protein for mutagenesis may be deduced from comparing the region(s) to what is known from the study of other proteins, and may be aided by modeling information. For example, the region may be one that has a role in a functional site including, for example, in binding, catalysis, or another function. Regions involved in binding may include, for example, a hypervariable region or complementarity determining region (CDR) of an antigen binding molecule.

In an exemplary method to select amino acid residues in an antibody or binding fragment thereof for mutation, the amino acid residues may be assigned to a proximity group. For example, each amino acid in an antibody heavy and/or light chain variable region may be assigned to one of the following unique groups, which includes, contacting (C), peripheral (P), supporting (S), interfacial (I), or distant (D) residues, as shown, for example, on the "prox" lines of FIGS. 2A, 2B, 2C, 2D, 3A, and/or 3B. For example, each of the more-than-200 amino-acid positions in an antibody's variable light chain and heavy chain has been designated as a member of one of these five novel groups. The "prox" line as shown in FIG. 3A or 3B is useful for any variable region sequence, irrespective of the present disclosure provides methods for mutagenesis of one or more defined region(s) within a protein. The region(s) may be important to a protein's structure or function. These region(s) can be deduced, for example, from what structural and/or functional aspects are known or specific amino acid sequence, such that residues can be selected as candidates for change (e.g., any and/or all contacting (C) residues). Additionally or alternatively, methods are provided that identify the presence of conspicuous amino-acid residues which may be candidates for change. Conspicuous amino acid changes may differ in charge or size or chemical functionality from the corresponding residues in the selected sequence (e.g., consensus or germline sequence) and represent positions where amino acid changes may enhance affinity.

Exemplary methods for characterization of amino acid residues in an antibody binding domain may include: a determination of each amino acid residue's proximity group as designated on the "prox" line of FIGS. 2A, 2B, 2C, 2D, 3A and/or 3B and additionally or alternatively a determination of each amino acid residue's conspicuousness as calculated by the methods provided in the present disclosure.

A. Determination of Proximity Groups

The characterization process may determine the proximity group for each amino-acid position simply by inspecting the corresponding symbol ("CPSI.:") on the "prox" lines as shown, for example, in FIGS. 2A, 2B, 2C and/or 2D. In some embodiments, the antibody's light-chain and/or heavy-chain sequences are aligned with appropriate sequences (e.g., such as consensus or germline sequences) and also with the "prox" lines of the present methods (FIGS. 2A, 2B, 2C and/or 2D), Each position in the light chain and heavy chain has been assigned to one of five novel groups designated as contacting (C), peripheral (P), supporting (S), interfacial (I), or distant (D) on the "prox" lines, for example, of FIGS. 2A, 2B, 2C, 2D, 3A, and/or 3B according to the methods disclosed herein. These Figures (e.g., 2A, 2B, 2C, 2D, 3A and/or 3B) contain a disc line to reflect disconnection from any significant effect upon an antibody's binding site, and an outw line to reflect outward-orientation on an antibody's surface.

Table 1 shows five proximity groups, as well as a novel designation of disconnection (as shown on a "disc" line, for example, in FIGS. 2A, 2B, 2C, 2D, 3A and/or 3B) and outward-orientation (shown as an "outw" line, for example, in FIGS. 2A, 2B, 2C, 2D, 3A and/or 3B) as defined for each group. The number of positions of each type of proximity group for an exemplary antibody (e.g., ING-1, as described herein) in a light chain, a heavy chain, and both chains together are shown in Table 2.

TABLE 1

| Proximity | Abbr | Disc/Outw | | |
|---|---|---|---|---|
| Contacting | C | −/+ | −/o | |
| Peripheral | P | o/+ | o/o | |
| Supporting | S | −/− | o/− | |
| Interfacial | I | −/= | o/= | +/= |
| Distant | • | +/+ | +/o | +/− p c |

TABLE 2

| Proximity | L | H | L + H |
|---|---|---|---|
| Contacting | 16 | 21 | 37 |
| Peripheral | 3 | 8 | 11 |
| Supporting | 14 | 16 | 30 |
| Interfacial | 9 | 10 | 19 |
| Distant | 70 | 63 | 133 |

Without being bound by a theory of the invention, it has been hypothesized that amino acid residues designated as contacting (C) are located within the combining site (see, e.g., "−" on the "disc" line of FIGS. 2A, 2B, 2C and/or 2D), and their sidechains are mostly outward-oriented (see, e.g., "+" or "○" on the outw line). It has been further hypothesized that these are generally surface-exposed residues in the CDR loops themselves, so their sidechains are very favorably situated for making direct contact with corresponding residues on a binding partner.

Without being bound by a theory of the invention, it has been hypothesized that amino acid residues designated as peripheral (P) are slightly disconnected from the binding site (see, e.g., "○" on the "disc" line), and their sidechains are mostly outward-oriented (see, e.g., "+" or "○" on the outw line). Many of these are framework residues with variable orientation, which are located at curves or twists in the protein chain not too far from CDR loops. Although they may normally not make direct contact with a binding partner, they may possibly make contact if a particular binding partner is bound preferentially toward one side of the binding site instead of being centered.

Without being bound by a theory of the invention, it has been hypothesized that amino acid residues designated as supporting (S) are either directly within or close to the combining site (see, e.g., "−" or "○" on the "disc" line), and their sidechains are inward-oriented (see, e.g., "−" on the outw line). It has been further hypothesized that many of these residues are buried in the Vernier-zone platform directly underneath a combining site, so that their nonpolar sidechains are able to act as conformation-stabilizing "anchors" for CDR loops which rest on top of them.

Without being bound by a theory of the invention, it has been hypothesized that amino acid residues designated as interfacial (I) may be located anywhere in relation to the binding site (see, e.g., "+" or "○" or "−" on the "disc" line), but their sidechains form the interface between the light and heavy subunits of the variable domain (see, e.g., "=" on the outw line). It has been further hypothesized that amino acid changes of these residues may cause the two subunits to pivot or rotate relative to one another along their shared hydrophobic interfacial surface, producing strong allosteric effects upon an entire binding site, for example, all six CDR loops may be forced to change their conformation in response.

Without being bound by a theory of the invention, it has been hypothesized that amino acid residues designated as distant (D) are of two different types, with those of the first type being disconnected from a combining site and its targeted epitope (see, e.g., "+" on the "disc" line), and their sidechains may have any orientation except interfacial (see, e.g., "+" or "○" or "−" but not "=" on the outw line). It is further hypothesized that amino acid changes at these positions generally will have little or no effect on enhanced affinity to a binding partner.

B. Determination of Conspicuousness

In some embodiments, alternatively or additionally with determination of the proximity groups by inspection of the "prox" lines, the characterization process may involve a calculation of the conspicuousness value for each amino-acid position. The conspicuousness value of a sidechain at a particular antibody position is hypothesized to represent the degree to which it appears strikingly different or unusually outstanding in comparison with selected sequences (e.g., a consensus or germline sequence). Without being bound by a theory of the invention, this value indicates the likelihood that this particular residue may be a somatic mutation which was necessary to confer binding partner specific affinity upon an antibody. Consequently, the conspicuousness value also correlates with the hypothesis that a new engineered amino acid substitution at or near this position could possibly lead to forming or strengthening a bond with a residue on a binding partner surface.

Conspicuousness values are calculated by comparing each sidechain of a candidate antibody with the corresponding sidechain of an appropriate consensus or germline sequence, for example, from a mutual alignment. For example, numerical values for conspicuousness can be calculated readily for each amino-acid position in a given antibody, according to the following formula: add 1 point for each three units of difference in size (e.g., divide the absolute value of the size-difference by 3 and drop the decimal without rounding); add 1 point for a shift from one sidechain class to another; add 1 point for each unit (absolute value) of difference in charge, and add 1 point for nonidentity (see, e.g., FIG. 4).

For example, where a single antibody sequence is aligned or compared with a single consensus or germline sequence, there is one "pair" of sequences being compared. The conspicuousness value for each amino-acid position in the alignment or comparison is the sum of the points for chemical function and physical size and nonidentity at that position. Where more than two sequences are aligned or compared together at the same time, each of the antibody sequences may form a separate "pair" with each of the consensus or germline sequences. The conspicuousness values are calculated as described (e.g., sum of function and size and nonidentity) for each pair of sequences being aligned or compared, and then the overall conspicuousness value for each amino acid position in the whole alignment is the sum of the values obtained from each pair at that position, while also adding in a value for repeated identical mutations.

It is hypothesized that nonidentity simply marks an amino-acid position as minimally conspicuous if it displays any kind of difference when compared with a corresponding consensus or germline position. Even a conservative mutation (e.g., from leucine to isoleucine or valine) may suggest a possible bond with a binding partner, especially if a slight change of size or shape was necessary to fine-tune steric relationships between the two molecules.

An exemplary calculation of conspicuousness is illustrated as follows. Four monoclonal antibodies to the same epitope were isolated, and portions of their heavy chains were mutually aligned with a germline sequence, between Kabat positions 25 and 57 [Mendez et al., Nature Genetics, 15:146-152 (1997)] (see, Table 3). Since this alignment contains more than two sequences, each of the four antibody sequences can separately form a "pair" with the one germline sequence. Thus, conspicuousness values are calculated separately for each of the four pairs, and then totaled at each amino-acid position, while also adding in the additional values for repeated identical mutations.

TABLE 3

```
prox:   PSSCSCCCCSISI.I.:...I.ISSCSCCCCCC

pos:        30        40        50

germ:   GSISSG̅GYYWSWIRQH̅PGKGLEWIGY̅IYYSGST
        (SEQ ID NO: 982)

mAb1:      N  D                  S     N

mAb2:         D   T                    N

mAb3:     v   D        p         HL    N

mAb4:      N  D              DC
```

Three repetitions are shown in Table 3, at positions 28 and 31 and 56. In each of these cases, an identical amino acid (N or D) has appeared at the same location in more than one independently isolated antibody. Accordingly, as described herein, these positions are given very high conspicuousness in the affinity enhancement process. An additional 2 points are added for each repetition of an identical amino acid at a given position (e.g., four D's amount to three repetitions of the first D, so it is worth 3×2=6 points).

In an example, at position 50, the first pair (germ:mAb 1) gets 3 points (Y to S=2 for size+0 for class+0 for charge+1 for nonidentity), the second pair (germ:mAb2) gets 0 points (unmutated Y=0+0+0+0), the third pair (germ:mAb3) gets 3 points (Y to H=0 for size+1 for class+1 for charge+1 for nonidentity), and the fourth pair (germ:mAb4) gets 0 points (unmutated Y=0+0+0+0). The total conspicuousness for position 50 is the sum (3+0+3+0) of these, plus 0 extra points for no repeated identical mutations, which finally gives 6.

In another example, at position 28, the first pair gets 1 point (S to N=0+0+0+1), the second and third pairs get 0 points, and the fourth pair gets I point. Since the somatic mutation N appears at position 28 twice, it is repeated once, and thus gets 2 extra points. The total conspicuousness for position 28 is the sum (1+0+0+1), plus 2 points for one repetition, which finally gives 4.

In another example, at position 31, each of the four pairs gets 4 points (G to D=1+1+1+1). Since the somatic mutation D appears at position 31 four times, it is repeated three times, and thus gets 3×2=6 extra points. The total conspicuousness for position 28 is the sum (4+4+4+4), plus 6 points for three repetitions, which finally gives 22.

The conspicuousness points can be calculated (one pair at a time and then summed) for positions 28, 31, and 50 in the antibody sequence provided in Table 2.

Degenerate Primers and Kits

The present disclosure provides primers and kits that may comprise one or more of the novel degenerate codons of the present disclosure. These degenerate codons that may be used to mutagenize a nucleotide sequence encoding a protein including, for example, an antibody such as an IgG, a Fab or a ScFv. The degenerate codons may code for an equal representation of eighteen amino acid substitutions including, for example, alanine (Ala, A), arginine (Arg, R), asparagine (Asn, N), aspartic acid (Asp, D), glutamine (Gln, Q), glutamic acid (Glu, E), glycine (Gly, G), histidine (His, H), isoleucine (Ile, I), leucine (Leu, L), lysine (Lys, K), phenylalanine (Phe, F), proline (Pro, P), serine (Ser, S), threonine (Thr, T), tryptophan (Trp, W), tyrosine (Tyr, Y) or valine (Val, V). The degenerate codons of the present disclosure do not code for cysteine and/or methionine. A degenerate primer may be between 2-fold degenerate (e.g., comprise 2 oligonucleotide sequences that collectively code for 2 different amino acid residues at the same position) and 12-fold degenerate (e.g., comprise 12 oligonucleotide sequence that collectively code for 12 different amino acid residues at the same position).

A set of primers is provided that comprise a set of primers that each comprise at least one 2 to 12 fold degenerate codon, wherein each primer comprises at least two oligonucleotide sequences that are complementary to a sequence in a parent nucleic acid and code for an amino acid mutation with the exception of cysteine or methionine at one amino acid position encoded by the parent nucleic acid. In some embodiments, the primer set codes for eighteen amino acid changes at each of one or more positions in the parent nucleic acid. In some embodiments, the set of primers each comprise a degenerate codon which collectively code for alanine, arginine, asparagine, aspartic acid, glutamine, glutamine acid, glycine, histidine, isoleucine, leucine, lysine, phenylalanine, proline, serine, threonine, tryptophan, tyrosine and valine at each position. A set of primers may comprise 2 or more primers (e.g., 3 or 7 primers) and contains a number of oligonucleotides equal to the sum of the degeneracy of each primer in the set. For example, a set of primers that comprises a 2-fold and a 4-fold degenerate primer contains six oligonucleotide sequences.

Kits are also provided for mutagenesis of a position in a parent nucleic acid that comprise a set of primers a set of primers that each comprise at least one 2 to 12 fold degenerate codon, wherein each primer comprises at least two oligonucleotide sequences that are complementary to a sequence in a parent nucleic acid and code for an amino acid mutation with the exception of cysteine or methionine at one amino acid position encoded by the parent nucleic acid.

A set of three degenerate codons may be used to mutagenize an amino acid position encoded by a parent nucleotide sequence. These degenerate codons may include, for example, NHT or NHC (where N=A/G/C/T, H=A/C/T), which codes for phenylalanine/serine/tyrosine/leucine/proline/histidine/isoleucine/threonine/asparagine/valine/alanine/aspartic acid, VAG or VAA (where V=A/C/G), which codes for glutamine/lysine/glutamic acid, and BGG or DGG (where B=C/G/T, D=A/G/T), which codes for tryptophan/arginine/glycine. Alternatively, a set of seven degenerate codons may be used to mutagenize one or more selected positions in a parent nucleotide sequence. These degenerate codons may include, for example, ARG (where R=A/G), which codes for arginine/lysine, WMC (where W=A/T and M=A/C), which codes for serine/threonine/asparagine/tyrosine, CAS (where S=C/G), which codes for histidine/glutamine, GAS (where S=C/G), which codes for glutamic acid/aspartic acid, NTC (where N=A/G/C/T), which codes for leucine/phenylalanine/isoleucine/valine, KGG (where K=G/T), which codes for tryptophan/glycine, and SCG (where S=C/G), which codes for proline/alanine.

Alternate degenerate codons may be used to mutagenize one or more selected positions in a parent nucleotide sequence by modifying the degenerate codons described above. For example, ARG may be replaced with ARA, WMC may be replaced with WMT, CAS may be replaced with CAK (K=G,T), CAM (M=A or C), or CAW (W=A or T), NTC with NTT, SCG with SCA, SCC, or SCT. In addition, the primer listed as NTC or NTT may be replaced with two primers MTC, KTC (or MTT/KTT; MTC/KTT; MTT/KTC); STC, WTC (or STT/WTT; STT/WTC; STC/WTT); RTC, YTC (or RTT/YTT; RTC/YTT, RTT/YTC).

Methods for Targeted Mutagenesis

The methods of the present disclosure may be used to mutagenize a nucleic acid sequence coding for a protein including, for example, an antibody or binding fragment thereof (e.g., an IgG, Fab or scFv). When the parent nucleic acid sequence encodes an antibody variable region, preferred positions for selection and mutagenesis are those encoding one of more CDR amino acid residues. Particularly preferred is mutation of each of the CDR residues in a heavy and/or light chain variable region. Methods for mutagenesis of the present disclosure may selectively target one or more regions of a protein including, for example, one or more amino acid residues. The region(s) mutagenized by the methods of the present disclosure may comprise a functional domain of a protein such as a binding or catalytic domain. For example, the region may be a hypervariable region (e.g., complementarity-determining region or CDR) of an immunoglobulin, the catalytic site of an enzyme, or a binding domain.

The CDRs (e.g., LCDR1, LCDR2 and LCDR3 for the light chain and HCDR1, HCDR2 and HCDR3 for the heavy chain) may be defined according to any known method in the art including, for example, Kabat, Chothia or IMGT. According to Kabat, LCDR1 comprises amino acid residues 24 to 34, LCDR2 comprises amino acid residues 50 to 56, LCDR3 comprises amino acid residues 89 to 97, HCDR1 comprises amino acid residues 31 to 35b, HCDR2 comprises amino acid residues 50 to 65 and HCDR3 comprises amino acid residues 95 to 102. According to Chothia, LCDR1 comprises amino acid residues 24 to 34, LCDR2 comprises amino acid residues 50 to 56, LCDR3 comprises amino acid residues 89 to 97, HCDR1 comprises amino acid residues 26 to 32, HCDR2 comprises amino acid residues 52 to 56 and HCDR3 comprises amino acid residues 95 to 102. According to IMGT, LCDR1 comprises amino acid residues 27 to 32, LCDR2 comprises amino acid residues 50 to 52, LCDR3 comprises amino acid residues 89 to 97, HCDR1 comprises amino acid residues 26 to 33, HCDR2 comprises amino acid residues 51 to 57 and HCDR3 comprises amino cid residues 93 to 102. Residues numbers for the Kabat, Chothia and IMGT CDRs are given as Kabat position numbers.

The present disclosure provides methods of mutagenesis of a parent nucleic acid sequence encoding a protein by obtaining one or more primers that each comprise at least one 2 to 12 fold degenerate codon, wherein the primers are complementary to a sequence in the parent nucleic acid sequence and wherein the primers code for amino acid mutations at one amino acid position encoded by the parent nucleic acid sequence; and subjecting the parent nucleic acid sequence to replication or polymerase based amplification using the obtained primers, wherein replication or amplification of the parent nucleic acid sequence with the primers generates variant nucleic acid sequences and wherein the variant nucleic acid sequences comprise amino acid mutations at the one position in the parent nucleic acid sequence with the exception of cysteine and methionine.

Several different regions of a protein may be mutagenized simultaneously. This approach may enable the evaluation of amino acid substitutions in conformationally related regions such as the regions which, upon folding of the protein, are associated to make up a functional site such as the catalytic site of an enzyme or the binding site of an antibody. For example, the six hypervariable regions of an immunoglobulin, which make up the unique aspects of the antigen binding site (e.g., Fv region), can be mutagenized simultaneously, or separately within the $V_H$ or $V_L$ chains, to study the three dimensional interrelationship of selected amino acids in this site.

Mutations may be introduced into a parent nucleic acid sequence by PCR mutagenesis using primers that comprise one or more degenerate codons. For example, basic amino acid changes may be introduced using the degenerate codon ARG (R=A/G), which codes for arginine/lysine. Polar amino acid changes may be introduced using the degenerate codons WMC (W=A/T; M=A/C), which codes for serine/threonine/asparagine/tyrosine and/or CAS (S=C/G), which codes for histidine/glutamine. Acidic amino acid changes may be introduced using the degenerate codon GAS (S=C/G), which codes for glutamic acid/aspartic acid. Non-polar changes may be introduced using the degenerate codons NTC (N=A/G/C/T), which codes for leucine/phenylalanine/isoleucine/valine, KGG (K=G/T), which codes for tryptophan/glycine and/or SCG (S=C/G), which codes for proline/alanine.

An oligonucleotide comprising one or more of the degenerate codons of the present disclosure may be synthesized by known methods for DNA synthesis. Such methods may involve the use of solid phase beta-cyanoethyl phosphoramidite chemistry (see, e.g., U.S. Pat. No. 4,725,677).

Methods are provided for making modified proteins that comprise changes at one or more positions in a parent protein in order to modify one or more biological properties of the parent protein. For example, one or more positions in a parent antibody may be modified in order to enhance the binding affinity of an antibody by means of producing targeted amino acid changes in the antibody's variable domain. Engineered amino acid changes may be introduced at positions likely to produce enhanced affinity based upon an amino acid residue's proximity group.

In an exemplary method, amino acid changes are engineered at one or more amino acid residues categorized as preferably contacting (C), peripheral (P), supporting (S) and/or interfacial on the "prox" lines of FIGS. 2A, 2B, 3A, and/or 3B. In other embodiments, amino acid residues categorized in more than one group may be selected for change. Less preferably one or more distant (D) amino acid residues may additionally or alternatively be changed.

Modified proteins are synthesized by mutating the nucleic acid encoding a parent protein, inserting the modified nucleic acid into an appropriate cloning vector and expressing the modified nucleic acid to produce modified proteins. Exemplary protocols are described below.

1. Making Modified Nucleic Acid

Modified proteins that comprise one or more amino acid sequence changes (e.g., substitutions) relative to a parent protein sequence may be produced by methods known in the art using the degenerate primers of the present disclosure. For example, amino acids may be preferably incorporated into a position of interest by utilizing seven different degenerate codons. Basic amino acid changes can be produced with a single oligonucleotide that contains the codon mixture of ARG (R=A/G), encoding Arg/Lys. Polar amino acid changes can be produced with two oligonucleotides. For example, the first oligonucleotide contains the codon mixture WMC (W=A/T; M=A/C), encoding Ser/Thr/Asn/Tyr, while the second polar oligonucleotide utilizes the codon mixture CAS (S=C/G), encoding His/Gln. Acidic amino acid changes can be produced with a single codon mixture of GAS, encoding Glu/Asp. Non-polar functional amino acid changes can be produced with four oligonucleotide mixtures: NTC (N=A/G/C/T), encoding Leu/Phe/Ile/Val, KGG (K=G/T), encoding Trp/Gly, and SCG, encoding Pro/Ala.

In some embodiments, all seven of the degenerate primers are used to perform one PCR reaction. In other embodiments, each degenerate primer is used in a separate PCR reaction. Any combination of PCR primers may be used in a PCR reaction.

DNA encoding modified proteins may be prepared by a variety of methods known in the art. These methods include, but are not limited to, preparation by oligonucleotide-mediated (or site-directed) mutagenesis, PCR mutagenesis, and cassette mutagenesis of an earlier prepared modified protein or a parent protein. These techniques may utilize antibody nucleic acid (DNA or RNA), or nucleic acid complementary to the protein nucleic acid.

In an exemplary method, Kunkel mutagenesis may be performed by placing a plasmid that contains a protein to be mutated into an $ung^-$ $dut^-$ strain of *E. coli* bacteria. $Dut^-$ (lacking dUTPase) bacteria accumulate dUTP and $ung^-$ (lacking uracil deglycosidase) bcteria cannot remove dUTP that gets incorporated into new DNA strands. The end result is that the plasmid is converted to DNA that lacks T's and contains U's instead. The U-containing target DNA may then be incubated with a mutagenic primer that base pairs with the target except at the location of the desired mutation. This mixture may then be incubated with Klenow, dNTP's and later Ligase and ATP to produce double-stranded plasmid with one strand containing U's and the new one containing only T's. Finally, the hybrid old/new double-stranded DNA may be transformed into bacteria that destroy the old U-containing DNA and produce a T-containing strand using the new and mutagenized DNA strand as a template.

DNA encoding a modified protein with more than one amino acid to be changed may be generated in one of several ways. If the amino acids are located close together in the protein chain, they may be mutated simultaneously using one oligonucleotide that codes for all of the desired amino acid changes. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be changed. The oligonucleotides are then annealed to the single-stranded template DNA simultaneously, and the second strand of DNA that is synthesized from the template will encode all of the desired amino acid changes.

The alternative method involves two or more rounds of mutagenesis to produce the desired mutant antibody. The first round is as described for the modified variable domain which comprise one amino acid change: wild-type DNA is used for the template, an oligonucleotide encoding the first desired amino acid change(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid change(s) is then annealed to this template, and the resulting strand of DNA now encodes mutations from both the first and second rounds of mutagenesis. This resultant DNA can be used as a template in a third round of mutagenesis, and so on.

2. Insertion of DNA into a Cloning Vehicle

The cDNA or genomic DNA encoding the modified protein may be inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

For example, the cDNA or genomic DNA encoding the modified protein may be inserted into a modified phage vector (i.e. phagemid). Construction of phage display libraries exploits the bacteriophage's ability to display peptides and proteins on their surfaces, i.e., on their capsids. Often, filamentous phage such as M13, f1 or fd are used. Filamentous phage contain single-stranded DNA surrounded by multiple copies of genes encoding major and minor coat proteins, e.g., pill. Coat proteins are displayed on the capsid's outer surface. DNA sequences inserted in-frame with capsid protein genes are co-transcribed to generate fusion proteins or protein fragments displayed on the phage surface. Peptide phage libraries thus can display peptides representative of the diversity of the inserted genomic sequences. Significantly, these epitopes can be displayed in "natural" folded conformations. The peptides expressed on phage display libraries can then bind target molecules, i.e., they can specifically interact with binding partner molecules such as antibodies (Petersen (1995) *Mol. Gen. Genet.* 249:425-31), cell surface receptors (Kay (1993) *Gene* 128:59-65), and extracellular and intracellular proteins (Gram (1993) *J. Immunol. Methods* 161:169-76).

The concept of using filamentous phages, such as M13, fd or fl, for displaying peptides on phage capsid surfaces was first introduced by Smith (1985) Science 228:1315-1317. Peptides have been displayed on phage surfaces to identify many potential ligands (see, e.g., Cwirla (1990) *Proc. Natl. Acad. Sci. USA* 87:6378-6382). There are numerous systems and methods for generating phage display libraries described in the scientific and patent literature (see, e.g., Sambrook and Russell, Molecule Cloning: A Laboratory Manual, 3rd edition, Cold Spring Harbor Laboratory Press, Chapter 18, 2001; "Phage Display of Peptides and Proteins: A Laboratory Manual, Academic Press, San Diego, 1996; Crameri (1994) *Eur. J. Biochem.* 226:53-58; de Kruif (1995) *Proc. Natl. Acad. Sci. USA* 92:3938-42; McGregor (1996) *Mol. Biotechnol.* 6:155-162; Jacobsson (1996) *Biotechniques* 20:1070-1076; Jespers (1996) *Gene* 173:179-181; Jacobsson (1997) *Micro-*

*biol Res.* 152:121-128; Fack (1997) *J. Immunol. Methods* 206:43-52; Rossenu (1997) *J. Protein Chem.* 16:499-503; Katz (1997) *Annu. Rev. Biophys. Biomol. Struct.* 26:27-45; Rader (1997) *Curr. Opin. Biotechnol.* 8:503-508; Griffiths (1998) *Curr. Opin. Biotechnol.* 9:102-108).

Typically, exogenous nucleic acid to be displayed are inserted into a coat protein gene, e.g. gene III or gene VIII of the phage. The resultant fusion proteins are displayed on the surface of the capsid. Protein VIII is present in approximately 2700 copies per phage, compared to 3 to 5 copies for protein III (Jacobsson (1996), supra). Multivalent expression vectors, such as phagemids, can be used for manipulation of exogenous genomic or antibody encoding inserts and production of phage particles in bacteria (see, e.g., Felici (1991) *J. Mol. Biol.* 222:301-310).

Phagemid vectors are often employed for constructing the phage library. These vectors include the origin of DNA replication from the genome of a single-stranded filamentous bacteriophage, e.g., M13, f1 or fd. A phagemid can be used in the same way as an orthodox plasmid vector, but can also be used to produce filamentous bacteriophage particle that contain single-stranded copies of cloned segments of DNA.

Other phage can also be used. For example, T7 vectors can be employed in which the displayed product on the mature phage particle is released by cell lysis.

In addition to phage epitope display libraries, analogous epitope display libraries can also be used. For example, the methods of the disclosure can also use yeast surface displayed epitope libraries (see, e.g., Boder (1997) Nat. Biotechnol. 15:553-557), which can be constructed using such vectors as the pYD1 yeast expression vector. Other potential display systems include mammalian display vectors and *E. coli* libraries.

An modified protein including, for example, an antibody or antibody fragment, e.g., a scFv, Fab or Fv may be displayed on the surface of a phage using phage display techniques. Exemplary antibody phage display methods are known to those skilled in the art and are described, e.g., in Hoogenboom, *Overview of Antibody Phage-Display Technology and Its Applications*, from *Methods in Molecular Biology: Antibody Phase Display: Methods and Protocols* (2002) 178:1-37 (O'Brien and Aitken, eds., Human Press, Totowa, N.J.). For example, a library of antibodies or antibody fragments (e.g., scFvs, Fabs, Fvs with an engineered intermolecular disulfide bond to stabilize the $V_H$-$V_L$ pair, and diabodies) can be displayed on the surface of a filamentous phage, such as the nonlytic filamentous phage fd or M13. Antibodies or antibody fragments with the desired binding specificity can then be selected.

An antibody phage-display library can be prepared using methods known to those skilled in the art (see, e.g., Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.).

In some embodiments, cDNA is cloned into a phage display vector, such as a phagemid vector (e.g., pCES1, p XOMA Fab or pXOMA Fab-gIII). In certain embodiments, cDNA encoding both heavy and light chains may be present on the same vector. In some embodiments, cDNA encoding scFvs are cloned in frame with all or a portion of gene III, which encodes the minor phage coat protein pIII. The phagemid directs the expression of the scFv-pIII fusion on the phage surface. In other embodiments, cDNA encoding heavy chain (or light chain) may be cloned in frame with all or a portion of gene III, and cDNA encoding light chain (or heavy chain) is cloned downstream of a signal sequence in the same vector. The signal sequence directs expression of the light chain (or heavy chain) into the periplasm of the host cell, where the heavy and light chains assemble into Fab fragments. Alternatively, in certain embodiments, cDNA encoding heavy chain and cDNA encoding light chain may be present on separate vectors. In certain embodiments, heavy chain and light chain cDNA may be cloned separately, one into a phagemid and the other into a phage vector, which both contain signals for in vivo recombination in the host cell.

The techniques for constructing and analyzing phage display libraries uses recombinant technology well known to those of skill in the art. General techniques, e.g., manipulation of nucleic encoding libraries, epitopes, antibodies, and vectors of interest, generating libraries, subcloning into expression vectors, labeling probes, sequencing DNA, DNA hybridization are described in the scientific and patent literature, see e.g., Sambrook and Russell, eds., Molecular Cloning: a Laboratory Manual (3rd), Vols. 1-3, Cold Spring Harbor Laboratory Press, (2001); Current Protocols in Molecular Biology, Ausubel, ed. John Wiley & Sons, Inc., New York (1997-2001) ("Ausubel"); and, Laboratory Techniques in Biochemistry and Molecular Biology: Hybridization with Nucleic Acid Probes, Part I. Theory and Nucleic Acid Preparation, Tijssen, ed. Elsevier, N.Y. (1993). Sequencing methods typically use dideoxy sequencing, however, other methodologies are available and well known to those of skill in the art.

3. Transformation of Host Cells

Suitable host cells for cloning or expressing the vectors herein may include prokaryote, yeast, or higher eukaryote cells. Suitable prokaryotes include eubacteria, such as Gram-negative or Gram-positive organisms, for example, *E. coli, Bacilli* such as *B. subtilis, Pseudomonas* species such as *P. aeruginosa, Salmonella typhimurium*, or *Serratia marcescens*.

For example, recombinant phagemid or phage vectors may be introduced into a suitable bacterial host, such as *E. coli*. In some embodiments using phagemid, the host may be infected with helper phage to supply phage structural proteins, thereby allowing expression of phage particles carrying the antibody-pIII fusion protein on the phage surface.

Methods for Identifying a Modified Protein with Altered Activity as Compared to a Parent Protein Methods are provided for identifying a modified protein with altered activity as compared to a parent protein. For example, a modified antibody variable domain having enhanced binding affinity for a binding partner may be identified by contacting a parent antibody variable domain with the binding partner under conditions that permit binding; contacting modified antibody variable domains made by the methods of the present disclosure with the binding partner under conditions that permit binding; and determining binding affinity of the modified antibody variable domains and the parent antibody variable domain for the binding partner, wherein modified antibody variable domains that have a binding affinity for the binding partner greater than the binding affinity of the parent antibody variable domain for the binding partner are identified as having enhanced binding affinity.

Isolated antibody variable domains may exhibit binding affinity as single chains, in the absence of assembly into a heteromeric structure with their respective $V_H$ or $V_L$ subunits. As such, populations of $V_H$ and $V_L$ altered antibody variable domains can be expressed alone and screened for binding affinity having substantially the same or greater binding affinity compared to the parent antibody $V_H$ or $V_L$ variable domain.

Alternatively, populations of antibody $V_H$ and $V_L$ altered variable domains proteins can be co-expressed so that they self-assemble into heteromeric altered antibody variable domain binding fragments. The heteromeric binding fragment population can then be screened for species exhibiting enhanced binding affinity to a binding partner compared to the binding affinity of the parent antibody variable domain.

The expressed population of modified antibody variable domains can be screened for the identification of one or more altered antibody variable domain species which exhibit enhanced binding affinity to a binding partner as compared with the parent antibody variable domain. Screening can be accomplished using various methods well known in the art for determining the binding affinity of a protein or compound. Additionally, methods based on determining the relative affinity of binding molecules to their partner by comparing the amount of binding between the modified antibody variable domain and the binding partner can similarly be used for the identification of species exhibiting binding affinity substantially the same or greater than the parent antibody variable domain to the binding partner. The above methods can be performed, for example, in solution or in solid phase. Moreover, various formats of binding assays are well known in the art and include, for example, immobilization to filters such as nylon or nitrocellulose; two-dimensional arrays, enzyme linked immunosorbant assay (ELISA), radioimmuno-assay (RIA), panning and plasmon resonance (see, e.g., Sambrook et al., supra, and Ansubel et al., supra).

For the screening of populations of proteins such as the modified antibody variable domains produced by the methods of the disclosure, immobilization of the modified antibody variable domains to filters or other solid substrates is particularly advantageous because large numbers of different species can be efficiently screened for binding to a binding partner. Such filter lifts allow for the identification of modified antibody variable domains that exhibit enhanced binding affinity compared to the parent antibody variable domain to the binding partner. Alternatively, the modified antibody variable domains may be expressed on the surface of a cell or bacteriophage. For example, panning on an immobilized binding partner can be used to efficiently screen for the relative binding affinity of species within the population of modified antibody variable domains and for those which exhibit enhanced binding affinity to the binding partner than the parent antibody variable domain.

Another affinity method for screening populations of modified antibody variable domains is a capture lift assay that is useful for identifying a binding molecule having selective affinity for a ligand. This method employs the selective immobilization of modified antibody variable domains to a solid support and then screening of the selectively immobilized modified antibody variable domains for selective binding interactions against the binding partner. Selective immobilization functions to increase the sensitivity of the binding interaction being measured since initial immobilization of a population of modified antibody variable domains onto a solid support reduces non-specific binding interactions with irrelevant molecules or contaminants which can be present in the reaction.

Another method for screening populations or for measuring the affinity of individual modified antibody variable domains is through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates ($k_m$) and disassociation rates (koff).

Measurements of $k_m$ and $k_{off}$ values can be advantageous because they can identify modified antibody variable domains with enhanced binding affinity for a binding partner. For example, a modified antibody variable domain can be more efficacious because it has, for example, a higher $k_{on}$ valued compared to the parent antibody variable domain. Increased efficacy is conferred because molecules with higher $k_{on}$ values can specifically bind and inhibit their binding partner at a faster rate. Similarly, a modified antibody variable domain can be more efficacious because it exhibits a lower $k_{off}$ value compared to molecules having similar binding affinity. Increased efficacy observed with molecules having lower $k_{off}$ rates can be observed because, once bound, the molecules are slower to dissociate from their binding partner.

Methods for measuring the affinity, including association and disassociation rates using surface plasmon resonance are well known in the arts and can be found described in, for example, Jonsson and Malmquist, Advances in Biosensors, 2:291-336 (1992) and Wu et al. Proc. Natl. Acad. Sci. USA, 95:6037-6042 (1998).

Using any of the above described screening methods, a modified antibody variable domain having binding affinity substantially the same or greater than the parent variable domain is identified by detecting the binding of at least one altered variable domain within the population to its binding partner.

Detection methods for identification of species within the population of modified variable domains can be direct or indirect and can include, for example, the measurement of light emission, radioisotopes, calorimetric dyes and fluorochromes. Direct detection includes methods that operate without intermediates or secondary measuring procedures to assess the amount of the binding partner bound by the modified antibody variable domain. Such methods generally employ ligands that are themselves labeled by, for example, radioactive, light emitting or fluorescent moieties. In contrast, indirect detection includes methods that operate through an intermediate or secondary measuring procedure. These methods generally employ molecules that specifically react with the binding partner and can themselves be directly labeled or detected by a secondary reagent. For example, a modified antibody variable domain specific for a binding partner can be detected using an antibody capable of interacting with the modified antibody variable domain, again using the detection methods described above for direct detection. Indirect methods can additionally employ detection by enzymatic labels. Moreover, for the specific example of screening for catalytic antibodies, the disappearance of a substrate or the appearance of a product can be used as an indirect measure of binding affinity or catalytic activity.

In some embodiments, the modified antibody variable domain has a binding affinity for the binding partner greater than the binding affinity of the parent variable domain for the binding partner and thus is identified as having enhanced binding affinity.

In some embodiments, a modified antibody variable domain exhibits enhanced binding affinity to a binding partner compared to the binding affinity between the parent variable domain and the binding partner. In some embodiments, a modified variable domain exhibits an at least 10%, at least 15%, at least 25%, at least 50%, at least 75%, at least 100% (or two-fold), at least 5-fold, at least 10-fold, at least 50-fold, at least 100-fold, or more, higher affinity to a binding partner than the corresponding parent antibody variable domain.

In other embodiments, the modified antibody variable domain has a binding affinity for the binding partner less than the binding affinity of the parent antibody variable domain for the binding partner and thus is identified as having reduced binding affinity for the binding partner.

This disclosure is further illustrated by the following examples which are provided to facilitate the practice of the disclosed methods. These examples are not intended to limit the scope of the disclosure in any way.

EXAMPLES

Example 1

Design of Primers for Synthesis of Nucleic Acid Encoding Modified Protein

Each amino acid residue in a parent protein may be changed with other amino acid residues (e.g., alanine, arginine, asparagine, aspartic acid, glutamine, glutamine acid, glycine, histidine, isoleucine, leucine, lysine, phenylalanine, proline, serine, threonine, tryptophan, tyrosine and valine) by performing PCR with an oligonucleotide containing one of seven different degenerate codons (e.g., ARG (where R=A/G), WMC (where W=A/T and M=A/C), CAS (where S=C/G), GAS (where S=C/G), NTC (where N=A/G/C/T), KGG (where K=G/T) and SCG (where S=C/G)). For example, contacting residues identified from the “prox” lines in FIGS. 1, 3A and/or 3B may be changed with other amino acid residues by performing PCR with an oligonucleotide containing one of seven different degenerate codons (e.g., ARG (where R=A/G), WMC (where W=A/T and M=A/C), CAS (where S=C/G), GAS (where S=C/G), NTC (where N=A/G/C/T), KGG (where K=G/T) and SCG (where S=C/G)).

In an exemplary substitution method, use of seven primers, each comprising one of the seven degenerate codons, may be employed to change one or more contacting (C) amino acid positions in a parent nucleic acid molecule to 18 other amino acid residues. An alternate substitution method may employ the use of three primers each comprising a different degenerate codon to produce eighteen amino acid changes at one or more contacting resides in a parent nucleic acid molecule. For example, the codons may include: NHT (where N=A/G/C/T, H=A/C/T), which codes for Phe/Ser/Tyr/Leu/Pro/His/Ile/Thr/AsnNal/Ala/Asp; VAA (where V=A/C/G), which codes for Gln/Lys/Glu; and BGG (where B=C,G,T), which codes for Trp/Arg/Gly. This allows production of all eighteen amino acids at equal ratios if oligonucleotides comprising NHT is used at a 4:1:1 ratio with oligonucleotides comprising VAA and oligonucleotides comprising BGG, since NHT encodes twelve amino acids and VAA and BGG both encode three amino acids.

Primers containing one or more degenerate codons may be used to introduce a desired class of amino acid residue at a contacting (C) position by hybridizing to a parent nucleic acid (e.g., the nucleotide sequence encoding the degenerate codon pairs with a contacting (C) position to be changed). Basic amino acid changes can be produced at a contacting (C) position with a single oligonucleotide that contains the codon mixture of ARG (R=A/G), encoding Arg/Lys. Further, polar amino acid changes can be introduced at a contacting (C) position with two oligonucleotides. The first oligonucleotide contains the codon mixture WMC (W=A/T; M=A/C), encoding Ser/Thr/Asn/Tyr, while the second oligonucleotide utilizes the codon mixture CAS (S=C/G), encoding His/Gln. Additionally, acidic amino acid changes may be introduced at a contacting (C) position with a single codon mixture of GAS, encoding Glu/Asp. Last, non-polar amino acid changes may be introduced at a contacting (C) position with a mixture of three primers with degenerate codons: NTC (N=A/G/C/T), encoding Leu/Phe/Ile/Val, KGG (K=G/T), encoding Trp/Gly, and SCG, encoding Pro/Ala.

Example 2

Construction of a Library Containing Modified Proteins

Modified proteins containing amino acid changes at one or more positions in a parent protein may be synthesized by PCR amplification from a parent nucleic acid molecule using synthetic oligonucleotides containing a degenerate codon. For example, modified antibody variable domains containing amino acid changes at one or more contacting (C) residues present within an exemplary antibody, for example, ING-1 (a mouse-human chimeric antibody containing the Br-1 mouse variable region domains and human constant regions domains which selectively binds to Ep-CAM (U.S. Pat. 5,576,184), heavy chain sequence represented by SEQ ID NO: 579, light chain sequence represented by SEQ ID NO: 580) may be synthesized by PCR amplification from a parent nucleic acid molecule using synthetic oligonucleotides containing a degenerate codon (SEQ ID NO: 1-285 or SEQ ID NO: 583-699). Similarly, modified antibody variable domains containing amino acid changes at one or more contacting (C) residues present within an exemplary antibody, for example, IL-1 antibody (heavy chain sequence represented by SEQ ID NO: 581, kappa chain sequence represented by SEQ ID NO: 582) may be synthesized by PCR amplification from a parent nucleic acid molecule using synthetic oligonucleotides containing a degenerate codon (SEQ ID NO: 286-578 or SEQ ID NO: 700-806).

For example, each library oligonucleotide containing the degenerate codon described above for ING-1 may be used in a PCR reaction to synthesize a DNA fragment which incorporates an amino acid change and a 3' restriction site. In an exemplary method, PCR may be conducted at a contacting (C) position (e.g., H3-3) by utilizing the CDRH3 oligonucleotide H3-3NP2 (SEQ ID NO: 267): 5'-GCTACATATTTCTGTGCAAGATTTGGCTCTKGGGTGGACTACTGGGGTCAAGG-3', and the reverse primer NotI-R (SEQ ID NO: 285): 5'-AGCGGCCGCACAAGATTTGGGCTCAACTCTC-3') (see, FIG. 5) under standard conditions (see, e.g., Sambrook and Russell, Molecule Cloning: A Laboratory Manual, 3rd edition, Cold Spring Harbor Laboratory Press, 2001). After PCR amplification, fragments are obtained which comprise either a tryptophan or glycine residue at the internal codon (underlined above). Further, six other PCR reactions may be performed at the H3-3 position, utilizing SEQ ID NO: 285 with one of SEQ ID NOs: 262-266 and 268 under the conditions described above to obtain other amino acid changes at the site. Next, the products from these reactions may be combined at equal mass, except for reactions which used SEQ ID NO: 263 and 266 as a primer (this mixture is termed the pooled H3-3 library). Due to the degeneracy of these primers, twice the mass of the sample obtained with SEQ ID NO: 263 and 266 is added to produce an equimolar ratio of encoded amino acids.

An additional PCR reaction may be performed to create a fragment (called the H3-R fragment) which contains a 5' restriction site and an overlapping complementary region to the library fragments described above. As an example, for the H3-3 position, a PCR reaction may be performed utilizing the Asc-F2 (SEQ ID NO: 284) and one of the H3R (SEQ ID NO: 247) primer. The 3' portion of this molecule contains a region that is identical to the 5' portion of the molecules created above which permits the use of a PCR reaction to create a contiguous molecule containing a 5' and 3' restriction site.

A PCR reaction may be performed to fuse the above PCR products together into a single molecule. Products from the two PCR reactions described above may be melted and re-annealed to allow for the region of overlap from the two molecules to hybridize. For example, an equal mass of the pooled H3-3 library (approximately two uL of each pooled PCR reaction) and the H3-R fragment may be annealed at their regions of overlap. Next, amplification of annealed molecules with both the Asc-F2 primer (SEQ ID NO: 284) and the NotI-R primer (SEQ ID NO: 247) allows for the synthesis of a single contiguous molecule (see, e.g., Sambrook and Russell, Molecule Cloning: A Laboratory Manual, 3rd edition, Cold Spring Harbor Laboratory Press, 2001).

Figure 6:
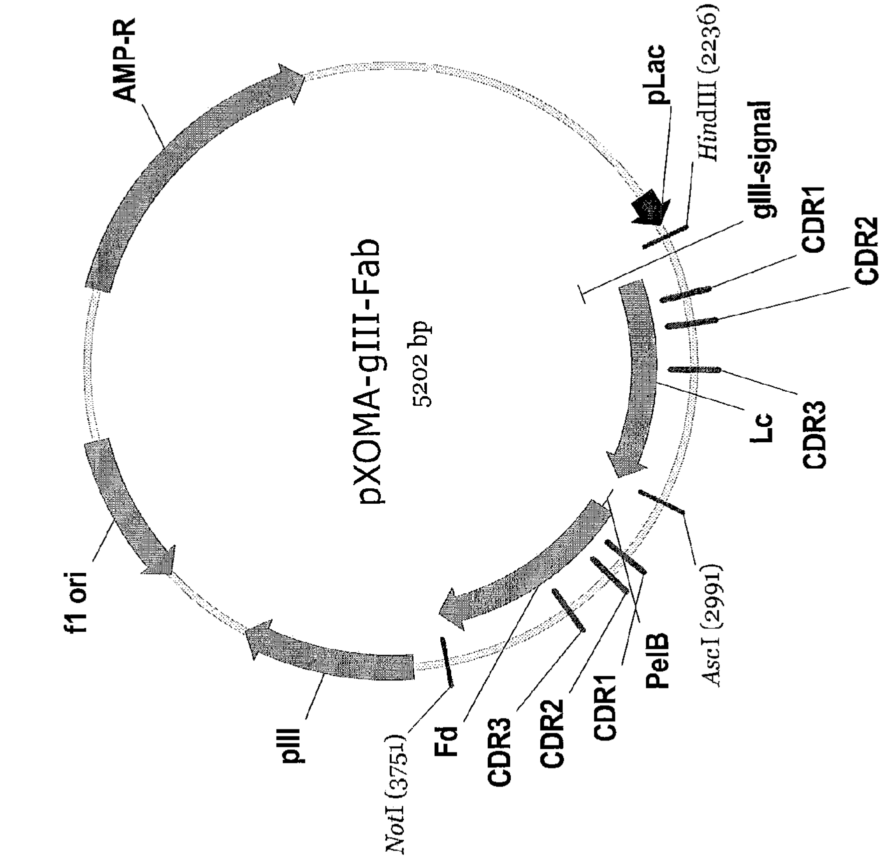
FIG. 6 depicts the plasmid map of the pXOMA-gIII-Fab vector. The vector is 5,202 base pairs in length and has AscI and NotI restriction sites flanking the heavy chain encoding sequences, and HindIII and AscI restriction sites flanking the light chain encoding sequences. The heavy chain encoding sequences are fused to pIII encoding sequences in the vector. The pXOMA-Fab vector is similar but lacks the pIII encoding sequences.

The DNA fragment synthesized by the methods above may be cloned into a pXOMA Fab or pXOMA Fab-gIII vector. Briefly, the DNA fragment is purified by using the QIAGEN® PCR purification kit and sequentially digesting the fragment with NotI (NEW ENGLAND BIOLABS®' Ipswich, Mass.) and AscI (NEW ENGLAND BIOLABS®' Ipswich, Mass.) (See, Methods in Molecular Biology, vol. 178: *Antibody Phage Display: Methods and Protocols* Edited by: P. M. O'Brien and R. Aitken, Humana Press, "Standard Protocols for the Construction of Fab Libraries, Clark, M. A., 39-58) (see, e.g., FIG. 6). Next, the vectors may be ligated with the mutagenized insert using T4 Ligase (NEW ENGLAND BIOLABS®' Ipswich, Mass.) and transformed into TG1 cells by electroporation.

Example 3

Selection of High Affinity Binders

Phage containing a modified proteins including, for example, modified antibody variable domains that bind to an antigen (e.g., Ep-Cam or IL-1β) with high affinity may be selected by standard panning protocols (see, e.g., Methods in Molecular Biology, vol. 178: *Antibody Phage Display: Methods and Protocols* Edited by: P. M. O'Brien and R. Aitken, Humana Press, "Panning of Antibody Phage-Display Libraries", Coomber, D. W. J. pp 133-145, and "Selection of Antibodies Against Biotinylated Antigens", Chames, P. et al. p. 147-157).

In an exemplary method, library phage for the panning procedure are amplified by inoculating fifty milliliters of 2YT with library TG1 cells and grown to an $OD_{600}$ of 0.6-0.8. Helper phage VCSM13 are added to the inoculated 2YT culture at a multiplicity of infection (M.O.I.) of 10 (e.g., in 50 mL of cells with $OD_{600}$=0.6 there are $0.6\times3^8\times50=9\times10^9$ cells, M.O.I. of 10 is therefore $9^{10}$ helper phage, which corresponds to about 10 μl of $1^{13}$ stock phage). The helper phage are used to infect the TG1 cells by gently mixing the phage with the cells with no shaking for thirty minutes. The culture is then shaken for an additional thirty minutes at 180 rpm. Following infection, the culture is spun down at 2500 rpm for ten minutes. The resulting cell pellet is resuspended in fifty milliliters of 2TYAmpKan and grown overnight at 30° C. and the supernatant is removed and discarded.

Exemplary methods of panning include coating one well of a NUNC® MAXISORP plate with fifty μl of Ep-Cam or IL-1β at 0.1 μg/ml in DULBECCO'S® PBS with Calcium and Magnesium chloride (Invitrogen, Carlsbad, Calif.) and incubating the plates overnight at 4° C. The wells are then blocked with 5% milk in PBS for one hour at room temperature. Separately 0.5 ml of phage supernatant from the overnight culture described above are blocked with 300 μL of 10% milk in PBS for one hour at room temperature. Blocked phage (e.g., approximately 200 μl) are added to the blocked wells in 3% BSA-PBS and incubated at room temperature with shaking for one to two hours. After incubation, the wells are emptied and washed five times with PBST quick wash (e.g., PBS+0.05% Tween 20), then washed five times with PBST five minute wash, followed by five washes with PBS quick wash and lastly washed five times with PBS five minute wash. Phage bound to the wells are eluted by incubating with 200 μL/well of freshly prepared 100 mM TEA (prepared by adding 140 μL of 7.18 M Triethylamine stock to ten ml $H_2O$ for 20 minutes at room temperature (see, e.g., Sambrook and Russell, Molecular Cloning: A Laboratory Manual, 3rd edition, Cold Spring Harbor Laboratory Press, 2001). The eluate is transferred to a Falcon tube containing 0.5 ml 2M TRIS-HCl pH 7.4. The pH of the eluate is checked with pH paper to ensure that it is about pH 7 and adjusted if necessary.

Eluted phage from the exemplary panning method are amplified by infecting TG1 cells. In an exemplary method, TG1 cells are grown to an $OD_{600}$=0.6 (e.g., mid log phase) and ten ml of the culture is added to the phage eluate from the panning method described above. The eluted phage are used to infect the TG1 cells at 37° C. for thirty minutes without shaking and then continued for an additional thirty minutes at 37° C. with shaking at 240 rpm. After the infection, the culture is centrifuged at 2500 rpm for five minutes. Next, the supernatant is removed and the cell pellet is resuspended in 700 μL of 2YTAG. The re-suspension is plated on two 15 cm 2YTAG agar plates and incubated at 30° C. overnight. After the overnight incubation, the cells are scraped from the two plates using five to ten milliliters of 2YTAG per plate, and transferred to a fifty milliliter falcon tube where they are used to make a glycerol stock.

In an alternative exemplary method, panning may be performed with biotinylated Ep-Cam or IL-1β. Briefly, two hundred microliters of streptavidin beads (Dynal) are blocked in 5% BSA-PBS (100 μl of the blocked beads are used for the de-selection and 100 μL for the selection). Using a magnet, the beads are removed from the 5% BSA-PBS and rinsed twice in PBS. To the rinsed beads is added one milliliter of 5% BSA-PBS and the beads are incubated at room temperature for one hour with very gentle rotation. After the incubation, the beads are split into two tubes, with the supernatant removed from one tube for the de-selection. Phage solution is added to the tube with beads designated for the de-selection and resuspended. The phage-bead solution is incubated at room temperature for forty-five minutes with gentle rotation. After the incubation, the phage supernatant (de-selected phage solution) is transferred to a new tube using a magnet. Next, the de-selected phage solution is incubated at room temperature for sixty minutes with one hundred pmols of biotinylated Ep-Cam or IL-1β. The phage-biotinylated Ep-Cam or IL-1β solution is then added to a new aliquot of streptavidin beads (with the supernatant removed) and incubated at room temperature for sixty minutes. After the incubation, the beads are separated from the supernatant using a magnet. Next the beads are washed five times with one ml of 0.5% BSA-PBST by adding the wash to the tube, closing the tube and resuspending the pellet, putting back in the magnet waiting a few seconds until the beads are attached to the magnet side of the tube and removing the wash with a pipetman. Further, the beads are washed five times in 0.5% BSA-PBST for five minutes for each wash, washed five times with one milliliter of 0.5% BSA-PBS, washed five times for five minutes each wash in five milliliters of 0.5% BSA, and washed one time with PBS. Bound phage are eluted by incubating the beads with 500 μL of freshly prepared 100 mM TEA (add 140 μL of 7.18 M Triethylamine stock to 10 ml $H_2O$) for thirty minutes at room temperature with gentle rotation. The eluate is separated from the beads by using a magnet and transferred to a fifty milliliter falcon tube containing 250 μl of 1M TRIS pH 7.4 to neutralize the TEA and can be used for infection and/or amplification (see, e.g., Sambrook and Russell, Molecular Cloning: A Laboratory Manual, 3rd edition, Cold Spring Harbor Laboratory Press, 2001). For example, log phase TG1 cells may be infected with phage eluate at 37° C. for one hour at ninety rpm. After infection of the cells, the culture is centrifuged at 2500 rpm for five minutes and the supernatant removed. Next, the cell pellet is resuspended in 700 μl of 2YTAG, plated onto two 15 cm 2YT-ampicillin-2% glucose agar plates and incubated at 30° C. overnight.

Example 4

Screening of an Affinity Matured Protein Using the DELFIA® Competition Assay Individual proteins including, for example, Fabs obtained from the affinity-based selection of libraries of the ING-1 antibody clone are tested for their ability to inhibit the binding of Ep-Cam to the parent chimeric ING-1 IgG antibody using a competitive screening assay (e.g., the microplate based competitive screening DELFIA® assay (PERKIN ELMER®' Waltham, Massachusetts)). Ninety-six well plates containing two hundred and fifty milliliters of 2YT media are inoculated with glycerol stock of Fab-expressing *E. coli* transformed with the pXOMA-Fab vector. The culture is grown at 37° C. until cloudy (approximate OD600=0.5) and inoculated with IPTG to a final concentration of 1 mM. The cultures are grown overnight at 30° C. In addition, a Costar plate 3922 (White) is coated with 1.25 ug/mL of parental ING-1 chimeric IgG O/N at 4° C.

Periplasmic extracts (PPE) of the overnight expression constructs are prepared by spinning the overnight expression plates at 3000 rpm for fifteen minutes, discarding supernatant and adding 60 microliters of PPB buffer to each well. The pellets are resuspended, and 90 microliters of cold PPB diluted 1:5 with cold water are added to each well. This mixture is incubated on ice for one hour and subsequently spun down at 3000 rpm for fifteen minutes. This PPE supernatant is transferred to a new plate. The PPE is diluted into 10% PPE in PBS, 5% PPE in PBS, and 1% PPE in PBS. For the coated Costar plate, it is washed three times with PBS-tween and blocked with 350 microliters of 3% BSA in PBS for one hour.

The blocked Costar plate is washed three times with PBS and then biotinylated Ep-Cam is added to the diluted PPE to a final concentration of 3 nM. The diluted PPE and biotinylated Ep-Cam solution is then added to the coated Costar plate and incubated for one and a half hours at room temperature. The plates are washed three times with PBST and fifty microliters of 1:250 dilution of Europrium-Streptavidin in Delfia Assay Buffer (PERKIN ELMER®' Waltham, Mass.) is added. The mixture is incubated at room temperature for one hour, and the Time-Resolved Fluorescence Plate reader is setup (Gemini microplate reader, Molecular Devices), interval 200-1600 microseconds, 20 reads/well, excitation 345 nm, emission 618 nm and cutoff 590 nm. The plates are washed seven times with Delfia Wash Buffer (PERKIN ELMER®' Waltham, Mass.), followed by the addition of fifty μl of Delfia Enhancement buffer (PERKIN ELMER®' Waltham, Mass.) and incubated for five minutes. The plates are read on the Gemini plate reader. Plates with decreased signal compared with control parental antibody show greater binding by the affinity matured Fab and can be further characterized by Biacore (e.g., Biacore 2000 or A100) and other affinity measuring techniques (see, e.g., Tables 4 and 5).

Similarly, XPA23 antibody clones may be tested for their ability to inhibit the binding of IL-1β to the parent chimeric XPA23 IgG using a competitive screening assay as described above.

TABLE 4

Delfia Screening of 10% Periplasmic Extract

| | 1 | 2 | 3 | 4 | 5 | 6 | 7 | 8 | 9 | 10 | 11 | 12 |
|---|---|---|---|---|---|---|---|---|---|---|---|---|
| A | 46.9 | 37.1 | 71.2 | 75.7 | 51.3 | 22.3 | 65.8 | 72.9 | 58.8 | 81.7 | 56.2 | 96.7 |
| B | **2.6** | 55.2 | 39.2 | 54.8 | 31.7 | 41.3 | 57.1 | 56.7 | 21.6 | 77.8 | **1.8** | 102.0 |
| C | 53.2 | 42.3 | 72.5 | 61.2 | 16.2 | 78.0 | 41.2 | 57.2 | 63.8 | 28.6 | 13.6 | 100.7 |
| D | 49.0 | 45.5 | **8.9** | **1.0** | 21.5 | 82.8 | 105.8 | 67.3 | 68.5 | 61.8 | 63.5 | 100.6 |
| E | 49.1 | 72.1 | 68.6 | **0.3** | 91.8 | 57.6 | 53.1 | **8.3** | 58.3 | 60.4 | 82.2 | −0.4 |
| F | 61.7 | 72.1 | 71.8 | 45.6 | 44.6 | 53.1 | 15.3 | 73.2 | 84.7 | 15.1 | 59.0 | 0.1 |
| G | 58.4 | 26.4 | **1.0** | 59.4 | 62.3 | 19.9 | **−0.1** | 49.0 | 52.4 | 76.2 | 46.8 | 0.3 |
| H | 36.1 | 67.7 | 65.2 | 27.4 | 34.3 | 50.3 | 60.0 | 60.1 | 56.8 | 83.0 | 49.3 | −0.4 |

Percentage of inhibition is shown in each well using the average signal from wells A12-D12 as positive control, 100% inhibition and the average signal in well E12-H12 as 0% inhibition negative control wells. Wells bolded show strong competition in the Delphia assay.

TABLE 5

Delfia Screening of 5% Periplasmic Extract

| | 1 | 2 | 3 | 4 | 5 | 6 | 7 | 8 | 9 | 10 | 11 | 12 |
|---|---|---|---|---|---|---|---|---|---|---|---|---|
| A | 58.4 | 59.3 | 86.6 | 87.8 | 74.8 | 52.4 | 71.7 | 84.4 | 68.6 | 84.8 | 74.2 | 99.4 |
| B | **14.5** | 73.0 | 71.5 | 77.5 | 63.1 | 75.4 | 79.2 | 76.4 | 53.2 | 82.6 | **44.9** | 101.8 |
| C | 56.2 | 56.3 | 92.3 | 76.5 | 55.1 | 94.0 | 81.1 | 79.9 | 77.6 | 60.2 | 53.7 | 100.5 |
| D | 46.8 | 57.8 | 43.0 | **33.0** | 52.4 | 92.6 | 115.3 | 91.6 | 74.7 | 77.1 | 74.7 | 98.2 |
| E | 58.8 | 60.1 | 82.5 | **28.5** | 101.3 | 88.5 | 71.6 | **51.9** | 76.2 | 74.9 | 94.8 | 0.2 |
| F | 58.3 | 65.8 | 69.2 | 64.6 | 67.3 | 78.0 | 65.3 | 87.7 | 88.2 | 38.9 | 70.8 | 0.1 |
| G | 52.8 | 47.4 | **22.2** | 72.2 | 65.8 | 55.7 | **10.0** | 68.1 | 69.2 | 73.5 | 64.6 | -0.2 |
| H | 42.2 | 68.8 | 68.5 | 46.3 | 62.7 | 63.6 | 73.7 | 70.9 | 76.2 | 85.1 | 68.7 | -1.1 |

Percentage of inhibition is shown in each well using the average signal from wells A12-D12 as positive control, 100% inhibition and the average signal in well E12-H12 as 0% inhibition negative control wells. Wells bolded show strong competition in the Delphia assay. Boxed wells retain strong inhibition and are prioritized for affinity testing.

Example 5

Screening of an Affinity Matured Protein Using Kinetic Titration Analysis

Kinetic properties of affinity matured proteins including, antibodies, for example, as represented by XPA23 clones such as Y208L may be determined by kinetic titration analysis. In an exemplary method, an antigen such as IL-1β is amine coupled to a CM5 sensor chip. Each sample (e.g., from lowest to highest concentration) may be injected for 240 seconds at a flow rate of 30 □l/min at a selected temperature (e.g., 25° C.). Sample are allowed to dissociate for 30 seconds except the highest concentration which may be permitted 300 seconds to dissociate. The assay is run at 25° C.

Biaevaluation software (e.g., Biacore 2000 evaluation software) is used to calculate dissociation rates of individual samples and the relative amount of sample bound to each test surface. The data is fit to an appropriate kinetic model (e.g., the kinetic titration model). For example, XPA23 had a ka=2.5e5 and a kd=1.2e-2 KD=4.6e-8, while the modified XPA23 Y208L mutant had a ka=3.57E+05kd=5.80E-03 KD=1.62E-08.

Example 6

ELISA Measurement for Fab Expression, EpCam Binding or IL-1 Binding

Additionally or alternatively to the Biacore assay described below in Example 10, an ELISA assay may be used for the identification of modified antibody variable domains that bind its binding partner or for verifying expression of Fab domains.

In an exemplary method, ELISA plates (e.g., Nunc MAXISORP™) are coated with 1 μg/ml EpCam, 1 μg/mL EpCam for EpCam ELISA, 1 μg/mL IL-1 (Peprotech), or anti-human IgG, F(ab')$_2$ fragment specific antibody (Jackson Immunoresearch) in PBS at 50 μg/ml. The ELISA plates are then covered and incubated at 4° C. overnight. After the incubation, the coated ELISA plates are washed three times with PBS. The plates are then filled with 370 μl of 3% milk (e.g., Carnation, nonfat) and incubated for one hour at room temperature. Separately, 150 μl of periplasmic extract is blocked by adding 50 μl of 15% milk and incubating the extract for one hour at room temperature. The blocked plates are washed three times with PBS and 50 μL of the blocked periplasmic extract is added to each well of the antigen coated ELISA plates. The plates are incubated for two hours at room temperature and then washed four times with TBST.

Secondary antibodies are added to each ELISA plate. For the Ep-Cam or IL-1 ELISA, 50 μl of mouse anti-human c-myc antibody (9E10 Ab, Roche) at 2.5 μg/ml in 3% milk is added to each well. For the anti-Fab ELISA, 50 μl of biotin-SP-conjugated anti-human IgG F(ab')2 fragment specific antibody (Jackson Immunoresearch) at 1:2000 dilution in 3% milk is added to each well. The plates from both ELISAs are incubated at room temperature for one hour. After the incubation, the plates are washed four times with TBST. After the washes, a tertiary antibody may be added to the plates in both ELISAs. For the Ep-Cam or IL-1 ELISA, 50 μl of goat anti-mouse IgG-HRP (Pierce) diluted 1:10,000 in 3% milk is added to each well. For the anti-Fab ELISA, 50 μl of extravidin-HRP conjugate (Sigma) at a 1:500 dilution in 3% milk is added to each well. Again the plates from both ELISAs are incubated for one hour at room temperature. After the incubation, the plates are washed four times with TBST. Next, 50 μl of the TMB substrate (Calbiochem) is added to each well and incubated until the color develops (do not incubate long enough to see the negative control turn blue). The reaction is stopped by adding 50 μl of 2N $H_2SO_4$ to each well and the plates are read at 450 nm.

Example 7

Methods for Off-Rate Ranking of Antibody Fragments

A high-throughput off-rate ranking method is used for rapid prioritization of modified proteins including, for example, modified antibody variable domains that bind to their binding partner by analyzing their relative off-rates (using, e.g., Biacore 2000 or A100).

In an exemplary method, modified antibody variable domains (e.g., Epcam-binding) are produced in ninety-six well plates by inoculating two hundred and fifty microliters of 2YT media with a glycerol stock of Fab-expressing *E. coli* transformed with a pXOMA-Fab vector comprising a modified Epcam-binding variable domain. The culture is grown at 37° C. until cloudy (e.g., approximate $OD_{600}$=0.5), inoculated with IPTG to a final concentration of 1 mM and grown overnight at 30° C.

Next, periplasmic extracts (PPE) of the overnight expression constructs are prepared by spinning the overnight expression plates at 3000 rpm for fifteen minutes, discarding the supernatant and adding 60 μl of PPB buffer to each well. The pellets are resuspended, and 90 μl of cold PPB diluted 1:5 with cold water is added to each well. This mixture is incubated on ice for one hour and subsequently spun down at 3000 rpm for fifteen minutes. The supernatant is transferred to a new plate and the periplasmic extracts are used for the Biacore (e.g., Biacore 2000 or A100) determination.

Figure 16:
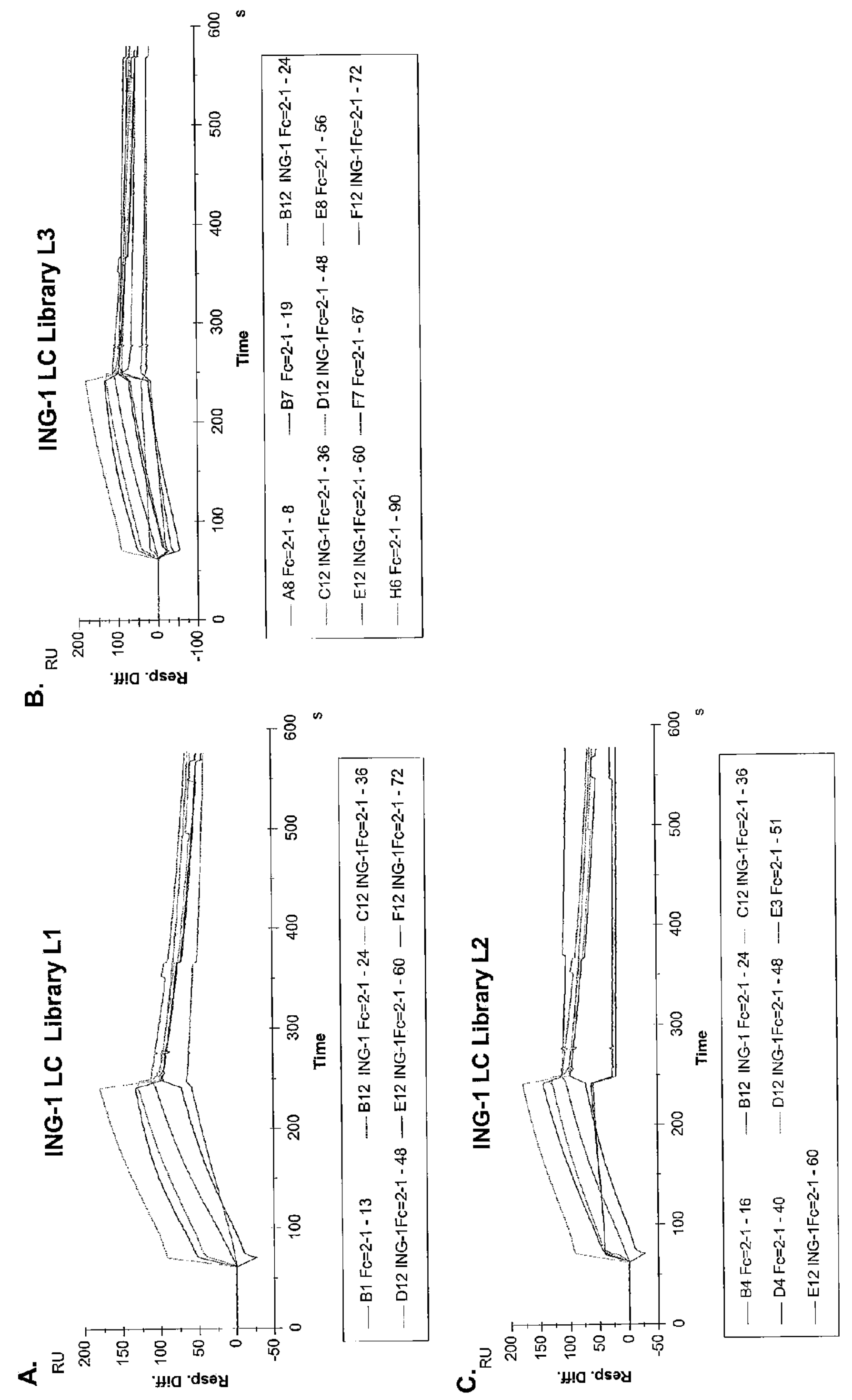
FIG. 16A-16C are sensogram profiles depicting ING-1 light chain binding to Ep-Cam.
Figure 17:
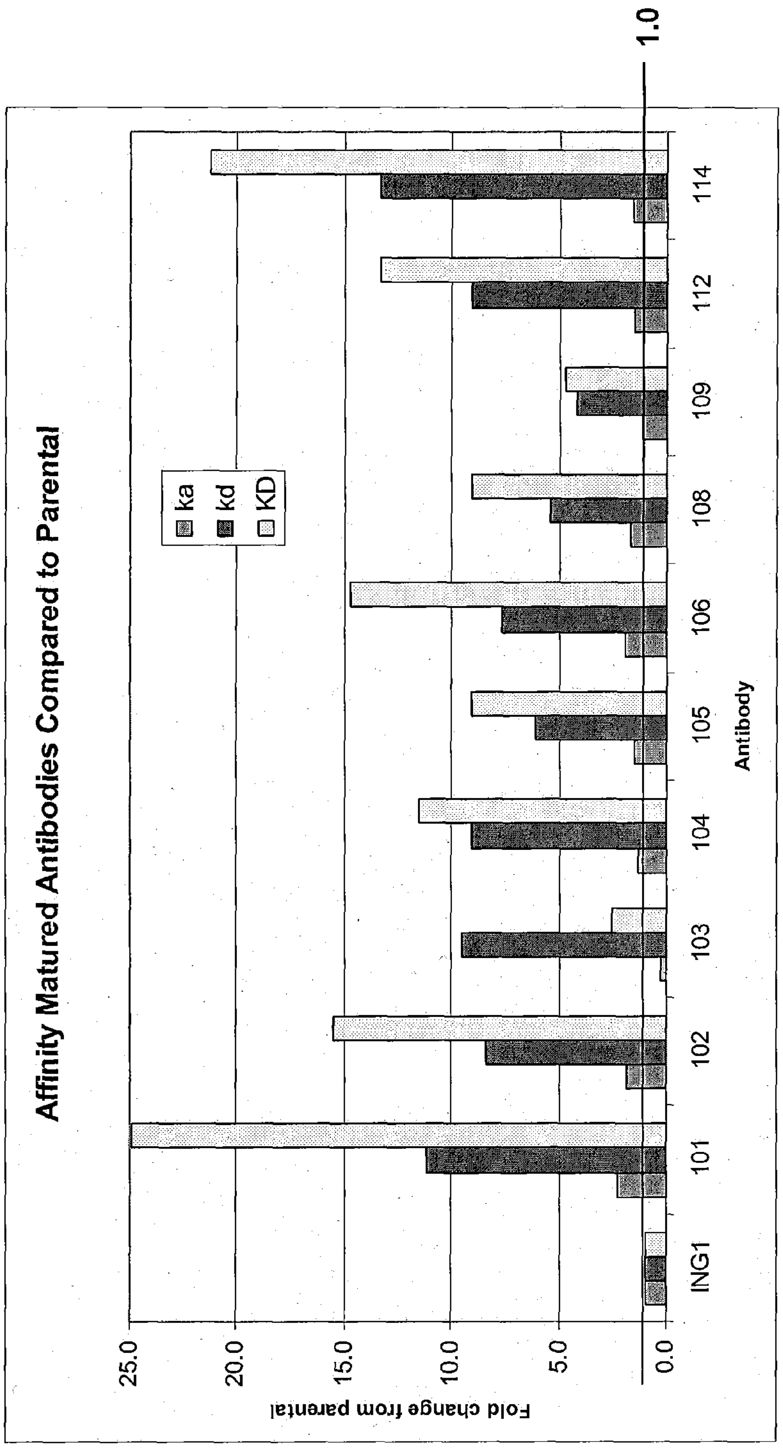
FIG. 17 depicts modified ING-1 antibodies each comprising two or more heavy chain mutations as compared to the parental antibody. Combinations of heavy chain mutations yield affinity improvements up to 25-fold over the parental ING-1 antibody. Affinity improvements are driven largely by improvements in $k_{off}$.

Epcam from the periplasmic extracts is amine coupled (e.g., 10 μg/mL Epcam in pH 4.5 acetate, seven minute injection at 5 μl/minute) to a CM5 sensor chip and periplasmic extracts containing the antibody fragments are injected over the sensor, resulting in binding of the Fab to the immobilized Epcam. Non specific binding of the antibody fragment to the sensor surface is corrected by subtracting the interaction of the antibody fragment with a blank flow cell (e.g., having no immobilized Epcam) from the interaction of the antibody fragment with the Epcam immobilized flow cell. The instrument settings are: a flow rate of 20 microliters/minute, an injection time of three minutes, a dissociation time of five minutes and an instrument temperature set to 25° C. Biaevaluation software is used to calculate dissociation rates of individual samples and the relative amount of sample bound to each test surface. Samples are then ranked according to their dissociation rates. Sensograms depicting the off-rates for heavy chains (FIG. 15) and light chains (FIG. 16) are shown. The off rates for the improved clones are tabulated for the heavy chain (FIG. 11) and the light chain (FIG. 12).

Likewise, modified XPA23 variable domains (e.g., IL-1β-binding) may be ranked according to their dissociation rates using the high-throughput off-rate ranking method described above. The instrument settings are: a flow rate of 30 microliters/minute, an injection time of three minutes, a dissociation time of ten minutes and an instrument temperature set to 25° C. The off rates for the improved clones are tabulated for the heavy chain (FIG. 13) and the light chain (FIG. 14).

Figure 18:
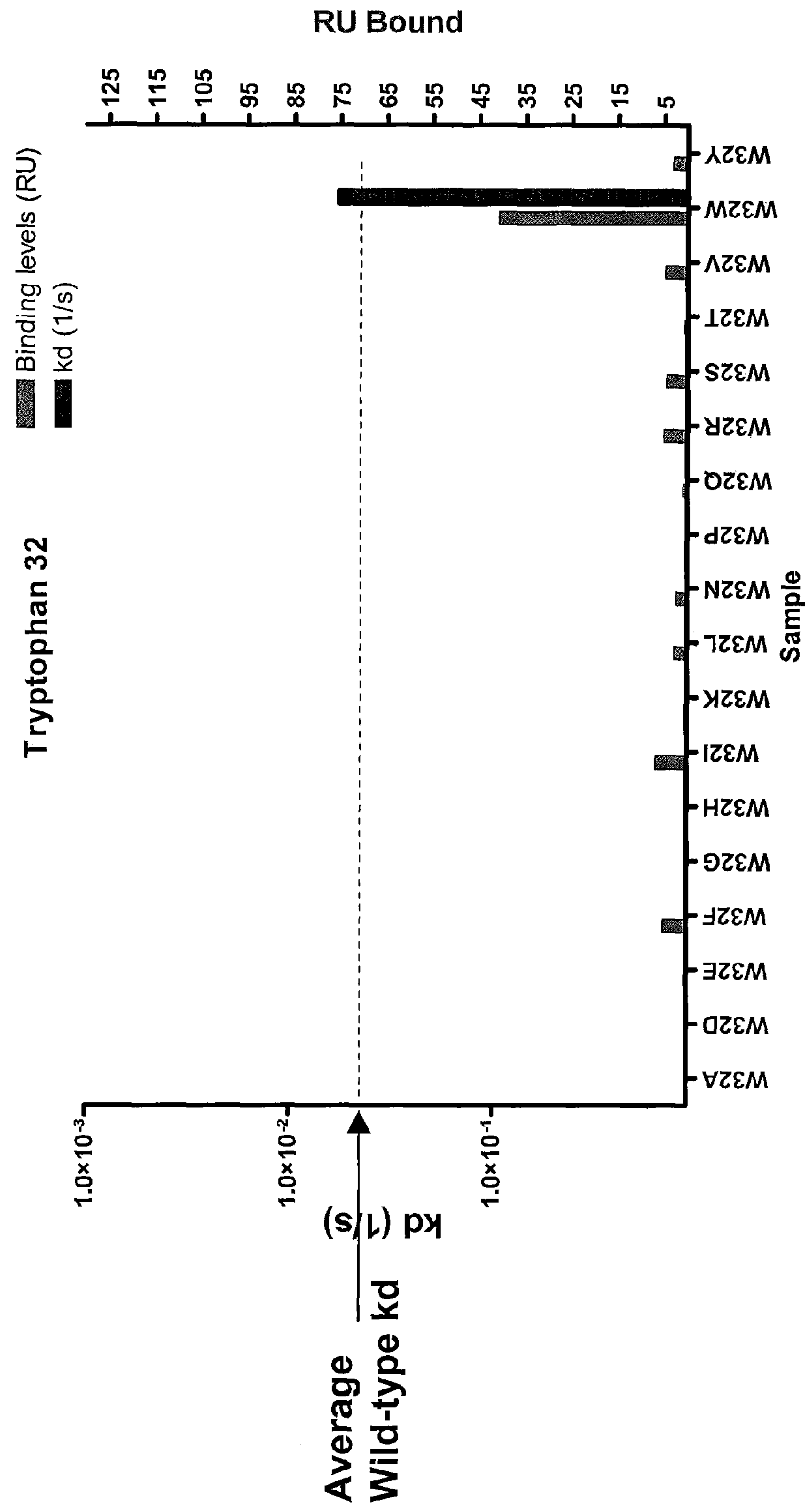
FIG. 18 shows amino acid substitutions at position 32 in the light chain variable region of XPA23. Generally the substitutions at position 30 decreased kd of the antibody-antigen interaction compared to the parental antibody.
Figure 19:
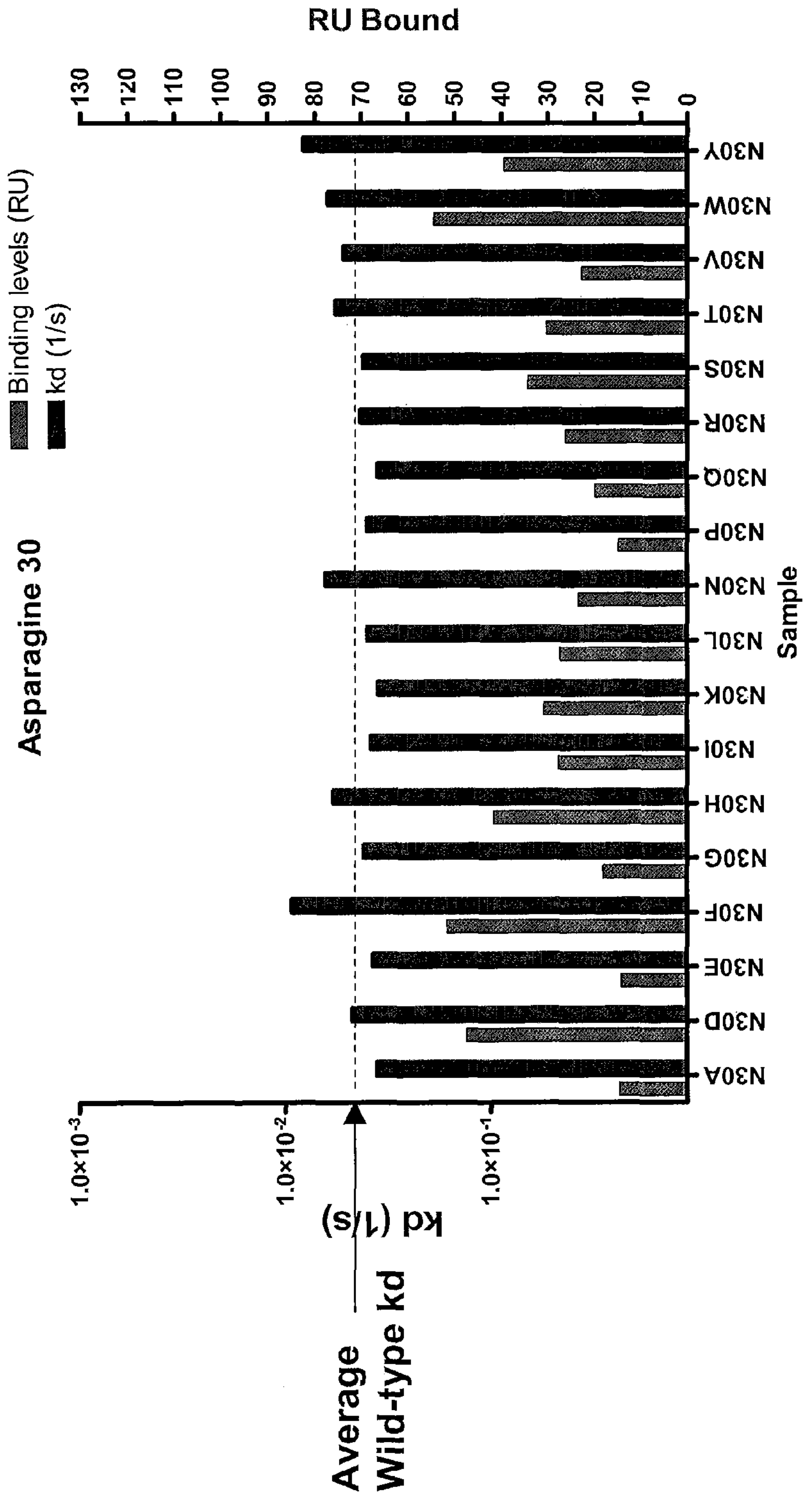
FIG. 19 shows amino acid substitutions at position 30 in the light chain variable region of XPA23. Generally the substitutions at position 30 resulted in a comparable kd of the antibody-antigen interaction compared to the parental antibody.
Figure 20:
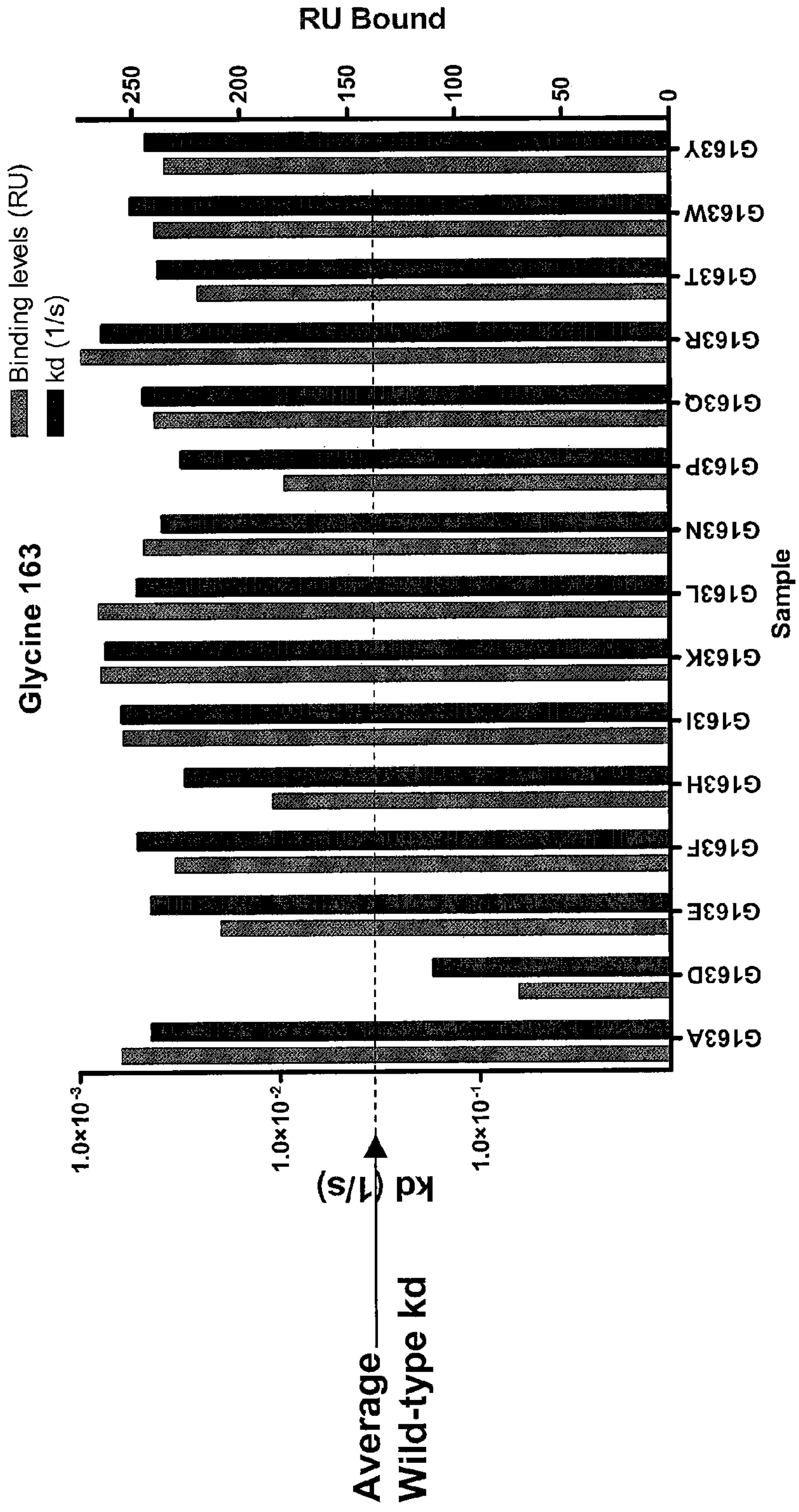
FIG. 20 shows amino acid substitutions at position 45 in the heavy chain variable region of XPA23. Generally the substitutions improved kd of the antibody-antigen interaction at this position compared to the parental antibody.

The modified antibody variable domains of the present disclosure may have a $k_{off}$ that is greater than (see, e.g., FIG. 20), less than (see, e.g., FIG. 18) or equal to (see, e.g., FIG. 19) than an unmodified antibody variable domain.

Example 8

Reformatting of Candidate Clones to IgG

Two of the improved off-rate clones from the $k_{off}$ analysis were reformatted into $IgG_1$ format by PCR amplification of the heavy and light chain variable domains and cloning the PCR amplified regions into a mammalian expression vector containing the Fc and the light chain constant domain respectively. The heavy chain is cloned into a mammalian expression vector containing a CMV promoter using Bsml and Nhel sites for the 5' and 3' ends respectively and is cloned in frame with the heavy chain secretion signal on the 5' end and the constant CH1,CH2, and CH3 portions of the IgG molecule on the 3' end. The amplification sequences are as follows: (ING-HC-IgGF 5'-ATATATTGCATTCCCAGATCCAGTTGGTGCAGTC-3') (SEQ ID NO: 983), ING-HC-1gGR (5'-ATATATGCTAGCTGAGCTGACGGTGACCGAGGTTCC-3') (SEQ ID NO: 984). The light chain is cloned into a similarly constructed expression vector utilizing a blunt 5' cloning site and the BsiWI site on the 3' end and is cloned in frame with the light chain secretion signal on the 5' end and the light chain constant region on the 3' end. The PCR amplification primer sequences are as follows: (ING-LC-IgGF 5'-CAAATTGTGATGACGCAGGC-3') (SEQ ID NO: 985) and (ING-LC-IgGR 5'-ATATATCGTACGTTICATCTCTAGTTIGGTGCC-3') (SEQ ID NO: 986). The PCRs are performed under standard conditions: see, e.g., Sambrook and Russell, Molecule Cloning: A Laboratory Manual, 3 rd edition, Cold Spring Harbor Laboratory Press, 2001. Improved off-rate clones reformatted into $IgG_1$ vectors are transiently co-transfected in a 2:1 light chain to heavy chain DNA ratio into HEK 292 cells using Lipofectamine 2000 (lnvitrogen) using the manufacturer's guidelines. Secreted IgGs secreted from HEK 292 cells are purified using protein A SEPHAROSE® (GE-AMERSHAM® Piscataway, NJ) using the manufacturer's guidelines-and tested by BIACORE® (e.g., Biacore 2000 or A100) for affinity (see, e.g., FIGS. 11 and 15) and Example 8.

Example 9

Expression and Testing of Modified Proteins with a Combination of Amino Acid Changes Modified proteins including, for example, antibody variable domains with improved off-rates and affinities as compared to a parent protein may be identified by employing the DELFIA® competition assay and/or BIACORE® (e.g., Biacore 2000 or A100) off-rate ranking. Clones with improved $k_{off}$ are sequenced and aligned by both their light and heavy chain. Identified amino acid changes in the light and heavy chain that increase affinity can be combined in one modified antibody variable domain for potential additive and synergistic combinations. Modifications for combination may utilize the residues that have improved off-rates greater than or equal to 4.9 fold compared with the parental antibodies (see, e.g., FIG. 11, 12). For any given amino acid position, the change that leads to the greatest improvement is chosen for study. This compilation is described in Table 6, and will lead to 21 combinations of heavy and light chains (e.g., 7 heavy chains combined in all variations with three light chains).

TABLE 6

Heavy and Light Chain CDR1, CDR2 and/or CDR3 Combinations

| CDR1 | CDR2 | CDR3 |
|---|---|---|
| | Heavy Chain Combinations | |
| G33F | wt | wt |
| wt | T53I | wt |
| wt | wt | G100R |
| G33F | T53I | wt |
| wt | T53I | G100R |
| G33F | wt | G100R |
| G33F | T53I | G100R |
| | Light Chain Combinations | |
| wt | Q55R | wt |
| wt | wt | E98T |
| wt | Q55R | E98T |

Alternatively, the initial modifications for combination may utilize the residues that have improved off-rates greater than or equal to approximately 2.5-fold compared with the parental antibodies (see, e.g., FIG. 13, 14). For any given amino acid change, the change that leads to the greatest improvement is chosen for study. The amino acids with greater than or equal to approximately 2.5 fold improved $k_{off}$ are compiled in Table 7. There are two amino acids in CDR1 (position 28), two amino acids in position 100, three amino acids in position 101, and five amino acids in position 102. In all, there are 60 (2×2×3×5=60) combinations.

TABLE 7

| Heavy Chain CDR1 and CDR3 Combinations | |
|---|---|
| CDR1 | CDR3 |
| 28T (wt) | 100 G(wt) |
| 28I | 100R |
| | 101S(wt) |
| | 101I |
| | 101G |
| | 102A(wt) |
| | 102Y |
| | 102F |
| | 102W |
| | 102G |

Figure 7:
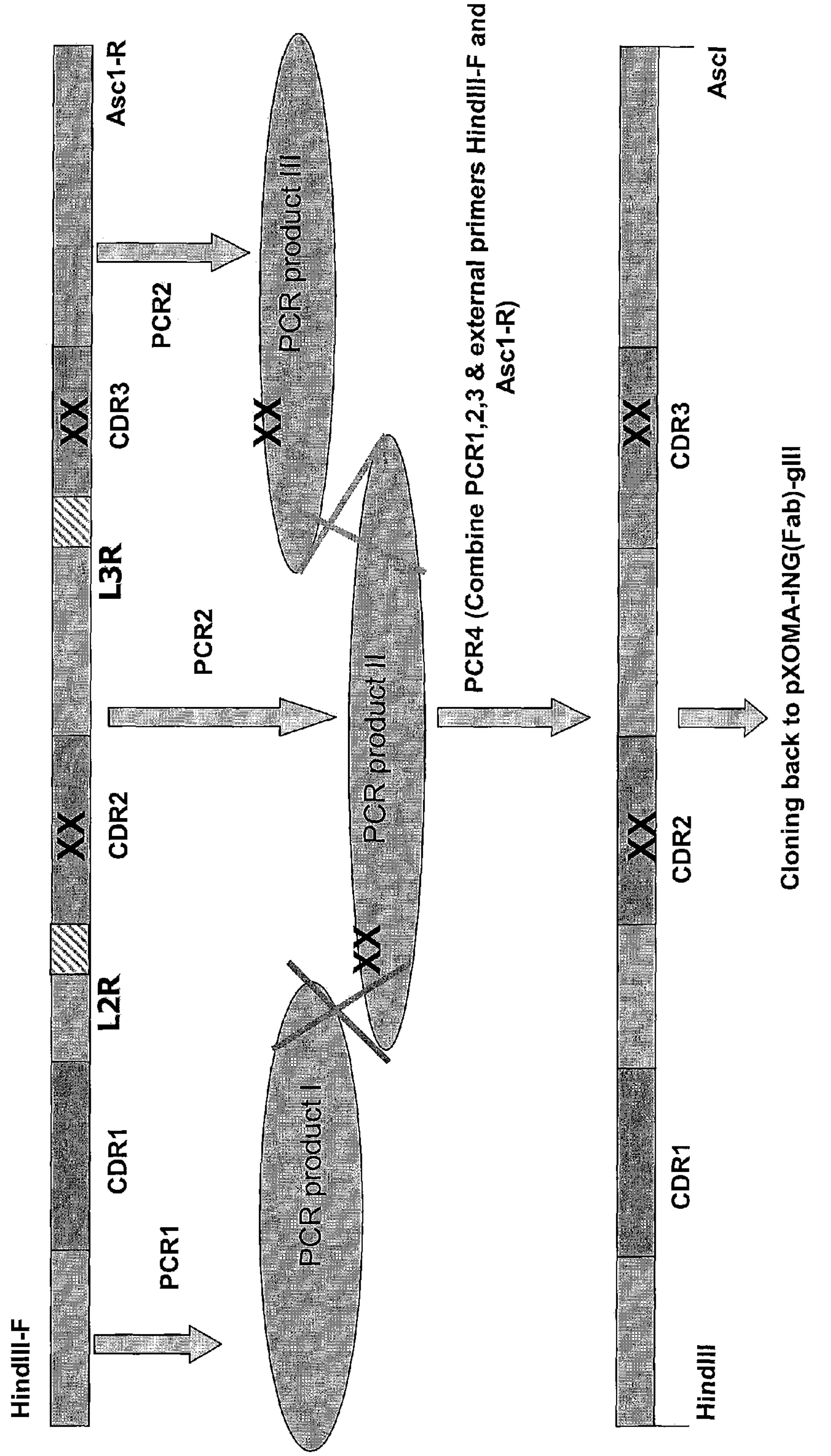
FIG. 7 depicts the strategy for creating the light chain combination variants.

A PCR based strategy may be used to create a modified antibody light chain containing more than one amino acid change (see, e.g., FIG. 7). In an exemplary method, PCR may be used to amplify three segments of the $V_k$ gene, two of which may be engineered to contain an amino acid change. For example, to create a light chain containing the mutations Q55R and E98T, PCR product 1 may be synthesized using the HindIII-F (SEQ ID NO: 814) and L2R primer (SEQ ID NO: 74), PCR product 2 may be synthesized using L2-Q55R primer (SEQ ID NO: 808) and the L3R primer (SEQ ID NO: 110) and PCR product 3 may be synthesized using L3-E98T primer (SEQ ID NO: 807)and the AscI-R primer (SEQ ID NO: 812). The PCR products are then melted and re-annealed such that their regions of overlap hybridize. Subsequently, all three PCR products may be joined into one molecule by PCR amplification using the forward primer from PCR product 1 (HindIII-For) (SEQ ID NO: 814) and the reverse primer from PCR product 3 (AscI-R) (SEQ ID NO: 812). In an exemplary method to create a heavy chain containing the mutations outlined above and described in FIG. 7, product 1 may be synthesized using the AscI-F (SEQ ID NO: 813) and H1R primer (SEQ ID NO: 146), PCR product 2 may be synthesized using H1-28TI primer and the H3R primer (SEQ ID NO: 247) and PCR product 3 may be synthesized using each H3 combination primer (6 primers, 6 rxns) and the NotI-R primer (SEQ ID NO: 285). The PCR products are then melted and re-annealed such that their regions of overlap hybridize. Subsequently, all three PCR products may be joined into one molecule by PCR amplification using the forward primer from PCR product 1 (AscI-F) (SEQ ID NO: 813) and the reverse primer from PCR product 3 (NotI-R) (SEQ ID NO: 285).

In an exemplary method, a 50 μL PCR reaction for the production of PCR product 1, 2 and 3 may be performed with 25 pmol of each of the forward and reverse primers, 10 ng of template DNA, 5 μL PFU buffer, 2.5 μL of 10 μM dNTPs, 1 μL PFU and water to 50 μL. The PCR reaction is heated to 94° C. for two minutes, followed by 25 cycles of 30 seconds at 94° C., 30 seconds at 54° C., and one minute at 72° C. After the 25 cycles, a final 72° C. incubation may be performed for five minutes.

An equal mass of the three PCR products may be combined in a PCR reaction to produce a modified variable domain with several amino acid changes which enhance affinity. Briefly, the PCR may be conducted by adding approximately 2 μL of each pooled PCR reaction to 5 μL PFU buffer, 25 pmol of both HindIII-f primer (SEQ ID NO: 814)and AscI-R primers (SEQ ID NO: 812), 2.5 μL of 10 μM dNTPs, 1 μL PFU polymerase and water to 100 μL. Next, the PCR reaction is heated to 94° C. for two minutes, followed by twenty-five cycles of thirty seconds at 94° C., 30 seconds at 54° C., and finally one minute at 72° C. After the twenty cycles, a final 72° C. incubation is performed for five minutes.

The resulting DNA fragment may be purified (e.g., using the QIAGEN® PCR purification kit (Valencia, Calif.)) and sequentially digested with HindIII (NEB) and then AscI (NEW ENGLAND BIOLABS®, Ipswich, Mass.) such that it may be cloned into the pXOMA Fab or pXOMA Fab-gIII vector.

Figure 8:
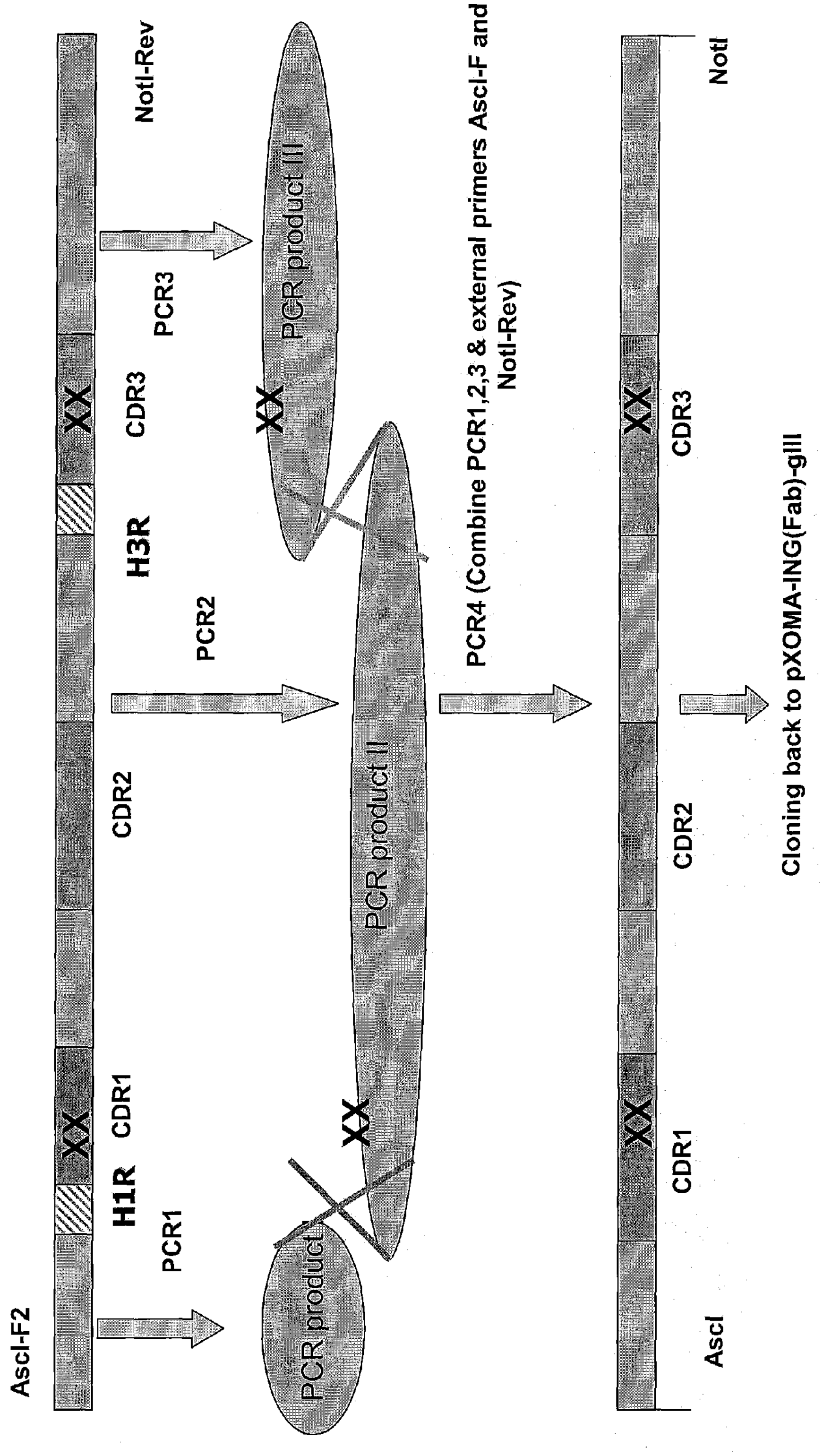
FIG. 8 depicts the strategy for creating the heavy chain combination variants.
Figure 10A:
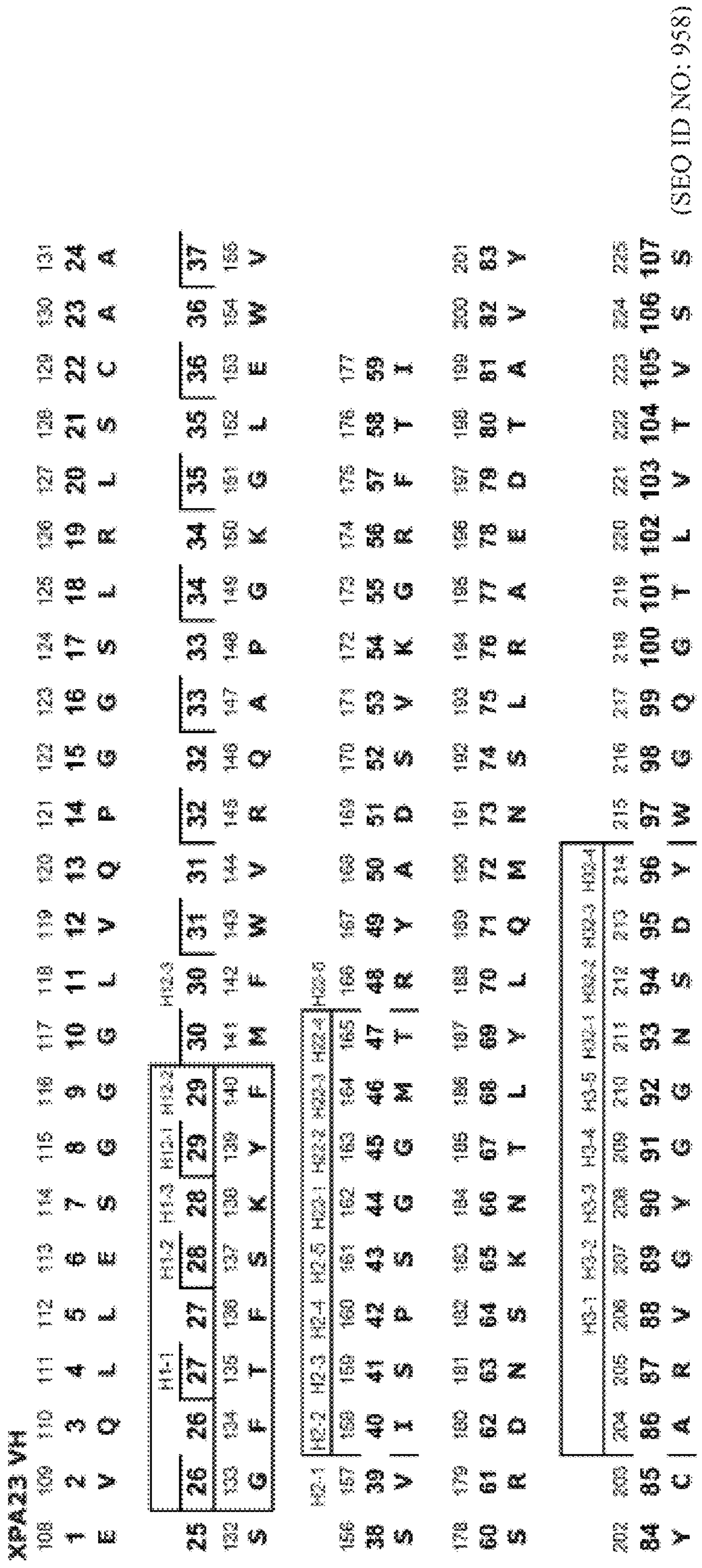

For the heavy chain modifications, a similar PCR based strategy may be used to create a modified antibody heavy chain containing more than one amino acid change (see, e.g., FIG. 8). In an exemplary method, PCR may be used to amplify four segments of the $V_H$ gene, three of which may be engineered to contain the G33F, T53I and G100R amino acid changes. For example, PCR product 1 may be synthesized using the AscI-F (SEQ ID NO: 813) and H1R primers (SEQ ID NO: 146), PCR product 2 may be synthesized using the H1-G33F primer (SEQ ID NO: 809) and H2R primer (SEQ ID NO: 182), PCR product 3 may be synthesized using H2-T3I primer (SEQ ID NO: 810) and H3R primer (SEQ ID NO: 247) and PCR product 4 may be synthesized using H3-G100R primer (SEQ ID NO: 811) and the NotI-R primer (SEQ ID NO: 285). The PCR products are then melted and re-annealed such that their regions of overlap hybridize. All four PCR products may then be joined into one molecule by PCR amplification using the forward primer from PCR product 1 (AscI-F) (SEQ ID NO: 813) and the reverse primer from PCR product 3 (NotI-R) (SEQ ID NO: 285).

In an exemplary method, a 50 μL PCR reaction for the production of PCR products 1, 2, 3 and 4 may be performed with 25 pmol each of the forward and reverse primers, 10 ng of template DNA, 5 μL PFU buffer, 2.5 μL of 10 μM dNTPs, 1 μL PFU and water to 50 μL. The PCR reaction is heated to 94° C. for 2 minutes, followed by 25 cycles of 30 sec at 94° C., 30 seconds at 54° C., and one minute at 72° C. After the 25 cycles, a final 72° C. incubation may be performed for five minutes.

An equal mass of the four PCR products may be combined in a PCR reaction to produce a modified variable domain with several amino acid changes which enhance affinity. Briefly, the PCR may be conducted by adding approximately 2 μL of each pooled PCR reaction to 5 μL PFU buffer, 25 pmol of both AscI-F primer (SEQ ID NO: 813) and NotI-R primer (SEQ ID NO: 285), 2.5 μL of 10 μM dNTPs, 1 μL PFU polymerase and water to 100 μL. Next, the PCR reaction is heated to 94° C. for two minutes, followed by twenty-five cycles of thirty seconds at 94° C., 30 seconds at 54° C., and finally one minute at 72° C. After the twenty cycles, a final 72° C. incubation is performed for five minutes.

The heavy chain PCR fragments and the vector will be digested with AscI (NEW ENGLAND BIOLABS°, Ipswich, Mass.) and NotI (NEW ENGLAND BIOLABS®, Ipswich, Mass.) such that it may be cloned into the pXOMA Fab or pXOMA Fab-gIII vector.

Example 10

Biacore Measurement of Protien Affinity

Proteins including, for example, IgGs that bind a binding partner (e.g., Epcam) are tested by BIACORE® for affinity (see, e.g., FIG. 15). For example, kinetic analysis of anti-Epcam mAb's are conducted on a Biacore 2000®.

In an exemplary method, the ING1 antibody is diluted to 0.5 μg/mL in HBS-EP running buffer and injected for two minutes at 5 μl/minute over a high density protein A/G surface. Next, six serial 3 fold dilutions of Epcam are prepared in running buffer and injected in triplicate in random order over the high density protein A/G surface with buffer injections evenly distributed throughout the run. The sample injections are then double referenced against the blank flow cells and buffer injections to correct for any bulk shift or non-specific binding. Data are then analyzed with the Biaevaluation software from Biacore and sensorgrams are fit utilizing the 1:1 langmuir model (see, e.g., FIG. 15).

Example 11

Construction of Arrays of Modified Proteins

Arrays of modified proteins including, for example, antibody variable domains (e.g., modified ING-1 variable domains) with amino acids changes at desired positions (e.g., contacting (C) residues) may be generated and tested for enhanced binding affinity compared to the parent protein (e.g., ING-1). Modified variable domains used in the array may be obtained directly from a library of modified variable domains as described in Example 2 or may first be screened for those modified variable domains that exhibit enhanced binding as compared to the parent variable domain as described in Examples 3, 4 and 5.

In an exemplary method, each contacting (C) residue in the heavy and light chain variable region of ING-1 is separately changed (e.g., by PCR mutagenesis) with alanine, arginine, asparagine, aspartic acid, glutamine, glutamine acid, glycine, histidine, isoleucine, leucine, lysine, phenylalanine, proline, serine, threonine, tryptophan, tyrosine and valine to generate modified ING-1 variable domains. CDNAs encoding the modified ING-1 variable domains are then inserted into a pXOMA vector and used to transform electrocompetent TG1 cells. The clones are plated on 2YT-$Amp_{100}$/2% Glucose plates (Teknova) and the plates filled with 250 μl of 2YT-$Amp_{100}$/well (Teknova). Each well is inoculated with a single colony comprising a single amino acid change at a contacting (C) residue. The colonies are grown by incubating the plates at 37° C. for two to four hours with shaking at 450 rpm. After the incubation, the plates are duplicated to sequencing plates by filling new deep-well culture plates (Thomson) with one milliliter of 2YT-$Amp_{100}Gluc_{2\%}$/well from the grown cultures. The Genetix 96-pin replicator is used to transfer cells from the master plate to the new sequencing plates. The sequencing plates are grown overnight at 37° C. with shaking at 450 rpm. After the incubation, the sequencing plate is spun down at 5000 rpm for ten minutes and the supernatant is discarded. Samples from the plate are sequenced (e.g., samples may be submitted for automated miniprep and automated sequencing (Elim biopharmaceuticals). After the incubation, Master Plates are made by adding glycerol to a final concentration of 15% to the wells on the glycerol plate and storing the plates at −80° C. The unique clones and their well position in the master plate are identified after sequencing results are returned.

Eighteen different clones, each containing an amino acid change at a contacting (C) residue in ING-1, are identified (typically 96 sequenced clones yield all eighteen clones). Unique clones from the master plates are rearrayed to a new 96-well master plate containing 2YT-$Amp_{100}$ by transferring ten microliters of glycerol stock from the master plate to the rearrayed master plate. Alternatively, automation, such as the QPIX II is used to transfer the glycerol stock containing the unique clones to the new master plate. The new rearrayed glycerol master plates are replicated into new expression plates to perform Biacore (e.g., Biacore A100) analysis (see, e.g., Table 8 and Table 9). Arrays may also be constructed for XPA 23 modified antibodies (see, e.g., Table 10 and 11).

TABLE 8

Biacore Analysis of Modified Light Chain Variable Regions[1, 2 3]

| | | | | | | | | | | | |
|---|---|---|---|---|---|---|---|---|---|---|---|
| | | | | | NP | | | | | | |
| | | | | Aromatic | | | | | | | |
| | Neg | | Pos | | Polar | | | | | | |
| | D | E | R | K | H | Y | W | F | Q | N | S |
| CDR1 K 27 | 1.26 | −1.00 | 1.26 | ? | 1.06 | nd | −1.00 | 1.62 | 1.52 | −1.00 | −1.00 |
| S 28 | 1.63 | 1.02 | **2.78** | 2.32 | 1.90 | 2.02 | nd | 2.38 | 1.99 | −1.00 | 1.08 |
| L 29 | −1.00 | −1.00 | −1.00 | nd | nd | −1.00 | −1.00 | −1.00 | −1.00 | 1.85 | **2.03** |
| L 30 | 1.47 | −1.00 | −1.00 | −1.00 | 1.45 | 1.53 | −1.00 | 1.56 | 1.60 | 1.45 | 1.43 |
| H 31 | 0.71 | 0.68 | 0.06 | 0.05 | 0.95 | **2.16** | 1.66 | nd | 0.57 | 0.50 | 0.82 |
| S 32 | 0.94 | nd | **1.79** | 1.32 | 1.13 | 1.37 | 1.27 | 1.64 | 1.10 | −1.00 | ? |
| N 33 | 0.49 | 0.65 | 0.71 | 0.70 | 0.73 | 0.80 | 1.04 | 0.93 | 0.73 | **1.38** | 0.48 |
| I 35 | 0.19 | 0.16 | 0.92 | 0.61 | 0.59 | 0.51 | 0.34 | 0.66 | 0.41 | 0.50 | 0.55 |
| T 36 | 0.05 | 1.60 | −1.00 | 1.15 | 0.79 | nd | 1.30 | nd | 1.04 | 0.74 | 1.10 |
| Y 37 | nd | 0.01 | nd | 0.02 | **4.07** | 0.95 | 0.85 | 0.63 | 0.02 | 0.06 | 0.09 |
| CDR2 Y 54 | 0.03 | 0.05 | −1.00 | **3.62** | −1.00 | 0.92 | 0.96 | 0.94 | 1.23 | −1.00 | 0.90 |
| Q 55 | 0.05 | 0.05 | **5.31** | 0.46 | 3.82 | nd | 4.11 | 0.86 | 0.95 | 0.36 | 0.56 |
| M 56 | 1.36 | 0.71 | 0.92 | 0.98 | 1.32 | 1.21 | 1.29 | **1.40** | 1.12 | 0.99 | 1.05 |
| S 57 | 0.95 | 0.93 | 1.17 | 1.54 | 1.01 | −1.00 | **2.34** | 0.96 | −1.00 | 1.17 | 1.00 |
| N 58 | nd | 0.97 | 1.77 | 1.40 | 1.16 | 1.43 | 1.99 | 1.03 | 1.55 | 0.95 | 1.65 |
| CDR3 L 97 | −1.00 | 0.75 | −1.00 | 0.61 | 0.42 | 0.98 | 1.59 | 0.93 | 0.91 | 0.48 | 0.79 |
| E 98 | 1.62 | 0.98 | 3.08 | 2.22 | 1.23 | 1.23 | 1.10 | 1.43 | 1.41 | −1.00 | −1.00 |
| L 99 | 0.02 | 0.01 | 0.04 | 0.02 | 0.05 | 1.00 | 0.89 | 0.43 | 0.02 | 2.00 | 0.04 |
| P 100 | 0.02 | 0.06 | 0.05 | 0.03 | 0.05 | **1.94** | 1.51 | 1.65 | 0.04 | 0.05 | 0.06 |
| R 101 | −1.00 | −1.00 | 0.93 | 0.04 | −1.00 | −1.00 | −1.00 | −1.00 | −1.00 | −1.00 | −1.00 |

TABLE 8-continued

Biacore Analysis of Modified Light Chain Variable Regions[1, 2 3]

| | | NP | | | | | | | | |
|---|---|---|---|---|---|---|---|---|---|---|
| | | Aliphatic | | | | Small | | | | NP |
| | | T | V | I | L | A | C | G | P | M |
| CDR1 | K 27 | −1.00 | nd | 1.15 | 1.39 | 1.10 | nd | 1.11 | **1.29** | nd |
| | S 28 | 1.19 | 2.15 | 2.35 | 2.60 | 1.53 | nd | nd | 2.42 | nd |
| | L 29 | nd | nd | −1.00 | ? | 1.97 | nd | 1.53 | −1.00 | nd |
| | L 30 | **1.89** | 1.69 | 0.96 | 0.97 | 1.27 | nd | 1.64 | 0.82 | nd |
| | H 31 | 1.94 | 1.17 | 1.14 | 0.59 | 1.26 | nd | 0.73 | 1.19 | nd |
| | S 32 | nd | 0.93 | 1.17 | 1.12 | 1.35 | nd | 1.39 | 0.83 | nd |
| | N 33 | 0.60 | −1.00 | nd | nd | 0.76 | nd | 0.72 | 0.67 | nd |
| | I 35 | 0.87 | 1.08 | nd | 0.60 | 0.46 | nd | 0.39 | 0.70 | nd |
| | T 36 | 0.94 | 0.98 | 0.76 | **1.64** | 1.02 | nd | 1.09 | 0.67 | nd |
| | Y 37 | −1.00 | −1.00 | 0.90 | nd | 0.04 | nd | 1.30 | nd | nd |
| CDR2 | Y 54 | 0.61 | 1.32 | −1.00 | 3.44 | 0.08 | nd | 1.85 | 0.86 | nd |
| | Q 55 | 0.66 | 1.53 | 1.42 | 0.71 | 0.64 | nd | 0.70 | 0.95 | nd |
| | M 56 | 0.80 | −1.00 | 1.37 | 0.74 | 0.86 | nd | 0.80 | 1.38 | nd |
| | S 57 | 0.86 | 0.89 | 0.98 | 1.38 | 1.15 | nd | −1.00 | nd | nd |
| | N 58 | 1.42 | 2.84 | 2.51 | 1.47 | 1.79 | nd | 1.87 | **3.47** | nd |
| CDR3 | L 97 | 0.54 | 1.44 | **2.62** | 0.93 | 0.50 | nd | −1.00 | 0.95 | nd |
| | E 98 | **4.90** | nd | nd | 2.82 | 1.35 | nd | 1.63 | −1.00 | nd |
| | L 99 | 0.09 | 1.04 | **2.07** | 0.93 | 1.43 | nd | 0.02 | 0.01 | nd |
| | P 100 | 0.08 | 0.14 | 0.14 | 0.03 | 0.05 | nd | 1.62 | 1.01 | nd |
| | R 101 | −1.00 | −1.00 | −1.00 | **1.33** | −1.00 | nd | −1.00 | −1.00 | nd |

[1]A value of −1 indicates no binding

[2]Bolded values indicate the highest affinity o affinity (as measured by how many "fold" differences in affinity. The mutant is in comparison to original, e.g., 2.0 as twice as strong and 0.5 as half as strong) obtained for an amino acid change at the position

[3]nd indicates that binding affinity was not determined

TABLE 9

Biacore Analysis of Modified Heavy Chain Variable Regions[1, 2, 3]

| | | | | | | NP | | | | | | |
|---|---|---|---|---|---|---|---|---|---|---|---|---|
| | | | | Aromatic | | | | | | | | |
| | | Neg | | Pos | | Polar | | | | | | |
| | | D | E | R | K | H | Y | W | F | Q | N | S |
| CDR1 | T 28 | 0.98 | 1.23 | 1.23 | **1.77** | 1.15 | 1.86 | 1.08 | 1.28 | −1.00 | 0.69 | 1.07 |
| | T 30 | 0.63 | 0.73 | **1.39** | 0.94 | nd | **2.00** | 1.26 | nd | nd | 0.73 | 0.91 |
| | K 31 | 0.66 | 0.54 | 0.76 | 0.96 | 0.78 | 1.00 | 1.02 | nd | nd | −1.00 | **0.49** |
| | Y 32 | nd | 0.08 | 0.43 | 0.08 | 0.60 | 0.84 | nd | **1.05** | 0.10 | nd | **0.01** |
| | G 33 | −1.00 | −1.00 | 0.03 | −1.00 | 0.02 | 6.16 | −1.00 | **7.19** | 0.06 | −1.00 | nd |
| CDR2 | W 50 | **3.27** | −1 | 0.10 | 0.04 | 0.02 | 0.04 | 0.97 | 0.09 | 0.01 | 0.03 | 0.02 |
| | N 52 | 0.02 | −1 | −1 | −1 | 0.02 | −1 | −1 | −1 | −1 | **0.98** | −1 |
| | T 53 | −1 | −1 | −1 | 1.79 | −1 | −1 | −1 | −1 | −1 | −1 | 0.17 |
| | Y 54 | 0.05 | 0.07 | **3.72** | 3.62 | 1.00 | 0.92 | 0.96 | 0.65 | 0.66 | 2.11 | 0.49 |
| | T 55 | 0.03 | −1 | 0.14 | 0.45 | 0.05 | 0.03 | 0.10 | 0.03 | 0.03 | 0.17 | 0.42 |
| | E 56 | 0.81 | 0.95 | 1.34 | 1.27 | **1.74** | 1.04 | 1.17 | 0.78 | 1.23 | 1.01 | 1.46 |
| | E 57 | 1.17 | 1.07 | **1.71** | nd | 1.16 | 1.37 | 1.39 | 1.06 | −1.00 | 1.57 | 1.41 |
| | P 58 | 0.54 | 0.44 | nd | 1.14 | nd | 0.99 | 1.11 | 0.98 | 1.11 | 0.90 | 1.07 |
| | T 59 | 0.87 | 0.51 | 1.22 | 1.43 | 0.40 | nd | **2.24** | 0.43 | −1.00 | 0.96 | nd |
| CDR3 | G 100 | −1 | −1 | **7.51** | 1.59 | −1 | −1 | −1 | −1 | −1.00 | 1.55 | 1.68 |
| | S 101 | 0.21 | 0.76 | nd | 2.20 | 1.35 | 1.79 | 1.22 | 1.16 | 2.18 | 0.97 | nd |
| | A 102 | 0.28 | 0.51 | 2.18 | 1.48 | 2.40 | 3.01 | 3.13 | 2.97 | 1.01 | 0.94 | 0.94 |
| | D 104 | nd | 0.14 | −1 | −1 | −1 | −1 | −1 | −1 | −1 | 0.73 | **1.87** |
| | Y 105 | −1 | −1 | 0.66 | −1 | **0.94** | nd | 0.84 | 0.91 | 0.87 | nd | 0.09 |

| | | NP | | | | | | | | |
|---|---|---|---|---|---|---|---|---|---|---|
| | | Aliphatic | | | | Small | | | | NP |
| | | T | V | I | L | A | C | G | P | M |
| CDR1 | T 28 | nd | 2.08 | **2.45** | nd | 1.56 | nd | 0.92 | **2.16** | nd |
| | T 30 | 0.93 | 1.30 | nd | 1.26 | 0.89 | nd | −1.00 | 0.93 | nd |
| | K 31 | nd | **1.41** | 1.17 | 0.60 | 0.39 | nd | 1.02 | nd | nd |
| | Y 32 | nd | 0.11 | 0.03 | 0.05 | 0.01 | nd | 0.02 | 0.01 | nd |
| | G 33 | **0.01** | 0.04 | 0.55 | 2.27 | 0.06 | nd | nd | 6.31 | nd |

TABLE 9-continued

Biacore Analysis of Modified Heavy Chain Variable Regions[1, 2, 3]

| | | | | | | | | | | |
|---|---|---|---|---|---|---|---|---|---|---|
| CDR2 | W 50 | 0.03 | 0.02 | 0.07 | 0.04 | 0.03 | nd | 0.03 | −1 | nd |
| | N 52 | −1 | −1 | −1 | −1 | −1 | nd | −1 | −1 | nd |
| | T 53 | 1.19 | 2.44 | **11.40** | nd | 9.03 | nd | −1 | −1 | nd |
| | Y 54 | 0.36 | 1.32 | 0.28 | 1.80 | 0.47 | nd | **3.72** | 0.86 | nd |
| | T 55 | nd | 0.28 | nd | **0.95** | nd | nd | 0.02 | nd | nd |
| | E 56 | 1.21 | 0.86 | 0.85 | 0.64 | 1.67 | nd | 1.37 | 0.01 | nd |
| | E 57 | 1.44 | nd | 1.34 | −1 | 1.65 | nd | 1.45 | −1.00 | nd |
| | P 58 | 1.00 | 1.01 | nd | 0.64 | 1.03 | nd | **1.31** | 1.06 | nd |
| | T 59 | 0.99 | 1.03 | 0.76 | 0.95 | nd | nd | 0.35 | −1.00 | nd |
| CDR3 | G 100 | 0.61 | 2.17 | nd | 0.65 | 1.99 | nd | nd | −1 | nd |
| | S 101 | 0.84 | 1.92 | **3.53** | −1 | 1.15 | nd | 3.31 | nd | nd |
| | A 102 | 0.68 | 1.20 | 0.79 | −1 | nd | nd | **3.58** | 0.87 | nd |
| | D 104 | −1 | −1 | nd | −1 | −1 | nd | 0.41 | −1 | nd |
| | Y 105 | 0.12 | 0.18 | 0.23 | 0.22 | 0.08 | nd | −1.00 | −1 | nd |

[1]A value −1 indicates no binding

[2]Bolded values indicate the highest affinity o affinity (as measured by how many "fold" differences in affinity. The mutant is in comparison to original, e.g., 2.0 as twice as strong and 0.5 as half as strong) obtained for an amino acid change at the position

[3]nd indicates that binding affinity was not determined

TABLE 10

Biacore Analysis of Modified C5A (XPA23) Light Chain Variable Regions[1, 2, 3]

| | | | | | | | | | | | | |
|---|---|---|---|---|---|---|---|---|---|---|---|---|
| | | | | | | NP | | | | | | |
| | | | | | | Aromatic | | | | | | |
| | | NEG | | Pos | | Polar | | | | | | |
| | | D | E | R | K | H | Y | W | F | Q | N | S |
| CDR1 | Q27 | 1.07 | 1.08 | 0.89 | −1.00 | 1.09 | nd | −1.00 | 2.96 | 1.06 | −1.00 | **3.30** |
| | D28 | 1.00 | 0.74 | 0.94 | 0.82 | 1.23 | 1.45 | 3.81 | 1.43 | nd | 1.00 | 5.25 |
| | N30 | 0.81 | 0.64 | 0.74 | 0.61 | 1.00 | 1.40 | 1.06 | **1.59** | 0.60 | 1.08 | 0.72 |
| | R31 | **11.11** | −1.00 | 1.06 | 1.18 | −1.00 | −1.00 | 0.43 | 0.92 | 0.27 | 0.38 | 0.44 |
| | W32 | −1.00 | −1.00 | −1.00 | −1.00 | −1.00 | −1.00 | **0.99** | −1.00 | −1.00 | −1.00 | −1.00 |
| CDR2 | H49 | 0.11 | −1.00 | 0.21 | 0.10 | **1.10** | 0.52 | 0.21 | 0.50 | −1.00 | 0.31 | 0.14 |
| | S50 | −1.00 | 0.02 | −1.00 | 0.10 | 0.05 | 0.05 | 0.02 | −1.00 | 0.21 | 0.25 | **1.04** |
| | A51 | 0.13 | 0.29 | 0.18 | nd | 0.61 | 0.45 | 0.24 | −1.00 | 0.24 | 0.30 | 0.95 |
| | T52 | 0.72 | 0.61 | **3.37** | 3.23 | 0.91 | 1.01 | 0.87 | 1.05 | 0.83 | 0.83 | 0.78 |
| | S53 | −1.00 | 1.13 | 3.29 | 4.07 | nd | 1.23 | 1.11 | 1.24 | 1.09 | 1.23 | 1.08 |
| CDR3 | A91 | 1.08 | 0.10 | −1.00 | nd | **1.12** | −1.00 | −1.00 | −1.00 | −1.00 | 0.10 | 0.90 |
| | D92 | 0.83 | 0.99 | −1.00 | 0.23 | 0.63 | −1.00 | 0.12 | 0.26 | 0.56 | 0.67 | **6.59** |
| | S93 | 4.59 | 3.71 | 0.91 | 0.86 | 1.08 | 1.45 | **5.49** | 1.32 | 1.54 | 3.76 | 1.20 |
| | F94 | −1.00 | −1.00 | −1.00 | −1.00 | −1.00 | −1.00 | −1.00 | **1.14** | −1.00 | −1.00 | −1.00 |
| | P95 | 1.32 | 0.88 | −1.00 | −1.00 | −1.00 | −1.00 | −1.00 | 0.98 | −1.00 | −1.00 | **4.05** |
| | L96 | −1.00 | −1.00 | −1.00 | −1.00 | 0.07 | −1.00 | **4.49** | 0.28 | 0.21 | 0.06 | 0.23 |

| | | | | | | | | | | |
|---|---|---|---|---|---|---|---|---|---|---|
| | | NP | | | | | | | | |
| | | Aliphatic | | | | Small | | | | NP |
| | | T | V | I | L | A | C | G | P | M |
| CDR1 | Q27 | 0.64 | −1.00 | 0.82 | 0.83 | 1.47 | nd | −1.00 | −1.00 | nd |
| | D28 | 1.19 | 0.85 | −1.00 | **9.64** | 0.88 | nd | 1.21 | 1.17 | nd |
| | N30 | 0.97 | 0.89 | 0.65 | 0.68 | 0.61 | nd | 0.71 | 0.69 | nd |
| | R31 | 0.24 | 0.44 | 0.68 | 0.51 | 8.48 | nd | 0.92 | −1.00 | nd |
| | W32 | −1.00 | −1.00 | −1.00 | −1.00 | −1.00 | nd | −1.00 | −1.00 | nd |
| CDR2 | H49 | −1.00 | −1.00 | −1.00 | 0.07 | 0.23 | nd | −1.00 | 0.86 | nd |
| | S50 | 0.87 | 0.21 | 0.25 | 0.49 | 0.13 | nd | 0.14 | −1.00 | nd |
| | A51 | 0.76 | 0.31 | −1.00 | 0.16 | 1.09 | nd | **3.84** | 0.13 | nd |
| | T52 | 1.02 | 0.82 | 0.80 | 0.78 | 0.66 | nd | −1.00 | 1.08 | nd |
| | S53 | 0.95 | 1.42 | 1.42 | 0.99 | 1.07 | nd | 1.03 | **4.92** | nd |
| CDR3 | A91 | 0.67 | 0.51 | −1.00 | 0.39 | −1.00 | nd | −1.00 | −1.00 | nd |
| | D92 | 0.34 | −1.00 | 0.33 | 0.14 | 0.40 | nd | 0.26 | −1.00 | nd |
| | S93 | 1.47 | 3.81 | 1.35 | 1.08 | 1.16 | nd | 0.75 | −1.00 | nd |
| | F94 | −1.00 | 0.20 | 0.88 | 0.55 | −1.00 | nd | −1.00 | 0.17 | nd |
| | P95 | −1.00 | −1.00 | −1.00 | −1.00 | 3.83 | nd | −1.00 | −1.00 | nd |
| | L96 | 0.06 | nd | 0.67 | 1.16 | 0.26 | nd | −1.00 | −1.00 | nd |

[1]A value of −1 indicates no binding

[2]Bolded values indicate the highest affinity (as measured by how many "fold" differences in affinity. The mutant is in comparison to original, e.g., 2.0 as twice as strong and 0.5 as half as strong) obtained for an amino acid change at the position

[3]nd indicates that binding affinity was not determined

TABLE 11

Biacore Analysis of Modified C5A (XPA23) Heavy Chain Variable Regions[1, 2, 3]

| | | | | | | NP | | | | | | |
|---|---|---|---|---|---|---|---|---|---|---|---|---|
| | | | | | | Aromatic | | | | | | |
| | | Neg | | Pos | | Polar | | | | | | |
| | | D | E | R | K | H | Y | W | F | Q | N | S |
| CDR1 | T28 | nd | −1.00 | −1.00 | −1.00 | −1.00 | nd | −1.00 | nd | −1.00 | nd | nd |
| | S30 | −1.00 | −1.00 | 0.10 | −1.00 | −1.00 | −1.00 | 0.77 | −1.00 | −1.00 | 0.15 | 0.85 |
| | K31 | 0.04 | −1.00 | 0.90 | **1.30** | 1.11 | 0.04 | 0.84 | 0.05 | −1.00 | −1.00 | −1.00 |
| | Y32 | 0.68 | 0.12 | nd | nd | 0.62 | nd | nd | 0.75 | −1.00 | 0.04 | **1.33** |
| | F33 | 0.92 | 0.86 | −1.00 | 0.85 | −1.00 | 0.77 | 0.79 | −1.00 | 0.78 | **0.97** | 0.73 |
| | F35 | 0.06 | −1.00 | −1.00 | 0.68 | −1.00 | 0.85 | −1.00 | −1.00 | −1.00 | 0.86 | 0.09 |
| CDR2 | V50 | −1.00 | −1.00 | −1.00 | −1.00 | −1.00 | −1.00 | −1.00 | −1.00 | −1.00 | 0.03 | −1.00 |
| | I51 | 0.07 | 0.73 | 0.10 | 0.11 | 0.08 | **1.75** | −1.00 | 0.90 | 0.83 | 0.68 | 0.69 |
| | S52 | −1.00 | −1.00 | −1.00 | −1.00 | −1.00 | −1.00 | −1.00 | −1.00 | −1.00 | −1.00 | nd |
| | P53 | −1.00 | 0.03 | nd | 0.04 | −1.00 | 0.03 | 0.05 | 0.05 | 0.03 | 0.06 | 0.03 |
| | S54 | 0.12 | 0.03 | 1.43 | **1.53** | nd | 0.99 | 1.07 | 0.87 | 1.01 | 0.08 | nd |
| | G55 | −1.00 | 0.11 | 0.95 | 0.11 | nd | 0.08 | nd | nd | 0.90 | 0.10 | **1.02** |
| | G56 | 0.05 | 1.21 | **2.11** | 2.05 | 0.82 | 1.27 | 1.51 | 1.41 | 1.31 | 1.06 | nd |
| | M57 | −1.00 | −1.00 | 0.06 | 0.04 | 0.08 | 0.86 | nd | **1.03** | 0.02 | 0.03 | 0.04 |
| | T58 | 0.12 | −1.00 | 1.14 | −1.00 | 0.98 | 1.01 | 0.93 | 1.04 | −1.00 | 0.90 | 0.82 |
| | R59 | −1.00 | −1.00 | −1.00 | 0.94 | −1.00 | −1.00 | 0.09 | 0.92 | 0.86 | 0.86 | 0.13 |
| CDR3 | V99 | nd | −1.00 | nd | −1.00 | nd | nd | nd | 0.03 | −1.00 | −1.00 | −1.00 |
| | G100 | −1.00 | nd | −1.00 | −1.00 | 0.06 | 0.09 | 0.05 | −1.00 | −1.00 | nd | **2.80** |
| | Y101 | −1.00 | 0.03 | 0.85 | nd | 0.04 | 1.00 | 0.81 | 0.85 | 0.06 | 0.06 | nd |
| | G102 | nd | −1.00 | −1.00 | −1.00 | −1.00 | −1.00 | −1.00 | nd | −1.00 | **1.17** | nd |
| | G103 | −1.00 | −1.00 | −1.00 | −1.00 | nd | nd | −1.00 | −1.00 | −1.00 | nd | nd |
| | N104 | −1.00 | −1.00 | −1.00 | −1.00 | 0.07 | −1.00 | −1.00 | −1.00 | 0.03 | 1.02 | 1.02 |
| | S105 | nd | 1.17 | −1.00 | nd | 0.05 | −1.00 | −1.00 | 1.25 | 0.98 | 0.85 | 1.09 |
| | D106 | **0.98** | 0.04 | 0.06 | 0.04 | 0.02 | −1.00 | −1.00 | −1.00 | 0.02 | 0.07 | 0.03 |
| | Y107 | 0.85 | 0.90 | 0.85 | 0.82 | −1.00 | −1.00 | 0.89 | 0.90 | 0.87 | −1.00 | 0.89 |

| | | NP | | | | | | | | |
|---|---|---|---|---|---|---|---|---|---|---|
| | | Aliphatic | | | | Small | | | | NP |
| | | T | V | I | L | A | C | G | P | M |
| CDR1 | T28 | −1.00 | nd | nd | nd | nd | nd | −1.00 | nd | nd |
| | S30 | 0.06 | −1.00 | 0.08 | **0.91** | 0.77 | nd | 0.13 | −1.00 | nd |
| | K31 | −1.00 | 0.81 | 0.74 | 1.08 | nd | nd | nd | −1.00 | nd |
| | Y32 | 0.80 | 1.07 | nd | 0.75 | −1.00 | nd | 1.00 | 0.68 | nd |
| | F33 | 0.78 | 0.76 | 0.75 | 0.88 | 0.75 | nd | 0.76 | 0.91 | nd |
| | F35 | 0.74 | **0.89** | 0.85 | 0.78 | 0.07 | nd | 0.04 | 0.06 | nd |
| CDR2 | V50 | 0.03 | **0.19** | 0.10 | 0.09 | 0.09 | nd | 0.03 | −1.00 | nd |
| | I51 | 0.86 | 0.99 | 0.95 | 0.79 | 1.04 | nd | 0.94 | −1.00 | nd |
| | S52 | 0.04 | 0.04 | −1.00 | −1.00 | **0.05** | nd | 0.03 | 0.05 | nd |
| | P53 | nd | **1.10** | 0.08 | 0.04 | 0.05 | nd | 0.02 | 0.94 | nd |
| | S54 | 0.14 | 1.00 | 0.86 | 0.91 | 1.00 | nd | 1.43 | 0.06 | nd |
| | G55 | nd | nd | 0.86 | 0.08 | nd | nd | 0.99 | nd | nd |
| | G56 | 1.11 | nd | 1.71 | 1.41 | 1.21 | nd | nd | 0.85 | nd |
| | M57 | 0.06 | 0.03 | 0.03 | 0.06 | 0.03 | nd | nd | −1.00 | nd |
| | T58 | 1.04 | 0.99 | 0.95 | 0.95 | 0.14 | nd | 0.95 | **1.81** | nd |
| | R59 | 0.76 | −1.00 | −1.00 | 0.08 | −1.00 | nd | **1.04** | 0.07 | nd |
| CDR3 | V99 | **0.10** | nd | nd | −1.00 | 0.03 | nd | nd | −1.00 | nd |
| | G100 | 0.12 | nd | nd | −1.00 | nd | nd | 1.02 | −1.00 | nd |
| | Y101 | 0.06 | 0.09 | 0.83 | **1.91** | 0.04 | nd | −1.00 | 0.04 | nd |
| | G102 | nd | −1.00 | nd | −1.00 | −1.00 | nd | nd | −1.00 | nd |
| | G103 | nd | **2.56** | nd | nd | 0.03 | nd | 0.93 | nd | nd |
| | N104 | 0.95 | 1.27 | nd | 1.19 | **1.61** | nd | 1.21 | nd | nd |
| | S105 | 0.11 | 0.08 | 0.07 | −1.00 | 0.84 | nd | 0.12 | **1.41** | nd |
| | D106 | −1.00 | −1.00 | −1.00 | −1.00 | −1.00 | nd | 0.03 | −1.00 | nd |
| | Y107 | 0.83 | 0.93 | **0.96** | 0.86 | 0.83 | nd | 0.10 | 0.04 | nd |

[1]A value of −1 indicates no binding

[2]Bolded values indicate the highest affinity o affinity (as measured by how many "fold" differences in affinity. The mutant is in comparison to original, e.g., 2.0 as twice as strong and 0.5 as half as strong) obtained for an amino acid change at the position

[3]nd indicates that binding affinity was not determined

Example 12

Construction of Arrays of Modified Proteins

Arrays of modified proteins including, for example, antibody variable domains (e.g., modified ING-1 variable domains) with amino acids changes at desired positions (e.g., contacting (C) residues) may be generated and tested for enhanced binding affinity compared to the parent protein (e.g., ING-1). Modified variable domains used in the array may be obtained directly from a library of modified variable domains as described in Example 2 or may first be screened for those modified variable domains that exhibit enhanced binding as compared to the parent variable domain as described in Examples 3, 4 and 5.

In an exemplary method, each contacting (C) residue in the heavy and light chain variable region of ING-1 is separately changed (e.g., by PCR mutagenesis) with alanine, arginine, asparagine, aspartic acid, glutamine, glutamine acid, glycine, histidine, isoleucine, leucine, lysine, phenylalanine, proline, serine, threonine, tryptophan, tyrosine and valine to generate modified ING-1 variable domains. cDNAs encoding the modified ING-1 variable domains are then inserted into a pXOMA vector and used to transform electrocompetent TG1 cells. The clones are plated on 2YT-Amp$_{100}$/2% Glucose plates (Teknova) and the plates filled with 250 μl of 2YT-Amp$_{100}$/well (Teknova). Each well is inoculated with a single colony comprising a single amino acid change at a contacting (C) residue. The colonies are grown by incubating the plates at 37° C. for two to four hours with shaking at 450 rpm. After the incubation, the plates are duplicated to expression plates by filling new plates (Costar) with two hundred and fifty microliters of 2YT-Amp100 media (Teknova). The Genetix 96-pin replicator is used to transfer cells from the Master plate to the new expression plates The culture is grown at 37° C. until cloudy (e.g., approximate OD$_{600}$=0.5), inoculated with IPTG to a final concentration of 1 mM and grown overnight at 30° C.

Next, periplasmic extracts (PPE) of the overnight expression constructs are prepared by spinning the overnight expression plates at 3000 rpm for fifteen minutes, discarding the supernatant and adding 60 μl of PPB buffer to each well. The pellets are resuspended, and 90 μl of cold PPB diluted 1:5 with cold water is added to each well. This mixture is incubated on ice for one hour and subsequently spun down at 3000 rpm for fifteen minutes. The supernatant is transferred to a new plate and the periplasmic extracts are used for the Biacore (e.g., Biacore A100) determination.

After Biacore determination, wells that contain clones with improved off rates are sequenced and further characterized (e.g. IgG reformatting and affinity determination).

Example 13

Affinity Optimization of Protein by Targeted Mutagenesis of Selected Amino Acid Residues Affinity optimized proteins including, for example, antibodies or fragments thereof may be obtained by mutation of one or more selected amino acid residues in a parent protein with other amino acid residues (e.g., alanine, arginine, asparagine, aspartic acid, glutamine, glutamic acid, glycine, histidine, isoleucine, leucine, lysine, phenylalanine, proline, serine, threonine, tryptophan, tyrosine or valine). Methods for optimization of an exemplary antibody variable domain may comprise the stages as set forth below.

A. Selection of Amino Acid Residues for Mutation

Amino acid residues at one or more positions in a parent antibody or binding fragment thereof are selected for mutagenesis. Such methods may include, for example, identifying the proximity assigned to amino acid positions in the variable domain of the antibody using the "prox" line as shown in FIGS. 3A, 3B, 3C and/or 3D. One or more amino acid resdies identified as C, P, S and/or I residues may be selected for mutation.

B. Design of Primers for Mutagenesis

Primers are designed to mutagenize a parent nucleic acid sequence that codes for an antibody or binding fragment thereof.

For a PCR-based mutagenesis method, a primer may be designed such that the forward primer sequence flanks both sides (e.g., 20 base pairs) of the position to be mutated. Additionally, it is preferred that the primer be 70 bases or les in length. A representative CDR comprising amino acid residues 1-8 is shown below.

```
aa#                     1    2    3    4    5    6    7    8
                        G    F    T    F    S    K    Y    F
5'-G TCTTTCTTGC GCTGCTTCCG GATTCACTTT CTCTAAGTAC TTTATGTTTT GGGTTCGCCAAGC-3'   (SEQ ID NO: 964)

3'-C AGAAAGAACG CGACGAAGGC CTAAGTGAAA GAGATTCATG AAATACAAAA CCCAAGCGGTTCG-5'   (SEQ ID NO: 965)
```

If the CDR is too long to incorporate all the desired mutations and remain under 70 nucleotides, the mutagenesis region may be broken up into two regions. An example of this process is shown below, where the 8 amino acid CDR as shown above is broken into two 4 amino acid regions (region 1 and region 2, respectively).

Region 1:

```
aa#                     1    2    3    4
                        G    F    T    F
5'-G TCTTTCTTGC GCTGCTTCCG GATTCACTTT CTCTAAGTAC TTTATGTTTT GGGTTC-3'   (SEQ ID NO: 966)

3'-C AGAAAGAACG CGACGAAGGC CTAAGTGAAA GAGATTCATG AAATACAAAA CCCAAG-5'   (SEQ ID NO: 967)
```

Region 2:

```
      aa#                 5  6  7  8
                          S  K  Y  F
5'-GCTGCTTCCG GATTCACTTT CTCTAAGTAC TTTATGTTTT GGGTTCGCCAAGC-3'(SEQ ID NO: 968)

3'-CGACGAAGGC CTAAGTGAAA GAGATTCATG AAATACAAAA CCCAAGCGGTTCG-5'(SEQ ID NO: 969)
```

Sets of primers may be constructed to incorporate all 18 amino acid mutations at each positon in region 2. Each codon selected for mutation may be replaced with NHT, VAA or BGG in the sense direction. Exemplary primer sets for mutation of each of positions 5-8 are shown below.

Mutation of the S position (aa5) in region 2 above may be accomplished by the following primers: R2-5-NHT 5'-GCTGCTTCCGGATTCACTTT-C NHTAAGTACTTTATGTTTTGGGTTCGCCAAGC-3'(SEQ ID NO: 970); R2-5-VAA 5'-GCTGCTTCCGGATTCACTTTC VAAAAGTACTTTATGTTTTGGGTTCGCCAAGC-3' (SEQ ID NO: 971); and R2-5-BGG 5'-GCTGCTTCCGGATTCACTTTC BGGAAGTAC-TTTATGT-TTTGGGTTCGCCAAGC-3' (SEQ ID NO: 972).

Mutation of the K position (aa6) in region 2 above may be accomplished by the following primers: R2-6-NHT 5'-GCTGCTTCCGGATTCACTTT CTCT NHTTACTTTATGTTTTGGGTTCGCCAAGC-3' (SEQ ID NO: 973); R2-6-VAA 5'-GCTGCTTCCGGATTCACTTTCTCT VAATACTTTATGTTTTGGGTTCGCCAAGC-3' (SEQ ID NO: 974); and R2-6-BGG 5'-GCTGCTTCCGGATTCACTTTCTCTBGGTAC TTTATGTTTTGGGTTCGCCAAGC-3' (SEQ ID NO: 975).

Mutation of the Y position (aa7) in region 2 above may be accomplished by the following primers: R2-7-NHT 5'-GCTGCTTCCGGATTCACTTT CTCTAAG NHTTTTATGTTTTGGGTTCGCCAAGC-3' (SEQ ID NO: 976); R2-7-VAA 5'-GCTGCTTCCGGATTCACTTTCTCTAAG VAATTTATGTTTTGGGTTCGCCAAGC-3' (SEQ ID NO: 977); and R2-7-BGG 5'-GCTGCTTCCGGATTCACTTTCTCTAAGBGG TTTATGTTTTGGGTTCGCCAAGC-3' (SEQ ID NO: 978).

Mutation of the F position (aa8) in region 2 above may be accomplished by the following primers: R2-8-NHT 5'-GCTGCTTCCGGATTCACTTT CTCTAAGTAC NHTATGTTTTGGGTTCGCCAAGC-3' (SEQ ID NO: 979); R2-8-VAA 5'-GCTGCTTCCGGATTCACTTTCTCTAAGTAC VAAATGTTTTGGGTTCGCCAAGC-3' (SEQ ID NO: 980); and R2-8-BGG 5'-GCTGCTTCCGGATTCACTTTCTCTAAGTAC BGGATGTTTTGGGTTCGCCAAGC-3' (SEQ ID NO: 981).

Alternatively, modified antibody variable domains containing amino acid changes at one or more contacting (C) residues present within an exemplary antibody may be synthesized by QUIKCHANGE™ site-directed mutagenesis (STRATAGENE, Tex.).

In an exemplary method, QUIKCHANGE™ site-directed mutagenesis may be performed to replace one or more codons in an antibody variable region (e.g., a CDR) such as XPA-23. Mutagenic primers are designed to contain the desired mutation and anneal to the same sequence on opposite strands of a plasmid comprising a nucleotide coding for XPA-23. Preferably, the desired mutation in the middle of the primer contains 20 bases of correct sequence on both sides of the nucleic acid flanking the mutation. The XPA-23 CDR1 coding region is shown below.

```
aa#              1   2  3  4   5  6  7   8
                 G   F  T  F   S  K  Y   F
5'-G TCTTTCTTGC GCTGCTTCCG GATTCACTTT CTCTAAGTAC TTTATGTTTT GGGTTCGCCAAGC-3' (SEQ ID NO: 851)

3'-C AGAAAGAACG CGACGAAGGC CTAAGTGAAA GAGATTCATG AAATACAAAA CCCAAGCGGTTCG-5' (SEQ ID NO: 852)
```

Primers for QUIKCHANGE™ site-directed mutagenesis are synthesized such that they are complementary to a parent nucleic acid sequence with the exception that they comprise a NHT, a VAA, or a BGG codon in the sense direction, and a ADN, a TTB, or a CCV codon in the antisense direction at the position to be mutagenized in the parent nucleic acid. Exemplary primers for mutagenesis of each of the eight amino acid residues in the XPA-23 heavy chain CDR1 are shown below and comprise a degenerate codon (underlined nucleotide triplet):

Mutation of the G position (aa1) may be accomplished by the following primers: 5'-GTCTTTCTTGCGCTGCTTCC NHTTTCACTTTCTCTAAGTACTTTATG-3' (SEQ ID NO: 853) and 3'-CAGAAAGAACGCGACGAAGG NDAAAGTGAAAG-AGATTCATGAAATAC-5' (SEQ ID NO: 854); 5'-GTCTTTCTTGCGCTGCTTCC VAAT-TCACTTTCTCTAAGTACTTTATG-3' (SEQ ID NO: 855) and 3'-CAGAAAGAACGC-GACGAAGG BTTAAGTGAAAGAGATTCATGAAATAC-5' (SEQ ID NO: 856); and 5'-GTC-TTTCTTGCGCTGCTTCC BGGTTCACTTTCTCTAAGTACTTTATG-3' (SEQ ID NO: 857) and 3'-CAGAAAGAACGCGACGAAGG VCCAAGTGAAAGAGATTCATGAA-ATAC-5' (SEQ ID NO: 858).

Mutation of the F position (aa2) may be accomplished by the following primers: 5'-CTTTCTTGCGCTGCTTCCGGA NHTACTTTCTCTAAGTACTTTATG-3' (SEQ ID NO: 859) and 3'-GAAAGAACGCGACGAAGGCCT NDATGAAAGAGATTCAT-GAAATAC-5' (SEQ ID NO: 860); 5'-CTTTCTTGCGCTGCTTCCGGA VAAACTTTC-TCTAAGTACTTTATG-3' (SEQ ID NO: 861) and 3'-GAAAGAACGCGACGAAGGC-CT BTTTGAAAGAGATTCATGAAATAC-5' (SEQ ID NO: 862); and 5'-CTTTCTTGC-GCTGCTTCCGGA BGGACTTTCTCTAAGTACTTTATG-3' (SEQ ID NO: 863) and 3'-GAAAGAACGCGACGAAGGCCT VCCTGAAAGAGATTCATGAAATAC-5' (SEQ ID NO: 864).

Mutation of the T (aa3) position may be accomplished by the following primers: 5'-CTTGCGCTGCTTCCGGATTC NHTTTCTCTAAGTACTTTATGTTTTG-3' (SEQ ID NO:

865) and 3'-GAACGCGACGAAGGCCTAAG NDAAAGAGATTCATGA-AATACAAAAC-5' (SEQ ID NO: 866); 5'-CTTGCGCTGCTTCCGGATT CVAATT-CTCTAAGTACTTTATGTTTTG-3' (SEQ ID NO: 867) and 3'-GAACGCGACGAAGGC-CTAAG BTTAAGAGATTCATGAAATACAAAAC-5' (SEQ ID NO: 868); and 5'-CTTGCGCTGCTTCCGGATTC BGGTTCTCTAAGTACTTTATGTTTTG-3' (SEQ ID NO: 869) and 3'-GAACGCGACGAAGGCCTAAG VCCAAGAGATTCATGAAATACAAAAC-5' (SEQ ID NO: 870).

Mutation of the F (aa4) position may be accomplished by the following primers: 5'-CGCTGCTTCCGGATTCACT NHTTCTAAGTACTTTATGTTTTGGG-3' (SEQ ID NO: 871) and 3'-GCGACGAAGGCCTAAGTGA NDAAGATTCATGAAA-TACAAAACCC-5' (SEQ ID NO: 872); 5'-CGCTGCTTCCGGATTCACT VAATCTAA-GTACTTTATGTTTTGGG-3' (SEQ ID NO: 873) and 3'-GCGACGAAGGCCTAAGTGA-BTTAGATTCATGAAATACAAAACCC-5' (SEQ ID NO: 874); and 5'-CGCTGCTTCC-GGATTCACT BGGTCTAAGTACTTTATGTTTTGGG-3' (SEQ ID NO: 875) and 3'-G CGACGAAGGCCTAAGTGA VCCAGATTCATGAAATACAAAACCC-5' (SEQ ID NO: 876).

Mutation of the S (aa5) position may be accomplished by the following primers: 5'-CTGCTTCCGGATTCACTTTC NHTAAGTACTTTATGTTTTGGGTTCG-3' (SEQ ID NO: 877) and 3'-GACGAAGGCCTAAGTGAAAG NDATTCATGAAAT-ACAAAACCCAAGC-5' (SEQ ID NO: 878); 5'-CTGCTTCCGGATTCACTTTC VAAAA-GTACTTTATGTTTTGGGTTCG-3'(SEQ ID NO: 879) and 3'-GACGAAGGCCT-AAGTGAAAG BTTTTCATGAAATACAAAACCCAAGC-5'(SEQ ID NO: 880); and 5'-CTGCTTCCGGATTCACTTTC BGGAAGTACTTTATGTTTTGGGTTCG-3'(SEQ ID NO: 881) and 3'-GACGAAGGCCTAAGTGAAAG VCCTTCATGAAATACAAAACCCAAGC-5'(SEQ ID NO: 882).

Mutation of the K (aa6) position may be accomplished by the following primers: 5'-CTTCCGGATTCACTTTCTCT NHTTACTTTATGTTTTGGGTTCGCC-3'(SEQ ID NO: 883) and 3'-GAAGGCCTAAGTGAAAGAGA NDAATGAAATACAAAAC-CCAAGCGG-5'(SEQ ID NO: 884); 5'-CTTCCGGATTCACTTTCTCT VAATACTTT-ATGTTTTGGGTTCGCC-3'(SEQ ID NO: 885) and 3'-GAAGGCCTAAGTGAAAGAG-A BTTATGAAATACAAAACCCAAGCGG-5'(SEQ ID NO: 886); and 5'-CTTCCGGA-TTCACTTTCTCT BGGTACTTTATGTTTTGGGTTCGCC-3'(SEQ ID NO: 887) and 3'-GAAGGCCTAAGTGAAAGAGA VCCATGAAATACAAAACCCAAGCGG-5'(SEQ ID NO: 888).

Mutation of the Y (aa7) position may be accomplished by the following primers: 5'-CCGGATTCACTTTCTCTAAG NHTTTTATGTTTTGGGTTCGCCAAG-3'(SEQ ID NO: 889) and 3'-GGCCTAAGTGAAAGAGATTC NDAAAATACAAAA-CCCAAGCGGTTC-5'(SEQ ID NO: 890); 5'-CCGGATTCACTTTCTCTAAG VAATT-TATGTTTTGGGTTCGCCAAG-3'(SEQ ID NO: 891) and 3'-GGCCTAAGTGAAAGA-GATTC BTTAAATACAAAACCCAAGCGGTTC-5'(SEQ ID NO: 892); and 5'-CCGGATTCACTTTCTCTAAG BGGTTTATGTTTTGGGTTCGCCAAG-3'(SEQ ID NO: 893) and 3'-GGCCTAAGTGAAAGAGATTC VCCAAATACAAAACCCAAGCGGTTC-5'(SEQ ID NO: 894).

Mutation of the F (aa8) position may be accomplished by the following primers: 5'-GGATTCACTTTCTCTAAGTAC NHTATGTTTTGGGTTCGCCAAGC-3' (SEQ ID NO: 895) and 3'-CCTAAGTGAAAGAGATTCATG NDATACAAAACCCAA-GCGGTTCG-5' (SEQ ID NO: 896); 5'-GGATTCACTTTCTCTAAGTAC VAAATGTTTT-GGGTTCGCCAAGC-3' (SEQ ID NO: 897) and 3'-CCTAAGTGAAAGAGATTCAT-G BTTTACAAAACCCAAGCGGTTCG-5' (SEQ ID NO: 898); and 5'-GGATTCACTTT-CTCTAAGTAC BGGATGTTTTGGGTTCGCCAAGC-3' (SEQ ID NO: 899) and 3'-CCTAAGTGAAAGAGATTCATG VCCTACAAAACCCAAGCGGTTCG-5' (SEQ ID NO: 900).

C. Synthesis of Full-Length Mutagenized Antibody

Full-length mutagenized antibodies may be produced by recombinant DNA technologies.

For the PCR-based method, a first PCR reaction (PCR1) is performed with a R2-rev primer and a 5'-SfiI primer, which incorporates a 5' SfiI restriction site into the amplified fragment. For each library oligonucleotide containing the mutations described above, the PCR2 reaction is performed to create the DNA fragment incorporating the primer mutation and the 3' SfiI restriction site. For the mutations in region 2, twelve PCR2 reactions will be performed with forward primers denoted R2-5 through R2-8 above (denoted primer-F in PCR2 below). The reverse primer for the mutagenic reaction will be 3'-SfiI. An appropriate amount of the following reagents may be used for PCR1: PfuUltra buffer; dNTPs [10 □M], template (10 ng total), 5'-SfiI [25 pmol], R2-rev [25 pmol], PfuUltra (2.5 U/□L), dH2O to 50 □L total. An appropriate amount of the following reagents may be used for PCR2: PfuUltra buffer, dNTPs [10 □M], template (10 ng total), Primer-F [10 pmol], 3'-SfiI [25 pmol], PfuUltra (2.5 U/□L), dH2O to 50 □L total. PCR1 and PCR2 may be conduced according to standard protocols includinig an initial denatural step, a number of cycles including a denaturation, annealing and extension step and a final extension step for appropriate times and temperatures.

A full-length antibody fragment may be produced by performing a separate reaction for each PCR2 product. For this step, an approximately equimolar amount of PCR product 1 and 2 is combined (e.g., 0.5 microliters of each PCR is combined). An appropriate amount of the following reagents may be used generation of a full-length antibody fragment: PfuUltra buffer, dNTPs [10 □M], PCR1 product, PCR2 product, PfuUltra (2.5 U/□L), dH2O to 50 □L total. PCR may be conduced according to standard protocols includinig an initial denatural step, a number of cycles including a denaturation, annealing and extension step for appropriate times and temperatures.

The full-length fragment may then be amplified by directly adding to the above reaction an appropriate amount of the following reagents: PfuUltra buffer, dNTPs [10 μM], 5'-SfiI [25 pmol], 3'-SfiI [25 pmol], PfuUltra (2.5 U/μL), dH2O to 50 μL total. PCR may be conduced according to standard protocols including an initial denaturation step, a number of cycles that comprise a denaturation, annealing and extension step for approapte times and temperatures and a final extension step. The PCR product may be examined on an agarose gel to ensure that the amplified DNA segment is the correct length.

Next, a vector and the DNA inserts obtained from the above PCR are digested with SfiI (NEB) according to the manufacturer's instructions and gel purified. The DNA synthesized fragment may be cloned into a pXOMA Fab or pXOMA Fab-gIII vector. Briefly, the DNA fragment is purified by using the QIAGEN® PCR purification kit and sequentially digesting the fragment with NotI (NEW ENGLAND BIOLABS®' Ipswich, Mass.) and AscI (NEW ENGLAND BIOLABS®' Ipswich, Mass.) (See, Methods in Molecular Biology, vol. 178: *Antibody Phage Display: Methods and Protocols* Edited by: P. M. O'Brien and R. Aitken, Humana Press, "Standard Protocols for the Construction of Fab Libraries, Clark, M. A., 39-58) (see, e.g., FIG. 6). Next, the vectors may be ligated with the mutagenized insert using T4 Ligase (NEW ENGLAND BIOLABS®' Ipswich, Mass.) and transformed into TG1 cells by electroporation.

Alternatively, for the DPN-based method, a double-stranded DNA (e.g., dsDNA) vector with an antibody insert isolated from a dam+ host is used as template for mutagenesis. DNA isolated from almost all *E. coli* strains is dam methylated and therefore susceptible to DpnI digestion. Two synthetic oligonucleotide primers containing the desired mutation each complementary to opposite strands of the vector, are extended during temperature cycling by DNA polymerase (e.g., PfuTurbo). PCR reactions may comprise an appropriate amout of PfuUltra buffer, dNTPs [10 mM] each dNTP, template (50 ng total), Primer-F [5 μM], Primer-R [5 μM], PfuUltra (2.5 U/μL), DMSO, and dH2O up to 50 μL total and be conducted with the following cycling parameters: an initial denaturation, subsequent cycles of denaturation, annealing and extension and a final extension step. Incorporation of the mutagenesis primers generates a mutated plasmid containing staggered nicks. Following temperature cycling, the PCR product is treated with DpnI and incubated at an appropriate temperature (e.g, at 37° C. for 4-5 hours). The DpnI endonuclease (target sequence: 5'-Gm6ATC-3') is specific for methylated and hemimethylated DNA and is used to digest the parental DNA template and to select for mutation-containing synthesized DNA. The nicked vector DNA containing the desired mutations is then transformed into supercompetent cells (e.g., XL1-Blue).

D. Sequencing of Mutagenized Antibodies

A library of mutagenized antibodies may comprise each of 18 unique amino acid mutations at each postion mutated. To identify all possible unique mutations an appropriate number of clones obtained from each degenerate codon are analyzed. For example, the NHT codon encodes 12 amino acids such that 72 clones from this reaction are sequenced for each mutated position. The VAA codon encodes 3 amino acids such that 12 clones are sequenced from this reaction for each mutated position. The BGG codon encodes 3 amino acids such that 12 clones from this reaction are sequenced for each mutated position. Unique clones are rearrayed into 96-well plates.

E. Expression of Mutagenized Antibodies

Mutagenized antibodies may be expressed. In an exemplary method, starting cultures may be produced by filling a plate (e.g., a 96 well plate) with an appropriate growth media (e.g., 2YTAG (2YT+2% glucose+100 □gs/ml Ampicillin) and inoculating the plate with glycerol stocks of the mutagenized antibodies. The cultures are then grown overnight (e.g., in an ATR plate shaker incubator at 37° C. with shaking at 450 rpm). Next, plates are filled with an appropriate growth medium (e.g., 1.2 mL per well of Superbroth+100 □gs·ml Ampicillin+0.2% glucose). The plates are then Innoculated with an appropriate amout of the overnight culture (e.g, 25 □L of overnight culture). The cultures are then grown with incubation (e.g., ATR plate shaker incubator at 37° C.) and shaking (e.g., at 700 rpm until Abs600nm=1.5). Expression in the cultures is then induced (e.g., by adding 12 uL of 100 mM IPTG per well to get a final concentration of 1 mM IPTG final) and incubated overnight (e.g., in an ATR plate shaker incubator at 30° C. with shaking at 700 rpm). Next, the plates are spun (e.g., at 4000 rpm using Beckman Coulter table top centrifuge for 10 minutes) and the supernatant decanted. The cells are then vortexed to disturb and loosen the pellet. The pellets are resuspended (e.g., with 75 □L per well of cold PPB) and incubated one ice (e.g., for 10 mintues). Next, water (e.g., 225 □L per well) is added and the cells resuspended. The suspension is incubated on ice (e.g., for 1 hour) and the plates are then spun (e.g., at 4000 rpm using Beckman Coulter table top centrifuge for 20 minutes). Last, the supernatants are collected for use in assays as described in detail below.

F. ELISA Screening of Mutagenized Antibodies

An assay including, for example, an ELISA may be performed to ensure that the mutagenized antibodies are capable of binding to their respective antigen.

In an exemplary ELISA, plates (e.g., 96-well Nunc Maxisorp plates) are coated with an antibody to the mutagenized antibody (e.g., 50 □L per well of 1 □g/ml Goat anti Human IgG $(Fab)_2$ Jackson immunoresearch, Cat. 109-005-006) and the plates are then incubated overnight at 4° C. After incubation, the plates may be washed (e.g., 3× with PBS-Tween at 350 □L/well) and then blocked (e.g., by adding 350 □L/well with 5% Milk+PBS).

Next, periplasmic extracts (PPE) containing the mutagenized antibody are blocked (e.g., by milk (diluted in PBS) to 200 □L of PPE to get a final milk percent of 5%). The PPEs are then mixed and incubated (e.g., at room temperature still for 1 hour) before using as samples to screen on ELISA and then washed (e.g., 3× with PBS-Tween at 350 □L/well). The blocked PPE samples (e.g., 50 □L) are then added to the blocked ELISA plates and incubated (e.g., at room temperature for 1-2 hours). Again the PPEs are washed (e.g., 3× with PBS-Tween at 350 □L/well). Next, an antibody specific for the mutagenized antibody is added to the PPEs (e.g., 50 □L/well of 1 □g/ml monoclonal anti-V5 antibody, Sigma Cat.#V8012-50UG) and the PPEs incubated (e.g., at room temperature for 1 hour). Again the PPEs are washed (e.g., 3× with PBS-Tween at 350 □L/well). Next, a secondary antibody conjugated to a enzymatic label is added to the PPEs (e.g., 1:10000 diluted Goat anti mouse HRP conjugated, Biorad, Cat. 170-5047) and incubated wth the PPEs (e.g., for 1 hour at room temperature). Again the PPEs are washed (e.g., 3× with PBS-Tween at 350 □L/well). Next, an appropriate amount of substrate for the enzymatic label is added to the PPEs (e.g., 50 □L/well of TMB, soluble, Calbiochem, Cat. 613544) and the enzyme is allowed time to act on the substrate (e.g., until sufficiently blue color develops). The reaction may be stopped by the addition of an agent that sequesters the substrate and/or and agent that inhibits the enzymatic activity of the secondary antibody (e.g, 50 □L per well of 2N $H_2SO_4$). Last, absorbance of the samples are read at 450 nm.

G. Ranking of Mutagenized Antibodies

Mutagenized antibodies may be ranked based on their dissociation rate from their respective antigen.

In an exemplary method, a Biacore A100 screening protocol may be used to rank mutagenized antibody clones. For example, a CM5 chip may be docked and normalized using normalization solution (e.g., using A100 normalization solution and use and an appropriate running buffer (e.g., HBS-N (0.01 M HEPES pH 7.4, 0.15 M NaCl). After normalization, software is set to immobilize antigen on desired spots of each flow cell. For antigen surface preparation the surface may be activated (e.g., with NHS/EDC mixture from the amine coupling kit for 5 minutes at 10 □l/min). Antigen is then diluted (e.g., in 10 mM sodium acetate buffer) and the surface of the CM5 chip is blocked (e.g., with 1 M ethanolamine HCl pH 8.5 for 5 min at 10 □l/min). Next, each sample comprising a mutagenized antibody is injected over the CM5 chip (e.g., for 3 min at 30 □l/min flow rate with 600 s dissociation) at an appropriate temperature (e.g., 25° C.). Biaevaluation software (e.g., Biacore A100 evaluation software) is then used to calculate dissociation rates of individual samples and the relative amount of sample bound to each test surface. The data is fit to an appropriate kinetic model (e.g., the kinetic titration model).

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention claimed is:

1. A method of mutagenesis of a parent nucleic acid encoding a protein to generate modified proteins, said method comprising (a) obtaining a primer set, wherein each primer of the primer set comprises degenerate codons and wherein none of the degenerate codons encode cysteine or methionine, comprising three primers that each comprise a degenerate codon, wherein the degenerate codons are: NHT or NHC (where N=A/G/C/T, and H=A/C/T); VAG or VAA (where V=A/C/G); and BGG or DGG (where B=C/G/T, D=A/G/T); or alternatively, seven primers that each comprise a degenerate codon, wherein the degenerate codons are: ARG or ARA (where R=A/G); WMC or WMT (where W=A/T and M=A/C); CAS, CAK, CAM or CAW (where S=C/G; K=G/T; M=A/C; and W=A/T); GAS (where S=C/G), NTC or NTT (where N=A/G/C/T); KGG (where K=G/T); and SCG, SCA, SCC or SCT (where S=C/G); wherein the degenerate codons of each primer set non-redundantly code for an equal representation of eighteen amino acid substitutions at each of one or more amino acid positions encoded by the parent nucleic acid, and wherein each primer of the three primers or seven primers comprise at least two oligonucleotide sequences that are complementary to a sequence in the parent nucleic acid; and (b) mutating the parent nucleic acid by replication or polymerase based amplification using the primer set obtained in (a), wherein replication or amplification of the parent nucleic acid with the primers generates mutated nucleic acids that encode said equal representation of eighteen amino acid substitutions in the modified proteins.

2. The method of claim 1, wherein the parent nucleic acid encodes a binding molecule.

3. The method of claim 2, wherein the binding molecule is an antibody or fragment thereof.

4. The method of claim 1 further comprising transforming the mutated nucleic acid sequences into competent cells.

5. A method of generating an array of nucleic acids encoding modified proteins, said method comprising:

(a) obtaining a collection of nucleic acids encoding modified proteins containing amino acid mutations at amino acid residues of a parent protein sequence by mutagenesis of a nucleic acid encoding the protein sequence using a primer set, wherein each primer of the primer set comprises degenerate codons and wherein none of the degenerate codons encode cysteine or methionine, wherein the primer set comprises:

three primers that each comprise a degenerate codon, wherein the degenerate codons are: NHT or NHC (where N=A/G/C/T, and H=A/C/T); VAG or VAA (where V=A/C/G); and BGG or DGG (where B=C/G/T, D=A/G/T); or alternatively, seven primers that each comprise a degenerate codon, wherein the degenerate codons are: ARG or ARA (where R=A/G); WMC or WMT (where W=A/T and M=A/C); CAS, CAK, CAM or CAW (where S=C/G, K=G/T, M=A/C, and W=A/T); GAS (where S=C/G), NTC or NTT (where N=A/G/C/T); KGG (where K=G/T); and SCG, SCA, SCC or SCT (where S=C/G); wherein the degenerate codons of each primer set non-redundantly code for an equal representation of eighteen amino acid substitutions at each of one or more amino acid positions encoded by the nucleic acid encoding the protein sequence, wherein each primer of the three primers or seven primers comprise at least two oligonucleotide sequences that are complementary to a sequence in the nucleic acid encoding the protein sequence;

(b) sequencing the collection of nucleic acids encoding the modified proteins; and (c) arranging each sequenced nucleic acid encoding a modified protein to generate an array of nucleic acids each encoding a modified protein.

6. The method of claim 5, wherein the parent protein sequence codes for a binding molecule.

7. The method of claim 6, wherein the binding molecule is an antibody or fragment thereof.

8. The method of claim 5 further comprising transforming the nucleic acid sequences encoding modified proteins into competent cells.

* * * * *

SEQUENCE LISTING

```
<160> NUMBER OF SEQ ID NOS: 989

<210> SEQ ID NO 1
<211> LENGTH: 20
<212> TYPE: DNA
<213> ORGANISM: human

<400> SEQUENCE: 1

actagagcgg caggagatgg                                                  20


<210> SEQ ID NO 2
<211> LENGTH: 55
<212> TYPE: DNA
<213> ORGANISM: Artificial Sequence
<220> FEATURE:
<223> OTHER INFORMATION: Synthesized: L1-1B primer

<400> SEQUENCE: 2

ccatctcctg ccgctctagt argagtctcc tacatagtaa tggcatcact tattt          55


<210> SEQ ID NO 3
<211> LENGTH: 55
<212> TYPE: DNA
<213> ORGANISM: Artificial Sequence
<220> FEATURE:
<223> OTHER INFORMATION: Synthesized: L1-1P1 (ING-1) primer

<400> SEQUENCE: 3

ccatctcctg ccgctctagt wmcagtctcc tacatagtaa tggcatcact tattt          55


<210> SEQ ID NO 4
<211> LENGTH: 55
<212> TYPE: DNA
<213> ORGANISM: Artificial Sequence
<220> FEATURE:
<223> OTHER INFORMATION: Synthesized: L1-1P2 (ING-1) primer

<400> SEQUENCE: 4

ccatctcctg ccgctctagt casagtctcc tacatagtaa tggcatcact tattt          55


<210> SEQ ID NO 5
<211> LENGTH: 55
<212> TYPE: DNA
<213> ORGANISM: Artificial Sequence
<220> FEATURE:
<223> OTHER INFORMATION: Synthesized: L1-1A (ING-1) primer

<400> SEQUENCE: 5

ccatctcctg ccgctctagt gasagtctcc tacatagtaa tggcatcact tattt          55


<210> SEQ ID NO 6
<211> LENGTH: 55
<212> TYPE: DNA
<213> ORGANISM: Artificial Sequence
<220> FEATURE:
```

<223> OTHER INFORMATION: Synthesized: L1-1NP1 (ING-1) primer
<220> FEATURE:
<221> NAME/KEY: misc_feature
<222> LOCATION: (21)..(21)
<223> OTHER INFORMATION: n is a, c, g, or t

<400> SEQUENCE: 6
ccatctcctg ccgctctagt ntcagtctcc tacatagtaa tggcatcact tattt 55

<210> SEQ ID NO 7
<211> LENGTH: 55
<212> TYPE: DNA
<213> ORGANISM: Artificial Sequence
<220> FEATURE:
<223> OTHER INFORMATION: Synthesized: L1-1NP2 (ING-1) primer

<400> SEQUENCE: 7
ccatctcctg ccgctctagt kggagtctcc tacatagtaa tggcatcact tattt 55

<210> SEQ ID NO 8
<211> LENGTH: 55
<212> TYPE: DNA
<213> ORGANISM: Artificial Sequence
<220> FEATURE:
<223> OTHER INFORMATION: Synthesized: L1-1NP3 primer

<400> SEQUENCE: 8
ccatctcctg ccgctctagt scgagtctcc tacatagtaa tggcatcact tattt 55

<210> SEQ ID NO 9
<211> LENGTH: 55
<212> TYPE: DNA
<213> ORGANISM: Artificial Sequence
<220> FEATURE:
<223> OTHER INFORMATION: Synthesized: L1-2B (ING-1) primer

<400> SEQUENCE: 9
ccatctcctg ccgctctagt aagargctcc tacatagtaa tggcatcact tattt 55

<210> SEQ ID NO 10
<211> LENGTH: 55
<212> TYPE: DNA
<213> ORGANISM: Artificial Sequence
<220> FEATURE:
<223> OTHER INFORMATION: Synthesized: L1-2P1 (ING-1) primer

<400> SEQUENCE: 10
ccatctcctg ccgctctagt aagwmcctcc tacatagtaa tggcatcact tattt 55

<210> SEQ ID NO 11
<211> LENGTH: 55
<212> TYPE: DNA
<213> ORGANISM: Artificial Sequence
<220> FEATURE:
<223> OTHER INFORMATION: Synthesized: L1-2P2 primer

<400> SEQUENCE: 11
ccatctcctg ccgctctagt aagcasctcc tacatagtaa tggcatcact tattt 55

<210> SEQ ID NO 12
<211> LENGTH: 55
<212> TYPE: DNA
<213> ORGANISM: Artificial Sequence
<220> FEATURE:
<223> OTHER INFORMATION: Synthesized: L1-2A primer

<400> SEQUENCE: 12
ccatctcctg ccgctctagt aaggasctcc tacatagtaa tggcatcact tattt 55

<210> SEQ ID NO 13
<211> LENGTH: 55
<212> TYPE: DNA
<213> ORGANISM: Artificial Sequence
<220> FEATURE:
<223> OTHER INFORMATION: Synthesized: L1-2NP1 (ING-1) primer
<220> FEATURE:
<221> NAME/KEY: misc_feature
<222> LOCATION: (24)..(24)
<223> OTHER INFORMATION: n is a, c, g, or t

<400> SEQUENCE: 13
ccatctcctg ccgctctagt aagntcctcc tacatagtaa tggcatcact tattt 55

<210> SEQ ID NO 14
<211> LENGTH: 55
<212> TYPE: DNA
<213> ORGANISM: Artificial Sequence
<220> FEATURE:
<223> OTHER INFORMATION: Synthesized: L1-2NP2 (ING-1) primer

<400> SEQUENCE: 14
ccatctcctg ccgctctagt aagkggctcc tacatagtaa tggcatcact tattt 55

<210> SEQ ID NO 15
<211> LENGTH: 55
<212> TYPE: DNA
<213> ORGANISM: Artificial Sequence
<220> FEATURE:
<223> OTHER INFORMATION: Synthesized: L1-2NP3 (ING-1) primer

<400> SEQUENCE: 15
ccatctcctg ccgctctagt aagscgctcc tacatagtaa tggcatcact tattt 55

<210> SEQ ID NO 16
<211> LENGTH: 55
<212> TYPE: DNA
<213> ORGANISM: Artificial Sequence
<220> FEATURE:
<223> OTHER INFORMATION: Synthesized: L1-3B (ING-1) primer

<400> SEQUENCE: 16
ccatctcctg ccgctctagt aagagtargc tacatagtaa tggcatcact tattt 55

<210> SEQ ID NO 17
<211> LENGTH: 55
<212> TYPE: DNA
<213> ORGANISM: Artificial Sequence
<220> FEATURE:
<223> OTHER INFORMATION: Synthesized: L1-3P1 (ING-1) primer

<400> SEQUENCE: 17
ccatctcctg ccgctctagt aagagtwmcc tacatagtaa tggcatcact tattt 55

<210> SEQ ID NO 18
<211> LENGTH: 55
<212> TYPE: DNA
<213> ORGANISM: Artificial Sequence
<220> FEATURE:
<223> OTHER INFORMATION: Synthesized: L1-3P2 (ING-1) primer

<400> SEQUENCE: 18
ccatctcctg ccgctctagt aagagtcasc tacatagtaa tggcatcact tattt 55

<210> SEQ ID NO 19
<211> LENGTH: 55
<212> TYPE: DNA
<213> ORGANISM: Artificial Sequence
<220> FEATURE:
<223> OTHER INFORMATION: Synthesized: L1-3A (ING-1) primer

<400> SEQUENCE: 19
ccatctcctg ccgctctagt aagagtgasc tacatagtaa tggcatcact tattt 55

<210> SEQ ID NO 20
<211> LENGTH: 55
<212> TYPE: DNA
<213> ORGANISM: Artificial Sequence
<220> FEATURE:
<223> OTHER INFORMATION: Synthesized: L1-3NP1 (ING-1) primer
<220> FEATURE:
<221> NAME/KEY: misc_feature
<222> LOCATION: (27)..(27)
<223> OTHER INFORMATION: n is a, c, g, or t

<400> SEQUENCE: 20
ccatctcctg ccgctctagt aagagtntcc tacatagtaa tggcatcact tattt 55

<210> SEQ ID NO 21
<211> LENGTH: 55
<212> TYPE: DNA
<213> ORGANISM: Artificial Sequence
<220> FEATURE:
<223> OTHER INFORMATION: Synthesized: L1-3NP2 (ING-1) primer

<400> SEQUENCE: 21
ccatctcctg ccgctctagt aagagtkggc tacatagtaa tggcatcact tattt 55

<210> SEQ ID NO 22
<211> LENGTH: 55
<212> TYPE: DNA
<213> ORGANISM: Artificial Sequence
<220> FEATURE:
<223> OTHER INFORMATION: Synthesized: L1-3NP3 (ING-1) primer

<400> SEQUENCE: 22
ccatctcctg ccgctctagt aagagtscgc tacatagtaa tggcatcact tattt 55

<210> SEQ ID NO 23
<211> LENGTH: 55
<212> TYPE: DNA
<213> ORGANISM: Artificial Sequence
<220> FEATURE:
<223> OTHER INFORMATION: Synthesized: L1-4B (ING-1) primer

<400> SEQUENCE: 23
ccatctcctg ccgctctagt aagagtctca rgcatagtaa tggcatcact tattt 55

<210> SEQ ID NO 24
<211> LENGTH: 55
<212> TYPE: DNA
<213> ORGANISM: Artificial Sequence
<220> FEATURE:
<223> OTHER INFORMATION: Synthesized: L1-4P1 (ING-1) primer

<400> SEQUENCE: 24
ccatctcctg ccgctctagt aagagtctcw mccatagtaa tggcatcact tattt 55

<210> SEQ ID NO 25
<211> LENGTH: 55

<212> TYPE: DNA
<213> ORGANISM: Artificial Sequence
<220> FEATURE:
<223> OTHER INFORMATION: Synthesized: L1-4P2 (ING-1) primer

<400> SEQUENCE: 25
ccatctcctg ccgctctagt aagagtctcc ascatagtaa tggcatcact tattt 55

<210> SEQ ID NO 26
<211> LENGTH: 55
<212> TYPE: DNA
<213> ORGANISM: Artificial Sequence
<220> FEATURE:
<223> OTHER INFORMATION: Synthesized: L1-4A primer

<400> SEQUENCE: 26
ccatctcctg ccgctctagt aagagtctcg ascatagtaa tggcatcact tattt 55

<210> SEQ ID NO 27
<211> LENGTH: 55
<212> TYPE: DNA
<213> ORGANISM: Artificial Sequence
<220> FEATURE:
<223> OTHER INFORMATION: Synthesized: L1-4NP1 (ING-1) primer
<220> FEATURE:
<221> NAME/KEY: misc_feature
<222> LOCATION: (30)..(30)
<223> OTHER INFORMATION: n is a, c, g, or t

<400> SEQUENCE: 27
ccatctcctg ccgctctagt aagagtctcn tccatagtaa tggcatcact tattt 55

<210> SEQ ID NO 28
<211> LENGTH: 55
<212> TYPE: DNA
<213> ORGANISM: Artificial Sequence
<220> FEATURE:
<223> OTHER INFORMATION: Synthesized: L1-4NP2 (ING-1) primer

<400> SEQUENCE: 28
ccatctcctg ccgctctagt aagagtctck ggcatagtaa tggcatcact tattt 55

<210> SEQ ID NO 29
<211> LENGTH: 55
<212> TYPE: DNA
<213> ORGANISM: Artificial Sequence
<220> FEATURE:
<223> OTHER INFORMATION: Synthesized: L1-4NP3 (ING-1) primer

<400> SEQUENCE: 29
ccatctcctg ccgctctagt aagagtctcs cgcatagtaa tggcatcact tattt 55

<210> SEQ ID NO 30
<211> LENGTH: 21
<212> TYPE: DNA
<213> ORGANISM: Artificial Sequence
<220> FEATURE:
<223> OTHER INFORMATION: Synthesized: L12-R (ING-1) primer

<400> SEQUENCE: 30
taggagactc ttactagagc g 21

<210> SEQ ID NO 31
<211> LENGTH: 54
<212> TYPE: DNA
<213> ORGANISM: Artificial Sequence
<220> FEATURE:

<223> OTHER INFORMATION: Synthesized: L12-1B (ING-1) primer

<400> SEQUENCE: 31
cgctctagta agagtctcct aargagtaat ggcatcactt atttgtattg gtat 54

<210> SEQ ID NO 32
<211> LENGTH: 54
<212> TYPE: DNA
<213> ORGANISM: Artificial Sequence
<220> FEATURE:
<223> OTHER INFORMATION: Synthesized: L12-1P1 (ING-1) primer

<400> SEQUENCE: 32
cgctctagta agagtctcct awmcagtaat ggcatcactt atttgtattg gtat 54

<210> SEQ ID NO 33
<211> LENGTH: 54
<212> TYPE: DNA
<213> ORGANISM: Artificial Sequence
<220> FEATURE:
<223> OTHER INFORMATION: Synthesized: L12-1P2 (ING-1) primer

<400> SEQUENCE: 33
cgctctagta agagtctcct acasagtaat ggcatcactt atttgtattg gtat 54

<210> SEQ ID NO 34
<211> LENGTH: 54
<212> TYPE: DNA
<213> ORGANISM: Artificial Sequence
<220> FEATURE:
<223> OTHER INFORMATION: Synthesized: L12-1A (ING-1) primer

<400> SEQUENCE: 34
cgctctagta agagtctcct agasagtaat ggcatcactt atttgtattg gtat 54

<210> SEQ ID NO 35
<211> LENGTH: 54
<212> TYPE: DNA
<213> ORGANISM: Artificial Sequence
<220> FEATURE:
<223> OTHER INFORMATION: Synthesized: L12-1NP1 (ING-1) primer
<220> FEATURE:
<221> NAME/KEY: misc_feature
<222> LOCATION: (22)..(22)
<223> OTHER INFORMATION: n is a, c, g, or t

<400> SEQUENCE: 35
cgctctagta agagtctcct antcagtaat ggcatcactt atttgtattg gtat 54

<210> SEQ ID NO 36
<211> LENGTH: 54
<212> TYPE: DNA
<213> ORGANISM: Artificial Sequence
<220> FEATURE:
<223> OTHER INFORMATION: Synthesized: L12-1NP2 (ING-1) primer

<400> SEQUENCE: 36
cgctctagta agagtctcct akggagtaat ggcatcactt atttgtattg gtat 54

<210> SEQ ID NO 37
<211> LENGTH: 54
<212> TYPE: DNA
<213> ORGANISM: Artificial Sequence
<220> FEATURE:
<223> OTHER INFORMATION: Synthesized: L12-1NP3 (ING-1) primer

<400> SEQUENCE: 37
cgctctagta agagtctcct ascgagtaat ggcatcactt atttgtattg gtat 54

<210> SEQ ID NO 38
<211> LENGTH: 54
<212> TYPE: DNA
<213> ORGANISM: Artificial Sequence
<220> FEATURE:
<223> OTHER INFORMATION: Synthesized: L12-2B (ING-1) primer

<400> SEQUENCE: 38
cgctctagta agagtctcct acatargaat ggcatcactt atttgtattg gtat 54

<210> SEQ ID NO 39
<211> LENGTH: 54
<212> TYPE: DNA
<213> ORGANISM: Artificial Sequence
<220> FEATURE:
<223> OTHER INFORMATION: Synthesized: L12-2P1 (ING-1) primer

<400> SEQUENCE: 39
cgctctagta agagtctcct acatwmcaat ggcatcactt atttgtattg gtat 54

<210> SEQ ID NO 40
<211> LENGTH: 54
<212> TYPE: DNA
<213> ORGANISM: Artificial Sequence
<220> FEATURE:
<223> OTHER INFORMATION: Synthesized: L12-2P2 (ING-1) primer

<400> SEQUENCE: 40
cgctctagta agagtctcct acatcasaat ggcatcactt atttgtattg gtat 54

<210> SEQ ID NO 41
<211> LENGTH: 54
<212> TYPE: DNA
<213> ORGANISM: Artificial Sequence
<220> FEATURE:
<223> OTHER INFORMATION: Synthesized: L12-2A (ING-1) primer

<400> SEQUENCE: 41
cgctctagta agagtctcct acatgasaat ggcatcactt atttgtattg gtat 54

<210> SEQ ID NO 42
<211> LENGTH: 54
<212> TYPE: DNA
<213> ORGANISM: Artificial Sequence
<220> FEATURE:
<223> OTHER INFORMATION: Synthesized: L12-2NP1 (ING-1) primer
<220> FEATURE:
<221> NAME/KEY: misc_feature
<222> LOCATION: (25)..(25)
<223> OTHER INFORMATION: n is a, c, g, or t

<400> SEQUENCE: 42
cgctctagta agagtctcct acatntcaat ggcatcactt atttgtattg gtat 54

<210> SEQ ID NO 43
<211> LENGTH: 54
<212> TYPE: DNA
<213> ORGANISM: Artificial Sequence
<220> FEATURE:
<223> OTHER INFORMATION: Synthesized: L12-2NP2 (ING-1) primer

<400> SEQUENCE: 43
cgctctagta agagtctcct acatkggaat ggcatcactt atttgtattg gtat 54

-continued

<210> SEQ ID NO 44
<211> LENGTH: 54
<212> TYPE: DNA
<213> ORGANISM: Artificial Sequence
<220> FEATURE:
<223> OTHER INFORMATION: Synthesized: L12-2NP3 (ING-1) primer

<400> SEQUENCE: 44
cgctctagta agagtctcct acatscgaat ggcatcactt atttgtattg gtat 54

<210> SEQ ID NO 45
<211> LENGTH: 54
<212> TYPE: DNA
<213> ORGANISM: Artificial Sequence
<220> FEATURE:
<223> OTHER INFORMATION: Synthesized: L12-3B (ING-1) primer

<400> SEQUENCE: 45
cgctctagta agagtctcct acatagtarg ggcatcactt atttgtattg gtat 54

<210> SEQ ID NO 46
<211> LENGTH: 54
<212> TYPE: DNA
<213> ORGANISM: Artificial Sequence
<220> FEATURE:
<223> OTHER INFORMATION: Synthesized: L12-3P1 (ING-1) primer

<400> SEQUENCE: 46
cgctctagta agagtctcct acatagtwmc ggcatcactt atttgtattg gtat 54

<210> SEQ ID NO 47
<211> LENGTH: 54
<212> TYPE: DNA
<213> ORGANISM: Artificial Sequence
<220> FEATURE:
<223> OTHER INFORMATION: Synthesized: L12-3P2 (ING-1) primer

<400> SEQUENCE: 47
cgctctagta agagtctcct acatagtcas ggcatcactt atttgtattg gtat 54

<210> SEQ ID NO 48
<211> LENGTH: 54
<212> TYPE: DNA
<213> ORGANISM: Artificial Sequence
<220> FEATURE:
<223> OTHER INFORMATION: Synthesized: L12-3A (ING-1) primer

<400> SEQUENCE: 48
cgctctagta agagtctcct acatagtgas ggcatcactt atttgtattg gtat 54

<210> SEQ ID NO 49
<211> LENGTH: 54
<212> TYPE: DNA
<213> ORGANISM: Artificial Sequence
<220> FEATURE:
<223> OTHER INFORMATION: Synthesized: L12-3NP1 (ING-1) primer
<220> FEATURE:
<221> NAME/KEY: misc_feature
<222> LOCATION: (28)..(28)
<223> OTHER INFORMATION: n is a, c, g, or t

<400> SEQUENCE: 49
cgctctagta agagtctcct acatagtntc ggcatcactt atttgtattg gtat 54

<210> SEQ ID NO 50
<211> LENGTH: 54

<212> TYPE: DNA
<213> ORGANISM: Artificial Sequence
<220> FEATURE:
<223> OTHER INFORMATION: Synthesized: L12-3NP2 (ING-1) primer

<400> SEQUENCE: 50
cgctctagta agagtctcct acatagtkgg ggcatcactt atttgtattg gtat 54

<210> SEQ ID NO 51
<211> LENGTH: 54
<212> TYPE: DNA
<213> ORGANISM: Artificial Sequence
<220> FEATURE:
<223> OTHER INFORMATION: Synthesized: L12-3NP3 (ING-1) primer

<400> SEQUENCE: 51
cgctctagta agagtctcct acatagtscg ggcatcactt atttgtattg gtat 54

<210> SEQ ID NO 52
<211> LENGTH: 22
<212> TYPE: DNA
<213> ORGANISM: Artificial Sequence
<220> FEATURE:
<223> OTHER INFORMATION: Synthesized: L13-R (ING-1) primer

<400> SEQUENCE: 52
gccattacta tgtaggagac tc 22

<210> SEQ ID NO 53
<211> LENGTH: 54
<212> TYPE: DNA
<213> ORGANISM: Artificial Sequence
<220> FEATURE:
<223> OTHER INFORMATION: Synthesized: L13-1B (ING-1) primer

<400> SEQUENCE: 53
gagtctccta catagtaatg gcargactta tttgtattgg tatttacaga agcc 54

<210> SEQ ID NO 54
<211> LENGTH: 54
<212> TYPE: DNA
<213> ORGANISM: Artificial Sequence
<220> FEATURE:
<223> OTHER INFORMATION: Synthesized: L13-1P1 (ING-1) primer

<400> SEQUENCE: 54
gagtctccta catagtaatg gcwmcactta tttgtattgg tatttacaga agcc 54

<210> SEQ ID NO 55
<211> LENGTH: 54
<212> TYPE: DNA
<213> ORGANISM: Artificial Sequence
<220> FEATURE:
<223> OTHER INFORMATION: Synthesized: L13-1P2 (ING-1) primer

<400> SEQUENCE: 55
gagtctccta catagtaatg gccasactta tttgtattgg tatttacaga agcc 54

<210> SEQ ID NO 56
<211> LENGTH: 54
<212> TYPE: DNA
<213> ORGANISM: Artificial Sequence
<220> FEATURE:
<223> OTHER INFORMATION: Synthesized: L13-1A (ING-1) primer

<400> SEQUENCE: 56
gagtctccta catagtaatg gcgasactta tttgtattgg tatttacaga agcc 54

<210> SEQ ID NO 57
<211> LENGTH: 54
<212> TYPE: DNA
<213> ORGANISM: Artificial Sequence
<220> FEATURE:
<223> OTHER INFORMATION: Synthesized: L13-1NP1 (ING-1) primer
<220> FEATURE:
<221> NAME/KEY: misc_feature
<222> LOCATION: (23)..(23)
<223> OTHER INFORMATION: n is a, c, g, or t

<400> SEQUENCE: 57
gagtctccta catagtaatg gcntcactta tttgtattgg tatttacaga agcc 54

<210> SEQ ID NO 58
<211> LENGTH: 54
<212> TYPE: DNA
<213> ORGANISM: Artificial Sequence
<220> FEATURE:
<223> OTHER INFORMATION: Synthesized: L13-1NP2 (ING-1) primer

<400> SEQUENCE: 58
gagtctccta catagtaatg gckggactta tttgtattgg tatttacaga agcc 54

<210> SEQ ID NO 59
<211> LENGTH: 54
<212> TYPE: DNA
<213> ORGANISM: Artificial Sequence
<220> FEATURE:
<223> OTHER INFORMATION: Synthesized: L13-1NP3 (ING-1) primer

<400> SEQUENCE: 59
gagtctccta catagtaatg gcscgactta tttgtattgg tatttacaga agcc 54

<210> SEQ ID NO 60
<211> LENGTH: 54
<212> TYPE: DNA
<213> ORGANISM: Artificial Sequence
<220> FEATURE:
<223> OTHER INFORMATION: Synthesized: L13-2B (ING-1) primer

<400> SEQUENCE: 60
gagtctccta catagtaatg gcatcargta tttgtattgg tatttacaga agcc 54

<210> SEQ ID NO 61
<211> LENGTH: 54
<212> TYPE: DNA
<213> ORGANISM: Artificial Sequence
<220> FEATURE:
<223> OTHER INFORMATION: Synthesized: L13-2P1 (ING-1) primer

<400> SEQUENCE: 61
gagtctccta catagtaatg gcatcwmcta tttgtattgg tatttacaga agcc 54

<210> SEQ ID NO 62
<211> LENGTH: 54
<212> TYPE: DNA
<213> ORGANISM: Artificial Sequence
<220> FEATURE:
<223> OTHER INFORMATION: Synthesized: L13-2P2 (ING-1) primer

<400> SEQUENCE: 62
gagtctccta catagtaatg gcatccasta tttgtattgg tatttacaga agcc 54

<210> SEQ ID NO 63
<211> LENGTH: 54
<212> TYPE: DNA
<213> ORGANISM: Artificial Sequence
<220> FEATURE:
<223> OTHER INFORMATION: Synthesized: L13-2A (ING-1) primer

<400> SEQUENCE: 63
gagtctccta catagtaatg gcatcgasta tttgtattgg tatttacaga agcc 54

<210> SEQ ID NO 64
<211> LENGTH: 54
<212> TYPE: DNA
<213> ORGANISM: Artificial Sequence
<220> FEATURE:
<223> OTHER INFORMATION: Synthesized: L13-2NP1 (ING-1) primer
<220> FEATURE:
<221> NAME/KEY: misc_feature
<222> LOCATION: (26)..(26)
<223> OTHER INFORMATION: n is a, c, g, or t

<400> SEQUENCE: 64
gagtctccta catagtaatg gcatcntcta tttgtattgg tatttacaga agcc 54

<210> SEQ ID NO 65
<211> LENGTH: 54
<212> TYPE: DNA
<213> ORGANISM: Artificial Sequence
<220> FEATURE:
<223> OTHER INFORMATION: Synthesized: L13-2NP2 (ING-1) primer

<400> SEQUENCE: 65
gagtctccta catagtaatg gcatckggta tttgtattgg tatttacaga agcc 54

<210> SEQ ID NO 66
<211> LENGTH: 54
<212> TYPE: DNA
<213> ORGANISM: Artificial Sequence
<220> FEATURE:
<223> OTHER INFORMATION: Synthesized: L13-2NP3 (ING-1) primer

<400> SEQUENCE: 66
gagtctccta catagtaatg gcatcscgta tttgtattgg tatttacaga agcc 54

<210> SEQ ID NO 67
<211> LENGTH: 54
<212> TYPE: DNA
<213> ORGANISM: Artificial Sequence
<220> FEATURE:
<223> OTHER INFORMATION: Synthesized: L13-3B (ING-1) primer

<400> SEQUENCE: 67
gagtctccta catagtaatg gcatcactar gttgtattgg tatttacaga agcc 54

<210> SEQ ID NO 68
<211> LENGTH: 54
<212> TYPE: DNA
<213> ORGANISM: Artificial Sequence
<220> FEATURE:
<223> OTHER INFORMATION: Synthesized: L13-3P1 (ING-1) primer

<400> SEQUENCE: 68
gagtctccta catagtaatg gcatcactwm cttgtattgg tatttacaga agcc 54

<210> SEQ ID NO 69
<211> LENGTH: 54
<212> TYPE: DNA

<213> ORGANISM: Artificial Sequence
<220> FEATURE:
<223> OTHER INFORMATION: Synthesized: L13-3P2 (ING-1) primer

<400> SEQUENCE: 69
gagtctccta catagtaatg gcatcactca sttgtattgg tatttacaga agcc 54

<210> SEQ ID NO 70
<211> LENGTH: 54
<212> TYPE: DNA
<213> ORGANISM: Artificial Sequence
<220> FEATURE:
<223> OTHER INFORMATION: Synthesized: L13-3A (ING-1) primer

<400> SEQUENCE: 70
gagtctccta catagtaatg gcatcactga sttgtattgg tatttacaga agcc 54

<210> SEQ ID NO 71
<211> LENGTH: 54
<212> TYPE: DNA
<213> ORGANISM: Artificial Sequence
<220> FEATURE:
<223> OTHER INFORMATION: Synthesized: L13-3NP1 (ING-1) primer
<220> FEATURE:
<221> NAME/KEY: misc_feature
<222> LOCATION: (29)..(29)
<223> OTHER INFORMATION: n is a, c, g, or t

<400> SEQUENCE: 71
gagtctccta catagtaatg gcatcactnt cttgtattgg tatttacaga agcc 54

<210> SEQ ID NO 72
<211> LENGTH: 54
<212> TYPE: DNA
<213> ORGANISM: Artificial Sequence
<220> FEATURE:
<223> OTHER INFORMATION: Synthesized: L13-3NP2 (ING-1) primer

<400> SEQUENCE: 72
gagtctccta catagtaatg gcatcactkg gttgtattgg tatttacaga agcc 54

<210> SEQ ID NO 73
<211> LENGTH: 54
<212> TYPE: DNA
<213> ORGANISM: Artificial Sequence
<220> FEATURE:
<223> OTHER INFORMATION: Synthesized: L13-3NP3 (ING-1) primer

<400> SEQUENCE: 73
gagtctccta catagtaatg gcatcactsc gttgtattgg tatttacaga agcc 54

<210> SEQ ID NO 74
<211> LENGTH: 21
<212> TYPE: DNA
<213> ORGANISM: Artificial Sequence
<220> FEATURE:
<223> OTHER INFORMATION: Synthesized: L2R (ING-1) primer
<220> FEATURE:
<221> NAME/KEY: misc_feature
<223> OTHER INFORMATION: Synthesized: L2R

<400> SEQUENCE: 74
aatcaggagc tgaggagact g 21

<210> SEQ ID NO 75
<211> LENGTH: 56
<212> TYPE: DNA

<213> ORGANISM: Artificial Sequence
<220> FEATURE:
<223> OTHER INFORMATION: Synthesized: L2-1B (ING-1) primer

<400> SEQUENCE: 75
cagtctcctc agctcctgat targcagatg tccaaccttg cctcaggagt cccaga 56

<210> SEQ ID NO 76
<211> LENGTH: 56
<212> TYPE: DNA
<213> ORGANISM: Artificial Sequence
<220> FEATURE:
<223> OTHER INFORMATION: Synthesized: L2-1P1 (ING-1) primer

<400> SEQUENCE: 76
cagtctcctc agctcctgat twmccagatg tccaaccttg cctcaggagt cccaga 56

<210> SEQ ID NO 77
<211> LENGTH: 56
<212> TYPE: DNA
<213> ORGANISM: Artificial Sequence
<220> FEATURE:
<223> OTHER INFORMATION: Synthesized: L2-1P2 (ING-1) primer

<400> SEQUENCE: 77
cagtctcctc agctcctgat tcascagatg tccaaccttg cctcaggagt cccaga 56

<210> SEQ ID NO 78
<211> LENGTH: 56
<212> TYPE: DNA
<213> ORGANISM: Artificial Sequence
<220> FEATURE:
<223> OTHER INFORMATION: Synthesized: L2-1A (ING-1) primer

<400> SEQUENCE: 78
cagtctcctc agctcctgat tgascagatg tccaaccttg cctcaggagt cccaga 56

<210> SEQ ID NO 79
<211> LENGTH: 56
<212> TYPE: DNA
<213> ORGANISM: Artificial Sequence
<220> FEATURE:
<223> OTHER INFORMATION: Synthesized: L2-1NP1 (ING-1) primer
<220> FEATURE:
<221> NAME/KEY: misc_feature
<222> LOCATION: (22)..(22)
<223> OTHER INFORMATION: n is a, c, g, or t

<400> SEQUENCE: 79
cagtctcctc agctcctgat tntccagatg tccaaccttg cctcaggagt cccaga 56

<210> SEQ ID NO 80
<211> LENGTH: 56
<212> TYPE: DNA
<213> ORGANISM: Artificial Sequence
<220> FEATURE:
<223> OTHER INFORMATION: Synthesized: L2-1NP2 (ING-1) primer

<400> SEQUENCE: 80
cagtctcctc agctcctgat tkggcagatg tccaaccttg cctcaggagt cccaga 56

<210> SEQ ID NO 81
<211> LENGTH: 56
<212> TYPE: DNA
<213> ORGANISM: Artificial Sequence
<220> FEATURE:
<223> OTHER INFORMATION: Synthesized: L2-1NP3 (ING-1) primer

<400> SEQUENCE: 81
cagtctcctc agctcctgat tscgcagatg tccaaccttg cctcaggagt cccaga 56

<210> SEQ ID NO 82
<211> LENGTH: 56
<212> TYPE: DNA
<213> ORGANISM: Artificial Sequence
<220> FEATURE:
<223> OTHER INFORMATION: Synthesized: L2-2B (ING-1) primer

<400> SEQUENCE: 82
cagtctcctc agctcctgat ttatargatg tccaaccttg cctcaggagt cccaga 56

<210> SEQ ID NO 83
<211> LENGTH: 56
<212> TYPE: DNA
<213> ORGANISM: Artificial Sequence
<220> FEATURE:
<223> OTHER INFORMATION: Synthesized: L2-2P1 (ING-1) primer

<400> SEQUENCE: 83
cagtctcctc agctcctgat ttatwmcatg tccaaccttg cctcaggagt cccaga 56

<210> SEQ ID NO 84
<211> LENGTH: 56
<212> TYPE: DNA
<213> ORGANISM: Artificial Sequence
<220> FEATURE:
<223> OTHER INFORMATION: Synthesized: L2-2P2 (ING-1) primer

<400> SEQUENCE: 84
cagtctcctc agctcctgat ttatcasatg tccaaccttg cctcaggagt cccaga 56

<210> SEQ ID NO 85
<211> LENGTH: 56
<212> TYPE: DNA
<213> ORGANISM: Artificial Sequence
<220> FEATURE:
<223> OTHER INFORMATION: Synthesized: L2-2A (ING-1) primer

<400> SEQUENCE: 85
cagtctcctc agctcctgat ttatgasatg tccaaccttg cctcaggagt cccaga 56

<210> SEQ ID NO 86
<211> LENGTH: 56
<212> TYPE: DNA
<213> ORGANISM: Artificial Sequence
<220> FEATURE:
<223> OTHER INFORMATION: Synthesized: L2-2NP1 (ING-1) primer
<220> FEATURE:
<221> NAME/KEY: misc_feature
<222> LOCATION: (25)..(25)
<223> OTHER INFORMATION: n is a, c, g, or t

<400> SEQUENCE: 86
cagtctcctc agctcctgat ttatntcatg tccaaccttg cctcaggagt cccaga 56

<210> SEQ ID NO 87
<211> LENGTH: 56
<212> TYPE: DNA
<213> ORGANISM: Artificial Sequence
<220> FEATURE:
<223> OTHER INFORMATION: Synthesized: L2-2NP2 (ING-1) primer

<400> SEQUENCE: 87

-continued cagtctcctc agctcctgat ttatkggatg tccaaccttg cctcaggagt cccaga 56

<210> SEQ ID NO 88
<211> LENGTH: 56
<212> TYPE: DNA
<213> ORGANISM: Artificial Sequence
<220> FEATURE:
<223> OTHER INFORMATION: Synthesized: L2-2NP3 (ING-1) primer

<400> SEQUENCE: 88
cagtctcctc agctcctgat ttatscgatg tccaaccttg cctcaggagt cccaga 56

<210> SEQ ID NO 89
<211> LENGTH: 56
<212> TYPE: DNA
<213> ORGANISM: Artificial Sequence
<220> FEATURE:
<223> OTHER INFORMATION: Synthesized: L2-3B (ING-1) primer

<400> SEQUENCE: 89
cagtctcctc agctcctgat ttatcagarg tccaaccttg cctcaggagt cccaga 56

<210> SEQ ID NO 90
<211> LENGTH: 56
<212> TYPE: DNA
<213> ORGANISM: Artificial Sequence
<220> FEATURE:
<223> OTHER INFORMATION: Synthesized: L2-3P1 (ING-1) primer

<400> SEQUENCE: 90
cagtctcctc agctcctgat ttatcagwmc tccaaccttg cctcaggagt cccaga 56

<210> SEQ ID NO 91
<211> LENGTH: 56
<212> TYPE: DNA
<213> ORGANISM: Artificial Sequence
<220> FEATURE:
<223> OTHER INFORMATION: Synthesized: L2-3P2 (ING-1) primer

<400> SEQUENCE: 91
cagtctcctc agctcctgat ttatcagcas tccaaccttg cctcaggagt cccaga 56

<210> SEQ ID NO 92
<211> LENGTH: 56
<212> TYPE: DNA
<213> ORGANISM: Artificial Sequence
<220> FEATURE:
<223> OTHER INFORMATION: Synthesized: L2-3A (ING-1) primer

<400> SEQUENCE: 92
cagtctcctc agctcctgat ttatcaggas tccaaccttg cctcaggagt cccaga 56

<210> SEQ ID NO 93
<211> LENGTH: 56
<212> TYPE: DNA
<213> ORGANISM: Artificial Sequence
<220> FEATURE:
<223> OTHER INFORMATION: Synthesized: L2-3NP1 (ING-1) primer
<220> FEATURE:
<221> NAME/KEY: misc_feature
<222> LOCATION: (28)..(28)
<223> OTHER INFORMATION: n is a, c, g, or t

<400> SEQUENCE: 93
cagtctcctc agctcctgat ttatcagntc tccaaccttg cctcaggagt cccaga 56

-continued

<210> SEQ ID NO 94
<211> LENGTH: 56
<212> TYPE: DNA
<213> ORGANISM: Artificial Sequence
<220> FEATURE:
<223> OTHER INFORMATION: Synthesized: L2-3NP2 (ING-1) primer

<400> SEQUENCE: 94
cagtctcctc agctcctgat ttatcagkgg tccaaccttg cctcaggagt cccaga 56

<210> SEQ ID NO 95
<211> LENGTH: 56
<212> TYPE: DNA
<213> ORGANISM: Artificial Sequence
<220> FEATURE:
<223> OTHER INFORMATION: Synthesized: L2-3NP3 (ING-1) primer

<400> SEQUENCE: 95
cagtctcctc agctcctgat ttatcagscg tccaaccttg cctcaggagt cccaga 56

<210> SEQ ID NO 96
<211> LENGTH: 56
<212> TYPE: DNA
<213> ORGANISM: Artificial Sequence
<220> FEATURE:
<223> OTHER INFORMATION: Synthesized: L2-4B (ING-1) primer

<400> SEQUENCE: 96
cagtctcctc agctcctgat ttatcagatg argaaccttg cctcaggagt cccaga 56

<210> SEQ ID NO 97
<211> LENGTH: 56
<212> TYPE: DNA
<213> ORGANISM: Artificial Sequence
<220> FEATURE:
<223> OTHER INFORMATION: Synthesized: L2-4P1 (ING-1) primer

<400> SEQUENCE: 97
cagtctcctc agctcctgat ttatcagatg wmcaaccttg cctcaggagt cccaga 56

<210> SEQ ID NO 98
<211> LENGTH: 56
<212> TYPE: DNA
<213> ORGANISM: Artificial Sequence
<220> FEATURE:
<223> OTHER INFORMATION: Synthesized: L2-4P2 (ING-1) primer

<400> SEQUENCE: 98
cagtctcctc agctcctgat ttatcagatg casaaccttg cctcaggagt cccaga 56

<210> SEQ ID NO 99
<211> LENGTH: 56
<212> TYPE: DNA
<213> ORGANISM: Artificial Sequence
<220> FEATURE:
<223> OTHER INFORMATION: Synthesized: L2-4A (ING-1) primer

<400> SEQUENCE: 99
cagtctcctc agctcctgat ttatcagatg gasaaccttg cctcaggagt cccaga 56

<210> SEQ ID NO 100
<211> LENGTH: 56
<212> TYPE: DNA
<213> ORGANISM: Artificial Sequence
<220> FEATURE:
<223> OTHER INFORMATION: Synthesized: L2-4NP1 (ING-1) primer
<220> FEATURE:

<221> NAME/KEY: misc_feature
<222> LOCATION: (31)..(31)
<223> OTHER INFORMATION: n is a, c, g, or t

<400> SEQUENCE: 100
cagtctcctc agctcctgat ttatcagatg ntcaaccttg cctcaggagt cccaga 56

<210> SEQ ID NO 101
<211> LENGTH: 56
<212> TYPE: DNA
<213> ORGANISM: Artificial Sequence
<220> FEATURE:
<223> OTHER INFORMATION: Synthesized: L2-4NP2 (ING-1) primer

<400> SEQUENCE: 101
cagtctcctc agctcctgat ttatcagatg kggaaccttg cctcaggagt cccaga 56

<210> SEQ ID NO 102
<211> LENGTH: 56
<212> TYPE: DNA
<213> ORGANISM: Artificial Sequence
<220> FEATURE:
<223> OTHER INFORMATION: Synthesized: L2-4NP3 (ING-1) primer

<400> SEQUENCE: 102
cagtctcctc agctcctgat ttatcagatg scgaaccttg cctcaggagt cccaga 56

<210> SEQ ID NO 103
<211> LENGTH: 56
<212> TYPE: DNA
<213> ORGANISM: Artificial Sequence
<220> FEATURE:
<223> OTHER INFORMATION: Synthesized: L2-5B (ING-1) primer

<400> SEQUENCE: 103
cagtctcctc agctcctgat ttatcagatg tccargcttg cctcaggagt cccaga 56

<210> SEQ ID NO 104
<211> LENGTH: 56
<212> TYPE: DNA
<213> ORGANISM: Artificial Sequence
<220> FEATURE:
<223> OTHER INFORMATION: Synthesized: L2-5P1 (ING-1) primer

<400> SEQUENCE: 104
cagtctcctc agctcctgat ttatcagatg tccwmccttg cctcaggagt cccaga 56

<210> SEQ ID NO 105
<211> LENGTH: 56
<212> TYPE: DNA
<213> ORGANISM: Artificial Sequence
<220> FEATURE:
<223> OTHER INFORMATION: Synthesized: L2-5P2 (ING-1) primer

<400> SEQUENCE: 105
cagtctcctc agctcctgat ttatcagatg tcccascttg cctcaggagt cccaga 56

<210> SEQ ID NO 106
<211> LENGTH: 56
<212> TYPE: DNA
<213> ORGANISM: Artificial Sequence
<220> FEATURE:
<223> OTHER INFORMATION: Synthesized: L2-5A (ING-1) primer

<400> SEQUENCE: 106
cagtctcctc agctcctgat ttatcagatg tccgascttg cctcaggagt cccaga 56

<210> SEQ ID NO 107
<211> LENGTH: 56
<212> TYPE: DNA
<213> ORGANISM: Artificial Sequence
<220> FEATURE:
<223> OTHER INFORMATION: Synthesized: L2-5NP1 (ING-1) primer
<220> FEATURE:
<221> NAME/KEY: misc_feature
<222> LOCATION: (34)..(34)
<223> OTHER INFORMATION: n is a, c, g, or t

<400> SEQUENCE: 107
cagtctcctc agctcctgat ttatcagatg tccntccttg cctcaggagt cccaga 56

<210> SEQ ID NO 108
<211> LENGTH: 56
<212> TYPE: DNA
<213> ORGANISM: Artificial Sequence
<220> FEATURE:
<223> OTHER INFORMATION: Synthesized: L2-5NP2 (ING-1) primer

<400> SEQUENCE: 108
cagtctcctc agctcctgat ttatcagatg tcckggcttg cctcaggagt cccaga 56

<210> SEQ ID NO 109
<211> LENGTH: 56
<212> TYPE: DNA
<213> ORGANISM: Artificial Sequence
<220> FEATURE:
<223> OTHER INFORMATION: Synthesized: L2-5NP3 (ING-1) primer

<400> SEQUENCE: 109
cagtctcctc agctcctgat ttatcagatg tccscgcttg cctcaggagt cccaga 56

<210> SEQ ID NO 110
<211> LENGTH: 24
<212> TYPE: DNA
<213> ORGANISM: Artificial Sequence
<220> FEATURE:
<223> OTHER INFORMATION: Synthesized: L3R (ING-1) primer

<400> SEQUENCE: 110
attttgagca cagtaataaa cacc 24

<210> SEQ ID NO 111
<211> LENGTH: 59
<212> TYPE: DNA
<213> ORGANISM: Artificial Sequence
<220> FEATURE:
<223> OTHER INFORMATION: Synthesized: L3-1B (ING-1) primer

<400> SEQUENCE: 111
ggtgtttatt actgtgctca aaatarggaa cttcctcgga cgttcggtgg aggcaccaa 59

<210> SEQ ID NO 112
<211> LENGTH: 59
<212> TYPE: DNA
<213> ORGANISM: Artificial Sequence
<220> FEATURE:
<223> OTHER INFORMATION: Synthesized: L3-1P1 (ING-1) primer

<400> SEQUENCE: 112
ggtgtttatt actgtgctca aaatwmcgaa cttcctcgga cgttcggtgg aggcaccaa 59

<210> SEQ ID NO 113

<211> LENGTH: 59
<212> TYPE: DNA
<213> ORGANISM: Artificial Sequence
<220> FEATURE:
<223> OTHER INFORMATION: Synthesized: L3-1P2 (ING-1) primer

<400> SEQUENCE: 113
ggtgtttatt actgtgctca aaatcasgaa cttcctcgga cgttcggtgg aggcaccaa 59

<210> SEQ ID NO 114
<211> LENGTH: 59
<212> TYPE: DNA
<213> ORGANISM: Artificial Sequence
<220> FEATURE:
<223> OTHER INFORMATION: Synthesized: L3-1A (ING-1) primer

<400> SEQUENCE: 114
ggtgtttatt actgtgctca aaatgasgaa cttcctcgga cgttcggtgg aggcaccaa 59

<210> SEQ ID NO 115
<211> LENGTH: 59
<212> TYPE: DNA
<213> ORGANISM: Artificial Sequence
<220> FEATURE:
<223> OTHER INFORMATION: Synthesized: L3-1NP1 (ING-1) primer
<220> FEATURE:
<221> NAME/KEY: misc_feature
<222> LOCATION: (25)..(25)
<223> OTHER INFORMATION: n is a, c, g, or t

<400> SEQUENCE: 115
ggtgtttatt actgtgctca aaatntcgaa cttcctcgga cgttcggtgg aggcaccaa 59

<210> SEQ ID NO 116
<211> LENGTH: 59
<212> TYPE: DNA
<213> ORGANISM: Artificial Sequence
<220> FEATURE:
<223> OTHER INFORMATION: Synthesized: L3-1NP2 (ING-1) primer

<400> SEQUENCE: 116
ggtgtttatt actgtgctca aaatkgggaa cttcctcgga cgttcggtgg aggcaccaa 59

<210> SEQ ID NO 117
<211> LENGTH: 59
<212> TYPE: DNA
<213> ORGANISM: Artificial Sequence
<220> FEATURE:
<223> OTHER INFORMATION: Synthesized: L3-1NP3 (ING-1) primer
<220> FEATURE:
<221> NAME/KEY: misc_feature
<223> OTHER INFORMATION: Synthesized: L3-1NP3

<400> SEQUENCE: 117
ggtgtttatt actgtgctca aaatscggaa cttcctcgga cgttcggtgg aggcaccaa 59

<210> SEQ ID NO 118
<211> LENGTH: 59
<212> TYPE: DNA
<213> ORGANISM: Artificial Sequence
<220> FEATURE:
<223> OTHER INFORMATION: Synthesized: L3-2B (ING-1) primer

<400> SEQUENCE: 118
ggtgtttatt actgtgctca aaatctaarg cttcctcgga cgttcggtgg aggcaccaa 59

<210> SEQ ID NO 119

<211> LENGTH: 59
<212> TYPE: DNA
<213> ORGANISM: Artificial Sequence
<220> FEATURE:
<223> OTHER INFORMATION: Synthesized: L3-2P1 (ING-1) primer

<400> SEQUENCE: 119
ggtgtttatt actgtgctca aaatctawmc cttcctcgga cgttcggtgg aggcaccaa 59

<210> SEQ ID NO 120
<211> LENGTH: 59
<212> TYPE: DNA
<213> ORGANISM: Artificial Sequence
<220> FEATURE:
<223> OTHER INFORMATION: Synthesized: L3-2P2 (ING-1) primer

<400> SEQUENCE: 120
ggtgtttatt actgtgctca aaatctacas cttcctcgga cgttcggtgg aggcaccaa 59

<210> SEQ ID NO 121
<211> LENGTH: 59
<212> TYPE: DNA
<213> ORGANISM: Artificial Sequence
<220> FEATURE:
<223> OTHER INFORMATION: Synthesized: L3-2A (ING-1) primer

<400> SEQUENCE: 121
ggtgtttatt actgtgctca aaatctagas cttcctcgga cgttcggtgg aggcaccaa 59

<210> SEQ ID NO 122
<211> LENGTH: 59
<212> TYPE: DNA
<213> ORGANISM: Artificial Sequence
<220> FEATURE:
<223> OTHER INFORMATION: Synthesized: L3-2NP1 (ING-1) primer
<220> FEATURE:
<221> NAME/KEY: misc_feature
<222> LOCATION: (28)..(28)
<223> OTHER INFORMATION: n is a, c, g, or t

<400> SEQUENCE: 122
ggtgtttatt actgtgctca aaatctantc cttcctcgga cgttcggtgg aggcaccaa 59

<210> SEQ ID NO 123
<211> LENGTH: 59
<212> TYPE: DNA
<213> ORGANISM: Artificial Sequence
<220> FEATURE:
<223> OTHER INFORMATION: Synthesized: L3-2NP2 (ING-1) primer

<400> SEQUENCE: 123
ggtgtttatt actgtgctca aaatctakgg cttcctcgga cgttcggtgg aggcaccaa 59

<210> SEQ ID NO 124
<211> LENGTH: 59
<212> TYPE: DNA
<213> ORGANISM: Artificial Sequence
<220> FEATURE:
<223> OTHER INFORMATION: Synthesized: L3-2NP3 (ING-1) primer

<400> SEQUENCE: 124
ggtgtttatt actgtgctca aaatctascg cttcctcgga cgttcggtgg aggcaccaa 59

<210> SEQ ID NO 125
<211> LENGTH: 59
<212> TYPE: DNA
<213> ORGANISM: Artificial Sequence
<220> FEATURE:
<223> OTHER INFORMATION: Synthesized: L3-3B (ING-1) primer

<400> SEQUENCE: 125
ggtgtttatt actgtgctca aaatctagaa argcctcgga cgttcggtgg aggcaccaa    59

<210> SEQ ID NO 126
<211> LENGTH: 59
<212> TYPE: DNA
<213> ORGANISM: Artificial Sequence
<220> FEATURE:
<223> OTHER INFORMATION: Synthesized: L3-3P1 (ING-1) primer

<400> SEQUENCE: 126
ggtgtttatt actgtgctca aaatctagaa wmccctcgga cgttcggtgg aggcaccaa    59

<210> SEQ ID NO 127
<211> LENGTH: 59
<212> TYPE: DNA
<213> ORGANISM: Artificial Sequence
<220> FEATURE:
<223> OTHER INFORMATION: Synthesized: L3-3P2 (ING-1) primer

<400> SEQUENCE: 127
ggtgtttatt actgtgctca aaatctagaa cascctcgga cgttcggtgg aggcaccaa    59

<210> SEQ ID NO 128
<211> LENGTH: 59
<212> TYPE: DNA
<213> ORGANISM: Artificial Sequence
<220> FEATURE:
<223> OTHER INFORMATION: Synthesized: L3-3A (ING-1) primer

<400> SEQUENCE: 128
ggtgtttatt actgtgctca aaatctagaa gascctcgga cgttcggtgg aggcaccaa    59

<210> SEQ ID NO 129
<211> LENGTH: 59
<212> TYPE: DNA
<213> ORGANISM: Artificial Sequence
<220> FEATURE:
<223> OTHER INFORMATION: Synthesized: L3-3NP1 (ING-1) primer
<220> FEATURE:
<221> NAME/KEY: misc_feature
<222> LOCATION: (31)..(31)
<223> OTHER INFORMATION: n is a, c, g, or t

<400> SEQUENCE: 129
ggtgtttatt actgtgctca aaatctagaa ntccctcgga cgttcggtgg aggcaccaa    59

<210> SEQ ID NO 130
<211> LENGTH: 59
<212> TYPE: DNA
<213> ORGANISM: Artificial Sequence
<220> FEATURE:
<223> OTHER INFORMATION: Synthesized: L3-3NP2 (ING-1) primer

<400> SEQUENCE: 130
ggtgtttatt actgtgctca aaatctagaa kggcctcgga cgttcggtgg aggcaccaa    59

<210> SEQ ID NO 131
<211> LENGTH: 59
<212> TYPE: DNA
<213> ORGANISM: Artificial Sequence
<220> FEATURE:
<223> OTHER INFORMATION: Synthesized: L3-3NP3 (ING-1) primer

<400> SEQUENCE: 131
ggtgtttatt actgtgctca aaatctagaa scgcctcgga cgttcggtgg aggcaccaa 59

<210> SEQ ID NO 132
<211> LENGTH: 59
<212> TYPE: DNA
<213> ORGANISM: Artificial Sequence
<220> FEATURE:
<223> OTHER INFORMATION: Synthesized: L3-4B (ING-1) primer

<400> SEQUENCE: 132
ggtgtttatt actgtgctca aaatctagaa cttargcgga cgttcggtgg aggcaccaa 59

<210> SEQ ID NO 133
<211> LENGTH: 59
<212> TYPE: DNA
<213> ORGANISM: Artificial Sequence
<220> FEATURE:
<223> OTHER INFORMATION: Synthesized: L3-4P1 (ING-1) primer

<400> SEQUENCE: 133
ggtgtttatt actgtgctca aaatctagaa cttwmccgga cgttcggtgg aggcaccaa 59

<210> SEQ ID NO 134
<211> LENGTH: 59
<212> TYPE: DNA
<213> ORGANISM: Artificial Sequence
<220> FEATURE:
<223> OTHER INFORMATION: Synthesized: L3-4P2 (ING-1) primer

<400> SEQUENCE: 134
ggtgtttatt actgtgctca aaatctagaa cttcascgga cgttcggtgg aggcaccaa 59

<210> SEQ ID NO 135
<211> LENGTH: 59
<212> TYPE: DNA
<213> ORGANISM: Artificial Sequence
<220> FEATURE:
<223> OTHER INFORMATION: Synthesized: L3-4A (ING-1) primer

<400> SEQUENCE: 135
ggtgtttatt actgtgctca aaatctagaa cttgascgga cgttcggtgg aggcaccaa 59

<210> SEQ ID NO 136
<211> LENGTH: 59
<212> TYPE: DNA
<213> ORGANISM: Artificial Sequence
<220> FEATURE:
<223> OTHER INFORMATION: Synthesized: L3-4NP1 (ING-1) primer
<220> FEATURE:
<221> NAME/KEY: misc_feature
<222> LOCATION: (34)..(34)
<223> OTHER INFORMATION: n is a, c, g, or t

<400> SEQUENCE: 136
ggtgtttatt actgtgctca aaatctagaa cttntccgga cgttcggtgg aggcaccaa 59

<210> SEQ ID NO 137
<211> LENGTH: 59
<212> TYPE: DNA
<213> ORGANISM: Artificial Sequence
<220> FEATURE:
<223> OTHER INFORMATION: Synthesized: L3-4NP2 (ING-1) primer

<400> SEQUENCE: 137
ggtgtttatt actgtgctca aaatctagaa cttkggcgga cgttcggtgg aggcaccaa 59

<210> SEQ ID NO 138
<211> LENGTH: 59
<212> TYPE: DNA
<213> ORGANISM: Artificial Sequence
<220> FEATURE:
<223> OTHER INFORMATION: Synthesized: L3-4NP3 (ING-1) primer

<400> SEQUENCE: 138
ggtgtttatt actgtgctca aaatctagaa cttscgcgga cgttcggtgg aggcaccaa 59

<210> SEQ ID NO 139
<211> LENGTH: 59
<212> TYPE: DNA
<213> ORGANISM: Artificial Sequence
<220> FEATURE:
<223> OTHER INFORMATION: Synthesized: L3-5B (ING-1) primer

<400> SEQUENCE: 139
ggtgtttatt actgtgctca aaatctagaa cttcctarga cgttcggtgg aggcaccaa 59

<210> SEQ ID NO 140
<211> LENGTH: 59
<212> TYPE: DNA
<213> ORGANISM: Artificial Sequence
<220> FEATURE:
<223> OTHER INFORMATION: Synthesized: L3-5P1 (ING-1) primer

<400> SEQUENCE: 140
ggtgtttatt actgtgctca aaatctagaa cttcctwmca cgttcggtgg aggcaccaa 59

<210> SEQ ID NO 141
<211> LENGTH: 59
<212> TYPE: DNA
<213> ORGANISM: Artificial Sequence
<220> FEATURE:
<223> OTHER INFORMATION: Synthesized: L3-5P2 (ING-1) primer

<400> SEQUENCE: 141
ggtgtttatt actgtgctca aaatctagaa cttcctcasa cgttcggtgg aggcaccaa 59

<210> SEQ ID NO 142
<211> LENGTH: 59
<212> TYPE: DNA
<213> ORGANISM: Artificial Sequence
<220> FEATURE:
<223> OTHER INFORMATION: Synthesized: L3-5A (ING-1) primer

<400> SEQUENCE: 142
ggtgtttatt actgtgctca aaatctagaa cttcctgasa cgttcggtgg aggcaccaa 59

<210> SEQ ID NO 143
<211> LENGTH: 59
<212> TYPE: DNA
<213> ORGANISM: Artificial Sequence
<220> FEATURE:
<223> OTHER INFORMATION: Synthesized: L3-5NP1 (ING-1) primer
<220> FEATURE:
<221> NAME/KEY: misc_feature
<222> LOCATION: (37)..(37)
<223> OTHER INFORMATION: n is a, c, g, or t

<400> SEQUENCE: 143
ggtgtttatt actgtgctca aaatctagaa cttcctntca cgttcggtgg aggcaccaa 59

<210> SEQ ID NO 144

<211> LENGTH: 59
<212> TYPE: DNA
<213> ORGANISM: Artificial Sequence
<220> FEATURE:
<223> OTHER INFORMATION: Synthesized: L3-5NP2 (ING-1) primer

<400> SEQUENCE: 144
ggtgtttatt actgtgctca aaatctagaa cttcctkgga cgttcggtgg aggcaccaa 59

<210> SEQ ID NO 145
<211> LENGTH: 59
<212> TYPE: DNA
<213> ORGANISM: Artificial Sequence
<220> FEATURE:
<223> OTHER INFORMATION: Synthesized: L3-5NP3 (ING-1) primer

<400> SEQUENCE: 145
ggtgtttatt actgtgctca aaatctagaa cttcctscga cgttcggtgg aggcaccaa 59

<210> SEQ ID NO 146
<211> LENGTH: 21
<212> TYPE: DNA
<213> ORGANISM: Artificial Sequence
<220> FEATURE:
<223> OTHER INFORMATION: Synthesized: H1R (ING-1) primer

<400> SEQUENCE: 146
atatccagaa gccttgcagg a 21

<210> SEQ ID NO 147
<211> LENGTH: 59
<212> TYPE: DNA
<213> ORGANISM: Artificial Sequence
<220> FEATURE:
<223> OTHER INFORMATION: Synthesized: H1-1B (ING-1) primer

<400> SEQUENCE: 147
tcctgcaagg cttctggata targttcaca aaatatggaa tgaactgggt gaagcaggc 59

<210> SEQ ID NO 148
<211> LENGTH: 59
<212> TYPE: DNA
<213> ORGANISM: Artificial Sequence
<220> FEATURE:
<223> OTHER INFORMATION: Synthesized: H1-1P1 (ING-1) primer

<400> SEQUENCE: 148
tcctgcaagg cttctggata twmcttcaca aaatatggaa tgaactgggt gaagcaggc 59

<210> SEQ ID NO 149
<211> LENGTH: 59
<212> TYPE: DNA
<213> ORGANISM: Artificial Sequence
<220> FEATURE:
<223> OTHER INFORMATION: Synthesized: H1-1P2 (ING-1) primer

<400> SEQUENCE: 149
tcctgcaagg cttctggata tcasttcaca aaatatggaa tgaactgggt gaagcaggc 59

<210> SEQ ID NO 150
<211> LENGTH: 59
<212> TYPE: DNA
<213> ORGANISM: Artificial Sequence
<220> FEATURE:
<223> OTHER INFORMATION: Synthesized: H1-1A (ING-1) primer

<400> SEQUENCE: 150
tcctgcaagg cttctggata tgasttcaca aaatatggaa tgaactgggt gaagcaggc 59

<210> SEQ ID NO 151
<211> LENGTH: 59
<212> TYPE: DNA
<213> ORGANISM: Artificial Sequence
<220> FEATURE:
<223> OTHER INFORMATION: Synthesized: H1-1NP1 (ING-1) primer
<220> FEATURE:
<221> NAME/KEY: misc_feature
<222> LOCATION: (22)..(22)
<223> OTHER INFORMATION: n is a, c, g, or t

<400> SEQUENCE: 151
tcctgcaagg cttctggata tntcttcaca aaatatggaa tgaactgggt gaagcaggc 59

<210> SEQ ID NO 152
<211> LENGTH: 59
<212> TYPE: DNA
<213> ORGANISM: Artificial Sequence
<220> FEATURE:
<223> OTHER INFORMATION: Synthesized: H1-1NP2 (ING-1) primer

<400> SEQUENCE: 152
tcctgcaagg cttctggata tkggttcaca aaatatggaa tgaactgggt gaagcaggc 59

<210> SEQ ID NO 153
<211> LENGTH: 59
<212> TYPE: DNA
<213> ORGANISM: Artificial Sequence
<220> FEATURE:
<223> OTHER INFORMATION: Synthesized: H1-1NP3 (ING-1) primer

<400> SEQUENCE: 153
tcctgcaagg cttctggata tscgttcaca aaatatggaa tgaactgggt gaagcaggc 59

<210> SEQ ID NO 154
<211> LENGTH: 59
<212> TYPE: DNA
<213> ORGANISM: Artificial Sequence
<220> FEATURE:
<223> OTHER INFORMATION: Synthesized: H1-2B (ING-1) primer

<400> SEQUENCE: 154
tcctgcaagg cttctggata taccttcarg aaatatggaa tgaactgggt gaagcaggc 59

<210> SEQ ID NO 155
<211> LENGTH: 59
<212> TYPE: DNA
<213> ORGANISM: Artificial Sequence
<220> FEATURE:
<223> OTHER INFORMATION: Synthesized: H1-2P1 (ING-1) primer

<400> SEQUENCE: 155
tcctgcaagg cttctggata taccttcwmc aaatatggaa tgaactgggt gaagcaggc 59

<210> SEQ ID NO 156
<211> LENGTH: 59
<212> TYPE: DNA
<213> ORGANISM: Artificial Sequence
<220> FEATURE:
<223> OTHER INFORMATION: Synthesized: H1-2P2 (ING-1) primer

<400> SEQUENCE: 156
tcctgcaagg cttctggata taccttccas aaatatggaa tgaactgggt gaagcaggc 59

<210> SEQ ID NO 157
<211> LENGTH: 59
<212> TYPE: DNA
<213> ORGANISM: Artificial Sequence
<220> FEATURE:
<223> OTHER INFORMATION: Synthesized: H1-2A (ING-1) primer

<400> SEQUENCE: 157
tcctgcaagg cttctggata taccttcgas aaatatggaa tgaactgggt gaagcaggc 59

<210> SEQ ID NO 158
<211> LENGTH: 59
<212> TYPE: DNA
<213> ORGANISM: Artificial Sequence
<220> FEATURE:
<223> OTHER INFORMATION: Synthesized: H1-2NP1 (ING-1) primer
<220> FEATURE:
<221> NAME/KEY: misc_feature
<222> LOCATION: (28)..(28)
<223> OTHER INFORMATION: n is a, c, g, or t

<400> SEQUENCE: 158
tcctgcaagg cttctggata taccttcntc aaatatggaa tgaactgggt gaagcaggc 59

<210> SEQ ID NO 159
<211> LENGTH: 59
<212> TYPE: DNA
<213> ORGANISM: Artificial Sequence
<220> FEATURE:
<223> OTHER INFORMATION: Synthesized: H1-2NP2 (ING-1) primer

<400> SEQUENCE: 159
tcctgcaagg cttctggata taccttckgg aaatatggaa tgaactgggt gaagcaggc 59

<210> SEQ ID NO 160
<211> LENGTH: 59
<212> TYPE: DNA
<213> ORGANISM: Artificial Sequence
<220> FEATURE:
<223> OTHER INFORMATION: Synthesized: H1-2NP3 (ING-1) primer

<400> SEQUENCE: 160
tcctgcaagg cttctggata taccttcscg aaatatggaa tgaactgggt gaagcaggc 59

<210> SEQ ID NO 161
<211> LENGTH: 59
<212> TYPE: DNA
<213> ORGANISM: Artificial Sequence
<220> FEATURE:
<223> OTHER INFORMATION: Synthesized: H1-3B (ING-1) primer

<400> SEQUENCE: 161
tcctgcaagg cttctggata taccttcaca argtatggaa tgaactgggt gaagcaggc 59

<210> SEQ ID NO 162
<211> LENGTH: 59
<212> TYPE: DNA
<213> ORGANISM: Artificial Sequence
<220> FEATURE:
<223> OTHER INFORMATION: Synthesized: H1-3P1 (ING-1) primer

<400> SEQUENCE: 162
tcctgcaagg cttctggata taccttcaca wmctatggaa tgaactgggt gaagcaggc 59

<210> SEQ ID NO 163
<211> LENGTH: 59

<212> TYPE: DNA
<213> ORGANISM: Artificial Sequence
<220> FEATURE:
<223> OTHER INFORMATION: Synthesized: H1-3P2 (ING-1) primer

<400> SEQUENCE: 163
tcctgcaagg cttctggata taccttcaca castatggaa tgaactgggt gaagcaggc 59

<210> SEQ ID NO 164
<211> LENGTH: 59
<212> TYPE: DNA
<213> ORGANISM: Artificial Sequence
<220> FEATURE:
<223> OTHER INFORMATION: Synthesized: H1-3A (ING-1) primer

<400> SEQUENCE: 164
tcctgcaagg cttctggata taccttcaca gastatggaa tgaactgggt gaagcaggc 59

<210> SEQ ID NO 165
<211> LENGTH: 59
<212> TYPE: DNA
<213> ORGANISM: Artificial Sequence
<220> FEATURE:
<223> OTHER INFORMATION: Synthesized: H1-3NP1 (ING-1) primer
<220> FEATURE:
<221> NAME/KEY: misc_feature
<222> LOCATION: (31)..(31)
<223> OTHER INFORMATION: n is a, c, g, or t

<400> SEQUENCE: 165
tcctgcaagg cttctggata taccttcaca ntctatggaa tgaactgggt gaagcaggc 59

<210> SEQ ID NO 166
<211> LENGTH: 59
<212> TYPE: DNA
<213> ORGANISM: Artificial Sequence
<220> FEATURE:
<223> OTHER INFORMATION: Synthesized: H1-3NP2 (ING-1) primer

<400> SEQUENCE: 166
tcctgcaagg cttctggata taccttcaca kggtatggaa tgaactgggt gaagcaggc 59

<210> SEQ ID NO 167
<211> LENGTH: 59
<212> TYPE: DNA
<213> ORGANISM: Artificial Sequence
<220> FEATURE:
<223> OTHER INFORMATION: Synthesized: H1-3NP3 (ING-1) primer

<400> SEQUENCE: 167
tcctgcaagg cttctggata taccttcaca scgtatggaa tgaactgggt gaagcaggc 59

<210> SEQ ID NO 168
<211> LENGTH: 59
<212> TYPE: DNA
<213> ORGANISM: Artificial Sequence
<220> FEATURE:
<223> OTHER INFORMATION: Synthesized: H1-4B (ING-1) primer

<400> SEQUENCE: 168
tcctgcaagg cttctggata taccttcaca aaaargggaa tgaactgggt gaagcaggc 59

<210> SEQ ID NO 169
<211> LENGTH: 59
<212> TYPE: DNA
<213> ORGANISM: Artificial Sequence
<220> FEATURE:

<223> OTHER INFORMATION: Synthesized: H1-4P1 (ING-1) primer

<400> SEQUENCE: 169
tcctgcaagg cttctggata taccttcaca aaawmcggaa tgaactgggt gaagcaggc 59

<210> SEQ ID NO 170
<211> LENGTH: 59
<212> TYPE: DNA
<213> ORGANISM: Artificial Sequence
<220> FEATURE:
<223> OTHER INFORMATION: Synthesized: H1-4P2 (ING-1) primer

<400> SEQUENCE: 170
tcctgcaagg cttctggata taccttcaca aaacasggaa tgaactgggt gaagcaggc 59

<210> SEQ ID NO 171
<211> LENGTH: 59
<212> TYPE: DNA
<213> ORGANISM: Artificial Sequence
<220> FEATURE:
<223> OTHER INFORMATION: Synthesized: H1-4A (ING-1) primer

<400> SEQUENCE: 171
tcctgcaagg cttctggata taccttcaca aaagasggaa tgaactgggt gaagcaggc 59

<210> SEQ ID NO 172
<211> LENGTH: 59
<212> TYPE: DNA
<213> ORGANISM: Artificial Sequence
<220> FEATURE:
<223> OTHER INFORMATION: Synthesized: H1-4NP1 (ING-1) primer
<220> FEATURE:
<221> NAME/KEY: misc_feature
<222> LOCATION: (34)..(34)
<223> OTHER INFORMATION: n is a, c, g, or t

<400> SEQUENCE: 172
tcctgcaagg cttctggata taccttcaca aaantcggaa tgaactgggt gaagcaggc 59

<210> SEQ ID NO 173
<211> LENGTH: 59
<212> TYPE: DNA
<213> ORGANISM: Artificial Sequence
<220> FEATURE:
<223> OTHER INFORMATION: Synthesized: H1-4NP2 (ING-1) primer

<400> SEQUENCE: 173
tcctgcaagg cttctggata taccttcaca aaakggggaa tgaactgggt gaagcaggc 59

<210> SEQ ID NO 174
<211> LENGTH: 59
<212> TYPE: DNA
<213> ORGANISM: Artificial Sequence
<220> FEATURE:
<223> OTHER INFORMATION: Synthesized: H1-4NP3 (ING-1) primer

<400> SEQUENCE: 174
tcctgcaagg cttctggata taccttcaca aaascgggaa tgaactgggt gaagcaggc 59

<210> SEQ ID NO 175
<211> LENGTH: 59
<212> TYPE: DNA
<213> ORGANISM: Artificial Sequence
<220> FEATURE:
<223> OTHER INFORMATION: Synthesized: H1-5B (ING-1) primer

<400> SEQUENCE: 175
tcctgcaagg cttctggata taccttcaca aaatatarga tgaactgggt gaagcaggc 59

<210> SEQ ID NO 176
<211> LENGTH: 59
<212> TYPE: DNA
<213> ORGANISM: Artificial Sequence
<220> FEATURE:
<223> OTHER INFORMATION: Synthesized: H1-5P1 (ING-1) primer

<400> SEQUENCE: 176
tcctgcaagg cttctggata taccttcaca aaatatwmca tgaactgggt gaagcaggc 59

<210> SEQ ID NO 177
<211> LENGTH: 59
<212> TYPE: DNA
<213> ORGANISM: Artificial Sequence
<220> FEATURE:
<223> OTHER INFORMATION: Synthesized: H1-5P2 (ING-1) primer

<400> SEQUENCE: 177
tcctgcaagg cttctggata taccttcaca aaatatcasa tgaactgggt gaagcaggc 59

<210> SEQ ID NO 178
<211> LENGTH: 59
<212> TYPE: DNA
<213> ORGANISM: Artificial Sequence
<220> FEATURE:
<223> OTHER INFORMATION: Synthesized: H1-5A (ING-1) primer

<400> SEQUENCE: 178
tcctgcaagg cttctggata taccttcaca aaatatgasa tgaactgggt gaagcaggc 59

<210> SEQ ID NO 179
<211> LENGTH: 59
<212> TYPE: DNA
<213> ORGANISM: Artificial Sequence
<220> FEATURE:
<223> OTHER INFORMATION: Synthesized: H1-5NP1 (ING-1) primer
<220> FEATURE:
<221> NAME/KEY: misc_feature
<222> LOCATION: (37)..(37)
<223> OTHER INFORMATION: n is a, c, g, or t

<400> SEQUENCE: 179
tcctgcaagg cttctggata taccttcaca aaatatntca tgaactgggt gaagcaggc 59

<210> SEQ ID NO 180
<211> LENGTH: 59
<212> TYPE: DNA
<213> ORGANISM: Artificial Sequence
<220> FEATURE:
<223> OTHER INFORMATION: Synthesized: H1-5NP2 (ING-1) primer

<400> SEQUENCE: 180
tcctgcaagg cttctggata taccttcaca aaatatkgga tgaactgggt gaagcaggc 59

<210> SEQ ID NO 181
<211> LENGTH: 59
<212> TYPE: DNA
<213> ORGANISM: Artificial Sequence
<220> FEATURE:
<223> OTHER INFORMATION: Synthesized: H1-5NP3 (ING-1) primer

<400> SEQUENCE: 181
tcctgcaagg cttctggata taccttcaca aaatatscga tgaactgggt gaagcaggc 59

<210> SEQ ID NO 182
<211> LENGTH: 21
<212> TYPE: DNA
<213> ORGANISM: Artificial Sequence
<220> FEATURE:
<223> OTHER INFORMATION: Synthesized: H2R (ING-1) primer

<400> SEQUENCE: 182
gcccatccac tttaaaccct t 21

<210> SEQ ID NO 183
<211> LENGTH: 58
<212> TYPE: DNA
<213> ORGANISM: Artificial Sequence
<220> FEATURE:
<223> OTHER INFORMATION: Synthesized: H2-1B (ING-1) primer

<400> SEQUENCE: 183
aagggtttaa agtggatggg cargataaac acctacactg aagagcctac atatggtg 58

<210> SEQ ID NO 184
<211> LENGTH: 58
<212> TYPE: DNA
<213> ORGANISM: Artificial Sequence
<220> FEATURE:
<223> OTHER INFORMATION: Synthesized: H2-1P1 (ING-1) primer

<400> SEQUENCE: 184
aagggtttaa agtggatggg cwmcataaac acctacactg aagagcctac atatggtg 58

<210> SEQ ID NO 185
<211> LENGTH: 58
<212> TYPE: DNA
<213> ORGANISM: Artificial Sequence
<220> FEATURE:
<223> OTHER INFORMATION: Synthesized: H2-1P2 (ING-1) primer

<400> SEQUENCE: 185
aagggtttaa agtggatggg ccasataaac acctacactg aagagcctac atatggtg 58

<210> SEQ ID NO 186
<211> LENGTH: 58
<212> TYPE: DNA
<213> ORGANISM: Artificial Sequence
<220> FEATURE:
<223> OTHER INFORMATION: Synthesized: H2-1A (ING-1) primer

<400> SEQUENCE: 186
aagggtttaa agtggatggg cgasataaac acctacactg aagagcctac atatggtg 58

<210> SEQ ID NO 187
<211> LENGTH: 58
<212> TYPE: DNA
<213> ORGANISM: Artificial Sequence
<220> FEATURE:
<223> OTHER INFORMATION: Synthesized: H2-1NP1 (ING-1) primer
<220> FEATURE:
<221> NAME/KEY: misc_feature
<222> LOCATION: (22)..(22)
<223> OTHER INFORMATION: n is a, c, g, or t

<400> SEQUENCE: 187
aagggtttaa agtggatggg cntcataaac acctacactg aagagcctac atatggtg 58

<210> SEQ ID NO 188
<211> LENGTH: 58

<212> TYPE: DNA
<213> ORGANISM: Artificial Sequence
<220> FEATURE:
<223> OTHER INFORMATION: Synthesized: H2-1NP2 (ING-1) primer

<400> SEQUENCE: 188
aagggtttaa agtggatggg ckggataaac acctacactg aagagcctac atatggtg 58

<210> SEQ ID NO 189
<211> LENGTH: 58
<212> TYPE: DNA
<213> ORGANISM: Artificial Sequence
<220> FEATURE:
<223> OTHER INFORMATION: Synthesized: H2-1NP3 (ING-1) primer

<400> SEQUENCE: 189
aagggtttaa agtggatggg cscgataaac acctacactg aagagcctac atatggtg 58

<210> SEQ ID NO 190
<211> LENGTH: 58
<212> TYPE: DNA
<213> ORGANISM: Artificial Sequence
<220> FEATURE:
<223> OTHER INFORMATION: Synthesized: H2-2B (ING-1) primer

<400> SEQUENCE: 190
aagggtttaa agtggatggg ctggataarg acctacactg aagagcctac atatggtg 58

<210> SEQ ID NO 191
<211> LENGTH: 58
<212> TYPE: DNA
<213> ORGANISM: Artificial Sequence
<220> FEATURE:
<223> OTHER INFORMATION: Synthesized: H2-2P1 (ING-1) primer

<400> SEQUENCE: 191
aagggtttaa agtggatggg ctggatawmc acctacactg aagagcctac atatggtg 58

<210> SEQ ID NO 192
<211> LENGTH: 58
<212> TYPE: DNA
<213> ORGANISM: Artificial Sequence
<220> FEATURE:
<223> OTHER INFORMATION: Synthesized: H2-2P2 (ING-1) primer

<400> SEQUENCE: 192
aagggtttaa agtggatggg ctggatacas acctacactg aagagcctac atatggtg 58

<210> SEQ ID NO 193
<211> LENGTH: 58
<212> TYPE: DNA
<213> ORGANISM: Artificial Sequence
<220> FEATURE:
<223> OTHER INFORMATION: Synthesized: H2-2A (ING-1) primer

<400> SEQUENCE: 193
aagggtttaa agtggatggg ctggatagas acctacactg aagagcctac atatggtg 58

<210> SEQ ID NO 194
<211> LENGTH: 58
<212> TYPE: DNA
<213> ORGANISM: Artificial Sequence
<220> FEATURE:
<223> OTHER INFORMATION: Synthesized: H2-2NP1 (ING-1) primer
<220> FEATURE:
<221> NAME/KEY: misc_feature
<222> LOCATION: (28)..(28)

<223> OTHER INFORMATION: n is a, c, g, or t

<400> SEQUENCE: 194
aagggtttaa agtggatggg ctggatantc acctacactg aagagcctac atatggtg 58

<210> SEQ ID NO 195
<211> LENGTH: 58
<212> TYPE: DNA
<213> ORGANISM: Artificial Sequence
<220> FEATURE:
<223> OTHER INFORMATION: Synthesized: H2-2NP2 (ING-1) primer

<400> SEQUENCE: 195
aagggtttaa agtggatggg ctggatakgg acctacactg aagagcctac atatggtg 58

<210> SEQ ID NO 196
<211> LENGTH: 58
<212> TYPE: DNA
<213> ORGANISM: Artificial Sequence
<220> FEATURE:
<223> OTHER INFORMATION: Synthesized: H2-2NP3 (ING-1) primer

<400> SEQUENCE: 196
aagggtttaa agtggatggg ctggatascg acctacactg aagagcctac atatggtg 58

<210> SEQ ID NO 197
<211> LENGTH: 58
<212> TYPE: DNA
<213> ORGANISM: Artificial Sequence
<220> FEATURE:
<223> OTHER INFORMATION: Synthesized: H2-3B (ING-1) primer

<400> SEQUENCE: 197
aagggtttaa agtggatggg ctggataaac argtacactg aagagcctac atatggtg 58

<210> SEQ ID NO 198
<211> LENGTH: 58
<212> TYPE: DNA
<213> ORGANISM: Artificial Sequence
<220> FEATURE:
<223> OTHER INFORMATION: Synthesized: H2-3P1 (ING-1) primer

<400> SEQUENCE: 198
aagggtttaa agtggatggg ctggataaac wmctacactg aagagcctac atatggtg 58

<210> SEQ ID NO 199
<211> LENGTH: 58
<212> TYPE: DNA
<213> ORGANISM: Artificial Sequence
<220> FEATURE:
<223> OTHER INFORMATION: Synthesized: H2-3P2 (ING-1) primer

<400> SEQUENCE: 199
aagggtttaa agtggatggg ctggataaac castacactg aagagcctac atatggtg 58

<210> SEQ ID NO 200
<211> LENGTH: 58
<212> TYPE: DNA
<213> ORGANISM: Artificial Sequence
<220> FEATURE:
<223> OTHER INFORMATION: Synthesized: H2-3A (ING-1) primer

<400> SEQUENCE: 200
aagggtttaa agtggatggg ctggataaac gastacactg aagagcctac atatggtg 58

<210> SEQ ID NO 201
<211> LENGTH: 58
<212> TYPE: DNA
<213> ORGANISM: Artificial Sequence
<220> FEATURE:
<223> OTHER INFORMATION: Synthesized: H2-3NP1 (ING-1) primer
<220> FEATURE:
<221> NAME/KEY: misc_feature
<222> LOCATION: (31)..(31)
<223> OTHER INFORMATION: n is a, c, g, or t

<400> SEQUENCE: 201
aagggtttaa agtggatggg ctggataaac ntctacactg aagagcctac atatggtg 58

<210> SEQ ID NO 202
<211> LENGTH: 58
<212> TYPE: DNA
<213> ORGANISM: Artificial Sequence
<220> FEATURE:
<223> OTHER INFORMATION: Synthesized: H2-3NP2 (ING-1) primer

<400> SEQUENCE: 202
aagggtttaa agtggatggg ctggataaac kggtacactg aagagcctac atatggtg 58

<210> SEQ ID NO 203
<211> LENGTH: 58
<212> TYPE: DNA
<213> ORGANISM: Artificial Sequence
<220> FEATURE:
<223> OTHER INFORMATION: Synthesized: H2-3NP3 (ING-1) primer

<400> SEQUENCE: 203
aagggtttaa agtggatggg ctggataaac scgtacactg aagagcctac atatggtg 58

<210> SEQ ID NO 204
<211> LENGTH: 58
<212> TYPE: DNA
<213> ORGANISM: Artificial Sequence
<220> FEATURE:
<223> OTHER INFORMATION: Synthesized: H2-4B (ING-1) primer

<400> SEQUENCE: 204
aagggtttaa agtggatggg ctggataaac accargactg aagagcctac atatggtg 58

<210> SEQ ID NO 205
<211> LENGTH: 58
<212> TYPE: DNA
<213> ORGANISM: Artificial Sequence
<220> FEATURE:
<223> OTHER INFORMATION: Synthesized: H2-4P1 (ING-1) primer

<400> SEQUENCE: 205
aagggtttaa agtggatggg ctggataaac accwmcactg aagagcctac atatggtg 58

<210> SEQ ID NO 206
<211> LENGTH: 58
<212> TYPE: DNA
<213> ORGANISM: Artificial Sequence
<220> FEATURE:
<223> OTHER INFORMATION: Synthesized: H2-4P2 (ING-1) primer

<400> SEQUENCE: 206
aagggtttaa agtggatggg ctggataaac acccasactg aagagcctac atatggtg 58

<210> SEQ ID NO 207
<211> LENGTH: 58
<212> TYPE: DNA

<213> ORGANISM: Artificial Sequence
<220> FEATURE:
<223> OTHER INFORMATION: Synthesized: H2-4A (ING-1) primer

<400> SEQUENCE: 207
aagggtttaa agtggatggg ctggataaac accgasactg aagagcctac atatggtg 58

<210> SEQ ID NO 208
<211> LENGTH: 58
<212> TYPE: DNA
<213> ORGANISM: Artificial Sequence
<220> FEATURE:
<223> OTHER INFORMATION: Synthesized: H2-4NP1 (ING-1) primer
<220> FEATURE:
<221> NAME/KEY: misc_feature
<222> LOCATION: (34)..(34)
<223> OTHER INFORMATION: n is a, c, g, or t

<400> SEQUENCE: 208
aagggtttaa agtggatggg ctggataaac accntcactg aagagcctac atatggtg 58

<210> SEQ ID NO 209
<211> LENGTH: 58
<212> TYPE: DNA
<213> ORGANISM: Artificial Sequence
<220> FEATURE:
<223> OTHER INFORMATION: Synthesized: H2-4NP2 (ING-1) primer

<400> SEQUENCE: 209
aagggtttaa agtggatggg ctggataaac acckggactg aagagcctac atatggtg 58

<210> SEQ ID NO 210
<211> LENGTH: 58
<212> TYPE: DNA
<213> ORGANISM: Artificial Sequence
<220> FEATURE:
<223> OTHER INFORMATION: Synthesized: H2-4NP3 (ING-1) primer

<400> SEQUENCE: 210
aagggtttaa agtggatggg ctggataaac accscgactg aagagcctac atatggtg 58

<210> SEQ ID NO 211
<211> LENGTH: 21
<212> TYPE: DNA
<213> ORGANISM: Artificial Sequence
<220> FEATURE:
<223> OTHER INFORMATION: Synthesized: H22-R (ING-1) primer

<400> SEQUENCE: 211
gtaggtgttt atccagccca t 21

<210> SEQ ID NO 212
<211> LENGTH: 58
<212> TYPE: DNA
<213> ORGANISM: Artificial Sequence
<220> FEATURE:
<223> OTHER INFORMATION: Synthesized: H22-1B (ING-1) primer

<400> SEQUENCE: 212
atgggctgga taaacaccta carggaagag cctacatatg gtgatgactt caagggac 58

<210> SEQ ID NO 213
<211> LENGTH: 58
<212> TYPE: DNA
<213> ORGANISM: Artificial Sequence
<220> FEATURE:
<223> OTHER INFORMATION: Synthesized: H22-1P1 (ING-1) primer

<400> SEQUENCE: 213
atgggctgga taaacaccta cwmcgaagag cctacatatg gtgatgactt caagggac 58

<210> SEQ ID NO 214
<211> LENGTH: 58
<212> TYPE: DNA
<213> ORGANISM: Artificial Sequence
<220> FEATURE:
<223> OTHER INFORMATION: Synthesized: H22-1P2 (ING-1) primer

<400> SEQUENCE: 214
atgggctgga taaacaccta ccasgaagag cctacatatg gtgatgactt caagggac 58

<210> SEQ ID NO 215
<211> LENGTH: 58
<212> TYPE: DNA
<213> ORGANISM: Artificial Sequence
<220> FEATURE:
<223> OTHER INFORMATION: Synthesized: H22-1A (ING-1) primer

<400> SEQUENCE: 215
atgggctgga taaacaccta cgasgaagag cctacatatg gtgatgactt caagggac 58

<210> SEQ ID NO 216
<211> LENGTH: 58
<212> TYPE: DNA
<213> ORGANISM: Artificial Sequence
<220> FEATURE:
<223> OTHER INFORMATION: Synthesized: H22-1NP1 (ING-1) primer
<220> FEATURE:
<221> NAME/KEY: misc_feature
<222> LOCATION: (22)..(22)
<223> OTHER INFORMATION: n is a, c, g, or t

<400> SEQUENCE: 216
atgggctgga taaacaccta cntcgaagag cctacatatg gtgatgactt caagggac 58

<210> SEQ ID NO 217
<211> LENGTH: 58
<212> TYPE: DNA
<213> ORGANISM: Artificial Sequence
<220> FEATURE:
<223> OTHER INFORMATION: Synthesized: H22-1NP2 (ING-1) primer

<400> SEQUENCE: 217
atgggctgga taaacaccta ckgggaagag cctacatatg gtgatgactt caagggac 58

<210> SEQ ID NO 218
<211> LENGTH: 58
<212> TYPE: DNA
<213> ORGANISM: Artificial Sequence
<220> FEATURE:
<223> OTHER INFORMATION: Synthesized: H22-1Np3 (ING-1) primer

<400> SEQUENCE: 218
atgggctgga taaacaccta cscggaagag cctacatatg gtgatgactt caagggac 58

<210> SEQ ID NO 219
<211> LENGTH: 58
<212> TYPE: DNA
<213> ORGANISM: Artificial Sequence
<220> FEATURE:
<223> OTHER INFORMATION: Synthesized: H22-2B (ING-1) primer

<400> SEQUENCE: 219
atgggctgga taaacaccta cactarggag cctacatatg gtgatgactt caagggac 58

<210> SEQ ID NO 220
<211> LENGTH: 58
<212> TYPE: DNA
<213> ORGANISM: Artificial Sequence
<220> FEATURE:
<223> OTHER INFORMATION: Synthesized: H22-2P1 (ING-1) primer

<400> SEQUENCE: 220
atgggctgga taaacaccta cactwmcgag cctacatatg gtgatgactt caagggac 58

<210> SEQ ID NO 221
<211> LENGTH: 58
<212> TYPE: DNA
<213> ORGANISM: Artificial Sequence
<220> FEATURE:
<223> OTHER INFORMATION: Synthesized: H22-2P2 (ING-1) primer

<400> SEQUENCE: 221
atgggctgga taaacaccta cactcasgag cctacatatg gtgatgactt caagggac 58

<210> SEQ ID NO 222
<211> LENGTH: 58
<212> TYPE: DNA
<213> ORGANISM: Artificial Sequence
<220> FEATURE:
<223> OTHER INFORMATION: Synthesized: H22-2A (ING-1) primer

<400> SEQUENCE: 222
atgggctgga taaacaccta cactgasgag cctacatatg gtgatgactt caagggac 58

<210> SEQ ID NO 223
<211> LENGTH: 58
<212> TYPE: DNA
<213> ORGANISM: Artificial Sequence
<220> FEATURE:
<223> OTHER INFORMATION: Synthesized: H22-2NP1 (ING-1) primer
<220> FEATURE:
<221> NAME/KEY: misc_feature
<222> LOCATION: (25)..(25)
<223> OTHER INFORMATION: n is a, c, g, or t

<400> SEQUENCE: 223
atgggctgga taaacaccta cactntcgag cctacatatg gtgatgactt caagggac 58

<210> SEQ ID NO 224
<211> LENGTH: 58
<212> TYPE: DNA
<213> ORGANISM: Artificial Sequence
<220> FEATURE:
<223> OTHER INFORMATION: Synthesized: H22-2NP2 (ING-1) primer

<400> SEQUENCE: 224
atgggctgga taaacaccta cactkgggag cctacatatg gtgatgactt caagggac 58

<210> SEQ ID NO 225
<211> LENGTH: 58
<212> TYPE: DNA
<213> ORGANISM: Artificial Sequence
<220> FEATURE:
<223> OTHER INFORMATION: Synthesized: H22-2NP3 (ING-1) primer

<400> SEQUENCE: 225
atgggctgga taaacaccta cactscggag cctacatatg gtgatgactt caagggac 58

<210> SEQ ID NO 226
<211> LENGTH: 58
<212> TYPE: DNA
<213> ORGANISM: Artificial Sequence
<220> FEATURE:
<223> OTHER INFORMATION: Synthesized: H22-3B (ING-1) primer

<400> SEQUENCE: 226
atgggctgga taaacaccta cactgaaarg cctacatatg gtgatgactt caagggac 58

<210> SEQ ID NO 227
<211> LENGTH: 58
<212> TYPE: DNA
<213> ORGANISM: Artificial Sequence
<220> FEATURE:
<223> OTHER INFORMATION: Synthesized: H22-3P1 (ING-1) primer

<400> SEQUENCE: 227
atgggctgga taaacaccta cactgaawmc cctacatatg gtgatgactt caagggac 58

<210> SEQ ID NO 228
<211> LENGTH: 58
<212> TYPE: DNA
<213> ORGANISM: Artificial Sequence
<220> FEATURE:
<223> OTHER INFORMATION: Synthesized: H22-3P2 (ING-1) primer

<400> SEQUENCE: 228
atgggctgga taaacaccta cactgaacas cctacatatg gtgatgactt caagggac 58

<210> SEQ ID NO 229
<211> LENGTH: 58
<212> TYPE: DNA
<213> ORGANISM: Artificial Sequence
<220> FEATURE:
<223> OTHER INFORMATION: Synthesized: H22-3A (ING-1) primer

<400> SEQUENCE: 229
atgggctgga taaacaccta cactgaagas cctacatatg gtgatgactt caagggac 58

<210> SEQ ID NO 230
<211> LENGTH: 58
<212> TYPE: DNA
<213> ORGANISM: Artificial Sequence
<220> FEATURE:
<223> OTHER INFORMATION: Synthesized: H22-3NP1 (ING-1) primer
<220> FEATURE:
<221> NAME/KEY: misc_feature
<222> LOCATION: (28)..(28)
<223> OTHER INFORMATION: n is a, c, g, or t

<400> SEQUENCE: 230
atgggctgga taaacaccta cactgaantc cctacatatg gtgatgactt caagggac 58

<210> SEQ ID NO 231
<211> LENGTH: 58
<212> TYPE: DNA
<213> ORGANISM: Artificial Sequence
<220> FEATURE:
<223> OTHER INFORMATION: Synthesized: H22-3NP2 (ING-1) primer

<400> SEQUENCE: 231
atgggctgga taaacaccta cactgaakgg cctacatatg gtgatgactt caagggac 58

<210> SEQ ID NO 232
<211> LENGTH: 58
<212> TYPE: DNA

<213> ORGANISM: Artificial Sequence
<220> FEATURE:
<223> OTHER INFORMATION: Synthesized: H22-3NP3 (ING-1) primer
<220> FEATURE:
<221> NAME/KEY: misc_feature
<223> OTHER INFORMATION: Synthesized: H22-3NP3

<400> SEQUENCE: 232
atgggctgga taaacaccta cactgaascg cctacatatg gtgatgactt caagggac 58

<210> SEQ ID NO 233
<211> LENGTH: 58
<212> TYPE: DNA
<213> ORGANISM: Artificial Sequence
<220> FEATURE:
<223> OTHER INFORMATION: Synthesized: H22-4B (ING-1) primer

<400> SEQUENCE: 233
atgggctgga taaacaccta cactgaagag argacatatg gtgatgactt caagggac 58

<210> SEQ ID NO 234
<211> LENGTH: 58
<212> TYPE: DNA
<213> ORGANISM: Artificial Sequence
<220> FEATURE:
<223> OTHER INFORMATION: Synthesized: H22-4P1 (ING-1) primer

<400> SEQUENCE: 234
atgggctgga taaacaccta cactgaagag wmcacatatg gtgatgactt caagggac 58

<210> SEQ ID NO 235
<211> LENGTH: 58
<212> TYPE: DNA
<213> ORGANISM: Artificial Sequence
<220> FEATURE:
<223> OTHER INFORMATION: Synthesized: H22-4P2 (ING-1) primer

<400> SEQUENCE: 235
atgggctgga taaacaccta cactgaagag casacatatg gtgatgactt caagggac 58

<210> SEQ ID NO 236
<211> LENGTH: 58
<212> TYPE: DNA
<213> ORGANISM: Artificial Sequence
<220> FEATURE:
<223> OTHER INFORMATION: Synthesized: H22-4A (ING-1) primer

<400> SEQUENCE: 236
atgggctgga taaacaccta cactgaagag gasacatatg gtgatgactt caagggac 58

<210> SEQ ID NO 237
<211> LENGTH: 58
<212> TYPE: DNA
<213> ORGANISM: Artificial Sequence
<220> FEATURE:
<223> OTHER INFORMATION: Synthesized: H22-4NP1 (ING-1) primer

<400> SEQUENCE: 237
atgggctgga taaacaccta cactgaagag gasacatatg gtgatgactt caagggac 58

<210> SEQ ID NO 238
<211> LENGTH: 58
<212> TYPE: DNA
<213> ORGANISM: Artificial Sequence
<220> FEATURE:
<223> OTHER INFORMATION: Synthesized: H22-4NP2 (ING-1) primer

<400> SEQUENCE: 238
atgggctgga taaacaccta cactgaagag kggacatatg gtgatgactt caagggac 58

<210> SEQ ID NO 239
<211> LENGTH: 58
<212> TYPE: DNA
<213> ORGANISM: Artificial Sequence
<220> FEATURE:
<223> OTHER INFORMATION: Synthesized: H22-4NP3 (ING-1) primer

<400> SEQUENCE: 239
atgggctgga taaacaccta cactgaagag scgacatatg gtgatgactt caagggac 58

<210> SEQ ID NO 240
<211> LENGTH: 58
<212> TYPE: DNA
<213> ORGANISM: Artificial Sequence
<220> FEATURE:
<223> OTHER INFORMATION: Synthesized: H22-5B (ING-1) primer

<400> SEQUENCE: 240
atgggctgga taaacaccta cactgaagag cctargtatg gtgatgactt caagggac 58

<210> SEQ ID NO 241
<211> LENGTH: 58
<212> TYPE: DNA
<213> ORGANISM: Artificial Sequence
<220> FEATURE:
<223> OTHER INFORMATION: Synthesized: H22-5P1 (ING-1) primer

<400> SEQUENCE: 241
atgggctgga taaacaccta cactgaagag cctwmctatg gtgatgactt caagggac 58

<210> SEQ ID NO 242
<211> LENGTH: 58
<212> TYPE: DNA
<213> ORGANISM: Artificial Sequence
<220> FEATURE:
<223> OTHER INFORMATION: Synthesized: H22-5P2 (ING-1) primer

<400> SEQUENCE: 242
atgggctgga taaacaccta cactgaagag cctcastatg gtgatgactt caagggac 58

<210> SEQ ID NO 243
<211> LENGTH: 58
<212> TYPE: DNA
<213> ORGANISM: Artificial Sequence
<220> FEATURE:
<223> OTHER INFORMATION: Synthesized: H22-5A (ING-1) primer

<400> SEQUENCE: 243
atgggctgga taaacaccta cactgaagag cctgastatg gtgatgactt caagggac 58

<210> SEQ ID NO 244
<211> LENGTH: 58
<212> TYPE: DNA
<213> ORGANISM: Artificial Sequence
<220> FEATURE:
<223> OTHER INFORMATION: Synthesized: H22-5NP1 (ING-1) primer
<220> FEATURE:
<221> NAME/KEY: misc_feature
<222> LOCATION: (34)..(34)
<223> OTHER INFORMATION: n is a, c, g, or t

<400> SEQUENCE: 244
atgggctgga taaacaccta cactgaagag cctntctatg gtgatgactt caagggac 58

<210> SEQ ID NO 245
<211> LENGTH: 58
<212> TYPE: DNA
<213> ORGANISM: Artificial Sequence
<220> FEATURE:
<223> OTHER INFORMATION: Synthesized: H22-5NP2 (ING-1) primer

<400> SEQUENCE: 245
atgggctgga taaacaccta cactgaagag cctkggtatg gtgatgactt caagggac 58

<210> SEQ ID NO 246
<211> LENGTH: 58
<212> TYPE: DNA
<213> ORGANISM: Artificial Sequence
<220> FEATURE:
<223> OTHER INFORMATION: Synthesized: H22-5NP3 (ING-1) primer

<400> SEQUENCE: 246
atgggctgga taaacaccta cactgaagag cctscgtatg gtgatgactt caagggac 58

<210> SEQ ID NO 247
<211> LENGTH: 24
<212> TYPE: DNA
<213> ORGANISM: Artificial Sequence
<220> FEATURE:
<223> OTHER INFORMATION: Synthesized: H3-R (ING-1) primer

<400> SEQUENCE: 247
aaatcttgca cagaaatatg tagc 24

<210> SEQ ID NO 248
<211> LENGTH: 53
<212> TYPE: DNA
<213> ORGANISM: Artificial Sequence
<220> FEATURE:
<223> OTHER INFORMATION: Synthesized: H3-1B (ING-1) primer

<400> SEQUENCE: 248
gctacatatt tctgtgcaag atttargtct gctgtggact actggggtca agg 53

<210> SEQ ID NO 249
<211> LENGTH: 53
<212> TYPE: DNA
<213> ORGANISM: Artificial Sequence
<220> FEATURE:
<223> OTHER INFORMATION: Synthesized: H3-1P1 (ING-1) primer

<400> SEQUENCE: 249
gctacatatt tctgtgcaag atttwmctct gctgtggact actggggtca agg 53

<210> SEQ ID NO 250
<211> LENGTH: 53
<212> TYPE: DNA
<213> ORGANISM: Artificial Sequence
<220> FEATURE:
<223> OTHER INFORMATION: Synthesized: H3-1P2 (ING-1) primer

<400> SEQUENCE: 250
gctacatatt tctgtgcaag atttcastct gctgtggact actggggtca agg 53

<210> SEQ ID NO 251
<211> LENGTH: 53
<212> TYPE: DNA
<213> ORGANISM: Artificial Sequence
<220> FEATURE:

<223> OTHER INFORMATION: Synthesized: H3-1A (ING-1) primer

<400> SEQUENCE: 251
gctacatatt tctgtgcaag atttgastct gctgtggact actggggtca agg 53

<210> SEQ ID NO 252
<211> LENGTH: 53
<212> TYPE: DNA
<213> ORGANISM: Artificial Sequence
<220> FEATURE:
<223> OTHER INFORMATION: Synthesized: H3-1NP1 (ING-1) primer
<220> FEATURE:
<221> NAME/KEY: misc_feature
<222> LOCATION: (25)..(25)
<223> OTHER INFORMATION: n is a, c, g, or t

<400> SEQUENCE: 252
gctacatatt tctgtgcaag atttntctct gctgtggact actggggtca agg 53

<210> SEQ ID NO 253
<211> LENGTH: 53
<212> TYPE: DNA
<213> ORGANISM: Artificial Sequence
<220> FEATURE:
<223> OTHER INFORMATION: Synthesized: H3-1NP2 (ING-1) primer

<400> SEQUENCE: 253
gctacatatt tctgtgcaag atttkggtct gctgtggact actggggtca agg 53

<210> SEQ ID NO 254
<211> LENGTH: 53
<212> TYPE: DNA
<213> ORGANISM: Artificial Sequence
<220> FEATURE:
<223> OTHER INFORMATION: Synthesized: H3-1NP3 (ING-1) primer

<400> SEQUENCE: 254
gctacatatt tctgtgcaag atttscgtct gctgtggact actggggtca agg 53

<210> SEQ ID NO 255
<211> LENGTH: 53
<212> TYPE: DNA
<213> ORGANISM: Artificial Sequence
<220> FEATURE:
<223> OTHER INFORMATION: Synthesized: H3-2B (ING-1) primer

<400> SEQUENCE: 255
gctacatatt tctgtgcaag atttggcarg gctgtggact actggggtca agg 53

<210> SEQ ID NO 256
<211> LENGTH: 53
<212> TYPE: DNA
<213> ORGANISM: Artificial Sequence
<220> FEATURE:
<223> OTHER INFORMATION: Synthesized: H3-2P1 (ING-1) primer

<400> SEQUENCE: 256
gctacatatt tctgtgcaag atttggcwmc gctgtggact actggggtca agg 53

<210> SEQ ID NO 257
<211> LENGTH: 53
<212> TYPE: DNA
<213> ORGANISM: Artificial Sequence
<220> FEATURE:
<223> OTHER INFORMATION: Synthesized: H3-2P2 (ING-1) primer

<400> SEQUENCE: 257

```
gctacatatt tctgtgcaag atttggccas gctgtggact actggggtca agg            53


<210> SEQ ID NO 258
<211> LENGTH: 53
<212> TYPE: DNA
<213> ORGANISM: Artificial Sequence
<220> FEATURE:
<223> OTHER INFORMATION: Synthesized: H3-2A (ING-1) primer

<400> SEQUENCE: 258

gctacatatt tctgtgcaag atttggcgas gctgtggact actggggtca agg            53


<210> SEQ ID NO 259
<211> LENGTH: 53
<212> TYPE: DNA
<213> ORGANISM: Artificial Sequence
<220> FEATURE:
<223> OTHER INFORMATION: Synthesized: H3-2NP1 (ING-1) primer
<220> FEATURE:
<221> NAME/KEY: misc_feature
<222> LOCATION: (28)..(28)
<223> OTHER INFORMATION: n is a, c, g, or t

<400> SEQUENCE: 259

gctacatatt tctgtgcaag atttggcntc gctgtggact actggggtca agg            53


<210> SEQ ID NO 260
<211> LENGTH: 53
<212> TYPE: DNA
<213> ORGANISM: Artificial Sequence
<220> FEATURE:
<223> OTHER INFORMATION: Synthesized: H3-2NP2 (ING-1) primer

<400> SEQUENCE: 260

gctacatatt tctgtgcaag atttggckgg gctgtggact actggggtca agg            53


<210> SEQ ID NO 261
<211> LENGTH: 53
<212> TYPE: DNA
<213> ORGANISM: Artificial Sequence
<220> FEATURE:
<223> OTHER INFORMATION: Synthesized: H3-2NP3 (ING-1) primer

<400> SEQUENCE: 261

gctacatatt tctgtgcaag atttggcscg gctgtggact actggggtca agg            53


<210> SEQ ID NO 262
<211> LENGTH: 53
<212> TYPE: DNA
<213> ORGANISM: Artificial Sequence
<220> FEATURE:
<223> OTHER INFORMATION: Synthesized: H3-3B (ING-1) primer

<400> SEQUENCE: 262

gctacatatt tctgtgcaag atttggctct arggtggact actggggtca agg            53


<210> SEQ ID NO 263
<211> LENGTH: 53
<212> TYPE: DNA
<213> ORGANISM: Artificial Sequence
<220> FEATURE:
<223> OTHER INFORMATION: Synthesized: H3-3P1 (ING-1) primer

<400> SEQUENCE: 263

gctacatatt tctgtgcaag atttggctct wmcgtggact actggggtca agg            53
```

<210> SEQ ID NO 264
<211> LENGTH: 53
<212> TYPE: DNA
<213> ORGANISM: Artificial Sequence
<220> FEATURE:
<223> OTHER INFORMATION: Synthesized: H3-3P2 (ING-1) primer

<400> SEQUENCE: 264
gctacatatt tctgtgcaag atttggctct casgtggact actggggtca agg 53

<210> SEQ ID NO 265
<211> LENGTH: 53
<212> TYPE: DNA
<213> ORGANISM: Artificial Sequence
<220> FEATURE:
<223> OTHER INFORMATION: Synthesized: H3-3A (ING-1) primer

<400> SEQUENCE: 265
gctacatatt tctgtgcaag atttggctct gasgtggact actggggtca agg 53

<210> SEQ ID NO 266
<211> LENGTH: 53
<212> TYPE: DNA
<213> ORGANISM: Artificial Sequence
<220> FEATURE:
<223> OTHER INFORMATION: Synthesized: H3-3NP1 (ING-1) primer
<220> FEATURE:
<221> NAME/KEY: misc_feature
<222> LOCATION: (31)..(31)
<223> OTHER INFORMATION: n is a, c, g, or t

<400> SEQUENCE: 266
gctacatatt tctgtgcaag atttggctct ntcgtggact actggggtca agg 53

<210> SEQ ID NO 267
<211> LENGTH: 53
<212> TYPE: DNA
<213> ORGANISM: Artificial Sequence
<220> FEATURE:
<223> OTHER INFORMATION: Synthesized: H3-3NP2 (ING-1) primer

<400> SEQUENCE: 267
gctacatatt tctgtgcaag atttggctct kgggtggact actggggtca agg 53

<210> SEQ ID NO 268
<211> LENGTH: 53
<212> TYPE: DNA
<213> ORGANISM: Artificial Sequence
<220> FEATURE:
<223> OTHER INFORMATION: Synthesized: H3-3NP3 (ING-1) primer

<400> SEQUENCE: 268
gctacatatt tctgtgcaag atttggctct scggtggact actggggtca agg 53

<210> SEQ ID NO 269
<211> LENGTH: 21
<212> TYPE: DNA
<213> ORGANISM: Artificial Sequence
<220> FEATURE:
<223> OTHER INFORMATION: Synthesized: H32-R (ING-1) primer

<400> SEQUENCE: 269
cacagcagag ccaaatcttg c 21

<210> SEQ ID NO 270
<211> LENGTH: 46

<212> TYPE: DNA
<213> ORGANISM: Artificial Sequence
<220> FEATURE:
<223> OTHER INFORMATION: Synthesized: H32-1B (ING-1) primer

<400> SEQUENCE: 270
gcaagatttg gctctgctgt gargtactgg ggtcaaggaa cctcgg 46

<210> SEQ ID NO 271
<211> LENGTH: 46
<212> TYPE: DNA
<213> ORGANISM: Artificial Sequence
<220> FEATURE:
<223> OTHER INFORMATION: Synthesized: H32-1P1 (ING-1) primer

<400> SEQUENCE: 271
gcaagatttg gctctgctgt gwmctactgg ggtcaaggaa cctcgg 46

<210> SEQ ID NO 272
<211> LENGTH: 46
<212> TYPE: DNA
<213> ORGANISM: Artificial Sequence
<220> FEATURE:
<223> OTHER INFORMATION: Synthesized: H32-1P2 (ING-1) primer

<400> SEQUENCE: 272
gcaagatttg gctctgctgt gcastactgg ggtcaaggaa cctcgg 46

<210> SEQ ID NO 273
<211> LENGTH: 46
<212> TYPE: DNA
<213> ORGANISM: Artificial Sequence
<220> FEATURE:
<223> OTHER INFORMATION: Synthesized: H32-1A (ING-1) primer

<400> SEQUENCE: 273
gcaagatttg gctctgctgt ggastactgg ggtcaaggaa cctcgg 46

<210> SEQ ID NO 274
<211> LENGTH: 46
<212> TYPE: DNA
<213> ORGANISM: Artificial Sequence
<220> FEATURE:
<223> OTHER INFORMATION: Synthesized: H32-1NP1 (ING-1) primer
<220> FEATURE:
<221> NAME/KEY: misc_feature
<222> LOCATION: (22)..(22)
<223> OTHER INFORMATION: n is a, c, g, or t

<400> SEQUENCE: 274
gcaagatttg gctctgctgt gntctactgg ggtcaaggaa cctcgg 46

<210> SEQ ID NO 275
<211> LENGTH: 46
<212> TYPE: DNA
<213> ORGANISM: Artificial Sequence
<220> FEATURE:
<223> OTHER INFORMATION: Synthesized: H32-1NP2 (ING-1) primer

<400> SEQUENCE: 275
gcaagatttg gctctgctgt gkggtactgg ggtcaaggaa cctcgg 46

<210> SEQ ID NO 276
<211> LENGTH: 46
<212> TYPE: DNA
<213> ORGANISM: Artificial Sequence
<220> FEATURE:

<223> OTHER INFORMATION: Synthesized: H32-1NP3 (ING-1) primer

<400> SEQUENCE: 276
gcaagatttg gctctgctgt gscgtactgg ggtcaaggaa cctcgg 46

<210> SEQ ID NO 277
<211> LENGTH: 46
<212> TYPE: DNA
<213> ORGANISM: Artificial Sequence
<220> FEATURE:
<223> OTHER INFORMATION: Synthesized: H32-2B (ING-1) primer

<400> SEQUENCE: 277
gcaagatttg gctctgctgt ggacargtgg ggtcaaggaa cctcgg 46

<210> SEQ ID NO 278
<211> LENGTH: 46
<212> TYPE: DNA
<213> ORGANISM: Artificial Sequence
<220> FEATURE:
<223> OTHER INFORMATION: Synthesized: H32-2P1 (ING-1) primer

<400> SEQUENCE: 278
gcaagatttg gctctgctgt ggacwmctgg ggtcaaggaa cctcgg 46

<210> SEQ ID NO 279
<211> LENGTH: 46
<212> TYPE: DNA
<213> ORGANISM: Artificial Sequence
<220> FEATURE:
<223> OTHER INFORMATION: Synthesized: H32-2P2 (ING-1) primer

<400> SEQUENCE: 279
gcaagatttg gctctgctgt ggaccastgg ggtcaaggaa cctcgg 46

<210> SEQ ID NO 280
<211> LENGTH: 46
<212> TYPE: DNA
<213> ORGANISM: Artificial Sequence
<220> FEATURE:
<223> OTHER INFORMATION: Synthesized: H32-2A (ING-1) primer

<400> SEQUENCE: 280
gcaagatttg gctctgctgt ggacgastgg ggtcaaggaa cctcgg 46

<210> SEQ ID NO 281
<211> LENGTH: 46
<212> TYPE: DNA
<213> ORGANISM: Artificial Sequence
<220> FEATURE:
<223> OTHER INFORMATION: Synthesized: H32-2NP1 (ING-1) primer
<220> FEATURE:
<221> NAME/KEY: misc_feature
<222> LOCATION: (25)..(25)
<223> OTHER INFORMATION: n is a, c, g, or t

<400> SEQUENCE: 281
gcaagatttg gctctgctgt ggacntctgg ggtcaaggaa cctcgg 46

<210> SEQ ID NO 282
<211> LENGTH: 46
<212> TYPE: DNA
<213> ORGANISM: Artificial Sequence
<220> FEATURE:
<223> OTHER INFORMATION: Synthesized: H32-2NP2 (ING-1) primer

<400> SEQUENCE: 282
gcaagatttg gctctgctgt ggackggtgg ggtcaaggaa cctcgg 46

<210> SEQ ID NO 283
<211> LENGTH: 46
<212> TYPE: DNA
<213> ORGANISM: Artificial Sequence
<220> FEATURE:
<223> OTHER INFORMATION: Synthesized: H32-2NP3 (ING-1) primer

<400> SEQUENCE: 283
gcaagatttg gctctgctgt ggacscgtgg ggtcaaggaa cctcgg 46

<210> SEQ ID NO 284
<211> LENGTH: 22
<212> TYPE: DNA
<213> ORGANISM: Artificial Sequence
<220> FEATURE:
<223> OTHER INFORMATION: Synthesized: Ascl-F2 (ING-1) primer

<400> SEQUENCE: 284
taataaggcg cgcctaacca tc 22

<210> SEQ ID NO 285
<211> LENGTH: 31
<212> TYPE: DNA
<213> ORGANISM: Artificial Sequence
<220> FEATURE:
<223> OTHER INFORMATION: notl-R (ING-1) primer

<400> SEQUENCE: 285
agcggccgca caagatttgg gctcaactct c 31

<210> SEQ ID NO 286
<211> LENGTH: 20
<212> TYPE: DNA
<213> ORGANISM: Artificial Sequence
<220> FEATURE:
<223> OTHER INFORMATION: Synthesized: L1R (XPA-23) primer

<400> SEQUENCE: 286
actcgcccga caaatgatgg 20

<210> SEQ ID NO 287
<211> LENGTH: 58
<212> TYPE: DNA
<213> ORGANISM: Artificial Sequence
<220> FEATURE:
<223> OTHER INFORMATION: Synthesized: L1-1B (XPA-23) primer

<400> SEQUENCE: 287
ccatcatttg tcgggcgagt arggatatta acaggtggtt agcctggtat cagcagac 58

<210> SEQ ID NO 288
<211> LENGTH: 58
<212> TYPE: DNA
<213> ORGANISM: Artificial Sequence
<220> FEATURE:
<223> OTHER INFORMATION: Synthesized: L1-1P1 (XPA-23) primer

<400> SEQUENCE: 288
ccatcatttg tcgggcgagt wmcgatatta acaggtggtt agcctggtat cagcagac 58

<210> SEQ ID NO 289
<211> LENGTH: 58
<212> TYPE: DNA

<213> ORGANISM: Artificial Sequence
<220> FEATURE:
<223> OTHER INFORMATION: Synthesized: L1-1P2 (XPA-23) primer

<400> SEQUENCE: 289
ccatcatttg tcgggcgagt casgatatta acaggtggtt agcctggtat cagcagac 58

<210> SEQ ID NO 290
<211> LENGTH: 58
<212> TYPE: DNA
<213> ORGANISM: Artificial Sequence
<220> FEATURE:
<223> OTHER INFORMATION: Synthesized: L1-1A (XPA-23) primer

<400> SEQUENCE: 290
ccatcatttg tcgggcgagt gasgatatta acaggtggtt agcctggtat cagcagac 58

<210> SEQ ID NO 291
<211> LENGTH: 58
<212> TYPE: DNA
<213> ORGANISM: Artificial Sequence
<220> FEATURE:
<223> OTHER INFORMATION: Synthesized: L1-1NP1 (XPA-23) primer
<220> FEATURE:
<221> NAME/KEY: misc_feature
<222> LOCATION: (21)..(21)
<223> OTHER INFORMATION: n is a, c, g, or t

<400> SEQUENCE: 291
ccatcatttg tcgggcgagt ntcgatatta acaggtggtt agcctggtat cagcagac 58

<210> SEQ ID NO 292
<211> LENGTH: 58
<212> TYPE: DNA
<213> ORGANISM: Artificial Sequence
<220> FEATURE:
<223> OTHER INFORMATION: Synthesized: L1-1NP2 (XPA-23) primer

<400> SEQUENCE: 292
ccatcatttg tcgggcgagt kgggatatta acaggtggtt agcctggtat cagcagac 58

<210> SEQ ID NO 293
<211> LENGTH: 58
<212> TYPE: DNA
<213> ORGANISM: Artificial Sequence
<220> FEATURE:
<223> OTHER INFORMATION: Synthesized: L1-1NP3 (XPA-23) primer

<400> SEQUENCE: 293
ccatcatttg tcgggcgagt scggatatta acaggtggtt agcctggtat cagcagac 58

<210> SEQ ID NO 294
<211> LENGTH: 58
<212> TYPE: DNA
<213> ORGANISM: Artificial Sequence
<220> FEATURE:
<223> OTHER INFORMATION: Synthesized: L1-2B (XPA-23) primer

<400> SEQUENCE: 294
ccatcatttg tcgggcgagt cagargatta acaggtggtt agcctggtat cagcagac 58

<210> SEQ ID NO 295
<211> LENGTH: 58
<212> TYPE: DNA
<213> ORGANISM: Artificial Sequence
<220> FEATURE:
<223> OTHER INFORMATION: Synthesized: L1-2P1 (XPA-23) primer

<400> SEQUENCE: 295
ccatcatttg tcgggcgagt cagwmcatta acaggtggtt agcctggtat cagcagac 58

<210> SEQ ID NO 296
<211> LENGTH: 58
<212> TYPE: DNA
<213> ORGANISM: Artificial Sequence
<220> FEATURE:
<223> OTHER INFORMATION: Synthesized: L1-2P2 (XPA-23) primer

<400> SEQUENCE: 296
ccatcatttg tcgggcgagt cagcasatta acaggtggtt agcctggtat cagcagac 58

<210> SEQ ID NO 297
<211> LENGTH: 58
<212> TYPE: DNA
<213> ORGANISM: Artificial Sequence
<220> FEATURE:
<223> OTHER INFORMATION: Synthesized: L1-2A (XPA-23) primer

<400> SEQUENCE: 297
ccatcatttg tcgggcgagt caggasatta acaggtggtt agcctggtat cagcagac 58

<210> SEQ ID NO 298
<211> LENGTH: 58
<212> TYPE: DNA
<213> ORGANISM: Artificial Sequence
<220> FEATURE:
<223> OTHER INFORMATION: Synthesized: L1-2NP1 (XPA-23) primer
<220> FEATURE:
<221> NAME/KEY: misc_feature
<222> LOCATION: (24)..(24)
<223> OTHER INFORMATION: n is a, c, g, or t

<400> SEQUENCE: 298
ccatcatttg tcgggcgagt cagntcatta acaggtggtt agcctggtat cagcagac 58

<210> SEQ ID NO 299
<211> LENGTH: 58
<212> TYPE: DNA
<213> ORGANISM: Artificial Sequence
<220> FEATURE:
<223> OTHER INFORMATION: Synthesized: L1-2NP2 (XPA-23) primer

<400> SEQUENCE: 299
ccatcatttg tcgggcgagt cagkggatta acaggtggtt agcctggtat cagcagac 58

<210> SEQ ID NO 300
<211> LENGTH: 58
<212> TYPE: DNA
<213> ORGANISM: Artificial Sequence
<220> FEATURE:
<223> OTHER INFORMATION: Synthesized: L1-2NP3 (XPA-23) primer

<400> SEQUENCE: 300
ccatcatttg tcgggcgagt cagscgatta acaggtggtt agcctggtat cagcagac 58

<210> SEQ ID NO 301
<211> LENGTH: 58
<212> TYPE: DNA
<213> ORGANISM: Artificial Sequence
<220> FEATURE:
<223> OTHER INFORMATION: Synthesized: L1-3B (XPA-23) primer

<400> SEQUENCE: 301
ccatcatttg tcgggcgagt caggatatta rgaggtggtt agcctggtat cagcagac 58

<210> SEQ ID NO 302
<211> LENGTH: 58
<212> TYPE: DNA
<213> ORGANISM: Artificial Sequence
<220> FEATURE:
<223> OTHER INFORMATION: Synthesized: L1-3P1 (XPA-23) primer

<400> SEQUENCE: 302
ccatcatttg tcgggcgagt caggatattw mcaggtggtt agcctggtat cagcagac 58

<210> SEQ ID NO 303
<211> LENGTH: 58
<212> TYPE: DNA
<213> ORGANISM: Artificial Sequence
<220> FEATURE:
<223> OTHER INFORMATION: Synthesized: L1-3P2 (XPA-23) primer

<400> SEQUENCE: 303
ccatcatttg tcgggcgagt caggatattc asaggtggtt agcctggtat cagcagac 58

<210> SEQ ID NO 304
<211> LENGTH: 58
<212> TYPE: DNA
<213> ORGANISM: Artificial Sequence
<220> FEATURE:
<223> OTHER INFORMATION: Synthesized: L1-3A (XPA-23) primer

<400> SEQUENCE: 304
ccatcatttg tcgggcgagt caggatattg asaggtggtt agcctggtat cagcagac 58

<210> SEQ ID NO 305
<211> LENGTH: 58
<212> TYPE: DNA
<213> ORGANISM: Artificial Sequence
<220> FEATURE:
<223> OTHER INFORMATION: Synthesized: L1-3NP1 (XPA-23) primer
<220> FEATURE:
<221> NAME/KEY: misc_feature
<222> LOCATION: (30)..(30)
<223> OTHER INFORMATION: n is a, c, g, or t

<400> SEQUENCE: 305
ccatcatttg tcgggcgagt caggatattn tcaggtggtt agcctggtat cagcagac 58

<210> SEQ ID NO 306
<211> LENGTH: 58
<212> TYPE: DNA
<213> ORGANISM: Artificial Sequence
<220> FEATURE:
<223> OTHER INFORMATION: Synthesized: L1-3NP2 (XPA-23) primer

<400> SEQUENCE: 306
ccatcatttg tcgggcgagt caggatattk ggaggtggtt agcctggtat cagcagac 58

<210> SEQ ID NO 307
<211> LENGTH: 58
<212> TYPE: DNA
<213> ORGANISM: Artificial Sequence
<220> FEATURE:
<223> OTHER INFORMATION: Synthesized: L1-3NP3 (XPA-23) primer

<400> SEQUENCE: 307
ccatcatttg tcgggcgagt caggatatts cgaggtggtt agcctggtat cagcagac 58

<210> SEQ ID NO 308
<211> LENGTH: 58
<212> TYPE: DNA
<213> ORGANISM: Artificial Sequence
<220> FEATURE:
<223> OTHER INFORMATION: Synthesized: L1-4B (XPA-23) primer

<400> SEQUENCE: 308
ccatcatttg tcgggcgagt caggatatta acargtggtt agcctggtat cagcagac 58

<210> SEQ ID NO 309
<211> LENGTH: 58
<212> TYPE: DNA
<213> ORGANISM: Artificial Sequence
<220> FEATURE:
<223> OTHER INFORMATION: Synthesized: L1-4P1 (XPA-23) primer

<400> SEQUENCE: 309
ccatcatttg tcgggcgagt caggatatta acwmctggtt agcctggtat cagcagac 58

<210> SEQ ID NO 310
<211> LENGTH: 58
<212> TYPE: DNA
<213> ORGANISM: Artificial Sequence
<220> FEATURE:
<223> OTHER INFORMATION: Synthesized: L1-4P2 (XPA-23) primer

<400> SEQUENCE: 310
ccatcatttg tcgggcgagt caggatatta accastggtt agcctggtat cagcagac 58

<210> SEQ ID NO 311
<211> LENGTH: 58
<212> TYPE: DNA
<213> ORGANISM: Artificial Sequence
<220> FEATURE:
<223> OTHER INFORMATION: Synthesized: L1-4A (XPA-23) primer

<400> SEQUENCE: 311
ccatcatttg tcgggcgagt caggatatta acgastggtt agcctggtat cagcagac 58

<210> SEQ ID NO 312
<211> LENGTH: 58
<212> TYPE: DNA
<213> ORGANISM: Artificial Sequence
<220> FEATURE:
<223> OTHER INFORMATION: Synthesized: L1-4NP1 (XPA-23) primer
<220> FEATURE:
<221> NAME/KEY: misc_feature
<222> LOCATION: (33)..(33)
<223> OTHER INFORMATION: n is a, c, g, or t

<400> SEQUENCE: 312
ccatcatttg tcgggcgagt caggatatta acntctggtt agcctggtat cagcagac 58

<210> SEQ ID NO 313
<211> LENGTH: 58
<212> TYPE: DNA
<213> ORGANISM: Artificial Sequence
<220> FEATURE:
<223> OTHER INFORMATION: Synthesized: L1-4NP2 (XPA-23) primer

<400> SEQUENCE: 313
ccatcatttg tcgggcgagt caggatatta ackggtggtt agcctggtat cagcagac 58

<210> SEQ ID NO 314
<211> LENGTH: 58
<212> TYPE: DNA

<213> ORGANISM: Artificial Sequence
<220> FEATURE:
<223> OTHER INFORMATION: Synthesized: L1-4NP3 (XPA-23) primer

<400> SEQUENCE: 314
ccatcatttg tcgggcgagt caggatatta acscgtggtt agcctggtat cagcagac 58

<210> SEQ ID NO 315
<211> LENGTH: 58
<212> TYPE: DNA
<213> ORGANISM: Artificial Sequence
<220> FEATURE:
<223> OTHER INFORMATION: Synthesized: L1-5B (XPA-23) primer

<400> SEQUENCE: 315
ccatcatttg tcgggcgagt caggatatta acaggargtt agcctggtat cagcagac 58

<210> SEQ ID NO 316
<211> LENGTH: 58
<212> TYPE: DNA
<213> ORGANISM: Artificial Sequence
<220> FEATURE:
<223> OTHER INFORMATION: Synthesized: L1-5P1 (XPA-23) primer

<400> SEQUENCE: 316
ccatcatttg tcgggcgagt caggatatta acaggwmctt agcctggtat cagcagac 58

<210> SEQ ID NO 317
<211> LENGTH: 58
<212> TYPE: DNA
<213> ORGANISM: Artificial Sequence
<220> FEATURE:
<223> OTHER INFORMATION: Synthesized: L1-5P2 (XPA-23) primer

<400> SEQUENCE: 317
ccatcatttg tcgggcgagt caggatatta acaggcastt agcctggtat cagcagac 58

<210> SEQ ID NO 318
<211> LENGTH: 58
<212> TYPE: DNA
<213> ORGANISM: Artificial Sequence
<220> FEATURE:
<223> OTHER INFORMATION: Synthesized: L1-5NP1 (XPA-23) primer
<220> FEATURE:
<221> NAME/KEY: misc_feature
<222> LOCATION: (36)..(36)
<223> OTHER INFORMATION: n is a, c, g, or t

<400> SEQUENCE: 318
ccatcatttg tcgggcgagt caggatatta acaggntctt agcctggtat cagcagac 58

<210> SEQ ID NO 319
<211> LENGTH: 58
<212> TYPE: DNA
<213> ORGANISM: Artificial Sequence
<220> FEATURE:
<223> OTHER INFORMATION: Synthesized: L1-5NP2 (XPA-23) primer

<400> SEQUENCE: 319
ccatcatttg tcgggcgagt caggatatta acaggkggtt agcctggtat cagcagac 58

<210> SEQ ID NO 320
<211> LENGTH: 58
<212> TYPE: DNA
<213> ORGANISM: Artificial Sequence
<220> FEATURE:
<223> OTHER INFORMATION: Synthesized: L1-5NP3 (XPA-23) primer

<400> SEQUENCE: 320
ccatcatttg tcgggcgagt caggatatta acaggscgtt agcctggtat cagcagac 58

<210> SEQ ID NO 321
<211> LENGTH: 20
<212> TYPE: DNA
<213> ORGANISM: Artificial Sequence
<220> FEATURE:
<223> OTHER INFORMATION: Synthesized: L2R (XPA-23) primer

<400> SEQUENCE: 321
gatcaggagc ttaggggcat 20

<210> SEQ ID NO 322
<211> LENGTH: 55
<212> TYPE: DNA
<213> ORGANISM: Artificial Sequence
<220> FEATURE:
<223> OTHER INFORMATION: Synthesized: L2-1B (XPA-23) primer

<400> SEQUENCE: 322
atgcccctaa gctcctgatc argtctgcaa ccagtctgca aagtggggtc ccatc 55

<210> SEQ ID NO 323
<211> LENGTH: 55
<212> TYPE: DNA
<213> ORGANISM: Artificial Sequence
<220> FEATURE:
<223> OTHER INFORMATION: Synthesized: L2-1P1 (XPA-23) primer

<400> SEQUENCE: 323
atgcccctaa gctcctgatc wmctctgcaa ccagtctgca aagtggggtc ccatc 55

<210> SEQ ID NO 324
<211> LENGTH: 55
<212> TYPE: DNA
<213> ORGANISM: Artificial Sequence
<220> FEATURE:
<223> OTHER INFORMATION: Synthesized: L2-1P2 (XPA-23) primer

<400> SEQUENCE: 324
atgcccctaa gctcctgatc castctgcaa ccagtctgca aagtggggtc ccatc 55

<210> SEQ ID NO 325
<211> LENGTH: 55
<212> TYPE: DNA
<213> ORGANISM: Artificial Sequence
<220> FEATURE:
<223> OTHER INFORMATION: Synthesized: L2-1A (XPA-23) primer

<400> SEQUENCE: 325
atgcccctaa gctcctgatc gastctgcaa ccagtctgca aagtggggtc ccatc 55

<210> SEQ ID NO 326
<211> LENGTH: 55
<212> TYPE: DNA
<213> ORGANISM: Artificial Sequence
<220> FEATURE:
<223> OTHER INFORMATION: Synthesized: L2-1NP1 (XPA-23) primer
<220> FEATURE:
<221> NAME/KEY: misc_feature
<222> LOCATION: (21)..(21)
<223> OTHER INFORMATION: n is a, c, g, or t

<400> SEQUENCE: 326
atgcccctaa gctcctgatc ntctctgcaa ccagtctgca aagtggggtc ccatc 55

<210> SEQ ID NO 327
<211> LENGTH: 55
<212> TYPE: DNA
<213> ORGANISM: Artificial Sequence
<220> FEATURE:
<223> OTHER INFORMATION: Synthesized: L2-1NP2 (XPA-23) primer

<400> SEQUENCE: 327
atgcccctaa gctcctgatc kggtctgcaa ccagtctgca aagtggggtc ccatc 55

<210> SEQ ID NO 328
<211> LENGTH: 55
<212> TYPE: DNA
<213> ORGANISM: Artificial Sequence
<220> FEATURE:
<223> OTHER INFORMATION: Synthesized: L2-1NP3 (XPA-23) primer

<400> SEQUENCE: 328
atgcccctaa gctcctgatc scgtctgcaa ccagtctgca aagtggggtc ccatc 55

<210> SEQ ID NO 329
<211> LENGTH: 55
<212> TYPE: DNA
<213> ORGANISM: Artificial Sequence
<220> FEATURE:
<223> OTHER INFORMATION: Synthesized: L2-2B (XPA-23) primer

<400> SEQUENCE: 329
atgcccctaa gctcctgatc catarggcaa ccagtctgca aagtggggtc ccatc 55

<210> SEQ ID NO 330
<211> LENGTH: 55
<212> TYPE: DNA
<213> ORGANISM: Artificial Sequence
<220> FEATURE:
<223> OTHER INFORMATION: Synthesized: L2-2P1 (XPA-23) primer

<400> SEQUENCE: 330
atgcccctaa gctcctgatc catwmcgcaa ccagtctgca aagtggggtc ccatc 55

<210> SEQ ID NO 331
<211> LENGTH: 55
<212> TYPE: DNA
<213> ORGANISM: Artificial Sequence
<220> FEATURE:
<223> OTHER INFORMATION: Synthesized: L2-2P2 (XPA-23) primer

<400> SEQUENCE: 331
atgcccctaa gctcctgatc catcasgcaa ccagtctgca aagtggggtc ccatc 55

<210> SEQ ID NO 332
<211> LENGTH: 55
<212> TYPE: DNA
<213> ORGANISM: Artificial Sequence
<220> FEATURE:
<223> OTHER INFORMATION: Synthesized: L2-2A (XPA-23) primer

<400> SEQUENCE: 332
atgcccctaa gctcctgatc catgasgcaa ccagtctgca aagtggggtc ccatc 55

<210> SEQ ID NO 333
<211> LENGTH: 55
<212> TYPE: DNA
<213> ORGANISM: Artificial Sequence
<220> FEATURE:
<223> OTHER INFORMATION: Synthesized: L2-2NP1 (XPA-23) primer
<220> FEATURE:
<221> NAME/KEY: misc_feature
<222> LOCATION: (24)..(24)
<223> OTHER INFORMATION: n is a, c, g, or t

<400> SEQUENCE: 333
atgcccctaa gctcctgatc catntcgcaa ccagtctgca aagtggggtc ccatc 55

<210> SEQ ID NO 334
<211> LENGTH: 55
<212> TYPE: DNA
<213> ORGANISM: Artificial Sequence
<220> FEATURE:
<223> OTHER INFORMATION: Synthesized: L2-2NP2 (XPA-23) primer

<400> SEQUENCE: 334
atgcccctaa gctcctgatc catkgggcaa ccagtctgca aagtggggtc ccatc 55

<210> SEQ ID NO 335
<211> LENGTH: 55
<212> TYPE: DNA
<213> ORGANISM: Artificial Sequence
<220> FEATURE:
<223> OTHER INFORMATION: Synthesized: L2-2NP3 (XPA-23) primer

<400> SEQUENCE: 335
atgcccctaa gctcctgatc catscggcaa ccagtctgca aagtggggtc ccatc 55

<210> SEQ ID NO 336
<211> LENGTH: 55
<212> TYPE: DNA
<213> ORGANISM: Artificial Sequence
<220> FEATURE:
<223> OTHER INFORMATION: Synthesized: L2-3B (XPA-23) primer

<400> SEQUENCE: 336
atgcccctaa gctcctgatc cattctarga ccagtctgca aagtggggtc ccatc 55

<210> SEQ ID NO 337
<211> LENGTH: 55
<212> TYPE: DNA
<213> ORGANISM: Artificial Sequence
<220> FEATURE:
<223> OTHER INFORMATION: Synthesized: L2-3P1 (XPA-23) primer

<400> SEQUENCE: 337
atgcccctaa gctcctgatc cattctwmca ccagtctgca aagtggggtc ccatc 55

<210> SEQ ID NO 338
<211> LENGTH: 55
<212> TYPE: DNA
<213> ORGANISM: Artificial Sequence
<220> FEATURE:
<223> OTHER INFORMATION: Synthesized: L2-3P2 (XPA-23) primer

<400> SEQUENCE: 338
atgcccctaa gctcctgatc cattctcasa ccagtctgca aagtggggtc ccatc 55

<210> SEQ ID NO 339
<211> LENGTH: 55
<212> TYPE: DNA
<213> ORGANISM: Artificial Sequence
<220> FEATURE:
<223> OTHER INFORMATION: Synthesized: L2-3A (XPA-23) primer

<400> SEQUENCE: 339
atgcccctaa gctcctgatc cattctgasa ccagtctgca aagtggggtc ccatc 55

<210> SEQ ID NO 340
<211> LENGTH: 55
<212> TYPE: DNA
<213> ORGANISM: Artificial Sequence
<220> FEATURE:
<223> OTHER INFORMATION: Synthesized: L2-3NP1 (XPA-23) primer
<220> FEATURE:
<221> NAME/KEY: misc_feature
<222> LOCATION: (27)..(27)
<223> OTHER INFORMATION: n is a, c, g, or t

<400> SEQUENCE: 340
atgcccctaa gctcctgatc cattctntca ccagtctgca aagtggggtc ccatc 55

<210> SEQ ID NO 341
<211> LENGTH: 55
<212> TYPE: DNA
<213> ORGANISM: Artificial Sequence
<220> FEATURE:
<223> OTHER INFORMATION: Synthesized: L2-3NP2 (XPA-23) primer

<400> SEQUENCE: 341
atgcccctaa gctcctgatc cattctkgga ccagtctgca aagtggggtc ccatc 55

<210> SEQ ID NO 342
<211> LENGTH: 55
<212> TYPE: DNA
<213> ORGANISM: Artificial Sequence
<220> FEATURE:
<223> OTHER INFORMATION: Synthesized: L2-3NP3 (XPA-23) primer

<400> SEQUENCE: 342
atgcccctaa gctcctgatc cattctscga ccagtctgca aagtggggtc ccatc 55

<210> SEQ ID NO 343
<211> LENGTH: 55
<212> TYPE: DNA
<213> ORGANISM: Artificial Sequence
<220> FEATURE:
<223> OTHER INFORMATION: Synthesized: L2-4B (XPA-23) primer

<400> SEQUENCE: 343
atgcccctaa gctcctgatc cattctgcaa rgagtctgca aagtggggtc ccatc 55

<210> SEQ ID NO 344
<211> LENGTH: 55
<212> TYPE: DNA
<213> ORGANISM: Artificial Sequence
<220> FEATURE:
<223> OTHER INFORMATION: Synthesized: L2-4P1 (XPA-23) primer

<400> SEQUENCE: 344
atgcccctaa gctcctgatc cattctgcaw mcagtctgca aagtggggtc ccatc 55

<210> SEQ ID NO 345
<211> LENGTH: 55
<212> TYPE: DNA
<213> ORGANISM: Artificial Sequence
<220> FEATURE:
<223> OTHER INFORMATION: Synthesized: L2-4P2 (XPA-23) primer

<400> SEQUENCE: 345
atgcccctaa gctcctgatc cattctgcac asagtctgca aagtggggtc ccatc 55

<210> SEQ ID NO 346
<211> LENGTH: 55
<212> TYPE: DNA
<213> ORGANISM: Artificial Sequence
<220> FEATURE:
<223> OTHER INFORMATION: Synthesized: L2-4A (XPA-23) primer

<400> SEQUENCE: 346
atgcccctaa gctcctgatc cattctgcag asagtctgca aagtggggtc ccatc 55

<210> SEQ ID NO 347
<211> LENGTH: 55
<212> TYPE: DNA
<213> ORGANISM: Artificial Sequence
<220> FEATURE:
<223> OTHER INFORMATION: Synthesized: L2-4NP1 (XPA-23) primer
<220> FEATURE:
<221> NAME/KEY: misc_feature
<222> LOCATION: (30)..(30)
<223> OTHER INFORMATION: n is a, c, g, or t

<400> SEQUENCE: 347
atgcccctaa gctcctgatc cattctgcan tcagtctgca aagtggggtc ccatc 55

<210> SEQ ID NO 348
<211> LENGTH: 55
<212> TYPE: DNA
<213> ORGANISM: Artificial Sequence
<220> FEATURE:
<223> OTHER INFORMATION: Synthesized: L2-4NP2 (XPA-23) primer

<400> SEQUENCE: 348
atgcccctaa gctcctgatc cattctgcak ggagtctgca aagtggggtc ccatc 55

<210> SEQ ID NO 349
<211> LENGTH: 55
<212> TYPE: DNA
<213> ORGANISM: Artificial Sequence
<220> FEATURE:
<223> OTHER INFORMATION: Synthesized: L2-4NP3 (XPA-23) primer

<400> SEQUENCE: 349
atgcccctaa gctcctgatc cattctgcas cgagtctgca aagtggggtc ccatc 55

<210> SEQ ID NO 350
<211> LENGTH: 55
<212> TYPE: DNA
<213> ORGANISM: Artificial Sequence
<220> FEATURE:
<223> OTHER INFORMATION: Synthesized: L2-5B (XPA-23) primer

<400> SEQUENCE: 350
atgcccctaa gctcctgatc cattctgcaa ccargctgca aagtggggtc ccatc 55

<210> SEQ ID NO 351
<211> LENGTH: 55
<212> TYPE: DNA
<213> ORGANISM: Artificial Sequence
<220> FEATURE:
<223> OTHER INFORMATION: Synthesized: L2-5P1 (XPA-23) primer

<400> SEQUENCE: 351
atgcccctaa gctcctgatc cattctgcaa ccwmcctgca aagtggggtc ccatc 55

<210> SEQ ID NO 352

<211> LENGTH: 55
<212> TYPE: DNA
<213> ORGANISM: Artificial Sequence
<220> FEATURE:
<223> OTHER INFORMATION: Synthesized: L2-5P2 (XPA-23) primer

<400> SEQUENCE: 352
atgcccctaa gctcctgatc cattctgcaa cccasctgca aagtggggtc ccatc 55

<210> SEQ ID NO 353
<211> LENGTH: 55
<212> TYPE: DNA
<213> ORGANISM: Artificial Sequence
<220> FEATURE:
<223> OTHER INFORMATION: Synthesized: L2-5A (XPA-23) primer

<400> SEQUENCE: 353
atgcccctaa gctcctgatc cattctgcaa ccgasctgca aagtggggtc ccatc 55

<210> SEQ ID NO 354
<211> LENGTH: 55
<212> TYPE: DNA
<213> ORGANISM: Artificial Sequence
<220> FEATURE:
<223> OTHER INFORMATION: Synthesized: L2-5NP1 (XPA-23) primer
<220> FEATURE:
<221> NAME/KEY: misc_feature
<222> LOCATION: (33)..(33)
<223> OTHER INFORMATION: n is a, c, g, or t

<400> SEQUENCE: 354
atgcccctaa gctcctgatc cattctgcaa ccntcctgca aagtggggtc ccatc 55

<210> SEQ ID NO 355
<211> LENGTH: 55
<212> TYPE: DNA
<213> ORGANISM: Artificial Sequence
<220> FEATURE:
<223> OTHER INFORMATION: Synthesized: L2-5NP2 (XPA-23) primer

<400> SEQUENCE: 355
atgcccctaa gctcctgatc cattctgcaa cckggctgca aagtggggtc ccatc 55

<210> SEQ ID NO 356
<211> LENGTH: 55
<212> TYPE: DNA
<213> ORGANISM: Artificial Sequence
<220> FEATURE:
<223> OTHER INFORMATION: Synthesized: L2-5NP3 (XPA-23) primer

<400> SEQUENCE: 356
atgcccctaa gctcctgatc cattctgcaa ccscgctgca aagtggggtc ccatc 55

<210> SEQ ID NO 357
<211> LENGTH: 21
<212> TYPE: DNA
<213> ORGANISM: Artificial Sequence
<220> FEATURE:
<223> OTHER INFORMATION: Synthesized: L3R (XPA-23) primer

<400> SEQUENCE: 357
ctgctgacaa tagtaagttg c 21

<210> SEQ ID NO 358
<211> LENGTH: 57
<212> TYPE: DNA
<213> ORGANISM: Artificial Sequence

```
<220> FEATURE:
<223> OTHER INFORMATION: Synthesized: L3-1B (XPA-23) primer

<400> SEQUENCE: 358

gcaacttact attgtcagca garggacagt ttcccgctca ctttcggcgg agggacc        57


<210> SEQ ID NO 359
<211> LENGTH: 57
<212> TYPE: DNA
<213> ORGANISM: Artificial Sequence
<220> FEATURE:
<223> OTHER INFORMATION: Synthesized: L3-1P1 (XPA-23) primer

<400> SEQUENCE: 359

gcaacttact attgtcagca gwmcgacagt ttcccgctca ctttcggcgg agggacc        57


<210> SEQ ID NO 360
<211> LENGTH: 57
<212> TYPE: DNA
<213> ORGANISM: Artificial Sequence
<220> FEATURE:
<223> OTHER INFORMATION: Synthesized: L3-1P2 (XPA-23) primer

<400> SEQUENCE: 360

gcaacttact attgtcagca gcasgacagt ttcccgctca ctttcggcgg agggacc        57


<210> SEQ ID NO 361
<211> LENGTH: 57
<212> TYPE: DNA
<213> ORGANISM: Artificial Sequence
<220> FEATURE:
<223> OTHER INFORMATION: Synthesized: L3-1A (XPA-23) primer

<400> SEQUENCE: 361

gcaacttact attgtcagca ggasgacagt ttcccgctca ctttcggcgg agggacc        57


<210> SEQ ID NO 362
<211> LENGTH: 57
<212> TYPE: DNA
<213> ORGANISM: Artificial Sequence
<220> FEATURE:
<223> OTHER INFORMATION: Synthesized: L3-1NP1 (XPA-23) primer
<220> FEATURE:
<221> NAME/KEY: misc_feature
<222> LOCATION: (22)..(22)
<223> OTHER INFORMATION: n is a, c, g, or t

<400> SEQUENCE: 362

gcaacttact attgtcagca gntcgacagt ttcccgctca ctttcggcgg agggacc        57


<210> SEQ ID NO 363
<211> LENGTH: 57
<212> TYPE: DNA
<213> ORGANISM: Artificial Sequence
<220> FEATURE:
<223> OTHER INFORMATION: Synthesized: L3-1NP2 (XPA-23) primer

<400> SEQUENCE: 363

gcaacttact attgtcagca gkgggacagt ttcccgctca ctttcggcgg agggacc        57


<210> SEQ ID NO 364
<211> LENGTH: 57
<212> TYPE: DNA
<213> ORGANISM: Artificial Sequence
<220> FEATURE:
<223> OTHER INFORMATION: Synthesized: L3-1NP3 (XPA-23) primer
```

<400> SEQUENCE: 364
gcaacttact attgtcagca gscggacagt ttcccgctca ctttcggcgg agggacc 57

<210> SEQ ID NO 365
<211> LENGTH: 57
<212> TYPE: DNA
<213> ORGANISM: Artificial Sequence
<220> FEATURE:
<223> OTHER INFORMATION: Synthesized: L3-2B (XPA-23) primer

<400> SEQUENCE: 365
gcaacttact attgtcagca ggctargagt ttcccgctca ctttcggcgg agggacc 57

<210> SEQ ID NO 366
<211> LENGTH: 57
<212> TYPE: DNA
<213> ORGANISM: Artificial Sequence
<220> FEATURE:
<223> OTHER INFORMATION: Synthesized: L3-2P1 (XPA-23) primer

<400> SEQUENCE: 366
gcaacttact attgtcagca ggctwmcagt ttcccgctca ctttcggcgg agggacc 57

<210> SEQ ID NO 367
<211> LENGTH: 57
<212> TYPE: DNA
<213> ORGANISM: Artificial Sequence
<220> FEATURE:
<223> OTHER INFORMATION: Synthesized: L3-2P2 (XPA-23) primer

<400> SEQUENCE: 367
gcaacttact attgtcagca ggctcasagt ttcccgctca ctttcggcgg agggacc 57

<210> SEQ ID NO 368
<211> LENGTH: 57
<212> TYPE: DNA
<213> ORGANISM: Artificial Sequence
<220> FEATURE:
<223> OTHER INFORMATION: Synthesized: L3-2A (XPA-23) primer

<400> SEQUENCE: 368
gcaacttact attgtcagca ggctgasagt ttcccgctca ctttcggcgg agggacc 57

<210> SEQ ID NO 369
<211> LENGTH: 57
<212> TYPE: DNA
<213> ORGANISM: Artificial Sequence
<220> FEATURE:
<223> OTHER INFORMATION: Synthesized: L3-2NP1 (XPA-23) primer
<220> FEATURE:
<221> NAME/KEY: misc_feature
<222> LOCATION: (25)..(25)
<223> OTHER INFORMATION: n is a, c, g, or t

<400> SEQUENCE: 369
gcaacttact attgtcagca ggctntcagt ttcccgctca ctttcggcgg agggacc 57

<210> SEQ ID NO 370
<211> LENGTH: 57
<212> TYPE: DNA
<213> ORGANISM: Artificial Sequence
<220> FEATURE:
<223> OTHER INFORMATION: Synthesized: L3-2NP2 (XPA-23) primer

<400> SEQUENCE: 370
gcaacttact attgtcagca ggctkggagt ttcccgctca ctttcggcgg agggacc 57

<210> SEQ ID NO 371
<211> LENGTH: 57
<212> TYPE: DNA
<213> ORGANISM: Artificial Sequence
<220> FEATURE:
<223> OTHER INFORMATION: Synthesized: L3-2NP3 (XPA-23) primer

<400> SEQUENCE: 371
gcaacttact attgtcagca ggctscgagt ttcccgctca ctttcggcgg agggacc 57

<210> SEQ ID NO 372
<211> LENGTH: 57
<212> TYPE: DNA
<213> ORGANISM: Artificial Sequence
<220> FEATURE:
<223> OTHER INFORMATION: Synthesized: L3-3B (XPA-23) primer

<400> SEQUENCE: 372
gcaacttact attgtcagca ggctgacarg ttcccgctca ctttcggcgg agggacc 57

<210> SEQ ID NO 373
<211> LENGTH: 57
<212> TYPE: DNA
<213> ORGANISM: Artificial Sequence
<220> FEATURE:
<223> OTHER INFORMATION: Synthesized: L3-3P1 (XPA-23) primer

<400> SEQUENCE: 373
gcaacttact attgtcagca ggctgacwmc ttcccgctca ctttcggcgg agggacc 57

<210> SEQ ID NO 374
<211> LENGTH: 57
<212> TYPE: DNA
<213> ORGANISM: Artificial Sequence
<220> FEATURE:
<223> OTHER INFORMATION: Synthesized: L3-3P2 (XPA-23) primer

<400> SEQUENCE: 374
gcaacttact attgtcagca ggctgaccas ttcccgctca ctttcggcgg agggacc 57

<210> SEQ ID NO 375
<211> LENGTH: 57
<212> TYPE: DNA
<213> ORGANISM: Artificial Sequence
<220> FEATURE:
<223> OTHER INFORMATION: Synthesized: L3-3A (XPA-23) primer

<400> SEQUENCE: 375
gcaacttact attgtcagca ggctgacgas ttcccgctca ctttcggcgg agggacc 57

<210> SEQ ID NO 376
<211> LENGTH: 57
<212> TYPE: DNA
<213> ORGANISM: Artificial Sequence
<220> FEATURE:
<223> OTHER INFORMATION: Synthesized: L3-3NP1 (XPA-23) primer
<220> FEATURE:
<221> NAME/KEY: misc_feature
<222> LOCATION: (28)..(28)
<223> OTHER INFORMATION: n is a, c, g, or t

<400> SEQUENCE: 376
gcaacttact attgtcagca ggctgacntc ttcccgctca ctttcggcgg agggacc 57

<210> SEQ ID NO 377

<211> LENGTH: 57
<212> TYPE: DNA
<213> ORGANISM: Artificial Sequence
<220> FEATURE:
<223> OTHER INFORMATION: Synthesized: L3-3NP2 (XPA-23) primer

<400> SEQUENCE: 377
gcaacttact attgtcagca ggctgackgg ttcccgctca ctttcggcgg agggacc 57

<210> SEQ ID NO 378
<211> LENGTH: 57
<212> TYPE: DNA
<213> ORGANISM: Artificial Sequence
<220> FEATURE:
<223> OTHER INFORMATION: Synthesized: L3-3NP3 (XPA-23) primer

<400> SEQUENCE: 378
gcaacttact attgtcagca ggctgacscg ttcccgctca ctttcggcgg agggacc 57

<210> SEQ ID NO 379
<211> LENGTH: 57
<212> TYPE: DNA
<213> ORGANISM: Artificial Sequence
<220> FEATURE:
<223> OTHER INFORMATION: Synthesized: L3-4B (XPA-23) primer

<400> SEQUENCE: 379
gcaacttact attgtcagca ggctgacagt argccgctca ctttcggcgg agggacc 57

<210> SEQ ID NO 380
<211> LENGTH: 57
<212> TYPE: DNA
<213> ORGANISM: Artificial Sequence
<220> FEATURE:
<223> OTHER INFORMATION: Synthesized: L3-4P1 (XPA-23) primer

<400> SEQUENCE: 380
gcaacttact attgtcagca ggctgacagt wmcccgctca ctttcggcgg agggacc 57

<210> SEQ ID NO 381
<211> LENGTH: 57
<212> TYPE: DNA
<213> ORGANISM: Artificial Sequence
<220> FEATURE:
<223> OTHER INFORMATION: Synthesized: L3-4P2 (XPA-23) primer

<400> SEQUENCE: 381
gcaacttact attgtcagca ggctgacagt casccgctca ctttcggcgg agggacc 57

<210> SEQ ID NO 382
<211> LENGTH: 57
<212> TYPE: DNA
<213> ORGANISM: Artificial Sequence
<220> FEATURE:
<223> OTHER INFORMATION: Synthesized: L3-4A (XPA-23) primer

<400> SEQUENCE: 382
gcaacttact attgtcagca ggctgacagt gasccgctca ctttcggcgg agggacc 57

<210> SEQ ID NO 383
<211> LENGTH: 57
<212> TYPE: DNA
<213> ORGANISM: Artificial Sequence
<220> FEATURE:
<223> OTHER INFORMATION: Synthesized: L3-4NP1 (XPA-23) primer
<220> FEATURE:
<221> NAME/KEY: misc_feature
<222> LOCATION: (31)..(31)
<223> OTHER INFORMATION: n is a, c, g, or t

<400> SEQUENCE: 383
gcaacttact attgtcagca ggctgacagt ntcccgctca ctttcggcgg agggacc 57

<210> SEQ ID NO 384
<211> LENGTH: 57
<212> TYPE: DNA
<213> ORGANISM: Artificial Sequence
<220> FEATURE:
<223> OTHER INFORMATION: Synthesized: L3-4NP2 (XPA-23) primer

<400> SEQUENCE: 384
gcaacttact attgtcagca ggctgacagt kggccgctca ctttcggcgg agggacc 57

<210> SEQ ID NO 385
<211> LENGTH: 57
<212> TYPE: DNA
<213> ORGANISM: Artificial Sequence
<220> FEATURE:
<223> OTHER INFORMATION: Synthesized: L3-4NP3 (XPA-23) primer

<400> SEQUENCE: 385
gcaacttact attgtcagca ggctgacagt scgccgctca ctttcggcgg agggacc 57

<210> SEQ ID NO 386
<211> LENGTH: 57
<212> TYPE: DNA
<213> ORGANISM: Artificial Sequence
<220> FEATURE:
<223> OTHER INFORMATION: Synthesized: L3-5B (XPA-23) primer

<400> SEQUENCE: 386
gcaacttact attgtcagca ggctgacagt ttcargctca ctttcggcgg agggacc 57

<210> SEQ ID NO 387
<211> LENGTH: 57
<212> TYPE: DNA
<213> ORGANISM: Artificial Sequence
<220> FEATURE:
<223> OTHER INFORMATION: Synthesized: L3-5P1 (XPA-23) primer

<400> SEQUENCE: 387
gcaacttact attgtcagca ggctgacagt ttcwmcctca ctttcggcgg agggacc 57

<210> SEQ ID NO 388
<211> LENGTH: 57
<212> TYPE: DNA
<213> ORGANISM: Artificial Sequence
<220> FEATURE:
<223> OTHER INFORMATION: Synthesized: L3-5P2 (XPA-23) primer

<400> SEQUENCE: 388
gcaacttact attgtcagca ggctgacagt ttccasctca ctttcggcgg agggacc 57

<210> SEQ ID NO 389
<211> LENGTH: 57
<212> TYPE: DNA
<213> ORGANISM: Artificial Sequence
<220> FEATURE:
<223> OTHER INFORMATION: Synthesized: L3-5A (XPA-23) primer

<400> SEQUENCE: 389
gcaacttact attgtcagca ggctgacagt ttcgasctca ctttcggcgg agggacc 57

<210> SEQ ID NO 390
<211> LENGTH: 57
<212> TYPE: DNA
<213> ORGANISM: Artificial Sequence
<220> FEATURE:
<223> OTHER INFORMATION: Synthesized: L3-5NP1 (XPA-23) primer
<220> FEATURE:
<221> NAME/KEY: misc_feature
<222> LOCATION: (34)..(34)
<223> OTHER INFORMATION: n is a, c, g, or t

<400> SEQUENCE: 390
gcaacttact attgtcagca ggctgacagt ttcntcctca ctttcggcgg agggacc 57

<210> SEQ ID NO 391
<211> LENGTH: 57
<212> TYPE: DNA
<213> ORGANISM: Artificial Sequence
<220> FEATURE:
<223> OTHER INFORMATION: Synthesized: L3-5NP2 (XPA-23) primer

<400> SEQUENCE: 391
gcaacttact attgtcagca ggctgacagt ttckggctca ctttcggcgg agggacc 57

<210> SEQ ID NO 392
<211> LENGTH: 57
<212> TYPE: DNA
<213> ORGANISM: Artificial Sequence
<220> FEATURE:
<223> OTHER INFORMATION: Synthesized: L3-5NP3 (XPA-23) primer

<400> SEQUENCE: 392
gcaacttact attgtcagca ggctgacagt ttcscgctca ctttcggcgg agggacc 57

<210> SEQ ID NO 393
<211> LENGTH: 57
<212> TYPE: DNA
<213> ORGANISM: Artificial Sequence
<220> FEATURE:
<223> OTHER INFORMATION: Synthesized: L3-6B (XPA-23) primer

<400> SEQUENCE: 393
gcaacttact attgtcagca ggctgacagt ttcccgarga ctttcggcgg agggacc 57

<210> SEQ ID NO 394
<211> LENGTH: 57
<212> TYPE: DNA
<213> ORGANISM: Artificial Sequence
<220> FEATURE:
<223> OTHER INFORMATION: Synthesized: L3-6P1 (XPA-23) primer

<400> SEQUENCE: 394
gcaacttact attgtcagca ggctgacagt ttcccgwmca ctttcggcgg agggacc 57

<210> SEQ ID NO 395
<211> LENGTH: 57
<212> TYPE: DNA
<213> ORGANISM: Artificial Sequence
<220> FEATURE:
<223> OTHER INFORMATION: Synthesized: L3-6P2 (XPA-23) primer

<400> SEQUENCE: 395
gcaacttact attgtcagca ggctgacagt ttcccgcasa ctttcggcgg agggacc 57

<210> SEQ ID NO 396
<211> LENGTH: 57

<212> TYPE: DNA
<213> ORGANISM: Artificial Sequence
<220> FEATURE:
<223> OTHER INFORMATION: Synthesized: L3-6A (XPA-23) primer

<400> SEQUENCE: 396
gcaacttact attgtcagca ggctgacagt ttcccggasa ctttcggcgg agggacc 57

<210> SEQ ID NO 397
<211> LENGTH: 57
<212> TYPE: DNA
<213> ORGANISM: Artificial Sequence
<220> FEATURE:
<223> OTHER INFORMATION: Synthesized: L3-6NP1 (XPA-23) primer
<220> FEATURE:
<221> NAME/KEY: misc_feature
<222> LOCATION: (37)..(37)
<223> OTHER INFORMATION: n is a, c, g, or t

<400> SEQUENCE: 397
gcaacttact attgtcagca ggctgacagt ttcccgntca ctttcggcgg agggacc 57

<210> SEQ ID NO 398
<211> LENGTH: 57
<212> TYPE: DNA
<213> ORGANISM: Artificial Sequence
<220> FEATURE:
<223> OTHER INFORMATION: Synthesized: L3-6NP2 (XPA-23) primer

<400> SEQUENCE: 398
gcaacttact attgtcagca ggctgacagt ttcccgkgga ctttcggcgg agggacc 57

<210> SEQ ID NO 399
<211> LENGTH: 57
<212> TYPE: DNA
<213> ORGANISM: Artificial Sequence
<220> FEATURE:
<223> OTHER INFORMATION: Synthesized: L3-6NP3 (XPA-23) primer

<400> SEQUENCE: 399
gcaacttact attgtcagca ggctgacagt ttcccgscga ctttcggcgg agggacc 57

<210> SEQ ID NO 400
<211> LENGTH: 20
<212> TYPE: DNA
<213> ORGANISM: Artificial Sequence
<220> FEATURE:
<223> OTHER INFORMATION: Synthesized: H1R (XPA-23) primer

<400> SEQUENCE: 400
gaatccggaa gcagcgcaag 20

<210> SEQ ID NO 401
<211> LENGTH: 54
<212> TYPE: DNA
<213> ORGANISM: Artificial Sequence
<220> FEATURE:
<223> OTHER INFORMATION: Synthesized: H1-1B (XPA-23) primer

<400> SEQUENCE: 401
cttgcgctgc ttccggattc argttctcta agtactttat gttttgggtt cgcc 54

<210> SEQ ID NO 402
<211> LENGTH: 54
<212> TYPE: DNA
<213> ORGANISM: Artificial Sequence
<220> FEATURE:

<223> OTHER INFORMATION: Synthesized: H1-1P1 (XPA-23) primer

<400> SEQUENCE: 402
cttgcgctgc ttccggattc wmcttctcta agtactttat gttttgggtt cgcc 54

<210> SEQ ID NO 403
<211> LENGTH: 54
<212> TYPE: DNA
<213> ORGANISM: Artificial Sequence
<220> FEATURE:
<223> OTHER INFORMATION: Synthesized: H1-1P2 (XPA-23) primer

<400> SEQUENCE: 403
cttgcgctgc ttccggattc casttctcta agtactttat gttttgggtt cgcc 54

<210> SEQ ID NO 404
<211> LENGTH: 54
<212> TYPE: DNA
<213> ORGANISM: Artificial Sequence
<220> FEATURE:
<223> OTHER INFORMATION: Synthesized: H1-1A (XPA-23) primer

<400> SEQUENCE: 404
cttgcgctgc ttccggattc gasttctcta agtactttat gttttgggtt cgcc 54

<210> SEQ ID NO 405
<211> LENGTH: 54
<212> TYPE: DNA
<213> ORGANISM: Artificial Sequence
<220> FEATURE:
<223> OTHER INFORMATION: Synthesized: H1-1NP1 (XPA-23) primer
<220> FEATURE:
<221> NAME/KEY: misc_feature
<222> LOCATION: (21)..(21)
<223> OTHER INFORMATION: n is a, c, g, or t

<400> SEQUENCE: 405
cttgcgctgc ttccggattc ntcttctcta agtactttat gttttgggtt cgcc 54

<210> SEQ ID NO 406
<211> LENGTH: 54
<212> TYPE: DNA
<213> ORGANISM: Artificial Sequence
<220> FEATURE:
<223> OTHER INFORMATION: Synthesized: H1-1NP3 (XPA-23) primer

<400> SEQUENCE: 406
cttgcgctgc ttccggattc scgttctcta agtactttat gttttgggtt cgcc 54

<210> SEQ ID NO 407
<211> LENGTH: 54
<212> TYPE: DNA
<213> ORGANISM: Artificial Sequence
<220> FEATURE:
<223> OTHER INFORMATION: Synthesized: H1-2B (XPA-23) primer

<400> SEQUENCE: 407
cttgcgctgc ttccggattc actttcarga agtactttat gttttgggtt cgcc 54

<210> SEQ ID NO 408
<211> LENGTH: 54
<212> TYPE: DNA
<213> ORGANISM: Artificial Sequence
<220> FEATURE:
<223> OTHER INFORMATION: Synthesized: H1-2P1 (XPA-23) primer

<400> SEQUENCE: 408
cttgcgctgc ttccggattc actttcwmca agtactttat gttttgggtt cgcc 54

<210> SEQ ID NO 409
<211> LENGTH: 54
<212> TYPE: DNA
<213> ORGANISM: Artificial Sequence
<220> FEATURE:
<223> OTHER INFORMATION: Synthesized: H1-2P2 (XPA-23) primer

<400> SEQUENCE: 409
cttgcgctgc ttccggattc actttccasa agtactttat gttttgggtt cgcc 54

<210> SEQ ID NO 410
<211> LENGTH: 54
<212> TYPE: DNA
<213> ORGANISM: Artificial Sequence
<220> FEATURE:
<223> OTHER INFORMATION: Synthesized: H1-2A (XPA-23) primer

<400> SEQUENCE: 410
cttgcgctgc ttccggattc actttcgasa agtactttat gttttgggtt cgcc 54

<210> SEQ ID NO 411
<211> LENGTH: 54
<212> TYPE: DNA
<213> ORGANISM: Artificial Sequence
<220> FEATURE:
<223> OTHER INFORMATION: Synthesized: H1-2NP1 (XPA-23) primer
<220> FEATURE:
<221> NAME/KEY: misc_feature
<222> LOCATION: (27)..(27)
<223> OTHER INFORMATION: n is a, c, g, or t

<400> SEQUENCE: 411
cttgcgctgc ttccggattc actttcntca agtactttat gttttgggtt cgcc 54

<210> SEQ ID NO 412
<211> LENGTH: 54
<212> TYPE: DNA
<213> ORGANISM: Artificial Sequence
<220> FEATURE:
<223> OTHER INFORMATION: Synthesized: H1-2NP2 (XPA-23) primer

<400> SEQUENCE: 412
cttgcgctgc ttccggattc actttckgga agtactttat gttttgggtt cgcc 54

<210> SEQ ID NO 413
<211> LENGTH: 54
<212> TYPE: DNA
<213> ORGANISM: Artificial Sequence
<220> FEATURE:
<223> OTHER INFORMATION: Synthesized: H1-2NP3 (XPA-23) primer

<400> SEQUENCE: 413
cttgcgctgc ttccggattc actttcscga agtactttat gttttgggtt cgcc 54

<210> SEQ ID NO 414
<211> LENGTH: 54
<212> TYPE: DNA
<213> ORGANISM: Artificial Sequence
<220> FEATURE:
<223> OTHER INFORMATION: Synthesized: H1-3B (XPA-23) primer

<400> SEQUENCE: 414
cttgcgctgc ttccggattc actttctcta rgtactttat gttttgggtt cgcc 54

<210> SEQ ID NO 415
<211> LENGTH: 54
<212> TYPE: DNA
<213> ORGANISM: Artificial Sequence
<220> FEATURE:
<223> OTHER INFORMATION: Synthesized: H1-3P1 (XPA-23) primer

<400> SEQUENCE: 415
cttgcgctgc ttccggattc actttctctw mctactttat gttttgggtt cgcc 54

<210> SEQ ID NO 416
<211> LENGTH: 54
<212> TYPE: DNA
<213> ORGANISM: Artificial Sequence
<220> FEATURE:
<223> OTHER INFORMATION: Synthesized: H1-3P2 (XPA-23) primer

<400> SEQUENCE: 416
cttgcgctgc ttccggattc actttctctc astactttat gttttgggtt cgcc 54

<210> SEQ ID NO 417
<211> LENGTH: 54
<212> TYPE: DNA
<213> ORGANISM: Artificial Sequence
<220> FEATURE:
<223> OTHER INFORMATION: Synthesized: H1-3A (XPA-23) primer

<400> SEQUENCE: 417
cttgcgctgc ttccggattc actttctctg astactttat gttttgggtt cgcc 54

<210> SEQ ID NO 418
<211> LENGTH: 54
<212> TYPE: DNA
<213> ORGANISM: Artificial Sequence
<220> FEATURE:
<223> OTHER INFORMATION: Synthesized: H1-3NP1 (XPA-23) primer
<220> FEATURE:
<221> NAME/KEY: misc_feature
<222> LOCATION: (30)..(30)
<223> OTHER INFORMATION: n is a, c, g, or t

<400> SEQUENCE: 418
cttgcgctgc ttccggattc actttctctn tctactttat gttttgggtt cgcc 54

<210> SEQ ID NO 419
<211> LENGTH: 54
<212> TYPE: DNA
<213> ORGANISM: Artificial Sequence
<220> FEATURE:
<223> OTHER INFORMATION: Synthesized: H1-3NP2 (XPA-23) primer

<400> SEQUENCE: 419
cttgcgctgc ttccggattc actttctctk ggtactttat gttttgggtt cgcc 54

<210> SEQ ID NO 420
<211> LENGTH: 54
<212> TYPE: DNA
<213> ORGANISM: Artificial Sequence
<220> FEATURE:
<223> OTHER INFORMATION: Synthesized: H1-3NP3 (XPA-23) primer

<400> SEQUENCE: 420
cttgcgctgc ttccggattc actttctcts cgtactttat gttttgggtt cgcc 54

<210> SEQ ID NO 421
<211> LENGTH: 22

<212> TYPE: DNA
<213> ORGANISM: Artificial Sequence
<220> FEATURE:
<223> OTHER INFORMATION: Synthesized: H12R (XPA-23) primer

<400> SEQUENCE: 421
cttagagaaa gtgaatccgg aa 22

<210> SEQ ID NO 422
<211> LENGTH: 53
<212> TYPE: DNA
<213> ORGANISM: Artificial Sequence
<220> FEATURE:
<223> OTHER INFORMATION: Synthesized: H12-1B (XPA-23) primer

<400> SEQUENCE: 422
ttccggattc actttctcta agargtttat gttttgggtt cgccaagctc ctg 53

<210> SEQ ID NO 423
<211> LENGTH: 53
<212> TYPE: DNA
<213> ORGANISM: Artificial Sequence
<220> FEATURE:
<223> OTHER INFORMATION: Synthesized: H12-1P1 (XPA-23) primer

<400> SEQUENCE: 423
ttccggattc actttctcta agwmctttat gttttgggtt cgccaagctc ctg 53

<210> SEQ ID NO 424
<211> LENGTH: 53
<212> TYPE: DNA
<213> ORGANISM: Artificial Sequence
<220> FEATURE:
<223> OTHER INFORMATION: Synthesized: H12-1P2 (XPA-23) primer

<400> SEQUENCE: 424
ttccggattc actttctcta agcastttat gttttgggtt cgccaagctc ctg 53

<210> SEQ ID NO 425
<211> LENGTH: 53
<212> TYPE: DNA
<213> ORGANISM: Artificial Sequence
<220> FEATURE:
<223> OTHER INFORMATION: Synthesized: H12-1A (XPA-23) primer

<400> SEQUENCE: 425
ttccggattc actttctcta aggastttat gttttgggtt cgccaagctc ctg 53

<210> SEQ ID NO 426
<211> LENGTH: 53
<212> TYPE: DNA
<213> ORGANISM: Artificial Sequence
<220> FEATURE:
<223> OTHER INFORMATION: Synthesized: H12-1NP1 (XPA-23) primer_
<220> FEATURE:
<221> NAME/KEY: misc_feature
<222> LOCATION: (23)..(23)
<223> OTHER INFORMATION: n is a, c, g, or t

<400> SEQUENCE: 426
ttccggattc actttctcta agntctttat gttttgggtt cgccaagctc ctg 53

<210> SEQ ID NO 427
<211> LENGTH: 53
<212> TYPE: DNA
<213> ORGANISM: Artificial Sequence
<220> FEATURE:

<223> OTHER INFORMATION: Synthesized: H12-1NP2 (XPA-23) primer

<400> SEQUENCE: 427
ttccggattc actttctcta agkggtttat gttttgggtt cgccaagctc ctg 53

<210> SEQ ID NO 428
<211> LENGTH: 53
<212> TYPE: DNA
<213> ORGANISM: Artificial Sequence
<220> FEATURE:
<223> OTHER INFORMATION: Synthesized: H12-1NP3 (XPA-23) primer

<400> SEQUENCE: 428
ttccggattc actttctcta agscgtttat gttttgggtt cgccaagctc ctg 53

<210> SEQ ID NO 429
<211> LENGTH: 53
<212> TYPE: DNA
<213> ORGANISM: Artificial Sequence
<220> FEATURE:
<223> OTHER INFORMATION: Synthesized: H12-2B (XPA-23) primer

<400> SEQUENCE: 429
ttccggattc actttctcta agtacargat gttttgggtt cgccaagctc ctg 53

<210> SEQ ID NO 430
<211> LENGTH: 53
<212> TYPE: DNA
<213> ORGANISM: Artificial Sequence
<220> FEATURE:
<223> OTHER INFORMATION: Synthesized: H12-2P1 (XPA-23) primer

<400> SEQUENCE: 430
ttccggattc actttctcta agtacwmcat gttttgggtt cgccaagctc ctg 53

<210> SEQ ID NO 431
<211> LENGTH: 53
<212> TYPE: DNA
<213> ORGANISM: Artificial Sequence
<220> FEATURE:
<223> OTHER INFORMATION: Synthesized: H12-2P2 (XPA- 23)

<400> SEQUENCE: 431
ttccggattc actttctcta agtaccasat gttttgggtt cgccaagctc ctg 53

<210> SEQ ID NO 432
<211> LENGTH: 53
<212> TYPE: DNA
<213> ORGANISM: Artificial Sequence
<220> FEATURE:
<223> OTHER INFORMATION: Synthesized: H12-2A (XPA-23) primer

<400> SEQUENCE: 432
ttccggattc actttctcta agtacgasat gttttgggtt cgccaagctc ctg 53

<210> SEQ ID NO 433
<211> LENGTH: 53
<212> TYPE: DNA
<213> ORGANISM: Artificial Sequence
<220> FEATURE:
<223> OTHER INFORMATION: Synthesized: H12-2NP1 (XPA-23) primer
<220> FEATURE:
<221> NAME/KEY: misc_feature
<222> LOCATION: (26)..(26)
<223> OTHER INFORMATION: n is a, c, g, or t

<400> SEQUENCE: 433
ttccggattc actttctcta agtacntcat gttttgggtt cgccaagctc ctg 53

<210> SEQ ID NO 434
<211> LENGTH: 53
<212> TYPE: DNA
<213> ORGANISM: Artificial Sequence
<220> FEATURE:
<223> OTHER INFORMATION: Synthesized: H12-2NP2 (XPA-23) primer

<400> SEQUENCE: 434
ttccggattc actttctcta agtackggat gttttgggtt cgccaagctc ctg 53

<210> SEQ ID NO 435
<211> LENGTH: 53
<212> TYPE: DNA
<213> ORGANISM: Artificial Sequence
<220> FEATURE:
<223> OTHER INFORMATION: Synthesized: H12-2NP3 (XPA-23) primer

<400> SEQUENCE: 435
ttccggattc actttctcta agtacscgat gttttgggtt cgccaagctc ctg 53

<210> SEQ ID NO 436
<211> LENGTH: 53
<212> TYPE: DNA
<213> ORGANISM: Artificial Sequence
<220> FEATURE:
<223> OTHER INFORMATION: Synthesized: H12-3B (XPA-23) primer

<400> SEQUENCE: 436
ttccggattc actttctcta agtactttat gargtgggtt cgccaagctc ctg 53

<210> SEQ ID NO 437
<211> LENGTH: 53
<212> TYPE: DNA
<213> ORGANISM: Artificial Sequence
<220> FEATURE:
<223> OTHER INFORMATION: Synthesized: H12-3P1 (XPA-23) primer

<400> SEQUENCE: 437
ttccggattc actttctcta agtactttat gwmctgggtt cgccaagctc ctg 53

<210> SEQ ID NO 438
<211> LENGTH: 53
<212> TYPE: DNA
<213> ORGANISM: Artificial Sequence
<220> FEATURE:
<223> OTHER INFORMATION: Synthesized: H12-3P2 (XPA-23) primer

<400> SEQUENCE: 438
ttccggattc actttctcta agtactttat gcastgggtt cgccaagctc ctg 53

<210> SEQ ID NO 439
<211> LENGTH: 53
<212> TYPE: DNA
<213> ORGANISM: Artificial Sequence
<220> FEATURE:
<223> OTHER INFORMATION: Synthesized: H12-3A (XPA-23) primer

<400> SEQUENCE: 439
ttccggattc actttctcta agtactttat ggastgggtt cgccaagctc ctg 53

<210> SEQ ID NO 440
<211> LENGTH: 53
<212> TYPE: DNA

<213> ORGANISM: Artificial Sequence
<220> FEATURE:
<223> OTHER INFORMATION: Synthesized: H12-3NP1 (XPA-23) primer
<220> FEATURE:
<221> NAME/KEY: misc_feature
<222> LOCATION: (32)..(32)
<223> OTHER INFORMATION: n is a, c, g, or t

<400> SEQUENCE: 440
ttccggattc actttctcta agtactttat gntctgggtt cgccaagctc ctg 53

<210> SEQ ID NO 441
<211> LENGTH: 53
<212> TYPE: DNA
<213> ORGANISM: Artificial Sequence
<220> FEATURE:
<223> OTHER INFORMATION: Synthesized: H12-3NP2 (XPA-23) primer

<400> SEQUENCE: 441
ttccggattc actttctcta agtactttat gkggtgggtt cgccaagctc ctg 53

<210> SEQ ID NO 442
<211> LENGTH: 53
<212> TYPE: DNA
<213> ORGANISM: Artificial Sequence
<220> FEATURE:
<223> OTHER INFORMATION: Synthesized: H12-3NP3 (XPA-23) primer

<400> SEQUENCE: 442
ttccggattc actttctcta agtactttat gscgtgggtt cgccaagctc ctg 53

<210> SEQ ID NO 443
<211> LENGTH: 22
<212> TYPE: DNA
<213> ORGANISM: Artificial Sequence
<220> FEATURE:
<223> OTHER INFORMATION: Synthesized: H2R (XPA-23) primer

<400> SEQUENCE: 443
agaaacccac tccaaacctt ta 22

<210> SEQ ID NO 444
<211> LENGTH: 57
<212> TYPE: DNA
<213> ORGANISM: Artificial Sequence
<220> FEATURE:
<223> OTHER INFORMATION: Synthesized: H2-1B (XPA-23) primer

<400> SEQUENCE: 444
taaaggtttg gagtgggttt ctargatctc tccttctggt ggcatgactc gttatgc 57

<210> SEQ ID NO 445
<211> LENGTH: 57
<212> TYPE: DNA
<213> ORGANISM: Artificial Sequence
<220> FEATURE:
<223> OTHER INFORMATION: Synthesized: H2-1P1 (XPA-23) primer

<400> SEQUENCE: 445
taaaggtttg gagtgggttt ctwmcatctc tccttctggt ggcatgactc gttatgc 57

<210> SEQ ID NO 446
<211> LENGTH: 57
<212> TYPE: DNA
<213> ORGANISM: Artificial Sequence
<220> FEATURE:
<223> OTHER INFORMATION: Synthesized: H2-1P2 (XPA-23) primer

<400> SEQUENCE: 446
taaaggtttg gagtgggttt ctcasatctc tccttctggt ggcatgactc gttatgc 57

<210> SEQ ID NO 447
<211> LENGTH: 57
<212> TYPE: DNA
<213> ORGANISM: Artificial Sequence
<220> FEATURE:
<223> OTHER INFORMATION: Synthesized: H2-1A (XPA-23) primer

<400> SEQUENCE: 447
taaaggtttg gagtgggttt ctgasatctc tccttctggt ggcatgactc gttatgc 57

<210> SEQ ID NO 448
<211> LENGTH: 57
<212> TYPE: DNA
<213> ORGANISM: Artificial Sequence
<220> FEATURE:
<223> OTHER INFORMATION: Synthesized: H2-1NP1 (XPA-23) primer
<220> FEATURE:
<221> NAME/KEY: misc_feature
<222> LOCATION: (23)..(23)
<223> OTHER INFORMATION: n is a, c, g, or t

<400> SEQUENCE: 448
taaaggtttg gagtgggttt ctntcatctc tccttctggt ggcatgactc gttatgc 57

<210> SEQ ID NO 449
<211> LENGTH: 57
<212> TYPE: DNA
<213> ORGANISM: Artificial Sequence
<220> FEATURE:
<223> OTHER INFORMATION: Synthesized: H2-1NP2 (XPA-23) primer

<400> SEQUENCE: 449
taaaggtttg gagtgggttt ctkggatctc tccttctggt ggcatgactc gttatgc 57

<210> SEQ ID NO 450
<211> LENGTH: 57
<212> TYPE: DNA
<213> ORGANISM: Artificial Sequence
<220> FEATURE:
<223> OTHER INFORMATION: Synthesized: H2-1NP3 (XPA-23) primer

<400> SEQUENCE: 450
taaaggtttg gagtgggttt ctscgatctc tccttctggt ggcatgactc gttatgc 57

<210> SEQ ID NO 451
<211> LENGTH: 57
<212> TYPE: DNA
<213> ORGANISM: Artificial Sequence
<220> FEATURE:
<223> OTHER INFORMATION: Synthesized: H2-2B (XPA-23) primer

<400> SEQUENCE: 451
taaaggtttg gagtgggttt ctgttargtc tccttctggt ggcatgactc gttatgc 57

<210> SEQ ID NO 452
<211> LENGTH: 57
<212> TYPE: DNA
<213> ORGANISM: Artificial Sequence
<220> FEATURE:
<223> OTHER INFORMATION: Synthesized: H2-2P1 (XPA-23) primer

<400> SEQUENCE: 452
taaaggtttg gagtgggttt ctgttwmctc tccttctggt ggcatgactc gttatgc 57

<210> SEQ ID NO 453
<211> LENGTH: 57
<212> TYPE: DNA
<213> ORGANISM: Artificial Sequence
<220> FEATURE:
<223> OTHER INFORMATION: Synthesized: H2-2P2 (XPA-23) primer

<400> SEQUENCE: 453
taaaggtttg gagtgggttt ctgttcastc tccttctggt ggcatgactc gttatgc 57

<210> SEQ ID NO 454
<211> LENGTH: 57
<212> TYPE: DNA
<213> ORGANISM: Artificial Sequence
<220> FEATURE:
<223> OTHER INFORMATION: Synthesized: H2-2A (XPA-23) primer

<400> SEQUENCE: 454
taaaggtttg gagtgggttt ctgttgastc tccttctggt ggcatgactc gttatgc 57

<210> SEQ ID NO 455
<211> LENGTH: 57
<212> TYPE: DNA
<213> ORGANISM: Artificial Sequence
<220> FEATURE:
<223> OTHER INFORMATION: Synthesized: H2-2NP1 (XPA-23) primer
<220> FEATURE:
<221> NAME/KEY: misc_feature
<222> LOCATION: (26)..(26)
<223> OTHER INFORMATION: n is a, c, g, or t

<400> SEQUENCE: 455
taaaggtttg gagtgggttt ctgttntctc tccttctggt ggcatgactc gttatgc 57

<210> SEQ ID NO 456
<211> LENGTH: 57
<212> TYPE: DNA
<213> ORGANISM: Artificial Sequence
<220> FEATURE:
<223> OTHER INFORMATION: Synthesized: H2-2NP2 (XPA-23) primer

<400> SEQUENCE: 456
taaaggtttg gagtgggttt ctgttkggtc tccttctggt ggcatgactc gttatgc 57

<210> SEQ ID NO 457
<211> LENGTH: 57
<212> TYPE: DNA
<213> ORGANISM: Artificial Sequence
<220> FEATURE:
<223> OTHER INFORMATION: Synthesized: H2-2NP3 (XPA-23) primer

<400> SEQUENCE: 457
taaaggtttg gagtgggttt ctgttscgtc tccttctggt ggcatgactc gttatgc 57

<210> SEQ ID NO 458
<211> LENGTH: 57
<212> TYPE: DNA
<213> ORGANISM: Artificial Sequence
<220> FEATURE:
<223> OTHER INFORMATION: Synthesized: H2-3B (XPA-23) primer

<400> SEQUENCE: 458
taaaggtttg gagtgggttt ctgttatcar gccttctggt ggcatgactc gttatgc 57

<210> SEQ ID NO 459
<211> LENGTH: 57
<212> TYPE: DNA
<213> ORGANISM: Artificial Sequence
<220> FEATURE:
<223> OTHER INFORMATION: Synthesized: H2-3P1 (XPA-23) primer

<400> SEQUENCE: 459
taaaggtttg gagtgggttt ctgttatcwm cccttctggt ggcatgactc gttatgc 57

<210> SEQ ID NO 460
<211> LENGTH: 57
<212> TYPE: DNA
<213> ORGANISM: Artificial Sequence
<220> FEATURE:
<223> OTHER INFORMATION: Synthesized: H2-3P2 (XPA-23) primer

<400> SEQUENCE: 460
taaaggtttg gagtgggttt ctgttatcca sccttctggt ggcatgactc gttatgc 57

<210> SEQ ID NO 461
<211> LENGTH: 57
<212> TYPE: DNA
<213> ORGANISM: Artificial Sequence
<220> FEATURE:
<223> OTHER INFORMATION: Synthesized: H2-3A (XPA-23) primer

<400> SEQUENCE: 461
taaaggtttg gagtgggttt ctgttatcga sccttctggt ggcatgactc gttatgc 57

<210> SEQ ID NO 462
<211> LENGTH: 57
<212> TYPE: DNA
<213> ORGANISM: Artificial Sequence
<220> FEATURE:
<223> OTHER INFORMATION: Synthesized: H2-3NP1 (XPA-23) primer
<220> FEATURE:
<221> NAME/KEY: misc_feature
<222> LOCATION: (29)..(29)
<223> OTHER INFORMATION: n is a, c, g, or t

<400> SEQUENCE: 462
taaaggtttg gagtgggttt ctgttatcnt cccttctggt ggcatgactc gttatgc 57

<210> SEQ ID NO 463
<211> LENGTH: 57
<212> TYPE: DNA
<213> ORGANISM: Artificial Sequence
<220> FEATURE:
<223> OTHER INFORMATION: Synthesized: H2-3NP2 (XPA-23) primer

<400> SEQUENCE: 463
taaaggtttg gagtgggttt ctgttatckg gccttctggt ggcatgactc gttatgc 57

<210> SEQ ID NO 464
<211> LENGTH: 57
<212> TYPE: DNA
<213> ORGANISM: Artificial Sequence
<220> FEATURE:
<223> OTHER INFORMATION: Synthesized: H2-3NP3 (XPA-23) primer

<400> SEQUENCE: 464
taaaggtttg gagtgggttt ctgttatcsc gccttctggt ggcatgactc gttatgc 57

<210> SEQ ID NO 465
<211> LENGTH: 57
<212> TYPE: DNA

<213> ORGANISM: Artificial Sequence
<220> FEATURE:
<223> OTHER INFORMATION: Synthesized: H2-4B (XPA-23) primer

<400> SEQUENCE: 465
taaaggtttg gagtgggttt ctgttatctc targtctggt ggcatgactc gttatgc 57

<210> SEQ ID NO 466
<211> LENGTH: 57
<212> TYPE: DNA
<213> ORGANISM: Artificial Sequence
<220> FEATURE:
<223> OTHER INFORMATION: Synthesized: H2-4P1 (XPA-23) primer

<400> SEQUENCE: 466
taaaggtttg gagtgggttt ctgttatctc twmctctggt ggcatgactc gttatgc 57

<210> SEQ ID NO 467
<211> LENGTH: 57
<212> TYPE: DNA
<213> ORGANISM: Artificial Sequence
<220> FEATURE:
<223> OTHER INFORMATION: Synthesized: H2-4P2 (XPA-23) primer

<400> SEQUENCE: 467
taaaggtttg gagtgggttt ctgttatctc tcastctggt ggcatgactc gttatgc 57

<210> SEQ ID NO 468
<211> LENGTH: 57
<212> TYPE: DNA
<213> ORGANISM: Artificial Sequence
<220> FEATURE:
<223> OTHER INFORMATION: Synthesized: H2-4A (XPA-23) primer

<400> SEQUENCE: 468
taaaggtttg gagtgggttt ctgttatctc tgastctggt ggcatgactc gttatgc 57

<210> SEQ ID NO 469
<211> LENGTH: 57
<212> TYPE: DNA
<213> ORGANISM: Artificial Sequence
<220> FEATURE:
<223> OTHER INFORMATION: Synthesized: H2-4NP1 (XPA-23) primer
<220> FEATURE:
<221> NAME/KEY: misc_feature
<222> LOCATION: (32)..(32)
<223> OTHER INFORMATION: n is a, c, g, or t

<400> SEQUENCE: 469
taaaggtttg gagtgggttt ctgttatctc tntctctggt ggcatgactc gttatgc 57

<210> SEQ ID NO 470
<211> LENGTH: 57
<212> TYPE: DNA
<213> ORGANISM: Artificial Sequence
<220> FEATURE:
<223> OTHER INFORMATION: Synthesized: H2-4NP2 (XPA-23) primer

<400> SEQUENCE: 470
taaaggtttg gagtgggttt ctgttatctc tkggtctggt ggcatgactc gttatgc 57

<210> SEQ ID NO 471
<211> LENGTH: 57
<212> TYPE: DNA
<213> ORGANISM: Artificial Sequence
<220> FEATURE:
<223> OTHER INFORMATION: Synthesized: H2-4NP3 (XPA-23) primer

<400> SEQUENCE: 471
taaaggtttg gagtgggttt ctgttatctc tscgtctggt ggcatgactc gttatgc 57

<210> SEQ ID NO 472
<211> LENGTH: 57
<212> TYPE: DNA
<213> ORGANISM: Artificial Sequence
<220> FEATURE:
<223> OTHER INFORMATION: Synthesized: H2-5B (XPA-23) primer

<400> SEQUENCE: 472
taaaggtttg gagtgggttt ctgttatctc tcctargggt ggcatgactc gttatgc 57

<210> SEQ ID NO 473
<211> LENGTH: 57
<212> TYPE: DNA
<213> ORGANISM: Artificial Sequence
<220> FEATURE:
<223> OTHER INFORMATION: Synthesized: H2-5P1 (XPA-23) primer

<400> SEQUENCE: 473
taaaggtttg gagtgggttt ctgttatctc tcctwmcggt ggcatgactc gttatgc 57

<210> SEQ ID NO 474
<211> LENGTH: 57
<212> TYPE: DNA
<213> ORGANISM: Artificial Sequence
<220> FEATURE:
<223> OTHER INFORMATION: Synthesized: H2-5P2 (XPA-23) primer

<400> SEQUENCE: 474
taaaggtttg gagtgggttt ctgttatctc tcctcasggt ggcatgactc gttatgc 57

<210> SEQ ID NO 475
<211> LENGTH: 57
<212> TYPE: DNA
<213> ORGANISM: Artificial Sequence
<220> FEATURE:
<223> OTHER INFORMATION: Synthesized: H2-5A (XPA-23) primer

<400> SEQUENCE: 475
taaaggtttg gagtgggttt ctgttatctc tcctgasggt ggcatgactc gttatgc 57

<210> SEQ ID NO 476
<211> LENGTH: 57
<212> TYPE: DNA
<213> ORGANISM: Artificial Sequence
<220> FEATURE:
<223> OTHER INFORMATION: Synthesized: H2-5NP1 (XPA-23) primer
<220> FEATURE:
<221> NAME/KEY: misc_feature
<222> LOCATION: (35)..(35)
<223> OTHER INFORMATION: n is a, c, g, or t

<400> SEQUENCE: 476
taaaggtttg gagtgggttt ctgttatctc tcctntcggt ggcatgactc gttatgc 57

<210> SEQ ID NO 477
<211> LENGTH: 57
<212> TYPE: DNA
<213> ORGANISM: Artificial Sequence
<220> FEATURE:
<223> OTHER INFORMATION: Synthesized: H2-5NP2 (XPA-23) primer

<400> SEQUENCE: 477

-continued taaaggtttg gagtgggttt ctgttatctc tcctkggggt ggcatgactc gttatgc 57

<210> SEQ ID NO 478
<211> LENGTH: 57
<212> TYPE: DNA
<213> ORGANISM: Artificial Sequence
<220> FEATURE:
<223> OTHER INFORMATION: Synthesized: H2-5NP3 (XPA-23) primer

<400> SEQUENCE: 478
taaaggtttg gagtgggttt ctgttatctc tcctscgggt ggcatgactc gttatgc 57

<210> SEQ ID NO 479
<211> LENGTH: 22
<212> TYPE: DNA
<213> ORGANISM: Artificial Sequence
<220> FEATURE:
<223> OTHER INFORMATION: Synthesized: H22-R (XPA-23) primer

<400> SEQUENCE: 479
agaaggagag ataacagaaa cc 22

<210> SEQ ID NO 480
<211> LENGTH: 59
<212> TYPE: DNA
<213> ORGANISM: Artificial Sequence
<220> FEATURE:
<223> OTHER INFORMATION: Synthesized: H22-1P1 (XPA-23) primer

<400> SEQUENCE: 480
ggtttctgtt atctctcctt ctwmcggcat gactcgttat gctgactccg ttaaaggtc 59

<210> SEQ ID NO 481
<211> LENGTH: 59
<212> TYPE: DNA
<213> ORGANISM: Artificial Sequence
<220> FEATURE:
<223> OTHER INFORMATION: Synthesized: H22-1P2 (XPA-23) primer

<400> SEQUENCE: 481
ggtttctgtt atctctcctt ctcasggcat gactcgttat gctgactccg ttaaaggtc 59

<210> SEQ ID NO 482
<211> LENGTH: 59
<212> TYPE: DNA
<213> ORGANISM: Artificial Sequence
<220> FEATURE:
<223> OTHER INFORMATION: Synthesized: H22-1A (XPA-23) primer

<400> SEQUENCE: 482
ggtttctgtt atctctcctt ctgasggcat gactcgttat gctgactccg ttaaaggtc 59

<210> SEQ ID NO 483
<211> LENGTH: 59
<212> TYPE: DNA
<213> ORGANISM: Artificial Sequence
<220> FEATURE:
<223> OTHER INFORMATION: Synthesized: H22-1NP1 (XPA-23) primer
<220> FEATURE:
<221> NAME/KEY: misc_feature
<222> LOCATION: (23)..(23)
<223> OTHER INFORMATION: n is a, c, g, or t

<400> SEQUENCE: 483
ggtttctgtt atctctcctt ctntcggcat gactcgttat gctgactccg ttaaaggtc 59

-continued

<210> SEQ ID NO 484
<211> LENGTH: 59
<212> TYPE: DNA
<213> ORGANISM: Artificial Sequence
<220> FEATURE:
<223> OTHER INFORMATION: Synthesized: H22-1NP2 (XPA-23) primer

<400> SEQUENCE: 484
ggtttctgtt atctctcctt ctkggggcat gactcgttat gctgactccg ttaaaggtc 59

<210> SEQ ID NO 485
<211> LENGTH: 59
<212> TYPE: DNA
<213> ORGANISM: Artificial Sequence
<220> FEATURE:
<223> OTHER INFORMATION: Synthesized: H22-1NP3 (XPA-23) primer

<400> SEQUENCE: 485
ggtttctgtt atctctcctt ctscgggcat gactcgttat gctgactccg ttaaaggtc 59

<210> SEQ ID NO 486
<211> LENGTH: 59
<212> TYPE: DNA
<213> ORGANISM: Artificial Sequence
<220> FEATURE:
<223> OTHER INFORMATION: Synthesized: H22-2B (XPA-23) primer

<400> SEQUENCE: 486
ggtttctgtt atctctcctt ctggtargat gactcgttat gctgactccg ttaaaggtc 59

<210> SEQ ID NO 487
<211> LENGTH: 59
<212> TYPE: DNA
<213> ORGANISM: Artificial Sequence
<220> FEATURE:
<223> OTHER INFORMATION: Synthesized: H22-2P1 (XPA-23) primer

<400> SEQUENCE: 487
ggtttctgtt atctctcctt ctggtwmcat gactcgttat gctgactccg ttaaaggtc 59

<210> SEQ ID NO 488
<211> LENGTH: 59
<212> TYPE: DNA
<213> ORGANISM: Artificial Sequence
<220> FEATURE:
<223> OTHER INFORMATION: Synthesized: H22-2P2 (XPA-23) primer

<400> SEQUENCE: 488
ggtttctgtt atctctcctt ctggtcasat gactcgttat gctgactccg ttaaaggtc 59

<210> SEQ ID NO 489
<211> LENGTH: 59
<212> TYPE: DNA
<213> ORGANISM: Artificial Sequence
<220> FEATURE:
<223> OTHER INFORMATION: Synthesized: H22-2A (XPA-23) primer

<400> SEQUENCE: 489
ggtttctgtt atctctcctt ctggtgasat gactcgttat gctgactccg ttaaaggtc 59

<210> SEQ ID NO 490
<211> LENGTH: 59
<212> TYPE: DNA
<213> ORGANISM: Artificial Sequence
<220> FEATURE:
<223> OTHER INFORMATION: Synthesized: H22-2NP1 (XPA-23) primer
<220> FEATURE:

<221> NAME/KEY: misc_feature
<222> LOCATION: (26)..(26)
<223> OTHER INFORMATION: n is a, c, g, or t

<400> SEQUENCE: 490
ggtttctgtt atctctcctt ctggtntcat gactcgttat gctgactccg ttaaaggtc 59

<210> SEQ ID NO 491
<211> LENGTH: 59
<212> TYPE: DNA
<213> ORGANISM: Artificial Sequence
<220> FEATURE:
<223> OTHER INFORMATION: Synthesized: H22-2NP2 (XPA-23) primer

<400> SEQUENCE: 491
ggtttctgtt atctctcctt ctggtkggat gactcgttat gctgactccg ttaaaggtc 59

<210> SEQ ID NO 492
<211> LENGTH: 59
<212> TYPE: DNA
<213> ORGANISM: Artificial Sequence
<220> FEATURE:
<223> OTHER INFORMATION: Synthesized: H22-2NP3 (XPA-23) primer

<400> SEQUENCE: 492
ggtttctgtt atctctcctt ctggtscgat gactcgttat gctgactccg ttaaaggtc 59

<210> SEQ ID NO 493
<211> LENGTH: 59
<212> TYPE: DNA
<213> ORGANISM: Artificial Sequence
<220> FEATURE:
<223> OTHER INFORMATION: Synthesized: H22-3B (XPA-23) primer

<400> SEQUENCE: 493
ggtttctgtt atctctcctt ctggtggcar gactcgttat gctgactccg ttaaaggtc 59

<210> SEQ ID NO 494
<211> LENGTH: 59
<212> TYPE: DNA
<213> ORGANISM: Artificial Sequence
<220> FEATURE:
<223> OTHER INFORMATION: Synthesized: H22-3P1 (XPA-23) primer

<400> SEQUENCE: 494
ggtttctgtt atctctcctt ctggtggcwm cactcgttat gctgactccg ttaaaggtc 59

<210> SEQ ID NO 495
<211> LENGTH: 59
<212> TYPE: DNA
<213> ORGANISM: Artificial Sequence
<220> FEATURE:
<223> OTHER INFORMATION: Synthesized: H22-3P2 (XPA-23) primer

<400> SEQUENCE: 495
ggtttctgtt atctctcctt ctggtggcca sactcgttat gctgactccg ttaaaggtc 59

<210> SEQ ID NO 496
<211> LENGTH: 59
<212> TYPE: DNA
<213> ORGANISM: Artificial Sequence
<220> FEATURE:
<223> OTHER INFORMATION: Synthesized: H22-3A (XPA-23) primer

<400> SEQUENCE: 496
ggtttctgtt atctctcctt ctggtggcga sactcgttat gctgactccg ttaaaggtc 59

<210> SEQ ID NO 497
<211> LENGTH: 59
<212> TYPE: DNA
<213> ORGANISM: Artificial Sequence
<220> FEATURE:
<223> OTHER INFORMATION: Synthesized: H22-3NP1 (XPA-23) primer
<220> FEATURE:
<221> NAME/KEY: misc_feature
<222> LOCATION: (29)..(29)
<223> OTHER INFORMATION: n is a, c, g, or t

<400> SEQUENCE: 497
ggtttctgtt atctctcctt ctggtggcnt cactcgttat gctgactccg ttaaaggtc 59

<210> SEQ ID NO 498
<211> LENGTH: 59
<212> TYPE: DNA
<213> ORGANISM: Artificial Sequence
<220> FEATURE:
<223> OTHER INFORMATION: Synthesized: H22-3NP2 (XPA-23) primer

<400> SEQUENCE: 498
ggtttctgtt atctctcctt ctggtggckg gactcgttat gctgactccg ttaaaggtc 59

<210> SEQ ID NO 499
<211> LENGTH: 59
<212> TYPE: DNA
<213> ORGANISM: Artificial Sequence
<220> FEATURE:
<223> OTHER INFORMATION: Synthesized: H22-3NP3 (XPA-23) primer

<400> SEQUENCE: 499
ggtttctgtt atctctcctt ctggtggcsc gactcgttat gctgactccg ttaaaggtc 59

<210> SEQ ID NO 500
<211> LENGTH: 59
<212> TYPE: DNA
<213> ORGANISM: Artificial Sequence
<220> FEATURE:
<223> OTHER INFORMATION: Synthesized: H22-4B (XPA-23) primer

<400> SEQUENCE: 500
ggtttctgtt atctctcctt ctggtggcat gargcgttat gctgactccg ttaaaggtc 59

<210> SEQ ID NO 501
<211> LENGTH: 59
<212> TYPE: DNA
<213> ORGANISM: Artificial Sequence
<220> FEATURE:
<223> OTHER INFORMATION: Synthesized: H22-4P1 (XPA-23) primer

<400> SEQUENCE: 501
ggtttctgtt atctctcctt ctggtggcat gwmccgttat gctgactccg ttaaaggtc 59

<210> SEQ ID NO 502
<211> LENGTH: 59
<212> TYPE: DNA
<213> ORGANISM: Artificial Sequence
<220> FEATURE:
<223> OTHER INFORMATION: Synthesized: H22-4P2 (XPA-23) primer

<400> SEQUENCE: 502
ggtttctgtt atctctcctt ctggtggcat gcascgttat gctgactccg ttaaaggtc 59

<210> SEQ ID NO 503

<211> LENGTH: 59
<212> TYPE: DNA
<213> ORGANISM: Artificial Sequence
<220> FEATURE:
<223> OTHER INFORMATION: Synthesized: H22-4A (XPA-23) primer

<400> SEQUENCE: 503
ggtttctgtt atctctcctt ctggtggcat ggascgttat gctgactccg ttaaaggtc 59

<210> SEQ ID NO 504
<211> LENGTH: 59
<212> TYPE: DNA
<213> ORGANISM: Artificial Sequence
<220> FEATURE:
<223> OTHER INFORMATION: Synthesized: H22-4NP1 (XPA-23) primer
<220> FEATURE:
<221> NAME/KEY: misc_feature
<222> LOCATION: (32)..(32)
<223> OTHER INFORMATION: n is a, c, g, or t

<400> SEQUENCE: 504
ggtttctgtt atctctcctt ctggtggcat gntccgttat gctgactccg ttaaaggtc 59

<210> SEQ ID NO 505
<211> LENGTH: 59
<212> TYPE: DNA
<213> ORGANISM: Artificial Sequence
<220> FEATURE:
<223> OTHER INFORMATION: Synthesized: H22-4NP2 (XPA-23) primer

<400> SEQUENCE: 505
ggtttctgtt atctctcctt ctggtggcat gkggcgttat gctgactccg ttaaaggtc 59

<210> SEQ ID NO 506
<211> LENGTH: 59
<212> TYPE: DNA
<213> ORGANISM: Artificial Sequence
<220> FEATURE:
<223> OTHER INFORMATION: Synthesized: H22-4NP3 (XPA-23) primer

<400> SEQUENCE: 506
ggtttctgtt atctctcctt ctggtggcat gscgcgttat gctgactccg ttaaaggtc 59

<210> SEQ ID NO 507
<211> LENGTH: 59
<212> TYPE: DNA
<213> ORGANISM: Artificial Sequence
<220> FEATURE:
<223> OTHER INFORMATION: Synthesized: H22-5B (XPA-23) primer

<400> SEQUENCE: 507
ggtttctgtt atctctcctt ctggtggcat gactargtat gctgactccg ttaaaggtc 59

<210> SEQ ID NO 508
<211> LENGTH: 59
<212> TYPE: DNA
<213> ORGANISM: Artificial Sequence
<220> FEATURE:
<223> OTHER INFORMATION: Synthesized: H22-5P1 (XPA-23) primer

<400> SEQUENCE: 508
ggtttctgtt atctctcctt ctggtggcat gactwmctat gctgactccg ttaaaggtc 59

<210> SEQ ID NO 509
<211> LENGTH: 59
<212> TYPE: DNA
<213> ORGANISM: Artificial Sequence
<220> FEATURE:
<223> OTHER INFORMATION: Synthesized: H22-5P2 (XPA-23) primer

<400> SEQUENCE: 509
ggtttctgtt atctctcctt ctggtggcat gactcastat gctgactccg ttaaaggtc 59

<210> SEQ ID NO 510
<211> LENGTH: 59
<212> TYPE: DNA
<213> ORGANISM: Artificial Sequence
<220> FEATURE:
<223> OTHER INFORMATION: Synthesized: H22-5A (XPA-23) primer

<400> SEQUENCE: 510
ggtttctgtt atctctcctt ctggtggcat gactgastat gctgactccg ttaaaggtc 59

<210> SEQ ID NO 511
<211> LENGTH: 59
<212> TYPE: DNA
<213> ORGANISM: Artificial Sequence
<220> FEATURE:
<223> OTHER INFORMATION: Synthesized: H22-5NP1 (XPA-23) primer
<220> FEATURE:
<221> NAME/KEY: misc_feature
<222> LOCATION: (35)..(35)
<223> OTHER INFORMATION: n is a, c, g, or t

<400> SEQUENCE: 511
ggtttctgtt atctctcctt ctggtggcat gactntctat gctgactccg ttaaaggtc 59

<210> SEQ ID NO 512
<211> LENGTH: 59
<212> TYPE: DNA
<213> ORGANISM: Artificial Sequence
<220> FEATURE:
<223> OTHER INFORMATION: Synthesized: H22-5NP2 (XPA-23) primer

<400> SEQUENCE: 512
ggtttctgtt atctctcctt ctggtggcat gactkggtat gctgactccg ttaaaggtc 59

<210> SEQ ID NO 513
<211> LENGTH: 59
<212> TYPE: DNA
<213> ORGANISM: Artificial Sequence
<220> FEATURE:
<223> OTHER INFORMATION: Synthesized: H22-5NP3 (XPA-23) primer

<400> SEQUENCE: 513
ggtttctgtt atctctcctt ctggtggcat gactscgtat gctgactccg ttaaaggtc 59

<210> SEQ ID NO 514
<211> LENGTH: 21
<212> TYPE: DNA
<213> ORGANISM: Artificial Sequence
<220> FEATURE:
<223> OTHER INFORMATION: Synthesized: H3-R (XPA-23) primer

<400> SEQUENCE: 514
tctcgcacaa tagtagactg c 21

<210> SEQ ID NO 515
<211> LENGTH: 56
<212> TYPE: DNA
<213> ORGANISM: Artificial Sequence
<220> FEATURE:
<223> OTHER INFORMATION: Synthesized: H3-1B (XPA-23) primer

<400> SEQUENCE: 515
gcagtctact attgtgcgag aargggctac ggtggtaact ctgactactg gggcca 56

<210> SEQ ID NO 516
<211> LENGTH: 56
<212> TYPE: DNA
<213> ORGANISM: Artificial Sequence
<220> FEATURE:
<223> OTHER INFORMATION: Synthesized: H3-1P1 (XPA-23) primer

<400> SEQUENCE: 516
gcagtctact attgtgcgag awmcggctac ggtggtaact ctgactactg gggcca 56

<210> SEQ ID NO 517
<211> LENGTH: 56
<212> TYPE: DNA
<213> ORGANISM: Artificial Sequence
<220> FEATURE:
<223> OTHER INFORMATION: Synthesized: H3-1P2 (XPA-23) primer

<400> SEQUENCE: 517
gcagtctact attgtgcgag acasggctac ggtggtaact ctgactactg gggcca 56

<210> SEQ ID NO 518
<211> LENGTH: 56
<212> TYPE: DNA
<213> ORGANISM: Artificial Sequence
<220> FEATURE:
<223> OTHER INFORMATION: Synthesized: H3-1A (XPA-23) primer

<400> SEQUENCE: 518
gcagtctact attgtgcgag agasggctac ggtggtaact ctgactactg gggcca 56

<210> SEQ ID NO 519
<211> LENGTH: 56
<212> TYPE: DNA
<213> ORGANISM: Artificial Sequence
<220> FEATURE:
<223> OTHER INFORMATION: Synthesized: H3-1NP1 (XPA-23) primer
<220> FEATURE:
<221> NAME/KEY: misc_feature
<222> LOCATION: (22)..(22)
<223> OTHER INFORMATION: n is a, c, g, or t

<400> SEQUENCE: 519
gcagtctact attgtgcgag antcggctac ggtggtaact ctgactactg gggcca 56

<210> SEQ ID NO 520
<211> LENGTH: 56
<212> TYPE: DNA
<213> ORGANISM: Artificial Sequence
<220> FEATURE:
<223> OTHER INFORMATION: Synthesized: H3-1NP2 (XPA-23) primer

<400> SEQUENCE: 520
gcagtctact attgtgcgag akggggctac ggtggtaact ctgactactg gggcca 56

<210> SEQ ID NO 521
<211> LENGTH: 56
<212> TYPE: DNA
<213> ORGANISM: Artificial Sequence
<220> FEATURE:
<223> OTHER INFORMATION: Synthesized: H3-1NP3 (XPA-23) primer

<400> SEQUENCE: 521
gcagtctact attgtgcgag ascgggctac ggtggtaact ctgactactg gggcca 56

<210> SEQ ID NO 522
<211> LENGTH: 56
<212> TYPE: DNA
<213> ORGANISM: Artificial Sequence
<220> FEATURE:
<223> OTHER INFORMATION: Synthesized: H3-2B (XPA-23) primer

<400> SEQUENCE: 522
gcagtctact attgtgcgag agtcargtac ggtggtaact ctgactactg gggcca 56

<210> SEQ ID NO 523
<211> LENGTH: 56
<212> TYPE: DNA
<213> ORGANISM: Artificial Sequence
<220> FEATURE:
<223> OTHER INFORMATION: Synthesized: H3-2P1 (XPA-23) primer

<400> SEQUENCE: 523
gcagtctact attgtgcgag agtcwmctac ggtggtaact ctgactactg gggcca 56

<210> SEQ ID NO 524
<211> LENGTH: 56
<212> TYPE: DNA
<213> ORGANISM: Artificial Sequence
<220> FEATURE:
<223> OTHER INFORMATION: Synthesized: H3-2P2 (XPA-23) primer

<400> SEQUENCE: 524
gcagtctact attgtgcgag agtccastac ggtggtaact ctgactactg gggcca 56

<210> SEQ ID NO 525
<211> LENGTH: 56
<212> TYPE: DNA
<213> ORGANISM: Artificial Sequence
<220> FEATURE:
<223> OTHER INFORMATION: Synthesized: H3-2A (XPA-23) primer

<400> SEQUENCE: 525
gcagtctact attgtgcgag agtcgastac ggtggtaact ctgactactg gggcca 56

<210> SEQ ID NO 526
<211> LENGTH: 56
<212> TYPE: DNA
<213> ORGANISM: Artificial Sequence
<220> FEATURE:
<223> OTHER INFORMATION: Synthesized: H3-2NP1 (XPA-23) primer
<220> FEATURE:
<221> NAME/KEY: misc_feature
<222> LOCATION: (25)..(25)
<223> OTHER INFORMATION: n is a, c, g, or t

<400> SEQUENCE: 526
gcagtctact attgtgcgag agtcntctac ggtggtaact ctgactactg gggcca 56

<210> SEQ ID NO 527
<211> LENGTH: 56
<212> TYPE: DNA
<213> ORGANISM: Artificial Sequence
<220> FEATURE:
<223> OTHER INFORMATION: Synthesized: H3-2NP2 (XPA-23) primer

<400> SEQUENCE: 527
gcagtctact attgtgcgag agtckggtac ggtggtaact ctgactactg gggcca 56

<210> SEQ ID NO 528

<211> LENGTH: 56
<212> TYPE: DNA
<213> ORGANISM: Artificial Sequence
<220> FEATURE:
<223> OTHER INFORMATION: Synthesized: H3-2NP3 (XPA-23) primer

<400> SEQUENCE: 528
gcagtctact attgtgcgag agtcscgtac ggtggtaact ctgactactg gggcca 56

<210> SEQ ID NO 529
<211> LENGTH: 56
<212> TYPE: DNA
<213> ORGANISM: Artificial Sequence
<220> FEATURE:
<223> OTHER INFORMATION: Synthesized: H3-3B (XPA-23) primer

<400> SEQUENCE: 529
gcagtctact attgtgcgag agtcggcarg ggtggtaact ctgactactg gggcca 56

<210> SEQ ID NO 530
<211> LENGTH: 56
<212> TYPE: DNA
<213> ORGANISM: Artificial Sequence
<220> FEATURE:
<223> OTHER INFORMATION: Synthesized: H3-3P1 (XPA-23) primer

<400> SEQUENCE: 530
gcagtctact attgtgcgag agtcggcwmc ggtggtaact ctgactactg gggcca 56

<210> SEQ ID NO 531
<211> LENGTH: 56
<212> TYPE: DNA
<213> ORGANISM: Artificial Sequence
<220> FEATURE:
<223> OTHER INFORMATION: Synthesized: H3-3P2 (XPA-23) primer

<400> SEQUENCE: 531
gcagtctact attgtgcgag agtcggccas ggtggtaact ctgactactg gggcca 56

<210> SEQ ID NO 532
<211> LENGTH: 56
<212> TYPE: DNA
<213> ORGANISM: Artificial Sequence
<220> FEATURE:
<223> OTHER INFORMATION: Synthesized: H3-3A (XPA-23) primer

<400> SEQUENCE: 532
gcagtctact attgtgcgag agtcggcgas ggtggtaact ctgactactg gggcca 56

<210> SEQ ID NO 533
<211> LENGTH: 56
<212> TYPE: DNA
<213> ORGANISM: Artificial Sequence
<220> FEATURE:
<223> OTHER INFORMATION: Synthesized: H3-3NP1 (XPA-23) primer
<220> FEATURE:
<221> NAME/KEY: misc_feature
<222> LOCATION: (28)..(28)
<223> OTHER INFORMATION: n is a, c, g, or t

<400> SEQUENCE: 533
gcagtctact attgtgcgag agtcggcntc ggtggtaact ctgactactg gggcca 56

<210> SEQ ID NO 534
<211> LENGTH: 56
<212> TYPE: DNA
<213> ORGANISM: Artificial Sequence
<220> FEATURE:
<223> OTHER INFORMATION: Synthesized: H3-3NP2 (XPA-23) primer

<400> SEQUENCE: 534
gcagtctact attgtgcgag agtcggckgg ggtggtaact ctgactactg gggcca 56

<210> SEQ ID NO 535
<211> LENGTH: 56
<212> TYPE: DNA
<213> ORGANISM: Artificial Sequence
<220> FEATURE:
<223> OTHER INFORMATION: Synthesized: H3-3NP3 (XPA-23) primer

<400> SEQUENCE: 535
gcagtctact attgtgcgag agtcggcscg ggtggtaact ctgactactg gggcca 56

<210> SEQ ID NO 536
<211> LENGTH: 56
<212> TYPE: DNA
<213> ORGANISM: Artificial Sequence
<220> FEATURE:
<223> OTHER INFORMATION: Synthesized: H3-4B (XPA-23) primer

<400> SEQUENCE: 536
gcagtctact attgtgcgag agtcggctac argggtaact ctgactactg gggcca 56

<210> SEQ ID NO 537
<211> LENGTH: 56
<212> TYPE: DNA
<213> ORGANISM: Artificial Sequence
<220> FEATURE:
<223> OTHER INFORMATION: Synthesized: H3-4P1 (XPA-23) primer

<400> SEQUENCE: 537
gcagtctact attgtgcgag agtcggctac wmcggtaact ctgactactg gggcca 56

<210> SEQ ID NO 538
<211> LENGTH: 56
<212> TYPE: DNA
<213> ORGANISM: Artificial Sequence
<220> FEATURE:
<223> OTHER INFORMATION: Synthesized: H3-4P2 (XPA-23) primer

<400> SEQUENCE: 538
gcagtctact attgtgcgag agtcggctac casggtaact ctgactactg gggcca 56

<210> SEQ ID NO 539
<211> LENGTH: 56
<212> TYPE: DNA
<213> ORGANISM: Artificial Sequence
<220> FEATURE:
<223> OTHER INFORMATION: Synthesized: H3-4A (XPA-23) primer

<400> SEQUENCE: 539
gcagtctact attgtgcgag agtcggctac gasggtaact ctgactactg gggcca 56

<210> SEQ ID NO 540
<211> LENGTH: 56
<212> TYPE: DNA
<213> ORGANISM: Artificial Sequence
<220> FEATURE:
<223> OTHER INFORMATION: Synthesized: H3-4NP1 (XPA-23) primer
<220> FEATURE:
<221> NAME/KEY: misc_feature
<222> LOCATION: (31)..(31)
<223> OTHER INFORMATION: n is a, c, g, or t

<400> SEQUENCE: 540
gcagtctact attgtgcgag agtcggctac ntcggtaact ctgactactg gggcca 56

<210> SEQ ID NO 541
<211> LENGTH: 56
<212> TYPE: DNA
<213> ORGANISM: Artificial Sequence
<220> FEATURE:
<223> OTHER INFORMATION: Synthesized: H3-4NP2 (XPA-23) primer

<400> SEQUENCE: 541
gcagtctact attgtgcgag agtcggctac kggggtaact ctgactactg gggcca 56

<210> SEQ ID NO 542
<211> LENGTH: 56
<212> TYPE: DNA
<213> ORGANISM: Artificial Sequence
<220> FEATURE:
<223> OTHER INFORMATION: Synthesized: H3-4NP3 (XPA-23) primer

<400> SEQUENCE: 542
gcagtctact attgtgcgag agtcggctac scgggtaact ctgactactg gggcca 56

<210> SEQ ID NO 543
<211> LENGTH: 56
<212> TYPE: DNA
<213> ORGANISM: Artificial Sequence
<220> FEATURE:
<223> OTHER INFORMATION: Synthesized: H3-5B (XPA-23) primer

<400> SEQUENCE: 543
gcagtctact attgtgcgag agtcggctac ggtargaact ctgactactg gggcca 56

<210> SEQ ID NO 544
<211> LENGTH: 56
<212> TYPE: DNA
<213> ORGANISM: Artificial Sequence
<220> FEATURE:
<223> OTHER INFORMATION: Synthesized: H3-5P1 (XPA-23) primer

<400> SEQUENCE: 544
gcagtctact attgtgcgag agtcggctac ggtwmcaact ctgactactg gggcca 56

<210> SEQ ID NO 545
<211> LENGTH: 56
<212> TYPE: DNA
<213> ORGANISM: Artificial Sequence
<220> FEATURE:
<223> OTHER INFORMATION: Synthesized: H3-5P2 (XPA-23) primer

<400> SEQUENCE: 545
gcagtctact attgtgcgag agtcggctac ggtcasaact ctgactactg gggcca 56

<210> SEQ ID NO 546
<211> LENGTH: 56
<212> TYPE: DNA
<213> ORGANISM: Artificial Sequence
<220> FEATURE:
<223> OTHER INFORMATION: Synthesized: H3-5A (XPA-23) primer

<400> SEQUENCE: 546
gcagtctact attgtgcgag agtcggctac ggtgasaact ctgactactg gggcca 56

<210> SEQ ID NO 547
<211> LENGTH: 56

<212> TYPE: DNA
<213> ORGANISM: Artificial Sequence
<220> FEATURE:
<223> OTHER INFORMATION: Synthesized: H3-5NP1 (XPA-23) primer
<220> FEATURE:
<221> NAME/KEY: misc_feature
<222> LOCATION: (34)..(34)
<223> OTHER INFORMATION: n is a, c, g, or t

<400> SEQUENCE: 547
gcagtctact attgtgcgag agtcggctac ggtntcaact ctgactactg gggcca 56

<210> SEQ ID NO 548
<211> LENGTH: 56
<212> TYPE: DNA
<213> ORGANISM: Artificial Sequence
<220> FEATURE:
<223> OTHER INFORMATION: Synthesized: H3-5NP2 (XPA-23) primer

<400> SEQUENCE: 548
gcagtctact attgtgcgag agtcggctac ggtkggaact ctgactactg gggcca 56

<210> SEQ ID NO 549
<211> LENGTH: 56
<212> TYPE: DNA
<213> ORGANISM: Artificial Sequence
<220> FEATURE:
<223> OTHER INFORMATION: Synthesized: H3-5NP3 (XPA-23) primer

<400> SEQUENCE: 549
gcagtctact attgtgcgag agtcggctac ggtscgaact ctgactactg gggcca 56

<210> SEQ ID NO 550
<211> LENGTH: 19
<212> TYPE: DNA
<213> ORGANISM: Artificial Sequence
<220> FEATURE:
<223> OTHER INFORMATION: Synthesized: H32R (XPA-23) primer

<400> SEQUENCE: 550
accaccgtag ccgactctc 19

<210> SEQ ID NO 551
<211> LENGTH: 49
<212> TYPE: DNA
<213> ORGANISM: Artificial Sequence
<220> FEATURE:
<223> OTHER INFORMATION: Synthesized: H32-1B (XPA-23) primer

<400> SEQUENCE: 551
gagagtcggc tacggtggta rgtctgacta ctggggccag ggaaccctg 49

<210> SEQ ID NO 552
<211> LENGTH: 49
<212> TYPE: DNA
<213> ORGANISM: Artificial Sequence
<220> FEATURE:
<223> OTHER INFORMATION: Synthesized: H32-1P1 (XPA-23) primer

<400> SEQUENCE: 552
gagagtcggc tacggtggtw mctctgacta ctggggccag ggaaccctg 49

<210> SEQ ID NO 553
<211> LENGTH: 49
<212> TYPE: DNA
<213> ORGANISM: Artificial Sequence
<220> FEATURE:

<223> OTHER INFORMATION: Synthesized: H32-1P2 (XPA-23) primer

<400> SEQUENCE: 553
gagagtcggc tacggtggtc astctgacta ctggggccag ggaaccctg 49

<210> SEQ ID NO 554
<211> LENGTH: 49
<212> TYPE: DNA
<213> ORGANISM: Artificial Sequence
<220> FEATURE:
<223> OTHER INFORMATION: Synthesized: H32-1A (XPA-23) primer

<400> SEQUENCE: 554
gagagtcggc tacggtggtg astctgacta ctggggccag ggaaccctg 49

<210> SEQ ID NO 555
<211> LENGTH: 49
<212> TYPE: DNA
<213> ORGANISM: Artificial Sequence
<220> FEATURE:
<223> OTHER INFORMATION: Synthesized: H32-1NP1 (XPA-23) primer
<220> FEATURE:
<221> NAME/KEY: misc_feature
<222> LOCATION: (20)..(20)
<223> OTHER INFORMATION: n is a, c, g, or t

<400> SEQUENCE: 555
gagagtcggc tacggtggtn tctctgacta ctggggccag ggaaccctg 49

<210> SEQ ID NO 556
<211> LENGTH: 49
<212> TYPE: DNA
<213> ORGANISM: Artificial Sequence
<220> FEATURE:
<223> OTHER INFORMATION: Synthesized: H32-1NP2 (XPA-23) primer

<400> SEQUENCE: 556
gagagtcggc tacggtggtk ggtctgacta ctggggccag ggaaccctg 49

<210> SEQ ID NO 557
<211> LENGTH: 49
<212> TYPE: DNA
<213> ORGANISM: Artificial Sequence
<220> FEATURE:
<223> OTHER INFORMATION: Synthesized: H32-1NP3 (XPA-23) primer

<400> SEQUENCE: 557
gagagtcggc tacggtggts cgtctgacta ctggggccag ggaaccctg 49

<210> SEQ ID NO 558
<211> LENGTH: 49
<212> TYPE: DNA
<213> ORGANISM: Artificial Sequence
<220> FEATURE:
<223> OTHER INFORMATION: Synthesized: H32-2B (XPA-23) primer

<400> SEQUENCE: 558
gagagtcggc tacggtggta acarggacta ctggggccag ggaaccctg 49

<210> SEQ ID NO 559
<211> LENGTH: 49
<212> TYPE: DNA
<213> ORGANISM: Artificial Sequence
<220> FEATURE:
<223> OTHER INFORMATION: Synthesized: H32-2P1 (XPA-23) primer

<400> SEQUENCE: 559
gagagtcggc tacggtggta acwmcgacta ctggggccag ggaaccctg 49

<210> SEQ ID NO 560
<211> LENGTH: 49
<212> TYPE: DNA
<213> ORGANISM: Artificial Sequence
<220> FEATURE:
<223> OTHER INFORMATION: Synthesized: H32-2P2 (XPA-23) primer

<400> SEQUENCE: 560
gagagtcggc tacggtggta accasgacta ctggggccag ggaaccctg 49

<210> SEQ ID NO 561
<211> LENGTH: 49
<212> TYPE: DNA
<213> ORGANISM: Artificial Sequence
<220> FEATURE:
<223> OTHER INFORMATION: Synthesized: H32-2A (XPA-23) primer

<400> SEQUENCE: 561
gagagtcggc tacggtggta acgasgacta ctggggccag ggaaccctg 49

<210> SEQ ID NO 562
<211> LENGTH: 49
<212> TYPE: DNA
<213> ORGANISM: Artificial Sequence
<220> FEATURE:
<223> OTHER INFORMATION: Synthesized: H32-2NP1 (XPA-23) primer
<220> FEATURE:
<221> NAME/KEY: misc_feature
<222> LOCATION: (23)..(23)
<223> OTHER INFORMATION: n is a, c, g, or t

<400> SEQUENCE: 562
gagagtcggc tacggtggta acntcgacta ctggggccag ggaaccctg 49

<210> SEQ ID NO 563
<211> LENGTH: 49
<212> TYPE: DNA
<213> ORGANISM: Artificial Sequence
<220> FEATURE:
<223> OTHER INFORMATION: Synthesized: H32-2NP2 (XPA-23) primer

<400> SEQUENCE: 563
gagagtcggc tacggtggta ackgggacta ctggggccag ggaaccctg 49

<210> SEQ ID NO 564
<211> LENGTH: 49
<212> TYPE: DNA
<213> ORGANISM: Artificial Sequence
<220> FEATURE:
<223> OTHER INFORMATION: Synthesized: H32-2NP3 (XPA-23) primer

<400> SEQUENCE: 564
gagagtcggc tacggtggta acscggacta ctggggccag ggaaccctg 49

<210> SEQ ID NO 565
<211> LENGTH: 49
<212> TYPE: DNA
<213> ORGANISM: Artificial Sequence
<220> FEATURE:
<223> OTHER INFORMATION: Synthesized: H32-3B (XPA-23) primer

<400> SEQUENCE: 565
gagagtcggc tacggtggta actctargta ctggggccag ggaaccctg 49

<210> SEQ ID NO 566
<211> LENGTH: 49
<212> TYPE: DNA
<213> ORGANISM: Artificial Sequence
<220> FEATURE:
<223> OTHER INFORMATION: Synthesized: H32-3P1 (XPA-23) primer

<400> SEQUENCE: 566
gagagtcggc tacggtggta actctwmcta ctggggccag ggaaccctg 49

<210> SEQ ID NO 567
<211> LENGTH: 49
<212> TYPE: DNA
<213> ORGANISM: Artificial Sequence
<220> FEATURE:
<223> OTHER INFORMATION: Synthesized: H32-3P2 (XPA-23) primer

<400> SEQUENCE: 567
gagagtcggc tacggtggta actctcasta ctggggccag ggaaccctg 49

<210> SEQ ID NO 568
<211> LENGTH: 49
<212> TYPE: DNA
<213> ORGANISM: Artificial Sequence
<220> FEATURE:
<223> OTHER INFORMATION: Synthesized: H32-3A (XPA-23) primer

<400> SEQUENCE: 568
gagagtcggc tacggtggta actctgasta ctggggccag ggaaccctg 49

<210> SEQ ID NO 569
<211> LENGTH: 49
<212> TYPE: DNA
<213> ORGANISM: Artificial Sequence
<220> FEATURE:
<223> OTHER INFORMATION: Synthesized: H32-3NP1 (XPA-23) primer
<220> FEATURE:
<221> NAME/KEY: misc_feature
<222> LOCATION: (26)..(26)
<223> OTHER INFORMATION: n is a, c, g, or t

<400> SEQUENCE: 569
gagagtcggc tacggtggta actctntcta ctggggccag ggaaccctg 49

<210> SEQ ID NO 570
<211> LENGTH: 49
<212> TYPE: DNA
<213> ORGANISM: Artificial Sequence
<220> FEATURE:
<223> OTHER INFORMATION: Synthesized: H32-3NP2 (XPA-23) primer

<400> SEQUENCE: 570
gagagtcggc tacggtggta actctkggta ctggggccag ggaaccctg 49

<210> SEQ ID NO 571
<211> LENGTH: 49
<212> TYPE: DNA
<213> ORGANISM: Artificial Sequence
<220> FEATURE:
<223> OTHER INFORMATION: Synthesized: H32-3NP3 (XPA-23) primer

<400> SEQUENCE: 571
gagagtcggc tacggtggta actctscgta ctggggccag ggaaccctg 49

<210> SEQ ID NO 572
<211> LENGTH: 49

-continued

<212> TYPE: DNA
<213> ORGANISM: Artificial Sequence
<220> FEATURE:
<223> OTHER INFORMATION: Synthesized: H32-4B (XPA-23) primer

<400> SEQUENCE: 572
gagagtcggc tacggtggta actctgacar gtggggccag ggaaccctg 49

<210> SEQ ID NO 573
<211> LENGTH: 49
<212> TYPE: DNA
<213> ORGANISM: Artificial Sequence
<220> FEATURE:
<223> OTHER INFORMATION: Synthesized: H32-4P1 (XPA-23) primer

<400> SEQUENCE: 573
gagagtcggc tacggtggta actctgacwm ctggggccag ggaaccctg 49

<210> SEQ ID NO 574
<211> LENGTH: 49
<212> TYPE: DNA
<213> ORGANISM: Artificial Sequence
<220> FEATURE:
<223> OTHER INFORMATION: Synthesized: H32-4P2 (XPA-23) primer

<400> SEQUENCE: 574
gagagtcggc tacggtggta actctgacca stggggccag ggaaccctg 49

<210> SEQ ID NO 575
<211> LENGTH: 49
<212> TYPE: DNA
<213> ORGANISM: Artificial Sequence
<220> FEATURE:
<223> OTHER INFORMATION: Synthesized: H32-4A (XPA-23) primer

<400> SEQUENCE: 575
gagagtcggc tacggtggta actctgacga stggggccag ggaaccctg 49

<210> SEQ ID NO 576
<211> LENGTH: 49
<212> TYPE: DNA
<213> ORGANISM: Artificial Sequence
<220> FEATURE:
<223> OTHER INFORMATION: Synthesized: H32-4NP1 (XPA-23) primer
<220> FEATURE:
<221> NAME/KEY: misc_feature
<222> LOCATION: (29)..(29)
<223> OTHER INFORMATION: n is a, c, g, or t

<400> SEQUENCE: 576
gagagtcggc tacggtggta actctgacnt ctggggccag ggaaccctg 49

<210> SEQ ID NO 577
<211> LENGTH: 49
<212> TYPE: DNA
<213> ORGANISM: Artificial Sequence
<220> FEATURE:
<223> OTHER INFORMATION: Synthesized: H32-4NP2 (XPA-23) primer

<400> SEQUENCE: 577
gagagtcggc tacggtggta actctgackg gtggggccag ggaaccctg 49

<210> SEQ ID NO 578
<211> LENGTH: 49
<212> TYPE: DNA
<213> ORGANISM: Artificial Sequence
<220> FEATURE:

<223> OTHER INFORMATION: Synthesized: H32-4NP3 (XPA-23) primer

<400> SEQUENCE: 578
gagagtcggc tacggtggta actctgacsc gtggggccag ggaaccctg 49

<210> SEQ ID NO 579
<211> LENGTH: 675
<212> TYPE: DNA
<213> ORGANISM: Artificial Sequence
<220> FEATURE:
<223> OTHER INFORMATION: Synthesized: ING-1 (heavy chain)

<400> SEQUENCE: 579
cagatccagt tggtgcagtc tggacctgag ctgaagaagc ctggagagac agtcaagatc 60
tcctgcaagg cttctggata taccttcaca aaatatggaa tgaactgggt gaagcaggct 120
ccaggaaagg gtttaaagtg gatgggctgg ataaacacct acactgaaga gccaacatat 180
ggtgatgact tcaagggacg gtttgccttc tctttggaaa cctctgccag cactgccaat 240
ttgcagatca acaacctcaa aagtgaggac acggctacat atttctgtgc aagatttggc 300
tctgctgtgg actactgggg tcaaggaacc tcggtcaccg tctcctcagc cagcacaaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gacaagagag ttgagcccaa atcttgtgac 660
aaaactcaca catga 675

<210> SEQ ID NO 580
<211> LENGTH: 675
<212> TYPE: DNA
<213> ORGANISM: Artificial Sequence
<220> FEATURE:
<223> OTHER INFORMATION: Synthesized: ING-1 (light chain)

<400> SEQUENCE: 580
caaccagcga tggcggatat tgtgatgacg caggctgcat tctccaatcc agtcactctt 60
ggaacatcag gttccatctc ctgcaggtct agtaagagtc tcctacatag taatggcatc 120
acttatttgt attggtatct gcagaagcca ggccagtctc ctcagctcct gatttatcag 180
atgtccaacc ttgcctcagg agtcccagac aggttcagta gcagtgggtc aggaactgat 240
ttcacactga gaatcagcag agtggaggct gaggatgtgg gtgtttatta ctgtgctcaa 300
aatctagaac ttcctcggac gttcggtgga ggcaccaagc ttgagatgaa acgaactgtg 360
gctgcaccat ctgtcttcat cttcccgcca tctgatgagc agttgaaatc tggaactgcc 420
tctgttgtgt gcctgctgaa taacttctat cccagagagg ccaaagtaca gtggaaggtg 480
gataacgccc tccaatcggg taactcccag gagagtgtca cagagcagga cagcaaggac 540
agcacctaca gcctcagcag caccctgacg ctgagcaaag cagactacga gaaacacaaa 600
gtctacgcct gcgaagtcac ccatcagggc ctgagctcgc ccgtcacaaa gagcttcaac 660
aggggagagt gttag 675

<210> SEQ ID NO 581
<211> LENGTH: 354
<212> TYPE: DNA
<213> ORGANISM: Artificial Sequence
<220> FEATURE:
<223> OTHER INFORMATION: Synthesized: IL-1 (XPA-23, heavy chain)

<400> SEQUENCE: 581
gaagttcaat tgttagagtc tggtggcggt cttgttcagc ctggtggttc tttacgtctt 60
tcttgcgctg cttccggatt cactttctct aagtacttta tgttttgggt tcgccaagct 120
cctggtaaag gtttggagtg ggtttctgtt atctctcctt ctggtggcat gactcgttat 180
gctgactccg ttaaaggtcg cttcactatc tctagagaca actctaagaa tactctctac 240
ttgcagatga acagcttaag ggctgaggac actgcagtct actattgtgc gagagtcggc 300
tacggtggta actctgacta ctggggccag ggaaccctgg tcaccgtctc aagc 354

<210> SEQ ID NO 582
<211> LENGTH: 324
<212> TYPE: DNA
<213> ORGANISM: Artificial Sequence
<220> FEATURE:
<223> OTHER INFORMATION: Synthesized: IL-1 (XPA-23, kappa chain)

<400> SEQUENCE: 582
caagacatcc agatgaccca gtctccctct tccgtgtctg catctgtagg agacagactc 60
accatcattt gtcgggcgag tcaggatatt aacaggtggt tagcctggta tcagcagaca 120
ccagggaatg cccctaagct cctgatccat tctgcaacca gtctgcaaag tggggtccca 180
tcaaggttta gcggcagtgg atctgggaca gatttcactc tcaccatcaa cagcctgcag 240
cctgaagatt ttgcaactta ctattgtcag caggctgaca gtttcccgct cactttcggc 300
ggagggacca aggtggagat caaa 324

<210> SEQ ID NO 583
<211> LENGTH: 59
<212> TYPE: DNA
<213> ORGANISM: Artificial Sequence
<220> FEATURE:
<223> OTHER INFORMATION: Synthesized: L3-1NHT (ING1)
<220> FEATURE:
<221> NAME/KEY: misc_feature
<222> LOCATION: (25)..(25)
<223> OTHER INFORMATION: n is a, c, g, or t

<400> SEQUENCE: 583
ggtgtttatt actgtgctca aaatnhtgaa cttcctcgga cgttcggtgg aggcaccaa 59

<210> SEQ ID NO 584
<211> LENGTH: 59
<212> TYPE: DNA
<213> ORGANISM: Artificial Sequence
<220> FEATURE:
<223> OTHER INFORMATION: Synthesized: L3-1VAA (ING1)

<400> SEQUENCE: 584
ggtgtttatt actgtgctca aaatvaagaa cttcctcgga cgttcggtgg aggcaccaa 59

<210> SEQ ID NO 585
<211> LENGTH: 59
<212> TYPE: DNA
<213> ORGANISM: Artificial Sequence
<220> FEATURE:
<223> OTHER INFORMATION: Synthesized: L3-1BGG (ING1)

<400> SEQUENCE: 585
ggtgtttatt actgtgctca aaatbgggaa cttcctcgga cgttcggtgg aggcaccaa 59

<210> SEQ ID NO 586
<211> LENGTH: 59
<212> TYPE: DNA
<213> ORGANISM: Artificial Sequence
<220> FEATURE:
<223> OTHER INFORMATION: Synthesized: L3-2NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 586
ggtgtttatt actgtgctca aaatctanht cttcctcgga cgttcggtgg aggcaccaa 59

<210> SEQ ID NO 587
<211> LENGTH: 59
<212> TYPE: DNA
<213> ORGANISM: Artificial Sequence
<220> FEATURE:
<223> OTHER INFORMATION: Synthesized: L3-2VAA (ING1)

<400> SEQUENCE: 587
ggtgtttatt actgtgctca aaatctavaa cttcctcgga cgttcggtgg aggcaccaa 59

<210> SEQ ID NO 588
<211> LENGTH: 59
<212> TYPE: DNA
<213> ORGANISM: Artificial Sequence
<220> FEATURE:
<223> OTHER INFORMATION: Synthesized: L3-2BGG (ING1)

<400> SEQUENCE: 588
ggtgtttatt actgtgctca aaatctabgg cttcctcgga cgttcggtgg aggcaccaa 59

<210> SEQ ID NO 589
<211> LENGTH: 59
<212> TYPE: DNA
<213> ORGANISM: Artificial Sequence
<220> FEATURE:
<223> OTHER INFORMATION: Synthesized: L3-3NHT (ING1)
<220> FEATURE:
<221> NAME/KEY: misc_feature
<222> LOCATION: (31)..(31)
<223> OTHER INFORMATION: n is a, c, g, or t

<400> SEQUENCE: 589
ggtgtttatt actgtgctca aaatctagaa nhtcctcgga cgttcggtgg aggcaccaa 59

<210> SEQ ID NO 590
<211> LENGTH: 59
<212> TYPE: DNA
<213> ORGANISM: Artificial Sequence
<220> FEATURE:
<223> OTHER INFORMATION: Synthesized: L3-3VAA (ING1)

<400> SEQUENCE: 590
ggtgtttatt actgtgctca aaatctagaa vaacctcgga cgttcggtgg aggcaccaa 59

<210> SEQ ID NO 591
<211> LENGTH: 59
<212> TYPE: DNA
<213> ORGANISM: Artificial Sequence
<220> FEATURE:
<223> OTHER INFORMATION: Synthesized: L3-3BGG (ING1)

<400> SEQUENCE: 591
ggtgtttatt actgtgctca aaatctagaa bggcctcgga cgttcggtgg aggcaccaa 59

<210> SEQ ID NO 592
<211> LENGTH: 59
<212> TYPE: DNA
<213> ORGANISM: Artificial Sequence
<220> FEATURE:
<223> OTHER INFORMATION: Synthesized: L3-4NHT (ING1)
<220> FEATURE:
<221> NAME/KEY: misc_feature
<222> LOCATION: (34)..(34)
<223> OTHER INFORMATION: n is a, c, g, or t

<400> SEQUENCE: 592
ggtgtttatt actgtgctca aaatctagaa cttnhtcgga cgttcggtgg aggcaccaa 59

<210> SEQ ID NO 593
<211> LENGTH: 59
<212> TYPE: DNA
<213> ORGANISM: Artificial Sequence
<220> FEATURE:
<223> OTHER INFORMATION: Synthesized: L3-4VAA (ING1)

<400> SEQUENCE: 593
ggtgtttatt actgtgctca aaatctagaa cttvaacgga cgttcggtgg aggcaccaa 59

<210> SEQ ID NO 594
<211> LENGTH: 59
<212> TYPE: DNA
<213> ORGANISM: Artificial Sequence
<220> FEATURE:
<223> OTHER INFORMATION: Synthesized: L3-4BGG (ING1)

<400> SEQUENCE: 594
ggtgtttatt actgtgctca aaatctagaa cttbggcgga cgttcggtgg aggcaccaa 59

<210> SEQ ID NO 595
<211> LENGTH: 59
<212> TYPE: DNA
<213> ORGANISM: Artificial Sequence
<220> FEATURE:
<223> OTHER INFORMATION: Synthesized: L3-5NHT (ING1)
<220> FEATURE:
<221> NAME/KEY: misc_feature
<222> LOCATION: (37)..(37)
<223> OTHER INFORMATION: n is a, c, g, or t

<400> SEQUENCE: 595
ggtgtttatt actgtgctca aaatctagaa cttcctnhta cgttcggtgg aggcaccaa 59

<210> SEQ ID NO 596
<211> LENGTH: 59
<212> TYPE: DNA
<213> ORGANISM: Artificial Sequence
<220> FEATURE:
<223> OTHER INFORMATION: Synthesized: L3-5VAA (ING1)

<400> SEQUENCE: 596
ggtgtttatt actgtgctca aaatctagaa cttcctvaaa cgttcggtgg aggcaccaa 59

<210> SEQ ID NO 597
<211> LENGTH: 59
<212> TYPE: DNA
<213> ORGANISM: Artificial Sequence
<220> FEATURE:
<223> OTHER INFORMATION: Synthesized: L3-5BGG (ING1)

<400> SEQUENCE: 597

-continued ggtgtttatt actgtgctca aaatctagaa cttcctbgga cgttcggtgg aggcaccaa 59

<210> SEQ ID NO 598
<211> LENGTH: 55
<212> TYPE: DNA
<213> ORGANISM: Artificial Sequence
<220> FEATURE:
<223> OTHER INFORMATION: Synthesized: L1-1NHT (ING1)
<220> FEATURE:
<221> NAME/KEY: misc_feature
<222> LOCATION: (21)..(21)
<223> OTHER INFORMATION: n is a, c, g, or t

<400> SEQUENCE: 598
ccatctcctg ccgctctagt nhtagtctcc tacatagtaa tggcatcact tattt 55

<210> SEQ ID NO 599
<211> LENGTH: 55
<212> TYPE: DNA
<213> ORGANISM: Artificial Sequence
<220> FEATURE:
<223> OTHER INFORMATION: Synthesized: L1-1VAA (ING1)

<400> SEQUENCE: 599
ccatctcctg ccgctctagt vaaagtctcc tacatagtaa tggcatcact tattt 55

<210> SEQ ID NO 600
<211> LENGTH: 55
<212> TYPE: DNA
<213> ORGANISM: Artificial Sequence
<220> FEATURE:
<223> OTHER INFORMATION: Synthesized: L1-1BGG (ING1)

<400> SEQUENCE: 600
ccatctcctg ccgctctagt bggagtctcc tacatagtaa tggcatcact tattt 55

<210> SEQ ID NO 601
<211> LENGTH: 55
<212> TYPE: DNA
<213> ORGANISM: Artificial Sequence
<220> FEATURE:
<223> OTHER INFORMATION: Synthesized: L1-2NHT (ING1)
<220> FEATURE:
<221> NAME/KEY: misc_feature
<222> LOCATION: (24)..(24)
<223> OTHER INFORMATION: n is a, c, g, or t

<400> SEQUENCE: 601
ccatctcctg ccgctctagt aagnhtctcc tacatagtaa tggcatcact tattt 55

<210> SEQ ID NO 602
<211> LENGTH: 55
<212> TYPE: DNA
<213> ORGANISM: Artificial Sequence
<220> FEATURE:
<223> OTHER INFORMATION: Synthesized: L1-2VAA (ING1)

<400> SEQUENCE: 602
ccatctcctg ccgctctagt aagvaactcc tacatagtaa tggcatcact tattt 55

<210> SEQ ID NO 603
<211> LENGTH: 55
<212> TYPE: DNA
<213> ORGANISM: Artificial Sequence
<220> FEATURE:
<223> OTHER INFORMATION: Synthesized: L1-2BGG (ING1)

<400> SEQUENCE: 603
ccatctcctg ccgctctagt aagbggctcc tacatagtaa tggcatcact tattt 55

<210> SEQ ID NO 604
<211> LENGTH: 55
<212> TYPE: DNA
<213> ORGANISM: Artificial Sequence
<220> FEATURE:
<223> OTHER INFORMATION: Synthesized: L1-3NHT (ING1)
<220> FEATURE:
<221> NAME/KEY: misc_feature
<222> LOCATION: (27)..(27)
<223> OTHER INFORMATION: n is a, c, g, or t

<400> SEQUENCE: 604
ccatctcctg ccgctctagt aagagtnhtc tacatagtaa tggcatcact tattt 55

<210> SEQ ID NO 605
<211> LENGTH: 55
<212> TYPE: DNA
<213> ORGANISM: Artificial Sequence
<220> FEATURE:
<223> OTHER INFORMATION: Synthesized: L1-3VAA (ING1)

<400> SEQUENCE: 605
ccatctcctg ccgctctagt aagagtvaac tacatagtaa tggcatcact tattt 55

<210> SEQ ID NO 606
<211> LENGTH: 55
<212> TYPE: DNA
<213> ORGANISM: Artificial Sequence
<220> FEATURE:
<223> OTHER INFORMATION: Synthesized: L1-3BGG (ING1)

<400> SEQUENCE: 606
ccatctcctg ccgctctagt aagagtbggc tacatagtaa tggcatcact tattt 55

<210> SEQ ID NO 607
<211> LENGTH: 55
<212> TYPE: DNA
<213> ORGANISM: Artificial Sequence
<220> FEATURE:
<223> OTHER INFORMATION: Synthesized: L1-4NHT (ING1)
<220> FEATURE:
<221> NAME/KEY: misc_feature
<222> LOCATION: (30)..(30)
<223> OTHER INFORMATION: n is a, c, g, or t

<400> SEQUENCE: 607
ccatctcctg ccgctctagt aagagtctcn htcatagtaa tggcatcact tattt 55

<210> SEQ ID NO 608
<211> LENGTH: 55
<212> TYPE: DNA
<213> ORGANISM: Artificial Sequence
<220> FEATURE:
<223> OTHER INFORMATION: Synthesized: L1-4VAA (ING1)

<400> SEQUENCE: 608
ccatctcctg ccgctctagt aagagtctcv aacatagtaa tggcatcact tattt 55

<210> SEQ ID NO 609
<211> LENGTH: 55
<212> TYPE: DNA
<213> ORGANISM: Artificial Sequence
<220> FEATURE:
<223> OTHER INFORMATION: Synthesized: L1-4BGG (ING1)

<400> SEQUENCE: 609
ccatctcctg ccgctctagt aagagtctcb ggcatagtaa tggcatcact tattt 55

<210> SEQ ID NO 610
<211> LENGTH: 54
<212> TYPE: DNA
<213> ORGANISM: Artificial Sequence
<220> FEATURE:
<223> OTHER INFORMATION: Synthesized: L12-1NHT (ING1)
<220> FEATURE:
<221> NAME/KEY: misc_feature
<222> LOCATION: (22)..(22)
<223> OTHER INFORMATION: n is a, c, g, or t

<400> SEQUENCE: 610
cgctctagta agagtctcct anhtagtaat ggcatcactt atttgtattg gtat 54

<210> SEQ ID NO 611
<211> LENGTH: 54
<212> TYPE: DNA
<213> ORGANISM: Artificial Sequence
<220> FEATURE:
<223> OTHER INFORMATION: Synthesized: L12-1VAA (ING1)

<400> SEQUENCE: 611
cgctctagta agagtctcct avaaagtaat ggcatcactt atttgtattg gtat 54

<210> SEQ ID NO 612
<211> LENGTH: 54
<212> TYPE: DNA
<213> ORGANISM: Artificial Sequence
<220> FEATURE:
<223> OTHER INFORMATION: Synthesized: L12-1BGG (ING1)

<400> SEQUENCE: 612
cgctctagta agagtctcct abggagtaat ggcatcactt atttgtattg gtat 54

<210> SEQ ID NO 613
<211> LENGTH: 54
<212> TYPE: DNA
<213> ORGANISM: Artificial Sequence
<220> FEATURE:
<223> OTHER INFORMATION: Synthesized: L12-2NHT (ING1)
<220> FEATURE:
<221> NAME/KEY: misc_feature
<222> LOCATION: (25)..(25)
<223> OTHER INFORMATION: n is a, c, g, or t

<400> SEQUENCE: 613
cgctctagta agagtctcct acatnhtaat ggcatcactt atttgtattg gtat 54

<210> SEQ ID NO 614
<211> LENGTH: 54
<212> TYPE: DNA
<213> ORGANISM: Artificial Sequence
<220> FEATURE:
<223> OTHER INFORMATION: Synthesized: L12-2VAA (ING1)

<400> SEQUENCE: 614
cgctctagta agagtctcct acatvaaaat ggcatcactt atttgtattg gtat 54

<210> SEQ ID NO 615
<211> LENGTH: 54
<212> TYPE: DNA
<213> ORGANISM: Artificial Sequence
<220> FEATURE:
<223> OTHER INFORMATION: Synthesized: L12-2BGG (ING1)

<400> SEQUENCE: 615
cgctctagta agagtctcct acatbggaat ggcatcactt atttgtattg gtat 54

<210> SEQ ID NO 616
<211> LENGTH: 54
<212> TYPE: DNA
<213> ORGANISM: Artificial Sequence
<220> FEATURE:
<223> OTHER INFORMATION: Synthesized: L12-3NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 616
cgctctagta agagtctcct acatagtnht ggcatcactt atttgtattg gtat 54

<210> SEQ ID NO 617
<211> LENGTH: 54
<212> TYPE: DNA
<213> ORGANISM: Artificial Sequence
<220> FEATURE:
<223> OTHER INFORMATION: Synthesized: L12-3VAA (ING1)

<400> SEQUENCE: 617
cgctctagta agagtctcct acatagtvaa ggcatcactt atttgtattg gtat 54

<210> SEQ ID NO 618
<211> LENGTH: 54
<212> TYPE: DNA
<213> ORGANISM: Artificial Sequence
<220> FEATURE:
<223> OTHER INFORMATION: Synthesized: L12-3BGG (ING1)

<400> SEQUENCE: 618
cgctctagta agagtctcct acatagtbgg ggcatcactt atttgtattg gtat 54

<210> SEQ ID NO 619
<211> LENGTH: 54
<212> TYPE: DNA
<213> ORGANISM: Artificial Sequence
<220> FEATURE:
<223> OTHER INFORMATION: Synthesized: L13-1NHT (ING1)
<220> FEATURE:
<221> NAME/KEY: misc_feature
<222> LOCATION: (23)..(23)
<223> OTHER INFORMATION: n is a, c, g, or t

<400> SEQUENCE: 619
gagtctccta catagtaatg gcnhtactta tttgtattgg tatttacaga agcc 54

<210> SEQ ID NO 620
<211> LENGTH: 54
<212> TYPE: DNA
<213> ORGANISM: Artificial Sequence
<220> FEATURE:
<223> OTHER INFORMATION: Synthesized: L13-1VAA (ING1)

<400> SEQUENCE: 620
gagtctccta catagtaatg gcvaaactta tttgtattgg tatttacaga agcc 54

<210> SEQ ID NO 621
<211> LENGTH: 54
<212> TYPE: DNA
<213> ORGANISM: Artificial Sequence
<220> FEATURE:

<223> OTHER INFORMATION: Synthesized: L13-1BGG (ING1)

<400> SEQUENCE: 621
gagtctccta catagtaatg gcbggactta tttgtattgg tatttacaga agcc 54

<210> SEQ ID NO 622
<211> LENGTH: 54
<212> TYPE: DNA
<213> ORGANISM: Artificial Sequence
<220> FEATURE:
<223> OTHER INFORMATION: Synthesized: L13-2NHT (ING1)
<220> FEATURE:
<221> NAME/KEY: misc_feature
<222> LOCATION: (26)..(26)
<223> OTHER INFORMATION: n is a, c, g, or t

<400> SEQUENCE: 622
gagtctccta catagtaatg gcatcnhtta tttgtattgg tatttacaga agcc 54

<210> SEQ ID NO 623
<211> LENGTH: 54
<212> TYPE: DNA
<213> ORGANISM: Artificial Sequence
<220> FEATURE:
<223> OTHER INFORMATION: Synthesized: L13-2VAA (ING1)

<400> SEQUENCE: 623
gagtctccta catagtaatg gcatcvaata tttgtattgg tatttacaga agcc 54

<210> SEQ ID NO 624
<211> LENGTH: 54
<212> TYPE: DNA
<213> ORGANISM: Artificial Sequence
<220> FEATURE:
<223> OTHER INFORMATION: Synthesized: L13-2BGG (ING1)

<400> SEQUENCE: 624
gagtctccta catagtaatg gcatcbggta tttgtattgg tatttacaga agcc 54

<210> SEQ ID NO 625
<211> LENGTH: 54
<212> TYPE: DNA
<213> ORGANISM: Artificial Sequence
<220> FEATURE:
<223> OTHER INFORMATION: Synthesized: L13-3NHT (ING1)
<220> FEATURE:
<221> NAME/KEY: misc_feature
<222> LOCATION: (29)..(29)
<223> OTHER INFORMATION: n is a, c, g, or t

<400> SEQUENCE: 625
gagtctccta catagtaatg gcatcactnh tttgtattgg tatttacaga agcc 54

<210> SEQ ID NO 626
<211> LENGTH: 54
<212> TYPE: DNA
<213> ORGANISM: Artificial Sequence
<220> FEATURE:
<223> OTHER INFORMATION: Synthesized: L13-3VAA (ING1)

<400> SEQUENCE: 626
gagtctccta catagtaatg gcatcactva attgtattgg tatttacaga agcc 54

<210> SEQ ID NO 627
<211> LENGTH: 54
<212> TYPE: DNA
<213> ORGANISM: Artificial Sequence
<220> FEATURE:
<223> OTHER INFORMATION: Synthesized: L13-3BGG (ING1)

<400> SEQUENCE: 627
gagtctccta catagtaatg gcatcactbg gttgtattgg tatttacaga agcc 54

<210> SEQ ID NO 628
<211> LENGTH: 56
<212> TYPE: DNA
<213> ORGANISM: Artificial Sequence
<220> FEATURE:
<223> OTHER INFORMATION: Synthesized: L2-1NHT (ING1)
<220> FEATURE:
<221> NAME/KEY: misc_feature
<222> LOCATION: (22)..(22)
<223> OTHER INFORMATION: n is a, c, g, or t

<400> SEQUENCE: 628
cagtctcctc agctcctgat tnhtcagatg tccaaccttg cctcaggagt cccaga 56

<210> SEQ ID NO 629
<211> LENGTH: 56
<212> TYPE: DNA
<213> ORGANISM: Artificial Sequence
<220> FEATURE:
<223> OTHER INFORMATION: Synthesized: L2-1VAA (ING1)

<400> SEQUENCE: 629
cagtctcctc agctcctgat tvaacagatg tccaaccttg cctcaggagt cccaga 56

<210> SEQ ID NO 630
<211> LENGTH: 56
<212> TYPE: DNA
<213> ORGANISM: Artificial Sequence
<220> FEATURE:
<223> OTHER INFORMATION: Synthesized: L2-1BGG (ING1)

<400> SEQUENCE: 630
cagtctcctc agctcctgat tbggcagatg tccaaccttg cctcaggagt cccaga 56

<210> SEQ ID NO 631
<211> LENGTH: 56
<212> TYPE: DNA
<213> ORGANISM: Artificial Sequence
<220> FEATURE:
<223> OTHER INFORMATION: Synthesized: L2-2NHT (ING1)
<220> FEATURE:
<221> NAME/KEY: misc_feature
<222> LOCATION: (25)..(25)
<223> OTHER INFORMATION: n is a, c, g, or t

<400> SEQUENCE: 631
cagtctcctc agctcctgat ttatnhtatg tccaaccttg cctcaggagt cccaga 56

<210> SEQ ID NO 632
<211> LENGTH: 56
<212> TYPE: DNA
<213> ORGANISM: Artificial Sequence
<220> FEATURE:
<223> OTHER INFORMATION: Synthesized: L2-2VAA (ING1)

<400> SEQUENCE: 632
cagtctcctc agctcctgat ttatvaaatg tccaaccttg cctcaggagt cccaga 56

<210> SEQ ID NO 633
<211> LENGTH: 56
<212> TYPE: DNA

<213> ORGANISM: Artificial Sequence
<220> FEATURE:
<223> OTHER INFORMATION: Synthesized: L2-2BGG (ING1)

<400> SEQUENCE: 633
cagtctcctc agctcctgat ttatbggatg tccaaccttg cctcaggagt cccaga 56

<210> SEQ ID NO 634
<211> LENGTH: 56
<212> TYPE: DNA
<213> ORGANISM: Artificial Sequence
<220> FEATURE:
<223> OTHER INFORMATION: Synthesized: L2-3NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 634
cagtctcctc agctcctgat ttatcagnht tccaaccttg cctcaggagt cccaga 56

<210> SEQ ID NO 635
<211> LENGTH: 56
<212> TYPE: DNA
<213> ORGANISM: Artificial Sequence
<220> FEATURE:
<223> OTHER INFORMATION: Synthesized: L2-3VAA (ING1)

<400> SEQUENCE: 635
cagtctcctc agctcctgat ttatcagvaa tccaaccttg cctcaggagt cccaga 56

<210> SEQ ID NO 636
<211> LENGTH: 56
<212> TYPE: DNA
<213> ORGANISM: Artificial Sequence
<220> FEATURE:
<223> OTHER INFORMATION: Synthesized: L2-3BGG (ING1)

<400> SEQUENCE: 636
cagtctcctc agctcctgat ttatcagbgg tccaaccttg cctcaggagt cccaga 56

<210> SEQ ID NO 637
<211> LENGTH: 56
<212> TYPE: DNA
<213> ORGANISM: Artificial Sequence
<220> FEATURE:
<223> OTHER INFORMATION: Synthesized: L2-4NHT (ING1)
<220> FEATURE:
<221> NAME/KEY: misc_feature
<222> LOCATION: (31)..(31)
<223> OTHER INFORMATION: n is a, c, g, or t

<400> SEQUENCE: 637
cagtctcctc agctcctgat ttatcagatg nhtaaccttg cctcaggagt cccaga 56

<210> SEQ ID NO 638
<211> LENGTH: 56
<212> TYPE: DNA
<213> ORGANISM: Artificial Sequence
<220> FEATURE:
<223> OTHER INFORMATION: Synthesized: L2-4VAA (ING1)

<400> SEQUENCE: 638
cagtctcctc agctcctgat ttatcagatg vaaaaccttg cctcaggagt cccaga 56

<210> SEQ ID NO 639
<211> LENGTH: 56

<212> TYPE: DNA
<213> ORGANISM: Artificial Sequence
<220> FEATURE:
<223> OTHER INFORMATION: Synthesized: L2-4BGG (ING1)

<400> SEQUENCE: 639
cagtctcctc agctcctgat ttatcagatg bggaaccttg cctcaggagt cccaga 56

<210> SEQ ID NO 640
<211> LENGTH: 56
<212> TYPE: DNA
<213> ORGANISM: Artificial Sequence
<220> FEATURE:
<223> OTHER INFORMATION: Synthesized: L2-5NHT (ING1)
<220> FEATURE:
<221> NAME/KEY: misc_feature
<222> LOCATION: (34)..(34)
<223> OTHER INFORMATION: n is a, c, g, or t

<400> SEQUENCE: 640
cagtctcctc agctcctgat ttatcagatg tccnhtcttg cctcaggagt cccaga 56

<210> SEQ ID NO 641
<211> LENGTH: 56
<212> TYPE: DNA
<213> ORGANISM: Artificial Sequence
<220> FEATURE:
<223> OTHER INFORMATION: Synthesized: L2-5VAA (ING1)

<400> SEQUENCE: 641
cagtctcctc agctcctgat ttatcagatg tccvaacttg cctcaggagt cccaga 56

<210> SEQ ID NO 642
<211> LENGTH: 56
<212> TYPE: DNA
<213> ORGANISM: Artificial Sequence
<220> FEATURE:
<223> OTHER INFORMATION: Synthesized: L2-5BGG (ING1)

<400> SEQUENCE: 642
cagtctcctc agctcctgat ttatcagatg tccbggcttg cctcaggagt cccaga 56

<210> SEQ ID NO 643
<211> LENGTH: 59
<212> TYPE: DNA
<213> ORGANISM: Artificial Sequence
<220> FEATURE:
<223> OTHER INFORMATION: Synthesized: H1-1NHT (ING1)
<220> FEATURE:
<221> NAME/KEY: misc_feature
<222> LOCATION: (22)..(22)
<223> OTHER INFORMATION: n is a, c, g, or t

<400> SEQUENCE: 643
tcctgcaagg cttctggata tnhtttcaca aaatatggaa tgaactgggt gaagcaggc 59

<210> SEQ ID NO 644
<211> LENGTH: 59
<212> TYPE: DNA
<213> ORGANISM: Artificial Sequence
<220> FEATURE:
<223> OTHER INFORMATION: Synthesized: H1-1VAA (ING1)

<400> SEQUENCE: 644
tcctgcaagg cttctggata tvaattcaca aaatatggaa tgaactgggt gaagcaggc 59

<210> SEQ ID NO 645

<211> LENGTH: 59
<212> TYPE: DNA
<213> ORGANISM: Artificial Sequence
<220> FEATURE:
<223> OTHER INFORMATION: Synthesized: H1-1BGG (ING1)

<400> SEQUENCE: 645
tcctgcaagg cttctggata tbggttcaca aaatatggaa tgaactgggt gaagcaggc 59

<210> SEQ ID NO 646
<211> LENGTH: 59
<212> TYPE: DNA
<213> ORGANISM: Artificial Sequence
<220> FEATURE:
<223> OTHER INFORMATION: Synthesized: H1-2NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 646
tcctgcaagg cttctggata taccttcnht aaatatggaa tgaactgggt gaagcaggc 59

<210> SEQ ID NO 647
<211> LENGTH: 59
<212> TYPE: DNA
<213> ORGANISM: Artificial Sequence
<220> FEATURE:
<223> OTHER INFORMATION: Synthesized: H1-2VAA (ING1)

<400> SEQUENCE: 647
tcctgcaagg cttctggata taccttcvaa aaatatggaa tgaactgggt gaagcaggc 59

<210> SEQ ID NO 648
<211> LENGTH: 59
<212> TYPE: DNA
<213> ORGANISM: Artificial Sequence
<220> FEATURE:
<223> OTHER INFORMATION: Synthesized: H1-2BGG (ING1)

<400> SEQUENCE: 648
tcctgcaagg cttctggata taccttcbgg aaatatggaa tgaactgggt gaagcaggc 59

<210> SEQ ID NO 649
<211> LENGTH: 59
<212> TYPE: DNA
<213> ORGANISM: Artificial Sequence
<220> FEATURE:
<223> OTHER INFORMATION: Synthesized: H1-3NHT (ING1)
<220> FEATURE:
<221> NAME/KEY: misc_feature
<222> LOCATION: (31)..(31)
<223> OTHER INFORMATION: n is a, c, g, or t

<400> SEQUENCE: 649
tcctgcaagg cttctggata taccttcaca nhttatggaa tgaactgggt gaagcaggc 59

<210> SEQ ID NO 650
<211> LENGTH: 59
<212> TYPE: DNA
<213> ORGANISM: Artificial Sequence
<220> FEATURE:
<223> OTHER INFORMATION: Synthesized: H1-3VAA (ING1)

<400> SEQUENCE: 650
tcctgcaagg cttctggata taccttcaca vaatatggaa tgaactgggt gaagcaggc 59

<210> SEQ ID NO 651
<211> LENGTH: 59
<212> TYPE: DNA
<213> ORGANISM: Artificial Sequence
<220> FEATURE:
<223> OTHER INFORMATION: Synthesized: H1-3BGG (ING1)

<400> SEQUENCE: 651
tcctgcaagg cttctggata taccttcaca bggtatggaa tgaactgggt gaagcaggc 59

<210> SEQ ID NO 652
<211> LENGTH: 59
<212> TYPE: DNA
<213> ORGANISM: Artificial Sequence
<220> FEATURE:
<223> OTHER INFORMATION: Synthesized: H1-4NHT (ING1)
<220> FEATURE:
<221> NAME/KEY: misc_feature
<222> LOCATION: (34)..(34)
<223> OTHER INFORMATION: n is a, c, g, or t

<400> SEQUENCE: 652
tcctgcaagg cttctggata taccttcaca aaanhtggaa tgaactgggt gaagcaggc 59

<210> SEQ ID NO 653
<211> LENGTH: 59
<212> TYPE: DNA
<213> ORGANISM: Artificial Sequence
<220> FEATURE:
<223> OTHER INFORMATION: Synthesized: H1-4VAA (ING1)

<400> SEQUENCE: 653
tcctgcaagg cttctggata taccttcaca aaavaaggaa tgaactgggt gaagcaggc 59

<210> SEQ ID NO 654
<211> LENGTH: 59
<212> TYPE: DNA
<213> ORGANISM: Artificial Sequence
<220> FEATURE:
<223> OTHER INFORMATION: Synthesized: H1-4BGG (ING1)

<400> SEQUENCE: 654
tcctgcaagg cttctggata taccttcaca aaabggggaa tgaactgggt gaagcaggc 59

<210> SEQ ID NO 655
<211> LENGTH: 59
<212> TYPE: DNA
<213> ORGANISM: Artificial Sequence
<220> FEATURE:
<223> OTHER INFORMATION: Synthesized: H1-5NHT (ING1)
<220> FEATURE:
<221> NAME/KEY: misc_feature
<222> LOCATION: (37)..(37)
<223> OTHER INFORMATION: n is a, c, g, or t

<400> SEQUENCE: 655
tcctgcaagg cttctggata taccttcaca aaatatnhta tgaactgggt gaagcaggc 59

<210> SEQ ID NO 656
<211> LENGTH: 59
<212> TYPE: DNA
<213> ORGANISM: Artificial Sequence
<220> FEATURE:
<223> OTHER INFORMATION: Synthesized: H1-5VAA (ING1)

<400> SEQUENCE: 656
tcctgcaagg cttctggata taccttcaca aaatatvaaa tgaactgggt gaagcaggc 59

<210> SEQ ID NO 657
<211> LENGTH: 59
<212> TYPE: DNA
<213> ORGANISM: Artificial Sequence
<220> FEATURE:
<223> OTHER INFORMATION: Synthesized: H1-5BGG (ING1)

<400> SEQUENCE: 657
tcctgcaagg cttctggata taccttcaca aaatatbgga tgaactgggt gaagcaggc 59

<210> SEQ ID NO 658
<211> LENGTH: 58
<212> TYPE: DNA
<213> ORGANISM: Artificial Sequence
<220> FEATURE:
<223> OTHER INFORMATION: Synthesized: H2-1NHT (ING1)
<220> FEATURE:
<221> NAME/KEY: misc_feature
<222> LOCATION: (22)..(22)
<223> OTHER INFORMATION: n is a, c, g, or t

<400> SEQUENCE: 658
aagggtttaa agtggatggg cnhtataaac acctacactg aagagcctac atatggtg 58

<210> SEQ ID NO 659
<211> LENGTH: 58
<212> TYPE: DNA
<213> ORGANISM: Artificial Sequence
<220> FEATURE:
<223> OTHER INFORMATION: Synthesized: H2-1VAA (ING1)

<400> SEQUENCE: 659
aagggtttaa agtggatggg cvaaataaac acctacactg aagagcctac atatggtg 58

<210> SEQ ID NO 660
<211> LENGTH: 58
<212> TYPE: DNA
<213> ORGANISM: Artificial Sequence
<220> FEATURE:
<223> OTHER INFORMATION: Synthesized: H2-1BGG (ING1)

<400> SEQUENCE: 660
aagggtttaa agtggatggg cbggataaac acctacactg aagagcctac atatggtg 58

<210> SEQ ID NO 661
<211> LENGTH: 58
<212> TYPE: DNA
<213> ORGANISM: Artificial Sequence
<220> FEATURE:
<223> OTHER INFORMATION: Synthesized: H2-2NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 661
aagggtttaa agtggatggg ctggatanht acctacactg aagagcctac atatggtg 58

<210> SEQ ID NO 662
<211> LENGTH: 58
<212> TYPE: DNA
<213> ORGANISM: Artificial Sequence
<220> FEATURE:
<223> OTHER INFORMATION: Synthesized: H2-2VAA (ING1)

<400> SEQUENCE: 662
aagggtttaa agtggatggg ctggatavaa acctacactg aagagcctac atatggtg 58

<210> SEQ ID NO 663
<211> LENGTH: 58
<212> TYPE: DNA
<213> ORGANISM: Artificial Sequence
<220> FEATURE:
<223> OTHER INFORMATION: Synthesized: H2-2BGG (ING1)

<400> SEQUENCE: 663
aagggtttaa agtggatggg ctggatabgg acctacactg aagagcctac atatggtg 58

<210> SEQ ID NO 664
<211> LENGTH: 58
<212> TYPE: DNA
<213> ORGANISM: Artificial Sequence
<220> FEATURE:
<223> OTHER INFORMATION: Synthesized: H2-3NHT (ING1)
<220> FEATURE:
<221> NAME/KEY: misc_feature
<222> LOCATION: (31)..(31)
<223> OTHER INFORMATION: n is a, c, g, or t

<400> SEQUENCE: 664
aagggtttaa agtggatggg ctggataaac nhttacactg aagagcctac atatggtg 58

<210> SEQ ID NO 665
<211> LENGTH: 58
<212> TYPE: DNA
<213> ORGANISM: Artificial Sequence
<220> FEATURE:
<223> OTHER INFORMATION: Synthesized: H2-3VAA (ING1)

<400> SEQUENCE: 665
aagggtttaa agtggatggg ctggataaac vaatacactg aagagcctac atatggtg 58

<210> SEQ ID NO 666
<211> LENGTH: 58
<212> TYPE: DNA
<213> ORGANISM: Artificial Sequence
<220> FEATURE:
<223> OTHER INFORMATION: Synthesized: H2-3BGG (ING1)

<400> SEQUENCE: 666
aagggtttaa agtggatggg ctggataaac bggtacactg aagagcctac atatggtg 58

<210> SEQ ID NO 667
<211> LENGTH: 58
<212> TYPE: DNA
<213> ORGANISM: Artificial Sequence
<220> FEATURE:
<223> OTHER INFORMATION: Synthesized: H2-4NHT (ING1)
<220> FEATURE:
<221> NAME/KEY: misc_feature
<222> LOCATION: (34)..(34)
<223> OTHER INFORMATION: n is a, c, g, or t

<400> SEQUENCE: 667
aagggtttaa agtggatggg ctggataaac accnhtactg aagagcctac atatggtg 58

<210> SEQ ID NO 668
<211> LENGTH: 58
<212> TYPE: DNA
<213> ORGANISM: Artificial Sequence
<220> FEATURE:
<223> OTHER INFORMATION: Synthesized: H2-4VAA (ING1)

<400> SEQUENCE: 668
aagggtttaa agtggatggg ctggataaac accvaaactg aagagcctac atatggtg 58

<210> SEQ ID NO 669
<211> LENGTH: 58
<212> TYPE: DNA
<213> ORGANISM: Artificial Sequence
<220> FEATURE:
<223> OTHER INFORMATION: Synthesized: H2-4BGG (ING1)

<400> SEQUENCE: 669
aagggtttaa agtggatggg ctggataaac accbggactg aagagcctac atatggtg 58

<210> SEQ ID NO 670
<211> LENGTH: 58
<212> TYPE: DNA
<213> ORGANISM: Artificial Sequence
<220> FEATURE:
<223> OTHER INFORMATION: Synthesized: H22-1NHT (ING1)
<220> FEATURE:
<221> NAME/KEY: misc_feature
<222> LOCATION: (22)..(22)
<223> OTHER INFORMATION: n is a, c, g, or t

<400> SEQUENCE: 670
atgggctgga taaacaccta cnhtgaagag cctacatatg gtgatgactt caagggac 58

<210> SEQ ID NO 671
<211> LENGTH: 58
<212> TYPE: DNA
<213> ORGANISM: Artificial Sequence
<220> FEATURE:
<223> OTHER INFORMATION: Synthesized: H22-1VAA (ING1)

<400> SEQUENCE: 671
atgggctgga taaacaccta cvaagaagag cctacatatg gtgatgactt caagggac 58

<210> SEQ ID NO 672
<211> LENGTH: 58
<212> TYPE: DNA
<213> ORGANISM: Artificial Sequence
<220> FEATURE:
<223> OTHER INFORMATION: Synthesized: H22-1BGG (ING1)

<400> SEQUENCE: 672
atgggctgga taaacaccta cbgggaagag cctacatatg gtgatgactt caagggac 58

<210> SEQ ID NO 673
<211> LENGTH: 58
<212> TYPE: DNA
<213> ORGANISM: Artificial Sequence
<220> FEATURE:
<223> OTHER INFORMATION: Synthesized: H22-2NHT (ING1)
<220> FEATURE:
<221> NAME/KEY: misc_feature
<222> LOCATION: (25)..(25)
<223> OTHER INFORMATION: n is a, c, g, or t

<400> SEQUENCE: 673
atgggctgga taaacaccta cactnhtgag cctacatatg gtgatgactt caagggac 58

<210> SEQ ID NO 674
<211> LENGTH: 58
<212> TYPE: DNA
<213> ORGANISM: Artificial Sequence
<220> FEATURE:
<223> OTHER INFORMATION: Synthesized: H22-2VAA (ING1)

<400> SEQUENCE: 674
atgggctgga taaacaccta cactvaagag cctacatatg gtgatgactt caagggac 58

<210> SEQ ID NO 675
<211> LENGTH: 58
<212> TYPE: DNA
<213> ORGANISM: Artificial Sequence
<220> FEATURE:
<223> OTHER INFORMATION: Synthesized: H22-2BGG (ING1)

<400> SEQUENCE: 675
atgggctgga taaacaccta cactbgggag cctacatatg gtgatgactt caagggac 58

<210> SEQ ID NO 676
<211> LENGTH: 58
<212> TYPE: DNA
<213> ORGANISM: Artificial Sequence
<220> FEATURE:
<223> OTHER INFORMATION: Synthesized: H22-3NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 676
atgggctgga taaacaccta cactgaanht cctacatatg gtgatgactt caagggac 58

<210> SEQ ID NO 677
<211> LENGTH: 58
<212> TYPE: DNA
<213> ORGANISM: Artificial Sequence
<220> FEATURE:
<223> OTHER INFORMATION: Synthesized: H22-3VAA (ING1)

<400> SEQUENCE: 677
atgggctgga taaacaccta cactgaavaa cctacatatg gtgatgactt caagggac 58

<210> SEQ ID NO 678
<211> LENGTH: 58
<212> TYPE: DNA
<213> ORGANISM: Artificial Sequence
<220> FEATURE:
<223> OTHER INFORMATION: Synthesized: H22-3BGG (ING1)

<400> SEQUENCE: 678
atgggctgga taaacaccta cactgaabgg cctacatatg gtgatgactt caagggac 58

<210> SEQ ID NO 679
<211> LENGTH: 58
<212> TYPE: DNA
<213> ORGANISM: Artificial Sequence
<220> FEATURE:
<223> OTHER INFORMATION: Synthesized: H22-4NHT (ING1)
<220> FEATURE:
<221> NAME/KEY: misc_feature
<222> LOCATION: (31)..(31)
<223> OTHER INFORMATION: n is a, c, g, or t

<400> SEQUENCE: 679
atgggctgga taaacaccta cactgaagag nhtacatatg gtgatgactt caagggac 58

<210> SEQ ID NO 680
<211> LENGTH: 58
<212> TYPE: DNA
<213> ORGANISM: Artificial Sequence
<220> FEATURE:
<223> OTHER INFORMATION: Synthesized: H22-4VAA (ING1)

<400> SEQUENCE: 680
atgggctgga taaacaccta cactgaagag vaaacatatg gtgatgactt caagggac 58

<210> SEQ ID NO 681
<211> LENGTH: 58
<212> TYPE: DNA
<213> ORGANISM: Artificial Sequence
<220> FEATURE:
<223> OTHER INFORMATION: Synthesized: H22-4BGG (ING1)

<400> SEQUENCE: 681
atgggctgga taaacaccta cactgaagag bggacatatg gtgatgactt caagggac 58

<210> SEQ ID NO 682
<211> LENGTH: 58
<212> TYPE: DNA
<213> ORGANISM: Artificial Sequence
<220> FEATURE:
<223> OTHER INFORMATION: Synthesized: H22-5NHT (ING1)
<220> FEATURE:
<221> NAME/KEY: misc_feature
<222> LOCATION: (34)..(34)
<223> OTHER INFORMATION: n is a, c, g, or t

<400> SEQUENCE: 682
atgggctgga taaacaccta cactgaagag cctnhttatg gtgatgactt caagggac 58

<210> SEQ ID NO 683
<211> LENGTH: 58
<212> TYPE: DNA
<213> ORGANISM: Artificial Sequence
<220> FEATURE:
<223> OTHER INFORMATION: Synthesized: H22-5VAA (ING1)

<400> SEQUENCE: 683
atgggctgga taaacaccta cactgaagag cctvaatatg gtgatgactt caagggac 58

<210> SEQ ID NO 684
<211> LENGTH: 58
<212> TYPE: DNA
<213> ORGANISM: Artificial Sequence
<220> FEATURE:
<223> OTHER INFORMATION: Synthesized: H22-5BGG (ING1)

<400> SEQUENCE: 684
atgggctgga taaacaccta cactgaagag cctbggtatg gtgatgactt caagggac 58

<210> SEQ ID NO 685
<211> LENGTH: 53
<212> TYPE: DNA
<213> ORGANISM: Artificial Sequence
<220> FEATURE:
<223> OTHER INFORMATION: Synthesized: H3-1NHT (ING1)
<220> FEATURE:
<221> NAME/KEY: misc_feature
<222> LOCATION: (25)..(25)
<223> OTHER INFORMATION: n is a, c, g, or t

<400> SEQUENCE: 685
gctacatatt tctgtgcaag atttnhttct gctgtggact actggggtca agg 53

<210> SEQ ID NO 686
<211> LENGTH: 53
<212> TYPE: DNA
<213> ORGANISM: Artificial Sequence
<220> FEATURE:
<223> OTHER INFORMATION: Synthesized: H3-1VAA (ING1)

<400> SEQUENCE: 686
gctacatatt tctgtgcaag atttvaatct gctgtggact actggggtca agg 53

<210> SEQ ID NO 687
<211> LENGTH: 53
<212> TYPE: DNA
<213> ORGANISM: Artificial Sequence
<220> FEATURE:
<223> OTHER INFORMATION: Synthesized: H3-1BGG (ING1)

<400> SEQUENCE: 687
gctacatatt tctgtgcaag atttbggtct gctgtggact actggggtca agg 53

<210> SEQ ID NO 688
<211> LENGTH: 53
<212> TYPE: DNA
<213> ORGANISM: Artificial Sequence
<220> FEATURE:
<223> OTHER INFORMATION: Synthesized: H3-2NHT (ING1)
<220> FEATURE:
<221> NAME/KEY: misc_feature
<222> LOCATION: (28)..(28)
<223> OTHER INFORMATION: n is a, c, g, or t

<400> SEQUENCE: 688
gctacatatt tctgtgcaag atttggcnht gctgtggact actggggtca agg 53

<210> SEQ ID NO 689
<211> LENGTH: 53
<212> TYPE: DNA
<213> ORGANISM: Artificial Sequence
<220> FEATURE:
<223> OTHER INFORMATION: Synthesized: H3-2VAA (ING1)

<400> SEQUENCE: 689
gctacatatt tctgtgcaag atttggcvaa gctgtggact actggggtca agg 53

<210> SEQ ID NO 690
<211> LENGTH: 53
<212> TYPE: DNA
<213> ORGANISM: Artificial Sequence
<220> FEATURE:
<223> OTHER INFORMATION: Synthesized: H3-2BGG (ING1)

<400> SEQUENCE: 690
gctacatatt tctgtgcaag atttggcbgg gctgtggact actggggtca agg 53

<210> SEQ ID NO 691
<211> LENGTH: 53
<212> TYPE: DNA
<213> ORGANISM: Artificial Sequence
<220> FEATURE:
<223> OTHER INFORMATION: Synthesized: H3-3NHT (ING1)
<220> FEATURE:
<221> NAME/KEY: misc_feature
<222> LOCATION: (31)..(31)
<223> OTHER INFORMATION: n is a, c, g, or t

<400> SEQUENCE: 691
gctacatatt tctgtgcaag atttggctct nhtgtggact actggggtca agg 53

<210> SEQ ID NO 692
<211> LENGTH: 53
<212> TYPE: DNA
<213> ORGANISM: Artificial Sequence
<220> FEATURE:

<223> OTHER INFORMATION: Synthesized: H3-3VAA (ING1)

<400> SEQUENCE: 692
gctacatatt tctgtgcaag atttggctct vaagtggact actggggtca agg 53

<210> SEQ ID NO 693
<211> LENGTH: 53
<212> TYPE: DNA
<213> ORGANISM: Artificial Sequence
<220> FEATURE:
<223> OTHER INFORMATION: Synthesized: H3-3BGG (ING1)

<400> SEQUENCE: 693
gctacatatt tctgtgcaag atttggctct bgggtggact actggggtca agg 53

<210> SEQ ID NO 694
<211> LENGTH: 46
<212> TYPE: DNA
<213> ORGANISM: Artificial Sequence
<220> FEATURE:
<223> OTHER INFORMATION: Synthesized: H32-1NHT (ING1)
<220> FEATURE:
<221> NAME/KEY: misc_feature
<222> LOCATION: (22)..(22)
<223> OTHER INFORMATION: n is a, c, g, or t

<400> SEQUENCE: 694
gcaagatttg gctctgctgt gnhttactgg ggtcaaggaa cctcgg 46

<210> SEQ ID NO 695
<211> LENGTH: 46
<212> TYPE: DNA
<213> ORGANISM: Artificial Sequence
<220> FEATURE:
<223> OTHER INFORMATION: Synthesized: H32-1VAA (ING1)

<400> SEQUENCE: 695
gcaagatttg gctctgctgt gvaatactgg ggtcaaggaa cctcgg 46

<210> SEQ ID NO 696
<211> LENGTH: 46
<212> TYPE: DNA
<213> ORGANISM: Artificial Sequence
<220> FEATURE:
<223> OTHER INFORMATION: Synthesized: H32-1BGG (ING1)

<400> SEQUENCE: 696
gcaagatttg gctctgctgt gbggtactgg ggtcaaggaa cctcgg 46

<210> SEQ ID NO 697
<211> LENGTH: 46
<212> TYPE: DNA
<213> ORGANISM: Artificial Sequence
<220> FEATURE:
<223> OTHER INFORMATION: Synthesized: H32-2NHT (ING1)
<220> FEATURE:
<221> NAME/KEY: misc_feature
<222> LOCATION: (25)..(25)
<223> OTHER INFORMATION: n is a, c, g, or t

<400> SEQUENCE: 697
gcaagatttg gctctgctgt ggacnhttgg ggtcaaggaa cctcgg 46

<210> SEQ ID NO 698
<211> LENGTH: 46
<212> TYPE: DNA
<213> ORGANISM: Artificial Sequence
<220> FEATURE:
<223> OTHER INFORMATION: Synthesized: H32-2VAA (ING1)

<400> SEQUENCE: 698
gcaagatttg gctctgctgt ggacvaatgg ggtcaaggaa cctcgg 46

<210> SEQ ID NO 699
<211> LENGTH: 46
<212> TYPE: DNA
<213> ORGANISM: Artificial Sequence
<220> FEATURE:
<223> OTHER INFORMATION: Synthesized: H32-2BGG (ING1)

<400> SEQUENCE: 699
gcaagatttg gctctgctgt ggacbggtgg ggtcaaggaa cctcgg 46

<210> SEQ ID NO 700
<211> LENGTH: 54
<212> TYPE: DNA
<213> ORGANISM: Artificial Sequence
<220> FEATURE:
<223> OTHER INFORMATION: Synthesized: H1-1NHT (IL1B) primer
<220> FEATURE:
<221> NAME/KEY: misc_feature
<222> LOCATION: (21)..(21)
<223> OTHER INFORMATION: n is a, c, g, or t

<400> SEQUENCE: 700
cttgcgctgc ttccggattc nhtttctcta agtactttat gttttgggtt cgcc 54

<210> SEQ ID NO 701
<211> LENGTH: 54
<212> TYPE: DNA
<213> ORGANISM: Artificial Sequence
<220> FEATURE:
<223> OTHER INFORMATION: Synthesized: H1-1VAA (IL1B) primer

<400> SEQUENCE: 701
cttgcgctgc ttccggattc vaattctcta agtactttat gttttgggtt cgcc 54

<210> SEQ ID NO 702
<211> LENGTH: 54
<212> TYPE: DNA
<213> ORGANISM: Artificial Sequence
<220> FEATURE:
<223> OTHER INFORMATION: Synthesized: H1-1BGG (IL1B) primer

<400> SEQUENCE: 702
cttgcgctgc ttccggattc bggttctcta agtactttat gttttgggtt cgcc 54

<210> SEQ ID NO 703
<211> LENGTH: 54
<212> TYPE: DNA
<213> ORGANISM: Artificial Sequence
<220> FEATURE:
<223> OTHER INFORMATION: Synthesized: H1-2NHT (IL1B) primer
<220> FEATURE:
<221> NAME/KEY: misc_feature
<222> LOCATION: (27)..(27)
<223> OTHER INFORMATION: n is a, c, g, or t

<400> SEQUENCE: 703
cttgcgctgc ttccggattc actttcnhta agtactttat gttttgggtt cgcc 54

<210> SEQ ID NO 704
<211> LENGTH: 54
<212> TYPE: DNA

<213> ORGANISM: Artificial Sequence
<220> FEATURE:
<223> OTHER INFORMATION: Synthesized: H1-2VAA (IL1B) primer

<400> SEQUENCE: 704
cttgcgctgc ttccggattc actttcvaaa agtactttat gttttgggtt cgcc 54

<210> SEQ ID NO 705
<211> LENGTH: 54
<212> TYPE: DNA
<213> ORGANISM: Artificial Sequence
<220> FEATURE:
<223> OTHER INFORMATION: Synthesized: H1-2BGG (IL1B) primer

<400> SEQUENCE: 705
cttgcgctgc ttccggattc actttcbgga agtactttat gttttgggtt cgcc 54

<210> SEQ ID NO 706
<211> LENGTH: 54
<212> TYPE: DNA
<213> ORGANISM: Artificial Sequence
<220> FEATURE:
<223> OTHER INFORMATION: Synthesized: H1-3NHT (IL1B) primer
<220> FEATURE:
<221> NAME/KEY: misc_feature
<222> LOCATION: (30)..(30)
<223> OTHER INFORMATION: n is a, c, g, or t

<400> SEQUENCE: 706
cttgcgctgc ttccggattc actttctctn httactttat gttttgggtt cgcc 54

<210> SEQ ID NO 707
<211> LENGTH: 54
<212> TYPE: DNA
<213> ORGANISM: Artificial Sequence
<220> FEATURE:
<223> OTHER INFORMATION: Synthesized: H1-3VAA (IL1B) primer

<400> SEQUENCE: 707
cttgcgctgc ttccggattc actttctctv aatactttat gttttgggtt cgcc 54

<210> SEQ ID NO 708
<211> LENGTH: 54
<212> TYPE: DNA
<213> ORGANISM: Artificial Sequence
<220> FEATURE:
<223> OTHER INFORMATION: Synthesized: H1-3BGG (IL1B) primer

<400> SEQUENCE: 708
cttgcgctgc ttccggattc actttctctb ggtactttat gttttgggtt cgcc 54

<210> SEQ ID NO 709
<211> LENGTH: 53
<212> TYPE: DNA
<213> ORGANISM: Artificial Sequence
<220> FEATURE:
<223> OTHER INFORMATION: Synthesized: H12-1NHT (IL1B) primer
<220> FEATURE:
<221> NAME/KEY: misc_feature
<222> LOCATION: (23)..(23)
<223> OTHER INFORMATION: n is a, c, g, or t

<400> SEQUENCE: 709
ttccggattc actttctcta agnhttttat gttttgggtt cgccaagctc ctg 53

<210> SEQ ID NO 710
<211> LENGTH: 53

<212> TYPE: DNA
<213> ORGANISM: Artificial Sequence
<220> FEATURE:
<223> OTHER INFORMATION: Synthesized: H12-1VAA (IL1B) primer

<400> SEQUENCE: 710
ttccggattc actttctcta agvaatttat gttttgggtt cgccaagctc ctg 53

<210> SEQ ID NO 711
<211> LENGTH: 53
<212> TYPE: DNA
<213> ORGANISM: Artificial Sequence
<220> FEATURE:
<223> OTHER INFORMATION: Synthesized: H12-1BGG (IL1B) primer

<400> SEQUENCE: 711
ttccggattc actttctcta agbggtttat gttttgggtt cgccaagctc ctg 53

<210> SEQ ID NO 712
<211> LENGTH: 53
<212> TYPE: DNA
<213> ORGANISM: Artificial Sequence
<220> FEATURE:
<223> OTHER INFORMATION: Synthesized: H12-2NHT (IL1B) primer
<220> FEATURE:
<221> NAME/KEY: misc_feature
<222> LOCATION: (26)..(26)
<223> OTHER INFORMATION: n is a, c, g, or t

<400> SEQUENCE: 712
ttccggattc actttctcta agtacnhtat gttttgggtt cgccaagctc ctg 53

<210> SEQ ID NO 713
<211> LENGTH: 53
<212> TYPE: DNA
<213> ORGANISM: Artificial Sequence
<220> FEATURE:
<223> OTHER INFORMATION: Synthesized: H12-2VAA (IL1B) primer

<400> SEQUENCE: 713
ttccggattc actttctcta agtacvaaat gttttgggtt cgccaagctc ctg 53

<210> SEQ ID NO 714
<211> LENGTH: 53
<212> TYPE: DNA
<213> ORGANISM: Artificial Sequence
<220> FEATURE:
<223> OTHER INFORMATION: Synthesized: H12-2BGG (IL1B) primer

<400> SEQUENCE: 714
ttccggattc actttctcta agtacbggat gttttgggtt cgccaagctc ctg 53

<210> SEQ ID NO 715
<211> LENGTH: 53
<212> TYPE: DNA
<213> ORGANISM: Artificial Sequence
<220> FEATURE:
<223> OTHER INFORMATION: Synthesized: H12-3NHT (IL1B) primer
<220> FEATURE:
<221> NAME/KEY: misc_feature
<222> LOCATION: (32)..(32)
<223> OTHER INFORMATION: n is a, c, g, or t

<400> SEQUENCE: 715
ttccggattc actttctcta agtactttat gnhttgggtt cgccaagctc ctg 53

<210> SEQ ID NO 716

<211> LENGTH: 53
<212> TYPE: DNA
<213> ORGANISM: Artificial Sequence
<220> FEATURE:
<223> OTHER INFORMATION: Synthesized: H12-3VAA (IL1B) primer

<400> SEQUENCE: 716
ttccggattc actttctcta agtactttat gvaatgggtt cgccaagctc ctg 53

<210> SEQ ID NO 717
<211> LENGTH: 53
<212> TYPE: DNA
<213> ORGANISM: Artificial Sequence
<220> FEATURE:
<223> OTHER INFORMATION: Synthesized: H12-3BGG (IL1B) primer

<400> SEQUENCE: 717
ttccggattc actttctcta agtactttat gbggtgggtt cgccaagctc ctg 53

<210> SEQ ID NO 718
<211> LENGTH: 57
<212> TYPE: DNA
<213> ORGANISM: Artificial Sequence
<220> FEATURE:
<223> OTHER INFORMATION: Synthesized: H2-1NHT (IL1B) primer
<220> FEATURE:
<221> NAME/KEY: misc_feature
<222> LOCATION: (23)..(23)
<223> OTHER INFORMATION: n is a, c, g, or t

<400> SEQUENCE: 718
taaaggtttg gagtgggttt ctnhtatctc tccttctggt ggcatgactc gttatgc 57

<210> SEQ ID NO 719
<211> LENGTH: 57
<212> TYPE: DNA
<213> ORGANISM: Artificial Sequence
<220> FEATURE:
<223> OTHER INFORMATION: Synthesized: H2-1VAA (IL1B) primer

<400> SEQUENCE: 719
taaaggtttg gagtgggttt ctvaaatctc tccttctggt ggcatgactc gttatgc 57

<210> SEQ ID NO 720
<211> LENGTH: 57
<212> TYPE: DNA
<213> ORGANISM: Artificial Sequence
<220> FEATURE:
<223> OTHER INFORMATION: Synthesized: H2-1BGG (IL1B) primer

<400> SEQUENCE: 720
taaaggtttg gagtgggttt ctbggatctc tccttctggt ggcatgactc gttatgc 57

<210> SEQ ID NO 721
<211> LENGTH: 57
<212> TYPE: DNA
<213> ORGANISM: Artificial Sequence
<220> FEATURE:
<223> OTHER INFORMATION: Synthesized: H2-2NHT (IL1B) primer
<220> FEATURE:
<221> NAME/KEY: misc_feature
<222> LOCATION: (26)..(26)
<223> OTHER INFORMATION: n is a, c, g, or t

<400> SEQUENCE: 721
taaaggtttg gagtgggttt ctgttnhttc tccttctggt ggcatgactc gttatgc 57

<210> SEQ ID NO 722
<211> LENGTH: 57
<212> TYPE: DNA
<213> ORGANISM: Artificial Sequence
<220> FEATURE:
<223> OTHER INFORMATION: Synthesized: H2-2VAA (IL1B) primer

<400> SEQUENCE: 722
taaaggtttg gagtgggttt ctgttvaatc tccttctggt ggcatgactc gttatgc 57

<210> SEQ ID NO 723
<211> LENGTH: 57
<212> TYPE: DNA
<213> ORGANISM: Artificial Sequence
<220> FEATURE:
<223> OTHER INFORMATION: Synthesized: H2-2BGG (IL1B) primer

<400> SEQUENCE: 723
taaaggtttg gagtgggttt ctgttbggtc tccttctggt ggcatgactc gttatgc 57

<210> SEQ ID NO 724
<211> LENGTH: 57
<212> TYPE: DNA
<213> ORGANISM: Artificial Sequence
<220> FEATURE:
<223> OTHER INFORMATION: Synthesized: H2-3NHT (IL1B) primer
<220> FEATURE:
<221> NAME/KEY: misc_feature
<222> LOCATION: (29)..(29)
<223> OTHER INFORMATION: n is a, c, g, or t

<400> SEQUENCE: 724
taaaggtttg gagtgggttt ctgttatcnh tccttctggt ggcatgactc gttatgc 57

<210> SEQ ID NO 725
<211> LENGTH: 57
<212> TYPE: DNA
<213> ORGANISM: Artificial Sequence
<220> FEATURE:
<223> OTHER INFORMATION: Synthesized: H2-3VAA (IL1B) primer

<400> SEQUENCE: 725
taaaggtttg gagtgggttt ctgttatcva accttctggt ggcatgactc gttatgc 57

<210> SEQ ID NO 726
<211> LENGTH: 57
<212> TYPE: DNA
<213> ORGANISM: Artificial Sequence
<220> FEATURE:
<223> OTHER INFORMATION: Synthesized: H2-3BGG (IL1B) primer

<400> SEQUENCE: 726
taaaggtttg gagtgggttt ctgttatcbg gccttctggt ggcatgactc gttatgc 57

<210> SEQ ID NO 727
<211> LENGTH: 57
<212> TYPE: DNA
<213> ORGANISM: Artificial Sequence
<220> FEATURE:
<223> OTHER INFORMATION: Synthesized: H2-4NHT (IL1B) primer
<220> FEATURE:
<221> NAME/KEY: misc_feature
<222> LOCATION: (32)..(32)
<223> OTHER INFORMATION: n is a, c, g, or t

<400> SEQUENCE: 727
taaaggtttg gagtgggttt ctgttatctc tnhttctggt ggcatgactc gttatgc 57

<210> SEQ ID NO 728
<211> LENGTH: 57
<212> TYPE: DNA
<213> ORGANISM: Artificial Sequence
<220> FEATURE:
<223> OTHER INFORMATION: Synthesized: H2-4VAA (IL1B) primer

<400> SEQUENCE: 728
taaaggtttg gagtgggttt ctgttatctc tvaatctggt ggcatgactc gttatgc 57

<210> SEQ ID NO 729
<211> LENGTH: 57
<212> TYPE: DNA
<213> ORGANISM: Artificial Sequence
<220> FEATURE:
<223> OTHER INFORMATION: Synthesized: H2-4BGG (IL1B) primer

<400> SEQUENCE: 729
taaaggtttg gagtgggttt ctgttatctc tbggtctggt ggcatgactc gttatgc 57

<210> SEQ ID NO 730
<211> LENGTH: 57
<212> TYPE: DNA
<213> ORGANISM: Artificial Sequence
<220> FEATURE:
<223> OTHER INFORMATION: Synthesized: H2-5NHT (IL1B) primer
<220> FEATURE:
<221> NAME/KEY: misc_feature
<222> LOCATION: (35)..(35)
<223> OTHER INFORMATION: n is a, c, g, or t

<400> SEQUENCE: 730
taaaggtttg gagtgggttt ctgttatctc tcctnhtggt ggcatgactc gttatgc 57

<210> SEQ ID NO 731
<211> LENGTH: 57
<212> TYPE: DNA
<213> ORGANISM: Artificial Sequence
<220> FEATURE:
<223> OTHER INFORMATION: Synthesized: H2-5VAA (IL1B) primer

<400> SEQUENCE: 731
taaaggtttg gagtgggttt ctgttatctc tcctvaaggt ggcatgactc gttatgc 57

<210> SEQ ID NO 732
<211> LENGTH: 57
<212> TYPE: DNA
<213> ORGANISM: Artificial Sequence
<220> FEATURE:
<223> OTHER INFORMATION: Synthesized: H2-5BGG (IL1B) primer

<400> SEQUENCE: 732
taaaggtttg gagtgggttt ctgttatctc tcctbggggt ggcatgactc gttatgc 57

<210> SEQ ID NO 733
<211> LENGTH: 59
<212> TYPE: DNA
<213> ORGANISM: Artificial Sequence
<220> FEATURE:
<223> OTHER INFORMATION: Synthesized: H22-1NHT (IL1B) primer
<220> FEATURE:
<221> NAME/KEY: misc_feature
<222> LOCATION: (23)..(23)
<223> OTHER INFORMATION: n is a, c, g, or t

<400> SEQUENCE: 733
ggtttctgtt atctctcctt ctnhtggcat gactcgttat gctgactccg ttaaaggtc 59

<210> SEQ ID NO 734
<211> LENGTH: 59
<212> TYPE: DNA
<213> ORGANISM: Artificial Sequence
<220> FEATURE:
<223> OTHER INFORMATION: Synthesized: H22-1VAA (IL1B) primer

<400> SEQUENCE: 734
ggtttctgtt atctctcctt ctvaaggcat gactcgttat gctgactccg ttaaaggtc 59

<210> SEQ ID NO 735
<211> LENGTH: 59
<212> TYPE: DNA
<213> ORGANISM: Artificial Sequence
<220> FEATURE:
<223> OTHER INFORMATION: Synthesized: H22-1BGG (IL1B) primer

<400> SEQUENCE: 735
ggtttctgtt atctctcctt ctbggggcat gactcgttat gctgactccg ttaaaggtc 59

<210> SEQ ID NO 736
<211> LENGTH: 59
<212> TYPE: DNA
<213> ORGANISM: Artificial Sequence
<220> FEATURE:
<223> OTHER INFORMATION: Synthesized: H22-2NHT (IL1B) primer
<220> FEATURE:
<221> NAME/KEY: misc_feature
<222> LOCATION: (26)..(26)
<223> OTHER INFORMATION: n is a, c, g, or t

<400> SEQUENCE: 736
ggtttctgtt atctctcctt ctggtnhtat gactcgttat gctgactccg ttaaaggtc 59

<210> SEQ ID NO 737
<211> LENGTH: 59
<212> TYPE: DNA
<213> ORGANISM: Artificial Sequence
<220> FEATURE:
<223> OTHER INFORMATION: Synthesized: H22-2VAA (IL1B) primer

<400> SEQUENCE: 737
ggtttctgtt atctctcctt ctggtvaaat gactcgttat gctgactccg ttaaaggtc 59

<210> SEQ ID NO 738
<211> LENGTH: 59
<212> TYPE: DNA
<213> ORGANISM: Artificial Sequence
<220> FEATURE:
<223> OTHER INFORMATION: Synthesized: H22-2BGG (IL1B) primer

<400> SEQUENCE: 738
ggtttctgtt atctctcctt ctggtbggat gactcgttat gctgactccg ttaaaggtc 59

<210> SEQ ID NO 739
<211> LENGTH: 59
<212> TYPE: DNA
<213> ORGANISM: Artificial Sequence
<220> FEATURE:
<223> OTHER INFORMATION: Synthesized: H22-3NHT (IL1B) primer
<220> FEATURE:
<221> NAME/KEY: misc_feature
<222> LOCATION: (29)..(29)
<223> OTHER INFORMATION: n is a, c, g, or t

<400> SEQUENCE: 739
ggtttctgtt atctctcctt ctggtggcnh tactcgttat gctgactccg ttaaaggtc 59

<210> SEQ ID NO 740
<211> LENGTH: 59
<212> TYPE: DNA
<213> ORGANISM: Artificial Sequence
<220> FEATURE:
<223> OTHER INFORMATION: Synthesized: H22-3VAA (IL1B) primer

<400> SEQUENCE: 740
ggtttctgtt atctctcctt ctggtggcva aactcgttat gctgactccg ttaaaggtc 59

<210> SEQ ID NO 741
<211> LENGTH: 59
<212> TYPE: DNA
<213> ORGANISM: Artificial Sequence
<220> FEATURE:
<223> OTHER INFORMATION: Synthesized: H22-3BGG (IL1B) primer

<400> SEQUENCE: 741
ggtttctgtt atctctcctt ctggtggcbg gactcgttat gctgactccg ttaaaggtc 59

<210> SEQ ID NO 742
<211> LENGTH: 59
<212> TYPE: DNA
<213> ORGANISM: Artificial Sequence
<220> FEATURE:
<223> OTHER INFORMATION: Synthesized: H22-4NHT (IL1B) primer
<220> FEATURE:
<221> NAME/KEY: misc_feature
<222> LOCATION: (32)..(32)
<223> OTHER INFORMATION: n is a, c, g, or t

<400> SEQUENCE: 742
ggtttctgtt atctctcctt ctggtggcat gnhtcgttat gctgactccg ttaaaggtc 59

<210> SEQ ID NO 743
<211> LENGTH: 59
<212> TYPE: DNA
<213> ORGANISM: Artificial Sequence
<220> FEATURE:
<223> OTHER INFORMATION: Synthesized: H22-4VAA (IL1B) primer

<400> SEQUENCE: 743
ggtttctgtt atctctcctt ctggtggcat gvaacgttat gctgactccg ttaaaggtc 59

<210> SEQ ID NO 744
<211> LENGTH: 59
<212> TYPE: DNA
<213> ORGANISM: Artificial Sequence
<220> FEATURE:
<223> OTHER INFORMATION: Synthesized: H22-4BGG (IL1B) primer

<400> SEQUENCE: 744
ggtttctgtt atctctcctt ctggtggcat gbggcgttat gctgactccg ttaaaggtc 59

<210> SEQ ID NO 745
<211> LENGTH: 59
<212> TYPE: DNA
<213> ORGANISM: Artificial Sequence
<220> FEATURE:
<223> OTHER INFORMATION: Synthesized: H22-5NHT (IL1B) primer
<220> FEATURE:
<221> NAME/KEY: misc_feature
<222> LOCATION: (35)..(35)
<223> OTHER INFORMATION: n is a, c, g, or t

<400> SEQUENCE: 745
ggtttctgtt atctctcctt ctggtggcat gactnhttat gctgactccg ttaaaggtc 59

<210> SEQ ID NO 746
<211> LENGTH: 59
<212> TYPE: DNA
<213> ORGANISM: Artificial Sequence
<220> FEATURE:
<223> OTHER INFORMATION: Synthesized: H22-5VAA (IL1B) primer

<400> SEQUENCE: 746
ggtttctgtt atctctcctt ctggtggcat gactvaatat gctgactccg ttaaaggtc 59

<210> SEQ ID NO 747
<211> LENGTH: 59
<212> TYPE: DNA
<213> ORGANISM: Artificial Sequence
<220> FEATURE:
<223> OTHER INFORMATION: Synthesized: H22-5BGG (IL1B) primer

<400> SEQUENCE: 747
ggtttctgtt atctctcctt ctggtggcat gactbggtat gctgactccg ttaaaggtc 59

<210> SEQ ID NO 748
<211> LENGTH: 56
<212> TYPE: DNA
<213> ORGANISM: Artificial Sequence
<220> FEATURE:
<223> OTHER INFORMATION: Synthesized: H3-1NHT (IL1B) primer
<220> FEATURE:
<221> NAME/KEY: misc_feature
<222> LOCATION: (22)..(22)
<223> OTHER INFORMATION: n is a, c, g, or t

<400> SEQUENCE: 748
gcagtctact attgtgcgag anhtggctac ggtggtaact ctgactactg gggcca 56

<210> SEQ ID NO 749
<211> LENGTH: 56
<212> TYPE: DNA
<213> ORGANISM: Artificial Sequence
<220> FEATURE:
<223> OTHER INFORMATION: Synthesized: H3-1VAA (IL1B) primer

<400> SEQUENCE: 749
gcagtctact attgtgcgag avaaggctac ggtggtaact ctgactactg gggcca 56

<210> SEQ ID NO 750
<211> LENGTH: 56
<212> TYPE: DNA
<213> ORGANISM: Artificial Sequence
<220> FEATURE:
<223> OTHER INFORMATION: Synthesized: H3-1BGG (IL1B) primer

<400> SEQUENCE: 750
gcagtctact attgtgcgag abggggctac ggtggtaact ctgactactg gggcca 56

<210> SEQ ID NO 751
<211> LENGTH: 56
<212> TYPE: DNA
<213> ORGANISM: Artificial Sequence
<220> FEATURE:
<223> OTHER INFORMATION: Synthesized: H3-2NHT (IL1B) primer
<220> FEATURE:
<221> NAME/KEY: misc_feature
<222> LOCATION: (25)..(25)
<223> OTHER INFORMATION: n is a, c, g, or t

<400> SEQUENCE: 751
gcagtctact attgtgcgag agtcnhttac ggtggtaact ctgactactg gggcca 56

<210> SEQ ID NO 752
<211> LENGTH: 56
<212> TYPE: DNA
<213> ORGANISM: Artificial Sequence
<220> FEATURE:
<223> OTHER INFORMATION: Synthesized: H3-2VAA (IL1B) primer

<400> SEQUENCE: 752
gcagtctact attgtgcgag agtcvaatac ggtggtaact ctgactactg gggcca 56

<210> SEQ ID NO 753
<211> LENGTH: 56
<212> TYPE: DNA
<213> ORGANISM: Artificial Sequence
<220> FEATURE:
<223> OTHER INFORMATION: Synthesized: H3-2BGG (IL1B) primer

<400> SEQUENCE: 753
gcagtctact attgtgcgag agtcbggtac ggtggtaact ctgactactg gggcca 56

<210> SEQ ID NO 754
<211> LENGTH: 56
<212> TYPE: DNA
<213> ORGANISM: Artificial Sequence
<220> FEATURE:
<223> OTHER INFORMATION: Synthesized: H3-3NHT (IL1B) primer
<220> FEATURE:
<221> NAME/KEY: misc_feature
<222> LOCATION: (28)..(28)
<223> OTHER INFORMATION: n is a, c, g, or t

<400> SEQUENCE: 754
gcagtctact attgtgcgag agtcggcnht ggtggtaact ctgactactg gggcca 56

<210> SEQ ID NO 755
<211> LENGTH: 56
<212> TYPE: DNA
<213> ORGANISM: Artificial Sequence
<220> FEATURE:
<223> OTHER INFORMATION: Synthesized: H3-3VAA (IL1B) primer

<400> SEQUENCE: 755
gcagtctact attgtgcgag agtcggcvaa ggtggtaact ctgactactg gggcca 56

<210> SEQ ID NO 756
<211> LENGTH: 56
<212> TYPE: DNA
<213> ORGANISM: Artificial Sequence
<220> FEATURE:
<223> OTHER INFORMATION: Synthesized: H3-3BGG (IL1B) primer

<400> SEQUENCE: 756
gcagtctact attgtgcgag agtcggcbgg ggtggtaact ctgactactg gggcca 56

<210> SEQ ID NO 757
<211> LENGTH: 56
<212> TYPE: DNA
<213> ORGANISM: Artificial Sequence
<220> FEATURE:
<223> OTHER INFORMATION: Synthesized: H3-4NHT (IL1B) primer
<220> FEATURE:
<221> NAME/KEY: misc_feature
<222> LOCATION: (31)..(31)
<223> OTHER INFORMATION: n is a, c, g, or t

<400> SEQUENCE: 757
gcagtctact attgtgcgag agtcggctac nhtggtaact ctgactactg gggcca 56

<210> SEQ ID NO 758
<211> LENGTH: 56
<212> TYPE: DNA
<213> ORGANISM: Artificial Sequence
<220> FEATURE:
<223> OTHER INFORMATION: Synthesized: H3-4VAA (IL1B) primer

<400> SEQUENCE: 758
gcagtctact attgtgcgag agtcggctac vaaggtaact ctgactactg gggcca 56

<210> SEQ ID NO 759
<211> LENGTH: 56
<212> TYPE: DNA
<213> ORGANISM: Artificial Sequence
<220> FEATURE:
<223> OTHER INFORMATION: Synthesized: H3-4BGG (IL1B) primer

<400> SEQUENCE: 759
gcagtctact attgtgcgag agtcggctac bggggtaact ctgactactg gggcca 56

<210> SEQ ID NO 760
<211> LENGTH: 56
<212> TYPE: DNA
<213> ORGANISM: Artificial Sequence
<220> FEATURE:
<223> OTHER INFORMATION: Synthesized: H3-5NHT (IL1B) primer
<220> FEATURE:
<221> NAME/KEY: misc_feature
<222> LOCATION: (34)..(34)
<223> OTHER INFORMATION: n is a, c, g, or t

<400> SEQUENCE: 760
gcagtctact attgtgcgag agtcggctac ggtnhtaact ctgactactg gggcca 56

<210> SEQ ID NO 761
<211> LENGTH: 56
<212> TYPE: DNA
<213> ORGANISM: Artificial Sequence
<220> FEATURE:
<223> OTHER INFORMATION: Synthesized: H3-5VAA (IL1B) primer

<400> SEQUENCE: 761
gcagtctact attgtgcgag agtcggctac ggtvaaaact ctgactactg gggcca 56

<210> SEQ ID NO 762
<211> LENGTH: 56
<212> TYPE: DNA
<213> ORGANISM: Artificial Sequence
<220> FEATURE:
<223> OTHER INFORMATION: Synthesized: H3-5BGG (IL1B) primer

<400> SEQUENCE: 762
gcagtctact attgtgcgag agtcggctac ggtbggaact ctgactactg gggcca 56

<210> SEQ ID NO 763
<211> LENGTH: 49
<212> TYPE: DNA
<213> ORGANISM: Artificial Sequence
<220> FEATURE:
<223> OTHER INFORMATION: Synthesized: H32-1NHT (IL1B) primer
<220> FEATURE:
<221> NAME/KEY: misc_feature
<222> LOCATION: (20)..(20)

<223> OTHER INFORMATION: n is a, c, g, or t

<400> SEQUENCE: 763
gagagtcggc tacggtggtn httctgacta ctggggccag ggaaccctg 49

<210> SEQ ID NO 764
<211> LENGTH: 49
<212> TYPE: DNA
<213> ORGANISM: Artificial Sequence
<220> FEATURE:
<223> OTHER INFORMATION: Synthesized: H32-1VAA (IL1B) primer

<400> SEQUENCE: 764
gagagtcggc tacggtggtv aatctgacta ctggggccag ggaaccctg 49

<210> SEQ ID NO 765
<211> LENGTH: 49
<212> TYPE: DNA
<213> ORGANISM: Artificial Sequence
<220> FEATURE:
<223> OTHER INFORMATION: Synthesized: H32-1BGG (IL1B) primer

<400> SEQUENCE: 765
gagagtcggc tacggtggtb ggtctgacta ctggggccag ggaaccctg 49

<210> SEQ ID NO 766
<211> LENGTH: 49
<212> TYPE: DNA
<213> ORGANISM: Artificial Sequence
<220> FEATURE:
<223> OTHER INFORMATION: Synthesized: H32-2NHT (IL1B) primer
<220> FEATURE:
<221> NAME/KEY: misc_feature
<222> LOCATION: (23)..(23)
<223> OTHER INFORMATION: n is a, c, g, or t

<400> SEQUENCE: 766
gagagtcggc tacggtggta acnhtgacta ctggggccag ggaaccctg 49

<210> SEQ ID NO 767
<211> LENGTH: 49
<212> TYPE: DNA
<213> ORGANISM: Artificial Sequence
<220> FEATURE:
<223> OTHER INFORMATION: Synthesized: H32-2VAA (IL1B) primer

<400> SEQUENCE: 767
gagagtcggc tacggtggta acvaagacta ctggggccag ggaaccctg 49

<210> SEQ ID NO 768
<211> LENGTH: 49
<212> TYPE: DNA
<213> ORGANISM: Artificial Sequence
<220> FEATURE:
<223> OTHER INFORMATION: Synthesized: H32-2BGG (IL1B) primer

<400> SEQUENCE: 768
gagagtcggc tacggtggta acbgggacta ctggggccag ggaaccctg 49

<210> SEQ ID NO 769
<211> LENGTH: 49
<212> TYPE: DNA
<213> ORGANISM: Artificial Sequence
<220> FEATURE:
<223> OTHER INFORMATION: Synthesized: H32-3VAA (IL1B) primer

<400> SEQUENCE: 769
gagagtcggc tacggtggta actctvaata ctggggccag ggaaccctg 49

<210> SEQ ID NO 770
<211> LENGTH: 49
<212> TYPE: DNA
<213> ORGANISM: Artificial Sequence
<220> FEATURE:
<223> OTHER INFORMATION: Synthesized: H32-3BGG (IL1B) primer

<400> SEQUENCE: 770
gagagtcggc tacggtggta actctbggta ctggggccag ggaaccctg 49

<210> SEQ ID NO 771
<211> LENGTH: 49
<212> TYPE: DNA
<213> ORGANISM: Artificial Sequence
<220> FEATURE:
<223> OTHER INFORMATION: Synthesized: H32-4NHT (IL1B) primer
<220> FEATURE:
<221> NAME/KEY: misc_feature
<222> LOCATION: (29)..(29)
<223> OTHER INFORMATION: n is a, c, g, or t

<400> SEQUENCE: 771
gagagtcggc tacggtggta actctgacnh ttggggccag ggaaccctg 49

<210> SEQ ID NO 772
<211> LENGTH: 49
<212> TYPE: DNA
<213> ORGANISM: Artificial Sequence
<220> FEATURE:
<223> OTHER INFORMATION: Synthesized: H32-4VAA (IL1B) primer

<400> SEQUENCE: 772
gagagtcggc tacggtggta actctgacva atggggccag ggaaccctg 49

<210> SEQ ID NO 773
<211> LENGTH: 49
<212> TYPE: DNA
<213> ORGANISM: Artificial Sequence
<220> FEATURE:
<223> OTHER INFORMATION: Synthesized: H32-4BGG (IL1B) primer

<400> SEQUENCE: 773
gagagtcggc tacggtggta actctgacbg gtggggccag ggaaccctg 49

<210> SEQ ID NO 774
<211> LENGTH: 58
<212> TYPE: DNA
<213> ORGANISM: Artificial Sequence
<220> FEATURE:
<223> OTHER INFORMATION: Synthesized: L1-1NHT (IL1B) primer
<220> FEATURE:
<221> NAME/KEY: misc_feature
<222> LOCATION: (21)..(21)
<223> OTHER INFORMATION: n is a, c, g, or t

<400> SEQUENCE: 774
ccatcatttg tcgggcgagt nhtgatatta acaggtggtt agcctggtat cagcagac 58

<210> SEQ ID NO 775
<211> LENGTH: 58
<212> TYPE: DNA
<213> ORGANISM: Artificial Sequence
<220> FEATURE:
<223> OTHER INFORMATION: Synthesized: L1-1VAA (IL1B) primer

<400> SEQUENCE: 775
ccatcatttg tcgggcgagt vaagatatta acaggtggtt agcctggtat cagcagac 58

<210> SEQ ID NO 776
<211> LENGTH: 58
<212> TYPE: DNA
<213> ORGANISM: Artificial Sequence
<220> FEATURE:
<223> OTHER INFORMATION: Synthesized: L1-1BGG (IL1B) primer

<400> SEQUENCE: 776
ccatcatttg tcgggcgagt bgggatatta acaggtggtt agcctggtat cagcagac 58

<210> SEQ ID NO 777
<211> LENGTH: 58
<212> TYPE: DNA
<213> ORGANISM: Artificial Sequence
<220> FEATURE:
<223> OTHER INFORMATION: Synthesized: L1-2NHT (IL1B) primer
<220> FEATURE:
<221> NAME/KEY: misc_feature
<222> LOCATION: (24)..(24)
<223> OTHER INFORMATION: n is a, c, g, or t

<400> SEQUENCE: 777
ccatcatttg tcgggcgagt cagnhtatta acaggtggtt agcctggtat cagcagac 58

<210> SEQ ID NO 778
<211> LENGTH: 58
<212> TYPE: DNA
<213> ORGANISM: Artificial Sequence
<220> FEATURE:
<223> OTHER INFORMATION: Synthesized: L1-2VAA (IL1B) primer

<400> SEQUENCE: 778
ccatcatttg tcgggcgagt cagvaaatta acaggtggtt agcctggtat cagcagac 58

<210> SEQ ID NO 779
<211> LENGTH: 58
<212> TYPE: DNA
<213> ORGANISM: Artificial Sequence
<220> FEATURE:
<223> OTHER INFORMATION: Synthesized: L1-2BGG (IL1B) primer

<400> SEQUENCE: 779
ccatcatttg tcgggcgagt cagbggatta acaggtggtt agcctggtat cagcagac 58

<210> SEQ ID NO 780
<211> LENGTH: 58
<212> TYPE: DNA
<213> ORGANISM: Artificial Sequence
<220> FEATURE:
<223> OTHER INFORMATION: Synthesized: L1-3NHT (IL1B) primer
<220> FEATURE:
<221> NAME/KEY: misc_feature
<222> LOCATION: (30)..(30)
<223> OTHER INFORMATION: n is a, c, g, or t

<400> SEQUENCE: 780
ccatcatttg tcgggcgagt caggatattn htaggtggtt agcctggtat cagcagac 58

<210> SEQ ID NO 781
<211> LENGTH: 58
<212> TYPE: DNA
<213> ORGANISM: Artificial Sequence
<220> FEATURE:
<223> OTHER INFORMATION: Synthesized: L1-3VAA (IL1B) primer

<400> SEQUENCE: 781
ccatcatttg tcgggcgagt caggatattv aaaggtggtt agcctggtat cagcagac 58

<210> SEQ ID NO 782
<211> LENGTH: 58
<212> TYPE: DNA
<213> ORGANISM: Artificial Sequence
<220> FEATURE:
<223> OTHER INFORMATION: Synthesized: L1-3BGG (IL1B) primer

<400> SEQUENCE: 782
ccatcatttg tcgggcgagt caggatattb ggaggtggtt agcctggtat cagcagac 58

<210> SEQ ID NO 783
<211> LENGTH: 58
<212> TYPE: DNA
<213> ORGANISM: Artificial Sequence
<220> FEATURE:
<223> OTHER INFORMATION: Synthesized: L1-4NHT (IL1B) primer
<220> FEATURE:
<221> NAME/KEY: misc_feature
<222> LOCATION: (33)..(33)
<223> OTHER INFORMATION: n is a, c, g, or t

<400> SEQUENCE: 783
ccatcatttg tcgggcgagt caggatatta acnhttggtt agcctggtat cagcagac 58

<210> SEQ ID NO 784
<211> LENGTH: 58
<212> TYPE: DNA
<213> ORGANISM: Artificial Sequence
<220> FEATURE:
<223> OTHER INFORMATION: Synthesized: L1-4VAA (IL1B) primer

<400> SEQUENCE: 784
ccatcatttg tcgggcgagt caggatatta acvaatggtt agcctggtat cagcagac 58

<210> SEQ ID NO 785
<211> LENGTH: 58
<212> TYPE: DNA
<213> ORGANISM: Artificial Sequence
<220> FEATURE:
<223> OTHER INFORMATION: Synthesized: L1-4BGG (IL1B) primer

<400> SEQUENCE: 785
ccatcatttg tcgggcgagt caggatatta acbggtggtt agcctggtat cagcagac 58

<210> SEQ ID NO 786
<211> LENGTH: 58
<212> TYPE: DNA
<213> ORGANISM: Artificial Sequence
<220> FEATURE:
<223> OTHER INFORMATION: Synthesized: L1-5NHT (IL1B) primer
<220> FEATURE:
<221> NAME/KEY: misc_feature
<222> LOCATION: (36)..(36)
<223> OTHER INFORMATION: n is a, c, g, or t

<400> SEQUENCE: 786
ccatcatttg tcgggcgagt caggatatta acaggnhttt agcctggtat cagcagac 58

<210> SEQ ID NO 787
<211> LENGTH: 58
<212> TYPE: DNA
<213> ORGANISM: Artificial Sequence
<220> FEATURE:

<223> OTHER INFORMATION: Synthesized: L1-5VAA (IL1B) primer

<400> SEQUENCE: 787
ccatcatttg tcgggcgagt caggatatta acaggvaatt agcctggtat cagcagac 58

<210> SEQ ID NO 788
<211> LENGTH: 55
<212> TYPE: DNA
<213> ORGANISM: Artificial Sequence
<220> FEATURE:
<223> OTHER INFORMATION: Synthesized: L1-5BGG (IL1B) primer

<400> SEQUENCE: 788
atgcccctaa gctcctgatc cattctgcaa ccbggctgca aagtggggtc ccatc 55

<210> SEQ ID NO 789
<211> LENGTH: 57
<212> TYPE: DNA
<213> ORGANISM: Artificial Sequence
<220> FEATURE:
<223> OTHER INFORMATION: Synthesized: L3-1NHT (IL1B) primer
<220> FEATURE:
<221> NAME/KEY: misc_feature
<222> LOCATION: (22)..(22)
<223> OTHER INFORMATION: n is a, c, g, or t

<400> SEQUENCE: 789
gcaacttact attgtcagca gnhtgacagt ttcccgctca ctttcggcgg agggacc 57

<210> SEQ ID NO 790
<211> LENGTH: 57
<212> TYPE: DNA
<213> ORGANISM: Artificial Sequence
<220> FEATURE:
<223> OTHER INFORMATION: Synthesized: L3-1VAA (IL1B) primer

<400> SEQUENCE: 790
gcaacttact attgtcagca gvaagacagt ttcccgctca ctttcggcgg agggacc 57

<210> SEQ ID NO 791
<211> LENGTH: 57
<212> TYPE: DNA
<213> ORGANISM: Artificial Sequence
<220> FEATURE:
<223> OTHER INFORMATION: Synthesized: L3-1BGG (IL1B) primer

<400> SEQUENCE: 791
gcaacttact attgtcagca gbgggacagt ttcccgctca ctttcggcgg agggacc 57

<210> SEQ ID NO 792
<211> LENGTH: 57
<212> TYPE: DNA
<213> ORGANISM: Artificial Sequence
<220> FEATURE:
<223> OTHER INFORMATION: Synthesized: L3-2NHT (IL1B) primer
<220> FEATURE:
<221> NAME/KEY: misc_feature
<222> LOCATION: (25)..(25)
<223> OTHER INFORMATION: n is a, c, g, or t

<400> SEQUENCE: 792
gcaacttact attgtcagca ggctnhtagt ttcccgctca ctttcggcgg agggacc 57

<210> SEQ ID NO 793
<211> LENGTH: 57
<212> TYPE: DNA
<213> ORGANISM: Artificial Sequence
<220> FEATURE:
<223> OTHER INFORMATION: Synthesized: L3-2VAA (IL1B) primer

<400> SEQUENCE: 793
gcaacttact attgtcagca ggctvaaagt ttcccgctca ctttcggcgg agggacc 57

<210> SEQ ID NO 794
<211> LENGTH: 57
<212> TYPE: DNA
<213> ORGANISM: Artificial Sequence
<220> FEATURE:
<223> OTHER INFORMATION: Synthesized: L3-2BGG (IL1B) primer

<400> SEQUENCE: 794
gcaacttact attgtcagca ggctbggagt ttcccgctca ctttcggcgg agggacc 57

<210> SEQ ID NO 795
<211> LENGTH: 57
<212> TYPE: DNA
<213> ORGANISM: Artificial Sequence
<220> FEATURE:
<223> OTHER INFORMATION: Synthesized: L3-3NHT (IL1B) primer
<220> FEATURE:
<221> NAME/KEY: misc_feature
<222> LOCATION: (28)..(28)
<223> OTHER INFORMATION: n is a, c, g, or t

<400> SEQUENCE: 795
gcaacttact attgtcagca ggctgacnht ttcccgctca ctttcggcgg agggacc 57

<210> SEQ ID NO 796
<211> LENGTH: 57
<212> TYPE: DNA
<213> ORGANISM: Artificial Sequence
<220> FEATURE:
<223> OTHER INFORMATION: Synthesized: L3-3VAA (IL1B) primer

<400> SEQUENCE: 796
gcaacttact attgtcagca ggctgacvaa ttcccgctca ctttcggcgg agggacc 57

<210> SEQ ID NO 797
<211> LENGTH: 57
<212> TYPE: DNA
<213> ORGANISM: Artificial Sequence
<220> FEATURE:
<223> OTHER INFORMATION: Synthesized: L3-3BGG (IL1B) primer

<400> SEQUENCE: 797
gcaacttact attgtcagca ggctgacbgg ttcccgctca ctttcggcgg agggacc 57

<210> SEQ ID NO 798
<211> LENGTH: 57
<212> TYPE: DNA
<213> ORGANISM: Artificial Sequence
<220> FEATURE:
<223> OTHER INFORMATION: Synthesized: L3-4NHT (IL1B) primer
<220> FEATURE:
<221> NAME/KEY: misc_feature
<222> LOCATION: (31)..(31)
<223> OTHER INFORMATION: n is a, c, g, or t

<400> SEQUENCE: 798
gcaacttact attgtcagca ggctgacagt nhtccgctca ctttcggcgg agggacc 57

<210> SEQ ID NO 799
<211> LENGTH: 57
<212> TYPE: DNA

<213> ORGANISM: Artificial Sequence
<220> FEATURE:
<223> OTHER INFORMATION: Synthesized: L3-4VAA (IL1B) primer

<400> SEQUENCE: 799
gcaacttact attgtcagca ggctgacagt vaaccgctca ctttcggcgg agggacc 57

<210> SEQ ID NO 800
<211> LENGTH: 57
<212> TYPE: DNA
<213> ORGANISM: Artificial Sequence
<220> FEATURE:
<223> OTHER INFORMATION: Synthesized: L3-4BGG (IL1B) primer

<400> SEQUENCE: 800
gcaacttact attgtcagca ggctgacagt bggccgctca ctttcggcgg agggacc 57

<210> SEQ ID NO 801
<211> LENGTH: 57
<212> TYPE: DNA
<213> ORGANISM: Artificial Sequence
<220> FEATURE:
<223> OTHER INFORMATION: Synthesized: L3-5NHT (IL1B) primer
<220> FEATURE:
<221> NAME/KEY: misc_feature
<222> LOCATION: (34)..(34)
<223> OTHER INFORMATION: n is a, c, g, or t

<400> SEQUENCE: 801
gcaacttact attgtcagca ggctgacagt ttcnhtctca ctttcggcgg agggacc 57

<210> SEQ ID NO 802
<211> LENGTH: 57
<212> TYPE: DNA
<213> ORGANISM: Artificial Sequence
<220> FEATURE:
<223> OTHER INFORMATION: Synthesized: L3-5VAA (IL1B) primer

<400> SEQUENCE: 802
gcaacttact attgtcagca ggctgacagt ttcvaactca ctttcggcgg agggacc 57

<210> SEQ ID NO 803
<211> LENGTH: 57
<212> TYPE: DNA
<213> ORGANISM: Artificial Sequence
<220> FEATURE:
<223> OTHER INFORMATION: Synthesized: L3-5BGG (IL1B) primer

<400> SEQUENCE: 803
gcaacttact attgtcagca ggctgacagt ttcbggctca ctttcggcgg agggacc 57

<210> SEQ ID NO 804
<211> LENGTH: 57
<212> TYPE: DNA
<213> ORGANISM: Artificial Sequence
<220> FEATURE:
<223> OTHER INFORMATION: Synthesized: L3-6NHT (IL1B) primer
<220> FEATURE:
<221> NAME/KEY: misc_feature
<222> LOCATION: (37)..(37)
<223> OTHER INFORMATION: n is a, c, g, or t

<400> SEQUENCE: 804
gcaacttact attgtcagca ggctgacagt ttcccgnhta ctttcggcgg agggacc 57

<210> SEQ ID NO 805
<211> LENGTH: 57

<212> TYPE: DNA
<213> ORGANISM: Artificial Sequence
<220> FEATURE:
<223> OTHER INFORMATION: Synthesized: L3-6VAA (IL1B) primer

<400> SEQUENCE: 805
gcaacttact attgtcagca ggctgacagt ttcccgvaaa ctttcggcgg agggacc 57

<210> SEQ ID NO 806
<211> LENGTH: 57
<212> TYPE: DNA
<213> ORGANISM: Artificial Sequence
<220> FEATURE:
<223> OTHER INFORMATION: Synthesized: L3-6BGG (IL1B) primer

<400> SEQUENCE: 806
gcaacttact attgtcagca ggctgacagt ttcccgbgga ctttcggcgg agggacc 57

<210> SEQ ID NO 807
<211> LENGTH: 59
<212> TYPE: DNA
<213> ORGANISM: Artificial Sequence
<220> FEATURE:
<223> OTHER INFORMATION: Synthesized: L3-E98T

<400> SEQUENCE: 807
ggtgtttatt actgtgctca aaatctaact cttcctcgga cgttcggtgg aggcaccaa 59

<210> SEQ ID NO 808
<211> LENGTH: 56
<212> TYPE: DNA
<213> ORGANISM: Artificial Sequence
<220> FEATURE:
<223> OTHER INFORMATION: Synthesized: L2-Q55R

<400> SEQUENCE: 808
cagtctcctc agctcctgat ttatcgaatg tccaaccttg cctcaggagt cccaga 56

<210> SEQ ID NO 809
<211> LENGTH: 59
<212> TYPE: DNA
<213> ORGANISM: Artificial Sequence
<220> FEATURE:
<223> OTHER INFORMATION: Synthesized: H1-G33F

<400> SEQUENCE: 809
tcctgcaagg cttctggata taccttcaca aaatatttca tgaactgggt gaagcaggc 59

<210> SEQ ID NO 810
<211> LENGTH: 58
<212> TYPE: DNA
<213> ORGANISM: Artificial Sequence
<220> FEATURE:
<223> OTHER INFORMATION: Synthesized: H2-T53I

<400> SEQUENCE: 810
aagggtttaa agtggatggg ctggataaac atctacactg aagagcctac atatggtg 58

<210> SEQ ID NO 811
<211> LENGTH: 53
<212> TYPE: DNA
<213> ORGANISM: Artificial Sequence
<220> FEATURE:
<223> OTHER INFORMATION: Synthesized: H3-G100R

<400> SEQUENCE: 811
gctacatatt tctgtgcaag atttcgttct gctgtggact actggggtca agg 53

<210> SEQ ID NO 812
<211> LENGTH: 40
<212> TYPE: DNA
<213> ORGANISM: Artificial Sequence
<220> FEATURE:
<223> OTHER INFORMATION: Synthesized: AscIR

<400> SEQUENCE: 812
atatatggcg cgccttatta acactctccc ctgttgaagc 40

<210> SEQ ID NO 813
<211> LENGTH: 21
<212> TYPE: DNA
<213> ORGANISM: Artificial Sequence
<220> FEATURE:
<223> OTHER INFORMATION: Synthesized: AscIF

<400> SEQUENCE: 813
taataaggcg cgcctaacca t 21

<210> SEQ ID NO 814
<211> LENGTH: 20
<212> TYPE: DNA
<213> ORGANISM: Artificial Sequence
<220> FEATURE:
<223> OTHER INFORMATION: Synthesized: HindIII-F

<400> SEQUENCE: 814
ttacgccaag ctttggagcc 20

<210> SEQ ID NO 815
<211> LENGTH: 112
<212> TYPE: PRT
<213> ORGANISM: Artificial Sequence
<220> FEATURE:
<223> OTHER INFORMATION: Synthesized: murING1 (light chain)

<400> SEQUENCE: 815

```
Asp Ile Val Met Thr Gln Ala Ala Phe Ser Asn Pro Val Thr Leu Gly
1               5                   10                  15

Thr Ser Gly Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Arg Thr Phe Gly Gly Gly Thr Lys Leu Glu Ile Lys
            100                 105                 110
```

<210> SEQ ID NO 816
<211> LENGTH: 115
<212> TYPE: PRT
<213> ORGANISM: Artificial Sequence
<220> FEATURE:
<223> OTHER INFORMATION: Synthesized: mK2 (light chain)

<400> SEQUENCE: 816

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr His Val Pro Pro Tyr Thr Phe Gly Gly Gly Thr Lys Leu Glu Ile
            100                 105                 110

Lys Arg Ala
        115


<210> SEQ ID NO 817
<211> LENGTH: 116
<212> TYPE: PRT
<213> ORGANISM: Artificial Sequence
<220> FEATURE:
<223> OTHER INFORMATION: Synthesized: murING1 (heavy chain)

<400> SEQUENCE: 817

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Ala Phe Ser Leu Glu Thr Ser Ala Ser Thr Ala Asn
65                  70                  75                  80

Leu Gln Ile Asn Asn Leu Lys Ser Glu Asp Thr Ala Thr Tyr Phe Cys
                85                  90                  95

Ala Arg Phe Gly Ser Ala Val Asp Tyr Trp Gly Gln Gly Thr Ser Val
            100                 105                 110

Thr Val Ser Ser
        115


<210> SEQ ID NO 818
<211> LENGTH: 129
<212> TYPE: PRT
<213> ORGANISM: Artificial Sequence
<220> FEATURE:
<223> OTHER INFORMATION: Synthesized: mH2a (heavy chain)
<220> FEATURE:
<221> NAME/KEY: misc_feature
<222> LOCATION: (100)..(101)
<223> OTHER INFORMATION: Synthesized: Xaa can be any naturally occurring
      amino acid
<220> FEATURE:
<221> NAME/KEY: misc_feature
<222> LOCATION: (107)..(107)
<223> OTHER INFORMATION: Synthesized: Xaa can be any naturally occurring
      amino acid
<220> FEATURE:
<221> NAME/KEY: misc_feature
<222> LOCATION: (109)..(109)
<223> OTHER INFORMATION: Synthesized: Xaa can be any naturally occurring
```

amino acid
<220> FEATURE:
<221> NAME/KEY: misc_feature
<222> LOCATION: (111)..(112)
<223> OTHER INFORMATION: Synthesized: Xaa can be any naturally occurring
amino acid

<400> SEQUENCE: 818

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Asp Tyr
20 25 30

Tyr Met Asn Asn Trp Val Lys Gln Ser Pro Gly Lys Ser Leu Glu Trp
35 40 45

Ile Gly Asp Ile Asn Pro Gly Asn Gly Gly Thr Ser Tyr Asn Gln Lys
50 55 60

Phe Lys Gly Lys Ala Thr Leu Thr Val Asp Lys Ser Ser Ser Thr Ala
65 70 75 80

Tyr Met Gln Leu Ser Ser Leu Thr Ser Glu Asp Ser Ala Val Tyr Tyr
85 90 95

Cys Ala Arg Xaa Xaa Tyr Tyr Ser Ser Ser Xaa Met Xaa Ala Xaa Xaa
100 105 110

Tyr Tyr Ala Phe Asp Tyr Trp Gly Gln Gly Thr Thr Val Thr Val Ser
115 120 125

Ser

<210> SEQ ID NO 819
<211> LENGTH: 113
<212> TYPE: PRT
<213> ORGANISM: Artificial Sequence
<220> FEATURE:
<223> OTHER INFORMATION: Synthesized: hK1

<400> SEQUENCE: 819

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Leu Val Ser Ile
20 25 30

Ser Asn Tyr Leu Ala Trp Tyr Gln Gln Lys Pro Gly Lys Ala Pro Lys
35 40 45

Leu Leu Ile Tyr Ala Ala Ser Ser Leu Glu Ser Gly Val Pro Ser Arg
50 55 60

Phe Ser Gly Ser Gly Ser Gly Thr Asp Phe Thr Leu Thr Ile Ser Ser
65 70 75 80

Leu Gln Pro Glu Asp Phe Ala Thr Tyr Tyr Cys Gln Gln Tyr Asn Ser
85 90 95

Leu Pro Glu Trp Thr Phe Gly Gln Gly Thr Lys Val Glu Ile Lys Arg
100 105 110

Thr

<210> SEQ ID NO 820
<211> LENGTH: 113
<212> TYPE: PRT
<213> ORGANISM: Artificial Sequence
<220> FEATURE:
<223> OTHER INFORMATION: Synthesized: hK2

<400> SEQUENCE: 820

Asp Ile Val Met Thr Gln Ser Pro Leu Ser Leu Pro Val Thr Pro Gly

```
1               5                   10                  15

Glu Pro Ala Ser Ile Ser Cys Arg Ser Ser Gln Ser Leu Leu His Ser
            20                  25                  30

Asp Gly Asn Asn Tyr Leu Asn Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Pro Arg Thr Phe Gly Gln Gly Thr Lys Val Glu Ile Lys Arg
            100                 105                 110

Thr


<210> SEQ ID NO 821
<211> LENGTH: 111
<212> TYPE: PRT
<213> ORGANISM: Artificial Sequence
<220> FEATURE:
<223> OTHER INFORMATION: Synthesized: hK3

<400> SEQUENCE: 821

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Leu Thr Phe Gly Gln Gly Thr Lys Val Glu Ile Lys Arg Thr
            100                 105                 110


<210> SEQ ID NO 822
<211> LENGTH: 114
<212> TYPE: PRT
<213> ORGANISM: Artificial Sequence
<220> FEATURE:
<223> OTHER INFORMATION: Synthesized: hK4

<400> SEQUENCE: 822

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
```

```
                85                  90                  95

Tyr Tyr Ser Thr Pro Thr Phe Gly Gln Gly Thr Lys Val Glu Ile Lys
            100                 105                 110

Arg Thr


<210> SEQ ID NO 823
<211> LENGTH: 115
<212> TYPE: PRT
<213> ORGANISM: Artificial Sequence
<220> FEATURE:
<223> OTHER INFORMATION: Synthesized: mK1

<400> SEQUENCE: 823

Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Arg Ala
        115


<210> SEQ ID NO 824
<211> LENGTH: 115
<212> TYPE: PRT
<213> ORGANISM: Artificial Sequence
<220> FEATURE:
<223> OTHER INFORMATION: Synthesized: mK2

<400> SEQUENCE: 824

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr His Val Pro Pro Tyr Thr Phe Gly Gly Gly Thr Lys Leu Glu Ile
            100                 105                 110

Lys Arg Ala
        115


<210> SEQ ID NO 825
<211> LENGTH: 114
<212> TYPE: PRT
```

```
<213> ORGANISM: Artificial Sequence
<220> FEATURE:
<223> OTHER INFORMATION: Synthesized: mK3

<400> SEQUENCE: 825

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Asp Ala Ala Thr Tyr Tyr Cys Gln Gln Ser Asn
                85                  90                  95

Glu Asp Pro Pro Trp Thr Phe Gly Gly Gly Thr Lys Leu Glu Ile Lys
            100                 105                 110

Arg Ala


<210> SEQ ID NO 826
<211> LENGTH: 112
<212> TYPE: PRT
<213> ORGANISM: Artificial Sequence
<220> FEATURE:
<223> OTHER INFORMATION: Synthesized: mK4
<220> FEATURE:
<221> NAME/KEY: misc_feature
<222> LOCATION: (43)..(43)
<223> OTHER INFORMATION: Synthesized: Xaa can be any naturally occurring
      amino acid
<220> FEATURE:
<221> NAME/KEY: misc_feature
<222> LOCATION: (97)..(97)
<223> OTHER INFORMATION: Synthesized: Xaa can be any naturally occurring
      amino acid

<400> SEQUENCE: 826

Glu Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Ser Ser
            20                  25                  30

Tyr Leu His Trp Tyr Gln Gln Lys Pro Gly Xaa Ser Pro Lys Leu Trp
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Xaa Gly Leu Thr Phe Gly Ala Gly Thr Lys Leu Glu Ile Lys Arg Ala
            100                 105                 110


<210> SEQ ID NO 827
<211> LENGTH: 111
<212> TYPE: PRT
<213> ORGANISM: Artificial Sequence
<220> FEATURE:
<223> OTHER INFORMATION: Synthesized: mK5

<400> SEQUENCE: 827
```

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Asp Ile Ser Asn
            20                  25                  30

Tyr Leu Asn Trp Tyr Gln Gln Lys Pro Gly Gly Ser Pro Lys Leu Leu
        35                  40                  45

Ile Tyr Tyr Ala Ser Arg Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Pro Arg Thr Phe Gly Gly Gly Thr Lys Leu Glu Ile Lys Arg Ala
            100                 105                 110


<210> SEQ ID NO 828
<211> LENGTH: 111
<212> TYPE: PRT
<213> ORGANISM: Artificial Sequence
<220> FEATURE:
<223> OTHER INFORMATION: Synthesized: mK6

<400> SEQUENCE: 828

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Met
                85                  90                  95

Pro Leu Thr Phe Gly Ala Gly Thr Lys Leu Glu Leu Lys Arg Ala
            100                 105                 110


<210> SEQ ID NO 829
<211> LENGTH: 118
<212> TYPE: PRT
<213> ORGANISM: Artificial Sequence
<220> FEATURE:
<223> OTHER INFORMATION: Synthesized: hL1
<220> FEATURE:
<221> NAME/KEY: misc_feature
<222> LOCATION: (78)..(78)
<223> OTHER INFORMATION: Synthesized: Xaa can be any naturally occurring
      amino acid
<220> FEATURE:
<221> NAME/KEY: misc_feature
<222> LOCATION: (100)..(100)
<223> OTHER INFORMATION: Synthesized: Xaa can be any naturally occurring
      amino acid

<400> SEQUENCE: 829

Glx Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Ile Gly Asn
            20                  25                  30
```

```
Asn Tyr Val Ser Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Xaa Gly Leu
65                  70                  75                  80

Gln Ser Glu Asp Glu Ala Asp Tyr Tyr Cys Ala Thr Trp Asp Asp Ser
                85                  90                  95

Leu Ser Ala Xaa Asn Ser Ala Pro Val Phe Gly Gly Gly Thr Lys Leu
            100                 105                 110

Thr Val Leu Gly Gln Pro
        115


<210> SEQ ID NO 830
<211> LENGTH: 114
<212> TYPE: PRT
<213> ORGANISM: Artificial Sequence
<220> FEATURE:
<223> OTHER INFORMATION: Synthesized: hL2
<220> FEATURE:
<221> NAME/KEY: misc_feature
<222> LOCATION: (98)..(99)
<223> OTHER INFORMATION: Synthesized: Xaa can be any naturally occurring
      amino acid
<220> FEATURE:
<221> NAME/KEY: misc_feature
<222> LOCATION: (108)..(108)
<223> OTHER INFORMATION: Synthesized: Xaa can be any naturally occurring
      amino acid

<400> SEQUENCE: 830

Glx Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ala Val Ser Trp Tyr Gln Gln His Pro Gly Lys Ala Pro Lys Leu
        35                  40                  45

Leu Ile Tyr Asp Val Thr Asp Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Gly Gly
                85                  90                  95

Ser Xaa Xaa Asn Val Phe Gly Gly Gly Thr Lys Xaa Thr Val Leu Gly
            100                 105                 110

Gln Pro


<210> SEQ ID NO 831
<211> LENGTH: 113
<212> TYPE: PRT
<213> ORGANISM: Artificial Sequence
<220> FEATURE:
<223> OTHER INFORMATION: Synthesized: hL3
<220> FEATURE:
<221> NAME/KEY: misc_feature
<222> LOCATION: (51)..(51)
<223> OTHER INFORMATION: Synthesized: Xaa can be any naturally occurring
      amino acid

<400> SEQUENCE: 831

Ser Tyr Glu Leu Thr Gln Pro Pro Ser Val Ser Val Ser Pro Gly Gln
1               5                   10                  15
```

Thr Ala Arg Ile Thr Cys Ser Gly Asp Asn Leu Gly Asp Lys Tyr Val
20 25 30

His Trp Tyr Gln Gln Lys Pro Gly Gln Ala Pro Val Leu Val Ile Tyr
35 40 45

Asp Asp Xaa Lys Arg Pro Ser Gly Ile Pro Glu Arg Phe Ser Gly Ser
50 55 60

Asn Ser Gly Asn Thr Ala Thr Leu Thr Ile Ser Gly Val Gln Ala Gly
65 70 75 80

Asp Glu Ala Asp Tyr Tyr Cys Gln Ala Trp Asp Ser Ser Ser Asp His
85 90 95

Pro Gly Val Val Phe Gly Gly Gly Thr Lys Leu Thr Val Leu Gly Gln
100 105 110

Pro

<210> SEQ ID NO 832
<211> LENGTH: 112
<212> TYPE: PRT
<213> ORGANISM: Artificial Sequence
<220> FEATURE:
<223> OTHER INFORMATION: Synthesized: hL4
<220> FEATURE:
<221> NAME/KEY: misc_feature
<222> LOCATION: (9)..(9)
<223> OTHER INFORMATION: Synthesized: Xaa can be any naturally occurring amino acid
<220> FEATURE:
<221> NAME/KEY: misc_feature
<222> LOCATION: (14)..(14)
<223> OTHER INFORMATION: Synthesized: Xaa can be any naturally occurring amino acid
<220> FEATURE:
<221> NAME/KEY: misc_feature
<222> LOCATION: (23)..(23)
<223> OTHER INFORMATION: Synthesized: Xaa can be any naturally occurring amino acid
<220> FEATURE:
<221> NAME/KEY: misc_feature
<222> LOCATION: (30)..(30)
<223> OTHER INFORMATION: Synthesized: Xaa can be any naturally occurring amino acid
<220> FEATURE:
<221> NAME/KEY: misc_feature
<222> LOCATION: (41)..(41)
<223> OTHER INFORMATION: Synthesized: Xaa can be any naturally occurring amino acid
<220> FEATURE:
<221> NAME/KEY: misc_feature
<222> LOCATION: (45)..(45)
<223> OTHER INFORMATION: Synthesized: Xaa can be any naturally occurring amino acid
<220> FEATURE:
<221> NAME/KEY: misc_feature
<222> LOCATION: (51)..(51)
<223> OTHER INFORMATION: Synthesized: Xaa can be any naturally occurring amino acid
<220> FEATURE:
<221> NAME/KEY: misc_feature
<222> LOCATION: (69)..(69)
<223> OTHER INFORMATION: Synthesized: Xaa can be any naturally occurring amino acid
<220> FEATURE:
<221> NAME/KEY: misc_feature
<222> LOCATION: (96)..(99)
<223> OTHER INFORMATION: Synthesized: Xaa can be any naturally occurring amino acid

<400> SEQUENCE: 832

Ser Glu Leu Thr Gln Pro Pro Ser Xaa Val Ser Val Ala Xaa Gly Gln
1 5 10 15

Thr Val Arg Ile Thr Cys Xaa Gly Asp Ser Asn Leu Gly Xaa Tyr Asp

```
            20                  25                  30

Ala Ser Trp Tyr Gln Gln Lys Pro Xaa Gln Ala Pro Xaa Leu Val Ile
        35                  40                  45

Tyr Gly Xaa Asn Asn Arg Pro Ser Gly Ile Pro Asp Arg Phe Ser Gly
    50                  55                  60

Ser Ser Ser Gly Xaa Thr Ala Ser Leu Thr Ile Thr Gly Ala Gln Ala
65                  70                  75                  80

Glu Asp Glu Ala Asp Tyr Tyr Cys Asn Ser Arg Asp Ser Ser Gly Xaa
                85                  90                  95

Xaa Xaa Xaa Phe Gly Gly Gly Thr Lys Leu Thr Val Leu Gly Gln Pro
            100                 105                 110


<210> SEQ ID NO 833
<211> LENGTH: 113
<212> TYPE: PRT
<213> ORGANISM: Artificial Sequence
<220> FEATURE:
<223> OTHER INFORMATION: Synthesized: hL5
<220> FEATURE:
<221> NAME/KEY: misc_feature
<222> LOCATION: (1)..(1)
<223> OTHER INFORMATION: Synthesized: Xaa can be any naturally occurring
      amino acid

<400> SEQUENCE: 833

Xaa Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Ala Gly Lys Ala Pro Lys Val
        35                  40                  45

Ile Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Glu Gly Ser
                85                  90                  95

Asp Asn Phe Val Phe Gly Thr Gly Thr Lys Val Thr Val Leu Gly Gln
            100                 105                 110

Pro


<210> SEQ ID NO 834
<211> LENGTH: 111
<212> TYPE: PRT
<213> ORGANISM: Artificial Sequence
<220> FEATURE:
<223> OTHER INFORMATION: Synthesized: hL6

<400> SEQUENCE: 834

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ser Ser Asn Ser Ala Ser Leu Thr Ile Ser Gly Leu Lys Thr
65                  70                  75                  80
```

Glu Asp Glu Ala Asp Tyr Tyr Cys Gln Ser Tyr Asp Ser Asn Asn His
85 90 95

Trp Val Phe Gly Gly Gly Thr Lys Leu Thr Val Leu Gly Gln Pro
100 105 110

<210> SEQ ID NO 835
<211> LENGTH: 116
<212> TYPE: PRT
<213> ORGANISM: Artificial Sequence
<220> FEATURE:
<223> OTHER INFORMATION: Synthesized: mL

<400> SEQUENCE: 835

Gln Ala Val Val Thr Gln Glu Ser Ala Leu Thr Thr Ser Pro Gly Glu
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Asp His Leu Phe Thr Gly
35 40 45

Leu Ile Gly Gly Thr Asn Asn Arg Ala Pro Gly Val Pro Ala Arg Phe
50 55 60

Ser Gly Ser Leu Ile Gly Asp Lys Ala Ala Leu Thr Ile Thr Gly Ala
65 70 75 80

Gln Thr Glu Asp Glu Ala Ile Tyr Phe Cys Ala Leu Trp Tyr Ser Asn
85 90 95

His Glu Gln Phe Val Trp Val Phe Gly Gly Gly Thr Lys Leu Thr Val
100 105 110

Leu Gly Gln Pro
115

<210> SEQ ID NO 836
<211> LENGTH: 129
<212> TYPE: PRT
<213> ORGANISM: Artificial Sequence
<220> FEATURE:
<223> OTHER INFORMATION: Synthesized: hH1
<220> FEATURE:
<221> NAME/KEY: misc_feature
<222> LOCATION: (115)..(115)
<223> OTHER INFORMATION: Synthesized: Xaa can be any naturally occurring amino acid

<400> SEQUENCE: 836

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Ala Ile Ser Trp Val Arg Gln Ala Pro Gly Gln Gly Leu Glu Trp Met
35 40 45

Gly Trp Ile Asn Pro Tyr Gly Asn Gly Asp Thr Asn Tyr Ala Gln Lys
50 55 60

Phe Gln Gly Arg Val Thr Ile Thr Ala Asp Thr Ser Thr Ser Thr Ala
65 70 75 80

Tyr Met Glu Leu Ser Ser Leu Arg Ser Glu Asp Thr Ala Val Tyr Tyr
85 90 95

Cys Ala Arg Ala Pro Gly Tyr Gly Ser Gly Gly Gly Cys Tyr Arg Gly
100 105 110

Asp Tyr Xaa Phe Asp Tyr Trp Gly Gln Gly Thr Leu Val Thr Val Ser
115 120 125

Ser

<210> SEQ ID NO 837
<211> LENGTH: 132
<212> TYPE: PRT
<213> ORGANISM: Artificial Sequence
<220> FEATURE:
<223> OTHER INFORMATION: Synthesized: hH2
<220> FEATURE:
<221> NAME/KEY: misc_feature
<222> LOCATION: (33)..(33)
<223> OTHER INFORMATION: Synthesized: Xaa can be any naturally occurring amino acid
<220> FEATURE:
<221> NAME/KEY: misc_feature
<222> LOCATION: (63)..(63)
<223> OTHER INFORMATION: Synthesized: Xaa can be any naturally occurring amino acid
<220> FEATURE:
<221> NAME/KEY: misc_feature
<222> LOCATION: (104)..(106)
<223> OTHER INFORMATION: Synthesized: Xaa can be any naturally occurring amino acid
<220> FEATURE:
<221> NAME/KEY: misc_feature
<222> LOCATION: (108)..(109)
<223> OTHER INFORMATION: Synthesized: Xaa can be any naturally occurring amino acid
<220> FEATURE:
<221> NAME/KEY: misc_feature
<222> LOCATION: (116)..(117)
<223> OTHER INFORMATION: Synthesized: Xaa can be any naturally occurring amino acid

<400> SEQUENCE: 837

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Ser Tyr
            20                  25                  30

Xaa Trp Ser Trp Asn Trp Ile Arg Gln Pro Pro Gly Lys Gly Leu Glu
        35                  40                  45

Trp Ile Gly Arg Ile Tyr Tyr Arg Ala Tyr Ser Gly Ser Thr Xaa Tyr
    50                  55                  60

Asn Pro Ser Leu Lys Ser Arg Val Thr Ile Ser Val Asp Thr Ser Lys
65                  70                  75                  80

Asn Gln Phe Ser Leu Lys Leu Ser Ser Val Thr Ala Ala Asp Thr Ala
                85                  90                  95

Val Tyr Tyr Cys Ala Arg Glu Xaa Xaa Xaa Gly Xaa Xaa Gly Asp Asp
            100                 105                 110

Tyr Tyr Tyr Xaa Xaa Gly Phe Asp Val Trp Gly Gln Gly Thr Leu Val
        115                 120                 125

Thr Val Ser Ser
    130
```

<210> SEQ ID NO 838
<211> LENGTH: 130
<212> TYPE: PRT
<213> ORGANISM: Artificial Sequence
<220> FEATURE:
<223> OTHER INFORMATION: Synthesized: hH3
<220> FEATURE:
<221> NAME/KEY: misc_feature
<222> LOCATION: (101)..(106)
<223> OTHER INFORMATION: Synthesized: Xaa can be any naturally occurring amino acid
<220> FEATURE:
<221> NAME/KEY: misc_feature
<222> LOCATION: (110)..(110)
<223> OTHER INFORMATION: Synthesized: Xaa can be any naturally occurring amino acid

<400> SEQUENCE: 838

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Val Ile Ser Gly Lys Thr Asp Gly Gly Ser Thr Tyr Tyr Ala Asp
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg Xaa Xaa Xaa Xaa Xaa Xaa Leu Ser Gly Xaa Tyr Tyr
100 105 110

Tyr Tyr His Tyr Phe Asp Tyr Trp Gly Gln Gly Thr Leu Val Thr Val
115 120 125

Ser Ser
130

<210> SEQ ID NO 839
<211> LENGTH: 130
<212> TYPE: PRT
<213> ORGANISM: Artificial Sequence
<220> FEATURE:
<223> OTHER INFORMATION: Synthesized: mH1a
<220> FEATURE:
<221> NAME/KEY: misc_feature
<222> LOCATION: (41)..(41)
<223> OTHER INFORMATION: Synthesized: Xaa can be any naturally occurring amino acid
<220> FEATURE:
<221> NAME/KEY: misc_feature
<222> LOCATION: (55)..(55)
<223> OTHER INFORMATION: Synthesized: Xaa can be any naturally occurring amino acid
<220> FEATURE:
<221> NAME/KEY: misc_feature
<222> LOCATION: (101)..(102)
<223> OTHER INFORMATION: Synthesized: Xaa can be any naturally occurring amino acid
<220> FEATURE:
<221> NAME/KEY: misc_feature
<222> LOCATION: (106)..(107)
<223> OTHER INFORMATION: Synthesized: Xaa can be any naturally occurring amino acid
<220> FEATURE:
<221> NAME/KEY: misc_feature
<222> LOCATION: (109)..(109)
<223> OTHER INFORMATION: Synthesized: Xaa can be any naturally occurring amino acid
<220> FEATURE:
<221> NAME/KEY: misc_feature
<222> LOCATION: (112)..(112)
<223> OTHER INFORMATION: Synthesized: Xaa can be any naturally occurring amino acid

<400> SEQUENCE: 839

Glu Val Gln Leu Gln Glu Ser Gly Pro Ser Leu Val Lys Pro Ser Gln
1 5 10 15

Thr Leu Ser Leu Thr Cys Ser Val Thr Gly Asp Ser Ile Thr Ser Gly
20 25 30

```
Tyr Trp Asn Asn Ser Trp Ile Arg Xaa Phe Pro Gly Asn Lys Leu Glu
        35                  40                  45

Trp Met Gly Tyr Ile Ser Xaa Tyr Ser Gly Ser Thr Tyr Tyr Asn Pro
    50                  55                  60

Ser Leu Lys Ser Arg Ile Ser Ile Thr Arg Asp Thr Ser Lys Asn Gln
65                  70                  75                  80

Tyr Phe Leu Gln Leu Asn Ser Val Thr Thr Glu Asp Thr Ala Thr Tyr
                85                  90                  95

Tyr Cys Ala Arg Xaa Xaa Tyr Gly Tyr Xaa Xaa Tyr Xaa Tyr Asp Xaa
            100                 105                 110

Tyr Tyr Tyr Tyr Phe Asp Tyr Trp Gly Gln Gly Thr Thr Val Thr Val
        115                 120                 125

Ser Ser
    130


<210> SEQ ID NO 840
<211> LENGTH: 129
<212> TYPE: PRT
<213> ORGANISM: Artificial Sequence
<220> FEATURE:
<223> OTHER INFORMATION: Synthesized: mH1b
<220> FEATURE:
<221> NAME/KEY: misc_feature
<222> LOCATION: (103)..(103)
<223> OTHER INFORMATION: Synthesized: Xaa can be any naturally occurring
      amino acid
<220> FEATURE:
<221> NAME/KEY: misc_feature
<222> LOCATION: (107)..(107)
<223> OTHER INFORMATION: Synthesized: Xaa can be any naturally occurring
      amino acid
<220> FEATURE:
<221> NAME/KEY: misc_feature
<222> LOCATION: (110)..(112)
<223> OTHER INFORMATION: Synthesized: Xaa can be any naturally occurring
      amino acid

<400> SEQUENCE: 840

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Val Ser Trp Val Arg Gln Pro Pro Gly Lys Gly Leu Glu
        35                  40                  45

Trp Leu Gly Val Ile Trp Ala Gly Gly Ser Thr Asn Tyr Asn Ser Ala
    50                  55                  60

Leu Met Ser Arg Leu Ser Ile Ser Lys Asp Asn Ser Lys Ser Gln Val
65                  70                  75                  80

Phe Leu Lys Met Asn Ser Leu Gln Thr Asp Asp Thr Ala Met Tyr Tyr
                85                  90                  95

Cys Ala Arg Asp Arg Gly Xaa Tyr Tyr Tyr Xaa Ser Gly Xaa Xaa Xaa
            100                 105                 110

Tyr Tyr Ala Met Asp Tyr Trp Gly Gln Gly Thr Ser Val Thr Val Ser
        115                 120                 125

Ser


<210> SEQ ID NO 841
<211> LENGTH: 129
<212> TYPE: PRT
<213> ORGANISM: Artificial Sequence
<220> FEATURE:
<223> OTHER INFORMATION: Synthesized: mH2a
```

<220> FEATURE:
<221> NAME/KEY: misc_feature
<222> LOCATION: (100)..(101)
<223> OTHER INFORMATION: Synthesized: Xaa can be any naturally occurring amino acid
<220> FEATURE:
<221> NAME/KEY: misc_feature
<222> LOCATION: (107)..(107)
<223> OTHER INFORMATION: Synthesized: Xaa can be any naturally occurring amino acid
<220> FEATURE:
<221> NAME/KEY: misc_feature
<222> LOCATION: (109)..(109)
<223> OTHER INFORMATION: Synthesized: Xaa can be any naturally occurring amino acid
<220> FEATURE:
<221> NAME/KEY: misc_feature
<222> LOCATION: (111)..(112)
<223> OTHER INFORMATION: Synthesized: Xaa can be any naturally occurring amino acid

<400> SEQUENCE: 841

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Asn Trp Val Lys Gln Ser Pro Gly Lys Ser Leu Glu Trp
        35                  40                  45

Ile Gly Asp Ile Asn Pro Gly Asn Gly Gly Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Xaa Xaa Tyr Tyr Ser Ser Ser Xaa Met Xaa Ala Xaa Xaa
            100                 105                 110

Tyr Tyr Ala Phe Asp Tyr Trp Gly Gln Gly Thr Thr Val Thr Val Ser
        115                 120                 125

Ser
```

<210> SEQ ID NO 842
<211> LENGTH: 127
<212> TYPE: PRT
<213> ORGANISM: Artificial Sequence
<220> FEATURE:
<223> OTHER INFORMATION: Synthesized: mH2b
<220> FEATURE:
<221> NAME/KEY: misc_feature
<222> LOCATION: (106)..(107)
<223> OTHER INFORMATION: Synthesized: Xaa can be any naturally occurring amino acid
<220> FEATURE:
<221> NAME/KEY: misc_feature
<222> LOCATION: (110)..(110)
<223> OTHER INFORMATION: Synthesized: Xaa can be any naturally occurring amino acid

<400> SEQUENCE: 842

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile Asp Pro Asn Ser Gly Gly Thr Asn Tyr Asn Glu Lys Phe
```

```
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Tyr Gly Gly Ser Ser Xaa Xaa Val Tyr Xaa Tyr Trp
            100                 105                 110

Tyr Phe Asp Tyr Trp Gly Gln Gly Thr Thr Val Thr Val Ser Ser
        115                 120                 125


<210> SEQ ID NO 843
<211> LENGTH: 125
<212> TYPE: PRT
<213> ORGANISM: Artificial Sequence
<220> FEATURE:
<223> OTHER INFORMATION: Synthesized: mH2c
<220> FEATURE:
<221> NAME/KEY: misc_feature
<222> LOCATION: (106)..(106)
<223> OTHER INFORMATION: Synthesized: Xaa can be any naturally occurring
      amino acid
<220> FEATURE:
<221> NAME/KEY: misc_feature
<222> LOCATION: (120)..(120)
<223> OTHER INFORMATION: Synthesized: Xaa can be any naturally occurring
      amino acid

<400> SEQUENCE: 843

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Tyr Tyr Tyr Tyr Asp Ser Xaa Val Gly Tyr Tyr Ala Met
            100                 105                 110

Asp Tyr Trp Gly Gln Gly Thr Xaa Val Thr Val Ser Ser
        115                 120                 125


<210> SEQ ID NO 844
<211> LENGTH: 130
<212> TYPE: PRT
<213> ORGANISM: Artificial Sequence
<220> FEATURE:
<223> OTHER INFORMATION: Synthesized: mH3a

<400> SEQUENCE: 844

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Ala Leu Glu Trp Ile
        35                  40                  45

Ala Ala Ser Arg Asn Lys Ala Asn Asp Tyr Thr Thr Glu Tyr Ser Ala
    50                  55                  60
```

```
Ser Val Lys Gly Arg Phe Thr Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Tyr Gly Ser Ser Tyr Tyr Glu Gly Pro
            100                 105                 110

Val Tyr Trp Tyr Phe Asp Val Trp Gly Ala Gly Thr Thr Val Thr Val
        115                 120                 125

Ser Ser
    130


<210> SEQ ID NO 845
<211> LENGTH: 127
<212> TYPE: PRT
<213> ORGANISM: Artificial Sequence
<220> FEATURE:
<223> OTHER INFORMATION: Synthesized: mH3b

<400> SEQUENCE: 845

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Lys Ala Asp Ser Ser Thr Ile Asn Tyr Thr Pro
    50                  55                  60

Ser Leu Lys Asp Lys Phe Ile Ile Ser Arg Asp Asn Ala Lys Asn Thr
65                  70                  75                  80

Leu Tyr Leu Gln Met Ser Lys Val Arg Ser Glu Asp Thr Ala Leu Tyr
                85                  90                  95

Tyr Cys Ala Arg Leu Gly Gly Tyr Gly Tyr Phe Gly Ser Ser Tyr Tyr
            100                 105                 110

Ala Met Asp Tyr Trp Gly Gln Gly Thr Thr Val Thr Val Ser Ser
        115                 120                 125


<210> SEQ ID NO 846
<211> LENGTH: 127
<212> TYPE: PRT
<213> ORGANISM: Artificial Sequence
<220> FEATURE:
<223> OTHER INFORMATION: Synthesized: mH3c
<220> FEATURE:
<221> NAME/KEY: misc_feature
<222> LOCATION: (36)..(37)
<223> OTHER INFORMATION: Synthesized: Xaa can be any naturally occurring
      amino acid
<220> FEATURE:
<221> NAME/KEY: misc_feature
<222> LOCATION: (108)..(108)
<223> OTHER INFORMATION: Synthesized: Xaa can be any naturally occurring
      amino acid
<220> FEATURE:
<221> NAME/KEY: misc_feature
<222> LOCATION: (112)..(112)
<223> OTHER INFORMATION: Synthesized: Xaa can be any naturally occurring
      amino acid

<400> SEQUENCE: 846

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
```

```
            20                  25                  30

Trp Met Asn Xaa Xaa Trp Val Arg Gln Ser Pro Glu Lys Gly Leu Glu
        35                  40                  45

Trp Val Ala Glu Ile Arg Leu Lys Ser Asp Asn Tyr Ala Thr His Tyr
    50                  55                  60

Ala Glu Ser Val Lys Gly Arg Phe Thr Ile Ser Arg Asp Asp Ser Lys
65                  70                  75                  80

Ser Ser Val Tyr Leu Gln Met Asn Asn Leu Arg Ala Glu Asp Thr Gly
                85                  90                  95

Ile Tyr Tyr Cys Thr Thr Gly Gly Tyr Gly Gly Xaa Arg Arg Ser Xaa
            100                 105                 110

Trp Phe Ala Tyr Trp Gly Gln Gly Thr Leu Val Thr Val Ser Ser
        115                 120                 125


<210> SEQ ID NO 847
<211> LENGTH: 129
<212> TYPE: PRT
<213> ORGANISM: Artificial Sequence
<220> FEATURE:
<223> OTHER INFORMATION: Synthesized: mH3d
<220> FEATURE:
<221> NAME/KEY: misc_feature
<222> LOCATION: (102)..(102)
<223> OTHER INFORMATION: Synthesized: Xaa can be any naturally occurring
      amino acid
<220> FEATURE:
<221> NAME/KEY: misc_feature
<222> LOCATION: (106)..(107)
<223> OTHER INFORMATION: Synthesized: Xaa can be any naturally occurring
      amino acid

<400> SEQUENCE: 847

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Lys Ser Gly Gly Gly Tyr Thr Tyr Tyr Pro Asp
    50                  55                  60

Ser Val Lys Gly Arg Phe Thr Ile Ser Arg Asp Asn Ala Lys Asn Thr
65                  70                  75                  80

Leu Tyr Leu Gln Met Ser Ser Leu Arg Ser Glu Asp Thr Ala Met Tyr
                85                  90                  95

Tyr Cys Ala Arg Gly Xaa Tyr Tyr Tyr Xaa Xaa Gly Ser Ala Pro Phe
            100                 105                 110

Asp Tyr Ala Met Asp Tyr Trp Gly Gln Gly Thr Ser Val Thr Val Ser
        115                 120                 125

Ser


<210> SEQ ID NO 848
<211> LENGTH: 128
<212> TYPE: PRT
<213> ORGANISM: Artificial Sequence
<220> FEATURE:
<223> OTHER INFORMATION: Synthesized: mH5a
<220> FEATURE:
<221> NAME/KEY: misc_feature
<222> LOCATION: (100)..(100)
<223> OTHER INFORMATION: Synthesized: Xaa can be any naturally occurring
      amino acid
<220> FEATURE:
```

<221> NAME/KEY: misc_feature
<222> LOCATION: (109)..(109)
<223> OTHER INFORMATION: Synthesized: Xaa can be any naturally occurring amino acid

<400> SEQUENCE: 848

```
Glu Val Gln Leu Gln Gln Ser Gly Ala Glu Leu Val Arg Ala Gly Ser
1               5                   10                  15

Ser Val Lys Met Ser Cys Lys Ala Ser Gly Tyr Thr Phe Thr Ser Tyr
            20                  25                  30

Gly Ile Asn Trp Val Lys Gln Arg Pro Gly Gln Gly Leu Glu Trp Ile
        35                  40                  45

Gly Tyr Ile Asn Pro Gly Asn Gly Tyr Thr Lys Tyr Asn Glu Lys Phe
    50                  55                  60

Lys Gly Lys Thr Thr Leu Thr Val Asp Lys Ser Ser Ser Thr Ala Tyr
65                  70                  75                  80

Met Gln Leu Arg Ser Leu Thr Ser Glu Asp Ser Ala Val Tyr Phe Cys
                85                  90                  95

Ala Arg Ser Xaa Tyr Tyr Gly Gly Ser Tyr Tyr Tyr Xaa Phe Ala Tyr
            100                 105                 110

Tyr Tyr Phe Asp Tyr Trp Gly Gln Gly Thr Thr Leu Thr Val Ser Ser
        115                 120                 125
```

<210> SEQ ID NO 849
<211> LENGTH: 114
<212> TYPE: PRT
<213> ORGANISM: Artificial Sequence
<220> FEATURE:
<223> OTHER INFORMATION: Synthesized: mH5b
<220> FEATURE:
<221> NAME/KEY: misc_feature
<222> LOCATION: (47)..(48)
<223> OTHER INFORMATION: Synthesized: Xaa can be any naturally occurring amino acid

<400> SEQUENCE: 849

```
Glu Val Gln Leu Gln Gln Ser Gly Ala Glu Leu Val Lys Ala Gly Ser
1               5                   10                  15

Ser Val Lys Met Ser Cys Ser Ala Thr Gly Tyr Thr Phe Ser Ser Tyr
            20                  25                  30

Gly Leu Tyr Trp Val Arg Gln Ala Pro Gly Gln Gly Leu Glu Xaa Xaa
        35                  40                  45

Gly Tyr Ile Ser Ser Ser Ser Ala Tyr Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Val Arg Val Ile Ser Arg Tyr Phe Asp Gly Trp Gly Gln Gly Thr
            100                 105                 110

Leu Val
```

<210> SEQ ID NO 850
<211> LENGTH: 132
<212> TYPE: PRT
<213> ORGANISM: Artificial Sequence
<220> FEATURE:
<223> OTHER INFORMATION: Synthesized: mHms
<220> FEATURE:
<221> NAME/KEY: misc_feature
<222> LOCATION: (1)..(1)

<223> OTHER INFORMATION: Synthesized: Xaa can be any naturally occurring amino acid
<220> FEATURE:
<221> NAME/KEY: misc_feature
<222> LOCATION: (68)..(68)
<223> OTHER INFORMATION: Synthesized: Xaa can be any naturally occurring amino acid
<220> FEATURE:
<221> NAME/KEY: misc_feature
<222> LOCATION: (103)..(103)
<223> OTHER INFORMATION: Synthesized: Xaa can be any naturally occurring amino acid
<220> FEATURE:
<221> NAME/KEY: misc_feature
<222> LOCATION: (112)..(114)
<223> OTHER INFORMATION: Synthesized: Xaa can be any naturally occurring amino acid

<400> SEQUENCE: 850

```
Xaa Val Gln Leu Val Glu Ser Gly Gly Gly Leu Val Lys Pro Gly Gly
1               5                   10                  15

Ser Val Lys Leu Ser Cys Lys Ala Ser Gly Phe Thr Phe Ser Ser Phe
            20                  25                  30

Gly Met Ser Asn Phe Trp Val Arg Gln Ala Pro Gly Lys Gly Leu Glu
        35                  40                  45

Trp Val Gly Trp Ile Asn Ser Lys Leu Gly Gly Gly Ala Ile Tyr Tyr
    50                  55                  60

Ala Asp Thr Xaa Lys Gly Arg Phe Thr Ile Ser Arg Asp Asn Ser Lys
65                  70                  75                  80

Ser Thr Leu Tyr Leu Gln Met Ser Ser Leu Arg Ser Glu Asp Thr Ala
                85                  90                  95

Thr Tyr Tyr Cys Ala Arg Xaa Gly Tyr Tyr Gly Gly Arg Arg Ser Xaa
            100                 105                 110

Xaa Xaa Ser Tyr Trp Tyr Phe Asp Tyr Trp Gly Gln Gly Thr Thr Val
        115                 120                 125

Thr Val Ser Ser
    130
```

<210> SEQ ID NO 851
<211> LENGTH: 63
<212> TYPE: DNA
<213> ORGANISM: Artificial Sequence
<220> FEATURE:
<223> OTHER INFORMATION: Synthesized: XPA CDR1 coding sequence

<400> SEQUENCE: 851

```
tctttcttgc gctgcttccg gattcacttt ctctaagtac tttatgtttt gggttcgcca     60

agc                                                                   63
```

<210> SEQ ID NO 852
<211> LENGTH: 63
<212> TYPE: DNA
<213> ORGANISM: Artificial Sequence
<220> FEATURE:
<223> OTHER INFORMATION: Synthesized: XPA CDR1 coding sequence (antisense)

<400> SEQUENCE: 852

```
agaaagaacg cgacgaaggc ctaagtgaaa gagattcatg aaatacaaaa cccaagcggt     60

tcg                                                                   63
```

<210> SEQ ID NO 853
<211> LENGTH: 47

<212> TYPE: DNA
<213> ORGANISM: Artificial Sequence
<220> FEATURE:
<223> OTHER INFORMATION: Synthesized: primer 1 for mutation of G position in XPA CDR1
<220> FEATURE:
<221> NAME/KEY: misc_feature
<222> LOCATION: (21)..(21)
<223> OTHER INFORMATION: n is a, c, g, or t

<400> SEQUENCE: 853
gtctttcttg cgctgcttcc nhtttcactt tctctaagta ctttatg 47

<210> SEQ ID NO 854
<211> LENGTH: 47
<212> TYPE: DNA
<213> ORGANISM: Artificial Sequence
<220> FEATURE:
<223> OTHER INFORMATION: Synthesized: primer 1 for mutation of G position in XPA CDR1 (antisense)
<220> FEATURE:
<221> NAME/KEY: misc_feature
<222> LOCATION: (21)..(21)
<223> OTHER INFORMATION: n is a, c, g, or t

<400> SEQUENCE: 854
cagaaagaac gcgacgaagg ndaaagtgaa agagattcat gaaatac 47

<210> SEQ ID NO 855
<211> LENGTH: 47
<212> TYPE: DNA
<213> ORGANISM: Artificial Sequence
<220> FEATURE:
<223> OTHER INFORMATION: Synthesized: primer 2 for mutation of G position in XPA CDR1

<400> SEQUENCE: 855
gtctttcttg cgctgcttcc vaattcactt tctctaagta ctttatg 47

<210> SEQ ID NO 856
<211> LENGTH: 47
<212> TYPE: DNA
<213> ORGANISM: Artificial Sequence
<220> FEATURE:
<223> OTHER INFORMATION: Synthesized: primer 2 for mutation of G position in XPA CDR1(antisense)

<400> SEQUENCE: 856
cagaaagaac gcgacgaagg bttaagtgaa agagattcat gaaatac 47

<210> SEQ ID NO 857
<211> LENGTH: 47
<212> TYPE: DNA
<213> ORGANISM: Artificial Sequence
<220> FEATURE:
<223> OTHER INFORMATION: Synthesized: primer 3 for mutation of G position in XPA CDR1

<400> SEQUENCE: 857
gtctttcttg cgctgcttcc bggttcactt tctctaagta ctttatg 47

<210> SEQ ID NO 858
<211> LENGTH: 47
<212> TYPE: DNA
<213> ORGANISM: Artificial Sequence
<220> FEATURE:
<223> OTHER INFORMATION: Synthesized: primer 3 for mutation of G position in XPA CDR1 (antisense)

<400> SEQUENCE: 858
cagaaagaac gcgacgaagg vccaagtgaa agagattcat gaaatac 47

<210> SEQ ID NO 859
<211> LENGTH: 45
<212> TYPE: DNA
<213> ORGANISM: Artificial Sequence
<220> FEATURE:
<223> OTHER INFORMATION: Synthesized: primer 1 for mutation of F position in XPA CDR1
<220> FEATURE:
<221> NAME/KEY: misc_feature
<222> LOCATION: (22)..(22)
<223> OTHER INFORMATION: n is a, c, g, or t

<400> SEQUENCE: 859
ctttcttgcg ctgcttccgg anhtactttc tctaagtact ttatg 45

<210> SEQ ID NO 860
<211> LENGTH: 45
<212> TYPE: DNA
<213> ORGANISM: Artificial Sequence
<220> FEATURE:
<223> OTHER INFORMATION: Synthesized: primer 1 for mutation of F position in XPA CDR1 (antisense)
<220> FEATURE:
<221> NAME/KEY: misc_feature
<222> LOCATION: (22)..(22)
<223> OTHER INFORMATION: n is a, c, g, or t

<400> SEQUENCE: 860
gaaagaacgc gacgaaggcc tndatgaaag agattcatga aatac 45

<210> SEQ ID NO 861
<211> LENGTH: 45
<212> TYPE: DNA
<213> ORGANISM: Artificial Sequence
<220> FEATURE:
<223> OTHER INFORMATION: Synthesized: primer 2 for mutation of F position in XPA CDR1

<400> SEQUENCE: 861
ctttcttgcg ctgcttccgg avaaactttc tctaagtact ttatg 45

<210> SEQ ID NO 862
<211> LENGTH: 45
<212> TYPE: DNA
<213> ORGANISM: Artificial Sequence
<220> FEATURE:
<223> OTHER INFORMATION: Synthesized: primer 2 for mutation of F position in XPA CDR1 (antisense)

<400> SEQUENCE: 862
gaaagaacgc gacgaaggcc tbtttgaaag agattcatga aatac 45

<210> SEQ ID NO 863
<211> LENGTH: 45
<212> TYPE: DNA
<213> ORGANISM: Artificial Sequence
<220> FEATURE:
<223> OTHER INFORMATION: Synthesized: primer 3 for mutation of F position in XPA CDR1

<400> SEQUENCE: 863
ctttcttgcg ctgcttccgg abggactttc tctaagtact ttatg 45

<210> SEQ ID NO 864

<211> LENGTH: 45
<212> TYPE: DNA
<213> ORGANISM: Artificial Sequence
<220> FEATURE:
<223> OTHER INFORMATION: Synthesized: primer 3 for mutation of F position in XPA CDR1 (antisense)

<400> SEQUENCE: 864
gaaagaacgc gacgaaggcc tvcctgaaag agattcatga aatac 45

<210> SEQ ID NO 865
<211> LENGTH: 46
<212> TYPE: DNA
<213> ORGANISM: Artificial Sequence
<220> FEATURE:
<223> OTHER INFORMATION: Synthesized: primer 1 for mutation of T position in XPA CDR1
<220> FEATURE:
<221> NAME/KEY: misc_feature
<222> LOCATION: (21)..(21)
<223> OTHER INFORMATION: n is a, c, g, or t

<400> SEQUENCE: 865
cttgcgctgc ttccggattc nhtttctcta agtactttat gttttg 46

<210> SEQ ID NO 866
<211> LENGTH: 46
<212> TYPE: DNA
<213> ORGANISM: Artificial Sequence
<220> FEATURE:
<223> OTHER INFORMATION: Synthesized: primer 1 for mutation of T position in XPA CDR1 (antisense)
<220> FEATURE:
<221> NAME/KEY: misc_feature
<222> LOCATION: (21)..(21)
<223> OTHER INFORMATION: n is a, c, g, or t

<400> SEQUENCE: 866
gaacgcgacg aaggcctaag ndaaagagat tcatgaaata caaaac 46

<210> SEQ ID NO 867
<211> LENGTH: 46
<212> TYPE: DNA
<213> ORGANISM: Artificial Sequence
<220> FEATURE:
<223> OTHER INFORMATION: Synthesized: primer 2 for mutation of T position in XPA CDR1

<400> SEQUENCE: 867
cttgcgctgc ttccggattc vaattctcta agtactttat gttttg 46

<210> SEQ ID NO 868
<211> LENGTH: 46
<212> TYPE: DNA
<213> ORGANISM: Artificial Sequence
<220> FEATURE:
<223> OTHER INFORMATION: Synthesized: primer 2 for mutation of T position in XPA CDR1 (antisense)

<400> SEQUENCE: 868
gaacgcgacg aaggcctaag bttaagagat tcatgaaata caaaac 46

<210> SEQ ID NO 869
<211> LENGTH: 46
<212> TYPE: DNA
<213> ORGANISM: Artificial Sequence
<220> FEATURE:
<223> OTHER INFORMATION: Synthesized: primer 3 for mutation of T position in XPA CDR1

<400> SEQUENCE: 869
cttgcgctgc ttccggattc bggttctcta agtactttat gttttg 46

<210> SEQ ID NO 870
<211> LENGTH: 46
<212> TYPE: DNA
<213> ORGANISM: Artificial Sequence
<220> FEATURE:
<223> OTHER INFORMATION: Synthesized: primer 3 for mutation of T position in XPA CDR1 (antisense)

<400> SEQUENCE: 870
gaacgcgacg aaggcctaag vccaagagat tcatgaaata caaaac 46

<210> SEQ ID NO 871
<211> LENGTH: 43
<212> TYPE: DNA
<213> ORGANISM: Artificial Sequence
<220> FEATURE:
<223> OTHER INFORMATION: Synthesized: primer 1 for mutation of F4 position in XPA CDR1
<220> FEATURE:
<221> NAME/KEY: misc_feature
<222> LOCATION: (19)..(19)
<223> OTHER INFORMATION: n is a, c, g, or t

<400> SEQUENCE: 871
gctgcttccg gattcactnh ttctaagtac tttatgtttt ggg 43

<210> SEQ ID NO 872
<211> LENGTH: 43
<212> TYPE: DNA
<213> ORGANISM: Artificial Sequence
<220> FEATURE:
<223> OTHER INFORMATION: Synthesized: primer 1 for mutation of F4 position in XPA CDR1 (antisense)
<220> FEATURE:
<221> NAME/KEY: misc_feature
<222> LOCATION: (19)..(19)
<223> OTHER INFORMATION: n is a, c, g, or t

<400> SEQUENCE: 872
cgacgaaggc ctaagtgand aagattcatg aaatacaaaa ccc 43

<210> SEQ ID NO 873
<211> LENGTH: 43
<212> TYPE: DNA
<213> ORGANISM: Artificial Sequence
<220> FEATURE:
<223> OTHER INFORMATION: Synthesized: primer 2 for mutation of F4 position in XPA CDR1

<400> SEQUENCE: 873
gctgcttccg gattcactva atctaagtac tttatgtttt ggg 43

<210> SEQ ID NO 874
<211> LENGTH: 43
<212> TYPE: DNA
<213> ORGANISM: Artificial Sequence
<220> FEATURE:
<223> OTHER INFORMATION: Synthesized: primer 2 for mutation of F4 position in XPA CDR1 (antisense)

<400> SEQUENCE: 874
cgacgaaggc ctaagtgabt tagattcatg aaatacaaaa ccc 43

<210> SEQ ID NO 875
<211> LENGTH: 43
<212> TYPE: DNA
<213> ORGANISM: Artificial Sequence
<220> FEATURE:
<223> OTHER INFORMATION: Synthesized: primer 3 for mutation of F4
position in XPA CDR1

<400> SEQUENCE: 875
gctgcttccg gattcactbg gtctaagtac tttatgtttt ggg 43

<210> SEQ ID NO 876
<211> LENGTH: 43
<212> TYPE: DNA
<213> ORGANISM: Artificial Sequence
<220> FEATURE:
<223> OTHER INFORMATION: Synthesized: primer 3 for mutation of F4
position in XPA CDR1 (antisense)

<400> SEQUENCE: 876
cgacgaaggc ctaagtgavc cagattcatg aaatacaaaa ccc 43

<210> SEQ ID NO 877
<211> LENGTH: 46
<212> TYPE: DNA
<213> ORGANISM: Artificial Sequence
<220> FEATURE:
<223> OTHER INFORMATION: Synthesized: primer 1 for mutation of S
position in XPA CDR1
<220> FEATURE:
<221> NAME/KEY: misc_feature
<222> LOCATION: (21)..(21)
<223> OTHER INFORMATION: n is a, c, g, or t

<400> SEQUENCE: 877
ctgcttccgg attcactttc nhtaagtact ttatgttttg ggttcg 46

<210> SEQ ID NO 878
<211> LENGTH: 46
<212> TYPE: DNA
<213> ORGANISM: Artificial Sequence
<220> FEATURE:
<223> OTHER INFORMATION: Synthesized: primer 1 for mutation of S
position in XPA CDR1 (antisense)
<220> FEATURE:
<221> NAME/KEY: misc_feature
<222> LOCATION: (21)..(21)
<223> OTHER INFORMATION: n is a, c, g, or t

<400> SEQUENCE: 878
gacgaaggcc taagtgaaag ndattcatga aatacaaaac ccaagc 46

<210> SEQ ID NO 879
<211> LENGTH: 46
<212> TYPE: DNA
<213> ORGANISM: Artificial Sequence
<220> FEATURE:
<223> OTHER INFORMATION: Synthesized: primer 2 for mutation of S
position in XPA CDR1

<400> SEQUENCE: 879
ctgcttccgg attcactttc vaaaagtact ttatgttttg ggttcg 46

<210> SEQ ID NO 880
<211> LENGTH: 46
<212> TYPE: DNA
<213> ORGANISM: Artificial Sequence
<220> FEATURE:
<223> OTHER INFORMATION: Synthesized: primer 2 for mutation of S position in XPA CDR1 (antisense)

<400> SEQUENCE: 880
gacgaaggcc taagtgaaag bttttcatga aatacaaaac ccaagc 46

<210> SEQ ID NO 881
<211> LENGTH: 46
<212> TYPE: DNA
<213> ORGANISM: Artificial Sequence
<220> FEATURE:
<223> OTHER INFORMATION: Synthesized: primer 3 for mutation of S position in XPA CDR1

<400> SEQUENCE: 881
ctgcttccgg attcactttc bggaagtact ttatgttttg ggttcg 46

<210> SEQ ID NO 882
<211> LENGTH: 46
<212> TYPE: DNA
<213> ORGANISM: Artificial Sequence
<220> FEATURE:
<223> OTHER INFORMATION: Synthesized: primer 3 for mutation of S position in XPA CDR1 (antisense)

<400> SEQUENCE: 882
gacgaaggcc taagtgaaag vccttcatga aatacaaaac ccaagc 46

<210> SEQ ID NO 883
<211> LENGTH: 45
<212> TYPE: DNA
<213> ORGANISM: Artificial Sequence
<220> FEATURE:
<223> OTHER INFORMATION: Synthesized: primer 1 for mutation of K position in XPA CDR1
<220> FEATURE:
<221> NAME/KEY: misc_feature
<222> LOCATION: (21)..(21)
<223> OTHER INFORMATION: n is a, c, g, or t

<400> SEQUENCE: 883
cttccggatt cactttctct nhttacttta tgttttgggt tcgcc 45

<210> SEQ ID NO 884
<211> LENGTH: 45
<212> TYPE: DNA
<213> ORGANISM: Artificial Sequence
<220> FEATURE:
<223> OTHER INFORMATION: Synthesized: primer 1 for mutation of K position in XPA CDR1 (antisense)
<220> FEATURE:
<221> NAME/KEY: misc_feature
<222> LOCATION: (21)..(21)
<223> OTHER INFORMATION: n is a, c, g, or t

<400> SEQUENCE: 884
gaaggcctaa gtgaaagaga ndaatgaaat acaaaaccca agcgg 45

<210> SEQ ID NO 885
<211> LENGTH: 45
<212> TYPE: DNA
<213> ORGANISM: Artificial Sequence
<220> FEATURE:
<223> OTHER INFORMATION: Synthesized: primer 2 for mutation of K position in XPA CDR1

<400> SEQUENCE: 885
cttccggatt cactttctct vaatacttta tgttttgggt tcgcc 45

<210> SEQ ID NO 886
<211> LENGTH: 45
<212> TYPE: DNA
<213> ORGANISM: Artificial Sequence
<220> FEATURE:
<223> OTHER INFORMATION: Synthesized: primer 2 for mutation of K position in XPA CDR1 (antisense)

<400> SEQUENCE: 886
gaaggcctaa gtgaaagaga bttatgaaat acaaaaccca agcgg 45

<210> SEQ ID NO 887
<211> LENGTH: 45
<212> TYPE: DNA
<213> ORGANISM: Artificial Sequence
<220> FEATURE:
<223> OTHER INFORMATION: Synthesized: primer 3 for mutation of K position in XPA CDR1

<400> SEQUENCE: 887
cttccggatt cactttctct bggtacttta tgttttgggt tcgcc 45

<210> SEQ ID NO 888
<211> LENGTH: 45
<212> TYPE: DNA
<213> ORGANISM: Artificial Sequence
<220> FEATURE:
<223> OTHER INFORMATION: Synthesized: primer 3 for mutation of K position in XPA CDR1 (antisense)

<400> SEQUENCE: 888
gaaggcctaa gtgaaagaga vccatgaaat acaaaaccca agcgg 45

<210> SEQ ID NO 889
<211> LENGTH: 45
<212> TYPE: DNA
<213> ORGANISM: Artificial Sequence
<220> FEATURE:
<223> OTHER INFORMATION: Synthesized: primer 1 for mutation of Y position in XPA CDR1
<220> FEATURE:
<221> NAME/KEY: misc_feature
<222> LOCATION: (21)..(21)
<223> OTHER INFORMATION: n is a, c, g, or t

<400> SEQUENCE: 889
ccggattcac tttctctaag nhttttatgt tttgggttcg ccaag 45

<210> SEQ ID NO 890
<211> LENGTH: 45
<212> TYPE: DNA
<213> ORGANISM: Artificial Sequence
<220> FEATURE:
<223> OTHER INFORMATION: Synthesized: primer 1 for mutation of Y position in XPA CDR1 (antisense)
<220> FEATURE:
<221> NAME/KEY: misc_feature
<222> LOCATION: (21)..(21)
<223> OTHER INFORMATION: n is a, c, g, or t

<400> SEQUENCE: 890
ggcctaagtg aaagagattc ndaaaataca aaacccaagc ggttc 45

<210> SEQ ID NO 891
<211> LENGTH: 45
<212> TYPE: DNA
<213> ORGANISM: Artificial Sequence
<220> FEATURE:

<223> OTHER INFORMATION: Synthesized: primer 2 for mutation of Y position in XPA CDR1

<400> SEQUENCE: 891
ccggattcac tttctctaag vaatttatgt tttgggttcg ccaag 45

<210> SEQ ID NO 892
<211> LENGTH: 45
<212> TYPE: DNA
<213> ORGANISM: Artificial Sequence
<220> FEATURE:
<223> OTHER INFORMATION: Synthesized: primer 2 for mutation of Y position in XPA CDR1 (Artificial Sequence)

<400> SEQUENCE: 892
ggcctaagtg aaagagattc bttaaataca aaacccaagc ggttc 45

<210> SEQ ID NO 893
<211> LENGTH: 45
<212> TYPE: DNA
<213> ORGANISM: Artificial Sequence
<220> FEATURE:
<223> OTHER INFORMATION: Synthesized: primer 3 for mutation of Y position in XPA CDR1

<400> SEQUENCE: 893
ccggattcac tttctctaag bggtttatgt tttgggttcg ccaag 45

<210> SEQ ID NO 894
<211> LENGTH: 45
<212> TYPE: DNA
<213> ORGANISM: Artificial Sequence
<220> FEATURE:
<223> OTHER INFORMATION: Synthesized: primer 3 for mutation of Y position in XPA CDR1 (antisense)

<400> SEQUENCE: 894
ggcctaagtg aaagagattc vccaaataca aaacccaagc ggttc 45

<210> SEQ ID NO 895
<211> LENGTH: 44
<212> TYPE: DNA
<213> ORGANISM: Artificial Sequence
<220> FEATURE:
<223> OTHER INFORMATION: Synthesized: primer 1 for mutation of F8 position in XPA CDR1
<220> FEATURE:
<221> NAME/KEY: misc_feature
<222> LOCATION: (22)..(22)
<223> OTHER INFORMATION: n is a, c, g, or t

<400> SEQUENCE: 895
ggattcactt tctctaagta cnhtatgttt tgggttcgcc aagc 44

<210> SEQ ID NO 896
<211> LENGTH: 44
<212> TYPE: DNA
<213> ORGANISM: Artificial Sequence
<220> FEATURE:
<223> OTHER INFORMATION: Synthesized: primer 1 for mutation of F8 position in XPA CDR1 (antisense)
<220> FEATURE:
<221> NAME/KEY: misc_feature
<222> LOCATION: (22)..(22)
<223> OTHER INFORMATION: n is a, c, g, or t

<400> SEQUENCE: 896
cctaagtgaa agagattcat gndatacaaa acccaagcgg ttcg 44

<210> SEQ ID NO 897
<211> LENGTH: 44
<212> TYPE: DNA
<213> ORGANISM: Artificial Sequence
<220> FEATURE:
<223> OTHER INFORMATION: Synthesized: primer 2 for mutation of F8 position in XPA CDR1

<400> SEQUENCE: 897
ggattcactt tctctaagta cvaaatgttt tgggttcgcc aagc 44

<210> SEQ ID NO 898
<211> LENGTH: 44
<212> TYPE: DNA
<213> ORGANISM: Artificial Sequence
<220> FEATURE:
<223> OTHER INFORMATION: Synthesized: primer 2 for mutation of F8 position in XPA CDR1 (antisense)

<400> SEQUENCE: 898
cctaagtgaa agagattcat gbtttacaaa acccaagcgg ttcg 44

<210> SEQ ID NO 899
<211> LENGTH: 44
<212> TYPE: DNA
<213> ORGANISM: Artificial Sequence
<220> FEATURE:
<223> OTHER INFORMATION: Synthesized: primer 3 for mutation of F8 position in XPA CDR1

<400> SEQUENCE: 899
ggattcactt tctctaagta cbggatgttt tgggttcgcc aagc 44

<210> SEQ ID NO 900
<211> LENGTH: 44
<212> TYPE: DNA
<213> ORGANISM: Artificial Sequence
<220> FEATURE:
<223> OTHER INFORMATION: Synthesized: primer 3 for mutation of F8 position in XPA CDR1 (Artificial Sequence)

<400> SEQUENCE: 900
cctaagtgaa agagattcat gvcctacaaa acccaagcgg ttcg 44

<210> SEQ ID NO 901
<211> LENGTH: 54
<212> TYPE: DNA
<213> ORGANISM: Artificial Sequence
<220> FEATURE:
<223> OTHER INFORMATION: Synthesized: H1-A combination primer

<400> SEQUENCE: 901
cttgcgctgc ttccggattc actttctcta aatactttat gttttgggtt cgcc 54

<210> SEQ ID NO 902
<211> LENGTH: 54
<212> TYPE: DNA
<213> ORGANISM: Artificial Sequence
<220> FEATURE:
<223> OTHER INFORMATION: Synthesized: H1-B combination primer

<400> SEQUENCE: 902
cttgcgctgc ttccggattc actttctctc ygtactttat gttttgggtt cgcc 54

<210> SEQ ID NO 903

<211> LENGTH: 54
<212> TYPE: DNA
<213> ORGANISM: Artificial Sequence
<220> FEATURE:
<223> OTHER INFORMATION: Synthesized: H1-C combination primer

<400> SEQUENCE: 903
cttgcgctgc ttccggattc actttctcty attactttat gttttgggtt cgcc 54

<210> SEQ ID NO 904
<211> LENGTH: 54
<212> TYPE: DNA
<213> ORGANISM: Artificial Sequence
<220> FEATURE:
<223> OTHER INFORMATION: Synthesized: H1-D combination primer

<400> SEQUENCE: 904
cttgcgctgc ttccggattc actttctctt ggtactttat gttttgggtt cgcc 54

<210> SEQ ID NO 905
<211> LENGTH: 59
<212> TYPE: DNA
<213> ORGANISM: Artificial Sequence
<220> FEATURE:
<223> OTHER INFORMATION: Synthesized: H2-A combination primer

<400> SEQUENCE: 905
gtgggtttct gttatctctc ctaaaggtmt catgactcgt tatgctgact ccgttaaag 59

<210> SEQ ID NO 906
<211> LENGTH: 59
<212> TYPE: DNA
<213> ORGANISM: Artificial Sequence
<220> FEATURE:
<223> OTHER INFORMATION: Synthesized: H2-B combination primer

<400> SEQUENCE: 906
gtgggtttct gttatctctc ctaaaggtma aatgactcgt tatgctgact ccgttaaag 59

<210> SEQ ID NO 907
<211> LENGTH: 59
<212> TYPE: DNA
<213> ORGANISM: Artificial Sequence
<220> FEATURE:
<223> OTHER INFORMATION: Synthesized: H2-C combination primer

<400> SEQUENCE: 907
gtgggtttct gttatctctc ctaaaggtsg tatgactcgt tatgctgact ccgttaaag 59

<210> SEQ ID NO 908
<211> LENGTH: 59
<212> TYPE: DNA
<213> ORGANISM: Artificial Sequence
<220> FEATURE:
<223> OTHER INFORMATION: Synthesized: H2-D combination primer

<400> SEQUENCE: 908
gtgggtttct gttatctctc cttctggtmt catgactcgt tatgctgact ccgttaaag 59

<210> SEQ ID NO 909
<211> LENGTH: 59
<212> TYPE: DNA
<213> ORGANISM: Artificial Sequence
<220> FEATURE:
<223> OTHER INFORMATION: Synthesized: H2-E combination primer

<400> SEQUENCE: 909
gtgggtttct gttatctctc cttctggtma aatgactcgt tatgctgact ccgttaaag 59

<210> SEQ ID NO 910
<211> LENGTH: 59
<212> TYPE: DNA
<213> ORGANISM: Artificial Sequence
<220> FEATURE:
<223> OTHER INFORMATION: Synthesized: H2-F combination primer

<400> SEQUENCE: 910
gtgggtttct gttatctctc cttctggtsg tatgactcgt tatgctgact ccgttaaag 59

<210> SEQ ID NO 911
<211> LENGTH: 54
<212> TYPE: DNA
<213> ORGANISM: Artificial Sequence
<220> FEATURE:
<223> OTHER INFORMATION: Synthesized: H3-A combination primer

<400> SEQUENCE: 911
ctattgtgcg agagtcggcc tgggtgkgaa tycagactac tggggccagg gaac 54

<210> SEQ ID NO 912
<211> LENGTH: 54
<212> TYPE: DNA
<213> ORGANISM: Artificial Sequence
<220> FEATURE:
<223> OTHER INFORMATION: Synthesized: H3-B combination primer

<400> SEQUENCE: 912
ctattgtgcg agagtcggcc tgggtgkgaa tgaggactac tggggccagg gaac 54

<210> SEQ ID NO 913
<211> LENGTH: 54
<212> TYPE: DNA
<213> ORGANISM: Artificial Sequence
<220> FEATURE:
<223> OTHER INFORMATION: Synthesized: H3-C combination primer

<400> SEQUENCE: 913
ctattgtgcg agagtcggcc tgggtgkggy gycagactac tggggccagg gaac 54

<210> SEQ ID NO 914
<211> LENGTH: 54
<212> TYPE: DNA
<213> ORGANISM: Artificial Sequence
<220> FEATURE:
<223> OTHER INFORMATION: Synthesized: H3-D combination primer

<400> SEQUENCE: 914
ctattgtgcg agagtcggcc tgggtgkggy ggaggactac tggggccagg gaac 54

<210> SEQ ID NO 915
<211> LENGTH: 54
<212> TYPE: DNA
<213> ORGANISM: Artificial Sequence
<220> FEATURE:
<223> OTHER INFORMATION: Synthesized: H3-E combination primer

<400> SEQUENCE: 915
ctattgtgcg agagtcggct atggtgkgaa tycagactac tggggccagg gaac 54

<210> SEQ ID NO 916
<211> LENGTH: 54
<212> TYPE: DNA

<213> ORGANISM: Artificial Sequence
<220> FEATURE:
<223> OTHER INFORMATION: Synthesized: H3-F combination primer

<400> SEQUENCE: 916
ctattgtgcg agagtcggct atggtgkgaa tgaggactac tggggccagg gaac 54

<210> SEQ ID NO 917
<211> LENGTH: 54
<212> TYPE: DNA
<213> ORGANISM: Artificial Sequence
<220> FEATURE:
<223> OTHER INFORMATION: Synthesized: H3-G combination primer

<400> SEQUENCE: 917
ctattgtgcg agagtcggct atggtgkggy gycagactac tggggccagg gaac 54

<210> SEQ ID NO 918
<211> LENGTH: 54
<212> TYPE: DNA
<213> ORGANISM: Artificial Sequence
<220> FEATURE:
<223> OTHER INFORMATION: Synthesized: H3-H combination primer

<400> SEQUENCE: 918
ctattgtgcg agagtcggct atggtgkggy ggaggactac tggggccagg gaac 54

<210> SEQ ID NO 919
<211> LENGTH: 21
<212> TYPE: DNA
<213> ORGANISM: Artificial Sequence
<220> FEATURE:
<223> OTHER INFORMATION: Synthesized: H1 fwd combination primer

<400> SEQUENCE: 919
gcttccggat tcactttctc t 21

<210> SEQ ID NO 920
<211> LENGTH: 21
<212> TYPE: DNA
<213> ORGANISM: Artificial Sequence
<220> FEATURE:
<223> OTHER INFORMATION: Synthesized: H1- rev combination primer

<400> SEQUENCE: 920
agagaaagtg aatccggaag c 21

<210> SEQ ID NO 921
<211> LENGTH: 20
<212> TYPE: DNA
<213> ORGANISM: Artificial Sequence
<220> FEATURE:
<223> OTHER INFORMATION: Synthesized: H2- fwd combination primer

<400> SEQUENCE: 921
gggtttctgt tatctctcct 20

<210> SEQ ID NO 922
<211> LENGTH: 20
<212> TYPE: DNA
<213> ORGANISM: Artificial Sequence
<220> FEATURE:
<223> OTHER INFORMATION: Synthesized: H2- rev combination primer

<400> SEQUENCE: 922
aggagagata acagaaaccc 20

<210> SEQ ID NO 923
<211> LENGTH: 19
<212> TYPE: DNA
<213> ORGANISM: Artificial Sequence
<220> FEATURE:
<223> OTHER INFORMATION: Synthesized: H3- fwd combination primer

<400> SEQUENCE: 923
ctattgtgcg agagtcggc 19

<210> SEQ ID NO 924
<211> LENGTH: 20
<212> TYPE: DNA
<213> ORGANISM: Artificial Sequence
<220> FEATURE:
<223> OTHER INFORMATION: Synthesized: H3- rev combination primer

<400> SEQUENCE: 924
gccgactctc gcacaatagt 20

<210> SEQ ID NO 925
<211> LENGTH: 20
<212> TYPE: DNA
<213> ORGANISM: Artificial Sequence
<220> FEATURE:
<223> OTHER INFORMATION: Synthesized: L1R combination primer

<400> SEQUENCE: 925
actcgcccga caaatgatgg 20

<210> SEQ ID NO 926
<211> LENGTH: 20
<212> TYPE: DNA
<213> ORGANISM: Artificial Sequence
<220> FEATURE:
<223> OTHER INFORMATION: Synthesized: L2R combination primer

<400> SEQUENCE: 926
gatcaggagc ttaggggcat 20

<210> SEQ ID NO 927
<211> LENGTH: 21
<212> TYPE: DNA
<213> ORGANISM: Artificial Sequence
<220> FEATURE:
<223> OTHER INFORMATION: Synthesized: L3R combination primer

<400> SEQUENCE: 927
ctgctgacaa tagtaagttg c 21

<210> SEQ ID NO 928
<211> LENGTH: 58
<212> TYPE: DNA
<213> ORGANISM: Artificial Sequence
<220> FEATURE:
<223> OTHER INFORMATION: Synthesized: L127Q28SLW30N combination primer

<400> SEQUENCE: 928
ccatcatttg tcgggcgagt cagtbgatta ataggtggtt agcctggtat cagcagac 58

<210> SEQ ID NO 929
<211> LENGTH: 58
<212> TYPE: DNA
<213> ORGANISM: Artificial Sequence
<220> FEATURE:

<223> OTHER INFORMATION: Synthesized: L127Q28D30N combination primer

<400> SEQUENCE: 929
ccatcatttg tcgggcgagt caggacatta ataggtggtt agcctggtat cagcagac 58

<210> SEQ ID NO 930
<211> LENGTH: 58
<212> TYPE: DNA
<213> ORGANISM: Artificial Sequence
<220> FEATURE:
<223> OTHER INFORMATION: Synthesized: L127Q28SLW30F combination primer

<400> SEQUENCE: 930
ccatcatttg tcgggcgagt cagtbgattt ttaggtggtt agcctggtat cagcagac 58

<210> SEQ ID NO 931
<211> LENGTH: 58
<212> TYPE: DNA
<213> ORGANISM: Artificial Sequence
<220> FEATURE:
<223> OTHER INFORMATION: Synthesized: L127Q28D30F combination primer

<400> SEQUENCE: 931
ccatcatttg tcgggcgagt caggacattt ttaggtggtt agcctggtat cagcagac 58

<210> SEQ ID NO 932
<211> LENGTH: 58
<212> TYPE: DNA
<213> ORGANISM: Artificial Sequence
<220> FEATURE:
<223> OTHER INFORMATION: Synthesized: L127SF28SLW30N combination primer

<400> SEQUENCE: 932
ccatcatttg tcgggcgagt tyttbgatta ataggtggtt agcctggtat cagcagac 58

<210> SEQ ID NO 933
<211> LENGTH: 58
<212> TYPE: DNA
<213> ORGANISM: Artificial Sequence
<220> FEATURE:
<223> OTHER INFORMATION: Synthesized: L127SF28D30N combination primer

<400> SEQUENCE: 933
ccatcatttg tcgggcgagt tytgacatta ataggtggtt agcctggtat cagcagac 58

<210> SEQ ID NO 934
<211> LENGTH: 58
<212> TYPE: DNA
<213> ORGANISM: Artificial Sequence
<220> FEATURE:
<223> OTHER INFORMATION: Synthesized: L127SF28SLW30F combination primer

<400> SEQUENCE: 934
ccatcatttg tcgggcgagt tyttbgattt ttaggtggtt agcctggtat cagcagac 58

<210> SEQ ID NO 935
<211> LENGTH: 58
<212> TYPE: DNA
<213> ORGANISM: Artificial Sequence
<220> FEATURE:
<223> OTHER INFORMATION: Synthesized: L127SF28D30F combination primer

<400> SEQUENCE: 935
ccatcatttg tcgggcgagt tytgacattt ttaggtggtt agcctggtat cagcagac 58

<210> SEQ ID NO 936
<211> LENGTH: 58
<212> TYPE: DNA
<213> ORGANISM: Artificial Sequence
<220> FEATURE:
<223> OTHER INFORMATION: Synthesized: L127G28SLW30N combination primer

<400> SEQUENCE: 936
ccatcatttg tcgggcgagt ggatbgatta ataggtggtt agcctggtat cagcagac 58

<210> SEQ ID NO 937
<211> LENGTH: 58
<212> TYPE: DNA
<213> ORGANISM: Artificial Sequence
<220> FEATURE:
<223> OTHER INFORMATION: Synthesized: L127G28D30N combination primer

<400> SEQUENCE: 937
ccatcatttg tcgggcgagt ggagacatta ataggtggtt agcctggtat cagcagac 58

<210> SEQ ID NO 938
<211> LENGTH: 58
<212> TYPE: DNA
<213> ORGANISM: Artificial Sequence
<220> FEATURE:
<223> OTHER INFORMATION: Synthesized: L127G28SLW30F combination primer

<400> SEQUENCE: 938
ccatcatttg tcgggcgagt ggatbgattt ttaggtggtt agcctggtat cagcagac 58

<210> SEQ ID NO 939
<211> LENGTH: 58
<212> TYPE: DNA
<213> ORGANISM: Artificial Sequence
<220> FEATURE:
<223> OTHER INFORMATION: Synthesized: L127G28D30F combination primer

<400> SEQUENCE: 939
ccatcatttg tcgggcgagt ggagacattt ttaggtggtt agcctggtat cagcagac 58

<210> SEQ ID NO 940
<211> LENGTH: 55
<212> TYPE: DNA
<213> ORGANISM: Artificial Sequence
<220> FEATURE:
<223> OTHER INFORMATION: Synthesized: L251GA53S combination primer

<400> SEQUENCE: 940
atgcccctaa gctcctgatc cattctgsta cctctctgca aagtggggtc ccatc 55

<210> SEQ ID NO 941
<211> LENGTH: 55
<212> TYPE: DNA
<213> ORGANISM: Artificial Sequence
<220> FEATURE:
<223> OTHER INFORMATION: Synthesized: L251GA53KR combination primer

<400> SEQUENCE: 941
atgcccctaa gctcctgatc cattctgsta ccargctgca aagtggggtc ccatc 55

<210> SEQ ID NO 942
<211> LENGTH: 57
<212> TYPE: DNA
<213> ORGANISM: Artificial Sequence
<220> FEATURE:
<223> OTHER INFORMATION: Synthesized: L392S93ED combination primer

<400> SEQUENCE: 942
gcaacttact attgtcagca ggcttcagak ttcbcatkga ctttcggcgg agggacc 57

<210> SEQ ID NO 943
<211> LENGTH: 57
<212> TYPE: DNA
<213> ORGANISM: Artificial Sequence
<220> FEATURE:
<223> OTHER INFORMATION: Synthesized: L392S93S combination primer

<400> SEQUENCE: 943
gcaacttact attgtcagca ggcttcatcg ttcbcatkga ctttcggcgg agggacc 57

<210> SEQ ID NO 944
<211> LENGTH: 57
<212> TYPE: DNA
<213> ORGANISM: Artificial Sequence
<220> FEATURE:
<223> OTHER INFORMATION: Synthesized: L392D93ED combination primer

<400> SEQUENCE: 944
gcaacttact attgtcagca ggctgatgak ttcbcatkga ctttcggcgg agggacc 57

<210> SEQ ID NO 945
<211> LENGTH: 57
<212> TYPE: DNA
<213> ORGANISM: Artificial Sequence
<220> FEATURE:
<223> OTHER INFORMATION: Synthesized: L392D93S combination primer

<400> SEQUENCE: 945
gcaacttact attgtcagca ggctgattcg ttcbcatkga ctttcggcgg agggacc 57

<210> SEQ ID NO 946
<211> LENGTH: 104
<212> TYPE: PRT
<213> ORGANISM: Artificial Sequence
<220> FEATURE:
<223> OTHER INFORMATION: Synthesized: Ca5 light chain variable region
<220> FEATURE:
<221> NAME/KEY: misc_feature
<222> LOCATION: (21)..(21)
<223> OTHER INFORMATION: Synthesized: Xaa can be any naturally occurring amino acid

<400> SEQUENCE: 946

```
Asp Ile Gln Met Thr Gln Ser Pro Ser Ser Val Ser Ala Ser Val Gly
1               5                   10                  15

Asp Arg Leu Thr Xaa Ile Cys Arg Ala Ser Gln Asp Ile Asn Arg Trp
            20                  25                  30

Leu Ala Trp Gln Gln Thr Pro Gly Asn Ala Pro Lys Leu Leu Ile His
        35                  40                  45

Ser Ala Thr Ser Leu Gln Ser Gly Val Pro Ser Arg Phe Ser Gly Ser
    50                  55                  60

Gly Ser Gly Thr Asp Phe Thr Leu Thr Ile Asn Ser Leu Met Asp Phe
65                  70                  75                  80

Ala Thr Tyr Tyr Cys Gln Gln Ala Asp Ser Phe Pro Leu Thr Phe Gly
                85                  90                  95

Gly Gly Thr Lys Val Glu Ile Lys
            100
```

<210> SEQ ID NO 947
<211> LENGTH: 106

<212> TYPE: PRT
<213> ORGANISM: Artificial Sequence
<220> FEATURE:
<223> OTHER INFORMATION: Synthesized: A8.2 light chain variable region

<400> SEQUENCE: 947

```
Asp Ile Gln Met Thr Gln Ser Pro Ser Ser Val Ser Ala Ser Ala Gly
1               5                   10                  15

Asp Arg Val Thr Ile Thr Cys Arg Ala Ser Gln Gly Ile Ser Thr Trp
            20                  25                  30

Leu Ala Trp Tyr Gln Gln Lys Pro Gly Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Phe Cys Gln Gln Gly Tyr Arg Phe Pro Phe Thr
                85                  90                  95

Phe Gly Pro Gly Thr Lys Val Glu Ile Lys
            100                 105
```

<210> SEQ ID NO 948
<211> LENGTH: 118
<212> TYPE: PRT
<213> ORGANISM: Artificial Sequence
<220> FEATURE:
<223> OTHER INFORMATION: Synthesized: Ca5 heavy chain variable region

<400> SEQUENCE: 948

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Phe Met Phe Trp Val Arg Gln Ala Pro Gly Lys Gly Leu Glu Trp Val
        35                  40                  45

Ser Val Ile Ser Pro Ser Gly Gly Met Thr Arg Tyr Ala Asp Ser Val
    50                  55                  60

Lys Gly Arg Pro Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Phe Gly Gly Asn Ser Asp Tyr Trp Gly Gln Gly Thr
            100                 105                 110

Leu Val Thr Val Ser Ser
        115
```

<210> SEQ ID NO 949
<211> LENGTH: 118
<212> TYPE: PRT
<213> ORGANISM: Artificial Sequence
<220> FEATURE:
<223> OTHER INFORMATION: Synthesized: A8.2 heavy chain variable region

<400> SEQUENCE: 949

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Asp Met His Trp Val Arg Gln Ala Pro Gly Lys Gly Leu Glu Trp Val
```

```
        35                  40                  45

Ser Tyr Ile Tyr Pro Ser Gly Gly Ile Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Gly Pro Asn Trp Phe Asp Pro Trp Gly Gln Gly Thr
            100                 105                 110

Leu Val Thr Val Ser Ser
        115
```

<210> SEQ ID NO 950
<211> LENGTH: 768
<212> TYPE: DNA
<213> ORGANISM: Artificial Sequence
<220> FEATURE:
<223> OTHER INFORMATION: Synthesized: ING-1 variable region DNA

<400> SEQUENCE: 950

```
ggcgcgccta accatctatt tcaaggagac agtcataatg aaatacctat tgcctacggc     60

agccgctgga ttgttattac tcgctgccca accagcgatg gcgcagatcc agttggtgca    120

gtctggacct gagctgaaga agcctggaga gacagtcaag atctcctgca aggcttctgg    180

atataccttc acaaaatatg gaatgaactg ggtgaagcag gctccaggaa agggtttaaa    240

gtggatgggc tggataaaca cctacactga agagcctaca tatggtgatg acttcaaggg    300

acggtttgcc ttctctttgg aaacctctgc cagcactgcc aatttgcaga tcaacaacct    360

caaaagtgag gacacggcta catatttctg tgcaagattt ggctctgctg tggactactg    420

gggtcaagga acctcggtca ccgtctcctc agcctccacc aagggcccat cggtcttccc    480

cctggcaccc tcctccaaga gcacctctgg gggcacagcg gccctgggct gcctggtcaa    540

ggactacttc cccgaaccgg tgacggtgtc gtggaactca ggcgccctga ccagcggcgt    600

tcataccttc ccggctgtcc tacagtcctc aggactctac tccctcagca gcgtggtgac    660

cgtgccctcc agcagcttgg gcacccagac ctacatctgc aacgtgaatc acaagcccag    720

caacaccaag gtggacaaga gagttgagcc caaatcttgt gcggccgc                 768
```

<210> SEQ ID NO 951
<211> LENGTH: 768
<212> TYPE: DNA
<213> ORGANISM: Artificial Sequence
<220> FEATURE:
<223> OTHER INFORMATION: Synthesized: ING-1 variable region DNA
      (antisense)

<400> SEQUENCE: 951

```
ccgcgcggat tggtagataa agttcctctg tcagtattac tttatggata acggatgccg     60

tcggcgacct aacaataatg agcgacgggt tggtcgctac cgcgtctagg tcaaccacgt    120

cagacctgga ctcgacttct tcggacctct ctgtcagttc tagaggacgt tccgaagacc    180

tatatggaag tgttttatac cttacttgac ccacttcgtc cgaggtcctt tcccaaattt    240

cacctacccg acctatttgt ggatgtgact tctcggatgt ataccactac tgaagttccc    300

tgccaaacgg aagagaaacc tttggagacg gtcgtgacgg ttaaacgtct agttgttgga    360

gttttcactc ctgtgccgat gtataaagac acgttctaaa ccgagacgac acctgatgac    420

cccagttcct tggagccagt ggcagaggag tcggaggtgg ttcccgggta gccagaaggg    480
```

```
ggaccgtggg aggaggttct cgtggagacc cccgtgtcgc cgggacccga cggaccagtt    540

cctgatgaag gggcttggcc actgccacag caccttgagt ccgcgggact ggtcgccgca    600

agtatggaag ggccgacagg atgtcaggag tcctgagatg agggagtcgt cgcaccactg    660

gcacgggagg tcgtcgaacc cgtgggtctg gatgtagacg ttgcacttag tgttcgggtc    720

gttgtggttc cacctgttct ctcaactcgg gtttagaaca cgccggcg                 768


<210> SEQ ID NO 952
<211> LENGTH: 116
<212> TYPE: PRT
<213> ORGANISM: Artificial Sequence
<220> FEATURE:
<223> OTHER INFORMATION: Synthesized: ING-1 KABAT HEAVY CHAIN (KABAT
      NUMBERING)

<400> SEQUENCE: 952

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Ala Phe Ser Leu Glu Thr Ser Ala Ser Thr Ala Asn
65                  70                  75                  80

Leu Gln Ile Asn Asn Leu Lys Ser Glu Asp Thr Ala Thr Tyr Phe Cys
                85                  90                  95

Ala Arg Phe Gly Ser Ala Val Asp Tyr Trp Gly Gln Gly Thr Ser Val
            100                 105                 110

Thr Val Ser Ser
        115


<210> SEQ ID NO 953
<211> LENGTH: 116
<212> TYPE: PRT
<213> ORGANISM: Artificial Sequence
<220> FEATURE:
<223> OTHER INFORMATION: Synthesized: ING-1 CHOTHIA HEAVY CHAIN

<400> SEQUENCE: 953

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Ala Phe Ser Leu Glu Thr Ser Ala Ser Thr Ala Asn
65                  70                  75                  80

Leu Gln Ile Asn Asn Leu Lys Ser Glu Asp Thr Ala Thr Tyr Phe Cys
                85                  90                  95

Ala Arg Phe Gly Ser Ala Val Asp Tyr Trp Gly Gln Gly Thr Ser Val
            100                 105                 110

Thr Val Ser Ser
        115
```

<210> SEQ ID NO 954
<211> LENGTH: 116
<212> TYPE: PRT
<213> ORGANISM: Artificial Sequence
<220> FEATURE:
<223> OTHER INFORMATION: Synthesized: ING-1 IMGT HEAVY CHAIN

<400> SEQUENCE: 954

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Ala Phe Ser Leu Glu Thr Ser Ala Ser Thr Ala Asn
65                  70                  75                  80

Leu Gln Ile Asn Asn Leu Lys Ser Glu Asp Thr Ala Thr Tyr Phe Cys
                85                  90                  95

Ala Arg Phe Gly Ser Ala Val Asp Tyr Trp Gly Gln Gly Thr Ser Val
            100                 105                 110

Thr Val Ser Ser
        115
```

<210> SEQ ID NO 955
<211> LENGTH: 113
<212> TYPE: PRT
<213> ORGANISM: Artificial Sequence
<220> FEATURE:
<223> OTHER INFORMATION: Synthesized: ING-1 KABAT LIGHT CHAIN (KABAT NUMBERING)

<400> SEQUENCE: 955

```
Gln Ile Val Met Thr Gln Ala Ala Phe Ser Asn Pro Val Thr Leu Gly
1               5                   10                  15

Thr Ser Gly Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Arg Thr Phe Gly Gly Gly Thr Lys Leu Glu Met Lys
            100                 105                 110

Arg
```

<210> SEQ ID NO 956
<211> LENGTH: 113
<212> TYPE: PRT
<213> ORGANISM: Artificial Sequence
<220> FEATURE:
<223> OTHER INFORMATION: Synthesized: ING-1 CHOTHIA LIGHT CHAIN

<400> SEQUENCE: 956

Gln Ile Val Met Thr Gln Ala Ala Phe Ser Asn Pro Val Thr Leu Gly
1 5 10 15

Thr Ser Gly Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Leu Leu Ile Tyr Gln Met Ser Asn Leu Ala Ser Gly Val Pro
50 55 60

Asp Arg Phe Ser Ser Ser Gly Ser Gly Thr Asp Phe Thr Leu Arg Ile
65 70 75 80

Ser Arg Val Glu Ala Glu Asp Val Gly Val Tyr Tyr Cys Ala Gln Asn
85 90 95

Leu Glu Leu Pro Arg Thr Phe Gly Gly Gly Thr Lys Leu Glu Met Lys
100 105 110

Arg

<210> SEQ ID NO 957
<211> LENGTH: 113
<212> TYPE: PRT
<213> ORGANISM: Artificial Sequence
<220> FEATURE:
<223> OTHER INFORMATION: Synthesized: ING-1 IMGT LIGHT CHAIN

<400> SEQUENCE: 957

Gln Ile Val Met Thr Gln Ala Ala Phe Ser Asn Pro Val Thr Leu Gly
1 5 10 15

Thr Ser Gly Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Leu Leu Ile Tyr Gln Met Ser Asn Leu Ala Ser Gly Val Pro
50 55 60

Asp Arg Phe Ser Ser Ser Gly Ser Gly Thr Asp Phe Thr Leu Arg Ile
65 70 75 80

Ser Arg Val Glu Ala Glu Asp Val Gly Val Tyr Tyr Cys Ala Gln Asn
85 90 95

Leu Glu Leu Pro Arg Thr Phe Gly Gly Gly Thr Lys Leu Glu Met Lys
100 105 110

Arg

<210> SEQ ID NO 958
<211> LENGTH: 118
<212> TYPE: PRT
<213> ORGANISM: Artificial Sequence
<220> FEATURE:
<223> OTHER INFORMATION: Synthesized: XPA23 KABAT HEAVY CHAIN (KABAT NUMBERING)

<400> SEQUENCE: 958

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Lys Tyr
20 25 30

Phe Met Phe Trp Val Arg Gln Ala Pro Gly Lys Gly Leu Glu Trp Val
35 40 45

Ser Val Ile Ser Pro Ser Gly Gly Met Thr Arg Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Tyr Gly Gly Asn Ser Asp Tyr Trp Gly Gln Gly Thr
            100                 105                 110

Leu Val Thr Val Ser Ser
        115
```

<210> SEQ ID NO 959
<211> LENGTH: 118
<212> TYPE: PRT
<213> ORGANISM: Artificial Sequence
<220> FEATURE:
<223> OTHER INFORMATION: Synthesized: XPA23 CHOTHIA HEAVY CHAIN

<400> SEQUENCE: 959

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Phe Met Phe Trp Val Arg Gln Ala Pro Gly Lys Gly Leu Glu Trp Val
        35                  40                  45

Ser Val Ile Ser Pro Ser Gly Gly Met Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Tyr Gly Gly Asn Ser Asp Tyr Trp Gly Gln Gly Thr
            100                 105                 110

Leu Val Thr Val Ser Ser
        115
```

<210> SEQ ID NO 960
<211> LENGTH: 118
<212> TYPE: PRT
<213> ORGANISM: Artificial Sequence
<220> FEATURE:
<223> OTHER INFORMATION: Synthesized: XPA23 IMGT HEAVY CHAIN

<400> SEQUENCE: 960

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Phe Met Phe Trp Val Arg Gln Ala Pro Gly Lys Gly Leu Glu Trp Val
        35                  40                  45

Ser Val Ile Ser Pro Ser Gly Gly Met Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Tyr Gly Gly Asn Ser Asp Tyr Trp Gly Gln Gly Thr
            100                 105                 110

Leu Val Thr Val Ser Ser
        115
```

<210> SEQ ID NO 961
<211> LENGTH: 108
<212> TYPE: PRT
<213> ORGANISM: Artificial Sequence
<220> FEATURE:
<223> OTHER INFORMATION: Synthesized: XPA23 KABAT LIGHT CHAIN (KABAT NUMBERING)

<400> SEQUENCE: 961

```
Asp Ile Gln Met Thr Gln Ser Pro Ser Ser Val Ser Ala Ser Val Gly
1               5                   10                  15

Asp Arg Leu Thr Ile Ile Cys Arg Ala Ser Gln Asp Ile Asn Arg Trp
            20                  25                  30

Leu Ala Trp Tyr Gln Gln Thr Pro Gly Asn Ala Pro Lys Leu Leu Ile
        35                  40                  45

His Ser Ala Thr Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys Arg
            100                 105
```

<210> SEQ ID NO 962
<211> LENGTH: 108
<212> TYPE: PRT
<213> ORGANISM: Artificial Sequence
<220> FEATURE:
<223> OTHER INFORMATION: Synthesized: XPA23 CHOTHIA LIGHT CHAIN

<400> SEQUENCE: 962

```
Asp Ile Gln Met Thr Gln Ser Pro Ser Ser Val Ser Ala Ser Val Gly
1               5                   10                  15

Asp Arg Leu Thr Ile Ile Cys Arg Ala Ser Gln Asp Ile Asn Arg Trp
            20                  25                  30

Leu Ala Trp Tyr Gln Gln Thr Pro Gly Asn Ala Pro Lys Leu Leu Ile
        35                  40                  45

His Ser Ala Thr Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Lys Val Glu Ile Lys Arg
            100                 105
```

<210> SEQ ID NO 963
<211> LENGTH: 108
<212> TYPE: PRT
<213> ORGANISM: Artificial Sequence
<220> FEATURE:
<223> OTHER INFORMATION: Synthesized: XPA23 IMGT LIGHT CHAIN

<400> SEQUENCE: 963

```
Asp Ile Gln Met Thr Gln Ser Pro Ser Ser Val Ser Ala Ser Val Gly
1               5                   10                  15

Asp Arg Leu Thr Ile Ile Cys Arg Ala Ser Gln Asp Ile Asn Arg Trp
            20                  25                  30
```

Leu Ala Trp Tyr Gln Gln Thr Pro Gly Asn Ala Pro Lys Leu Leu Ile
35 40 45

His Ser Ala Thr Ser Leu Gln Ser Gly Val Pro Ser Arg Phe Ser Gly
50 55 60

Ser Gly Ser Gly Thr Asp Phe Thr Leu Thr Ile Asn Ser Leu Gln Pro
65 70 75 80

Glu Asp Phe Ala Thr Tyr Tyr Cys Gln Gln Ala Asp Ser Phe Pro Leu
85 90 95

Thr Phe Gly Gly Gly Thr Lys Val Glu Ile Lys Arg
100 105

<210> SEQ ID NO 964
<211> LENGTH: 64
<212> TYPE: DNA
<213> ORGANISM: Artificial Sequence
<220> FEATURE:
<223> OTHER INFORMATION: Synthesized: Representative CDR region

<400> SEQUENCE: 964
gtctttcttg cgctgcttcc ggattcactt tctctaagta ctttatgttt tgggttcgcc 60
aagc 64

<210> SEQ ID NO 965
<211> LENGTH: 64
<212> TYPE: DNA
<213> ORGANISM: Artificial Sequence
<220> FEATURE:
<223> OTHER INFORMATION: Synthesized: Representative CDR region (antisense)

<400> SEQUENCE: 965
cagaaagaac gcgacgaagg cctaagtgaa agagattcat gaaatacaaa acccaagcgg 60
ttcg 64

<210> SEQ ID NO 966
<211> LENGTH: 57
<212> TYPE: DNA
<213> ORGANISM: Artificial Sequence
<220> FEATURE:
<223> OTHER INFORMATION: Synthesized: CDR region 1

<400> SEQUENCE: 966
gtctttcttg cgctgcttcc ggattcactt tctctaagta ctttatgttt tgggttc 57

<210> SEQ ID NO 967
<211> LENGTH: 57
<212> TYPE: DNA
<213> ORGANISM: Artificial Sequence
<220> FEATURE:
<223> OTHER INFORMATION: Synthesized: CDR region 1 (antisense)

<400> SEQUENCE: 967
cagaaagaac gcgacgaagg cctaagtgaa agagattcat gaaatacaaa acccaag 57

<210> SEQ ID NO 968
<211> LENGTH: 53
<212> TYPE: DNA
<213> ORGANISM: Artificial Sequence
<220> FEATURE:
<223> OTHER INFORMATION: Synthesized: CDR region 2

<400> SEQUENCE: 968
gctgcttccg gattcacttt ctctaagtac tttatgtttt gggttcgcca agc 53

<210> SEQ ID NO 969
<211> LENGTH: 53
<212> TYPE: DNA
<213> ORGANISM: Artificial Sequence
<220> FEATURE:
<223> OTHER INFORMATION: Synthesized: CDR region 2 (antisense)

<400> SEQUENCE: 969
cgacgaaggc ctaagtgaaa gagattcatg aaatacaaaa cccaagcggt tcg 53

<210> SEQ ID NO 970
<211> LENGTH: 53
<212> TYPE: DNA
<213> ORGANISM: Artificial Sequence
<220> FEATURE:
<223> OTHER INFORMATION: Synthesized: R2-5-NHT primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (23)..(23)
<223> OTHER INFORMATION: h is a, c or t

<400> SEQUENCE: 970
gctgcttccg gattcacttt cnhtaagtac tttatgtttt gggttcgcca agc 53

<210> SEQ ID NO 971
<211> LENGTH: 53
<212> TYPE: DNA
<213> ORGANISM: Artificial Sequence
<220> FEATURE:
<223> OTHER INFORMATION: Synthesized: R2-5-VAA primer
<220> FEATURE:
<221> NAME/KEY: misc_feature
<222> LOCATION: (22)..(22)
<223> OTHER INFORMATION: v is a, c or g

<400> SEQUENCE: 971
gctgcttccg gattcacttt cvaaaagtac tttatgtttt gggttcgcca agc 53

<210> SEQ ID NO 972
<211> LENGTH: 53
<212> TYPE: DNA
<213> ORGANISM: Artificial Sequence
<220> FEATURE:
<223> OTHER INFORMATION: Synthesized: R2-5-BGG primer
<220> FEATURE:
<221> NAME/KEY: misc_feature
<222> LOCATION: (22)..(22)
<223> OTHER INFORMATION: b is c, g or t

<400> SEQUENCE: 972
gctgcttccg gattcacttt cbggaagtac tttatgtttt gggttcgcca agc 53

<210> SEQ ID NO 973
<211> LENGTH: 53
<212> TYPE: DNA
<213> ORGANISM: Artificial Sequence
<220> FEATURE:
<223> OTHER INFORMATION: Synthesized: R2-6-NHT primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (26)..(26)
<223> OTHER INFORMATION: h is a, c or t

<400> SEQUENCE: 973
gctgcttccg gattcacttt ctctnhttac tttatgtttt gggttcgcca agc 53

<210> SEQ ID NO 974
<211> LENGTH: 53
<212> TYPE: DNA
<213> ORGANISM: Artificial Sequence
<220> FEATURE:
<223> OTHER INFORMATION: Synthesized: R2-6-VAA primer
<220> FEATURE:
<221> NAME/KEY: misc_feature
<222> LOCATION: (25)..(25)
<223> OTHER INFORMATION: v is a, c or g

<400> SEQUENCE: 974
gctgcttccg gattcacttt ctctvaatac tttatgtttt gggttcgcca agc 53

<210> SEQ ID NO 975
<211> LENGTH: 53
<212> TYPE: DNA
<213> ORGANISM: Artificial Sequence
<220> FEATURE:
<223> OTHER INFORMATION: Synthesized: R2-6-BGG primer
<220> FEATURE:
<221> NAME/KEY: misc_feature
<222> LOCATION: (25)..(25)
<223> OTHER INFORMATION: b is c, g or t

<400> SEQUENCE: 975
gctgcttccg gattcacttt ctctbggtac tttatgtttt gggttcgcca agc 53

<210> SEQ ID NO 976
<211> LENGTH: 53
<212> TYPE: DNA
<213> ORGANISM: Artificial Sequence
<220> FEATURE:
<223> OTHER INFORMATION: Synthesized: R2-7-NHT primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (29)..(29)
<223> OTHER INFORMATION: h is a, c or t

<400> SEQUENCE: 976
gctgcttccg gattcacttt ctctaagnht tttatgtttt gggttcgcca agc 53

<210> SEQ ID NO 977
<211> LENGTH: 53
<212> TYPE: DNA
<213> ORGANISM: Artificial Sequence
<220> FEATURE:
<223> OTHER INFORMATION: Synthesized: R2-7-VAA primer
<220> FEATURE:
<221> NAME/KEY: misc_feature
<222> LOCATION: (28)..(28)
<223> OTHER INFORMATION: v is a, c or g

<400> SEQUENCE: 977
gctgcttccg gattcacttt ctctaagvaa tttatgtttt gggttcgcca agc 53

<210> SEQ ID NO 978
<211> LENGTH: 53
<212> TYPE: DNA

<213> ORGANISM: Artificial Sequence
<220> FEATURE:
<223> OTHER INFORMATION: Synthesized: R2-7-BGG primer
<220> FEATURE:
<221> NAME/KEY: misc_feature
<222> LOCATION: (28)..(28)
<223> OTHER INFORMATION: b is c, g or t

<400> SEQUENCE: 978
gctgcttccg gattcacttt ctctaagbgg tttatgtttt gggttcgcca agc 53

<210> SEQ ID NO 979
<211> LENGTH: 53
<212> TYPE: DNA
<213> ORGANISM: Artificial Sequence
<220> FEATURE:
<223> OTHER INFORMATION: Synthesized: R2-8-NHT primer
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (32)..(32)
<223> OTHER INFORMATION: h is a, c or t

<400> SEQUENCE: 979
gctgcttccg gattcacttt ctctaagtac nhtatgtttt gggttcgcca agc 53

<210> SEQ ID NO 980
<211> LENGTH: 53
<212> TYPE: DNA
<213> ORGANISM: Artificial Sequence
<220> FEATURE:
<223> OTHER INFORMATION: Synthesized: R2-8-VAA primer
<220> FEATURE:
<221> NAME/KEY: misc_feature
<222> LOCATION: (31)..(31)
<223> OTHER INFORMATION: v is c, c or g

<400> SEQUENCE: 980
gctgcttccg gattcacttt ctctaagtac vaaatgtttt gggttcgcca agc 53

<210> SEQ ID NO 981
<211> LENGTH: 53
<212> TYPE: DNA
<213> ORGANISM: Artificial Sequence
<220> FEATURE:
<223> OTHER INFORMATION: Synthesized: R2-8-BGG primer
<220> FEATURE:
<221> NAME/KEY: misc_feature
<222> LOCATION: (31)..(31)
<223> OTHER INFORMATION: b is c, g or t

<400> SEQUENCE: 981
gctgcttccg gattcacttt ctctaagtac bggatgtttt gggttcgcca agc 53

<210> SEQ ID NO 982
<211> LENGTH: 33
<212> TYPE: PRT
<213> ORGANISM: Artificial sequence
<220> FEATURE:
<223> OTHER INFORMATION: Synthesized: germline sequence

<400> SEQUENCE: 982

```
Gly Ser Ile Ser Ser Gly Gly Tyr Tyr Trp Ser Trp Ile Arg Gln His
1               5                   10                  15

Pro Gly Lys Gly Leu Glu Trp Ile Gly Tyr Ile Tyr Tyr Ser Gly Ser
            20                  25                  30
```

Thr

<210> SEQ ID NO 983
<211> LENGTH: 34
<212> TYPE: DNA
<213> ORGANISM: Artificial sequence
<220> FEATURE:
<223> OTHER INFORMATION: Synthesized: ING-HC-IgGF primer

<400> SEQUENCE: 983
atatattgca ttcccagatc cagttggtgc agtc 34

<210> SEQ ID NO 984
<211> LENGTH: 36
<212> TYPE: DNA
<213> ORGANISM: Artificial sequence
<220> FEATURE:
<223> OTHER INFORMATION: Synthesized: ING-HC-IgGR primer

<400> SEQUENCE: 984
atatatgcta gctgagctga cggtgaccga ggttcc 36

<210> SEQ ID NO 985
<211> LENGTH: 20
<212> TYPE: DNA
<213> ORGANISM: Artificial sequence
<220> FEATURE:
<223> OTHER INFORMATION: Synthesized: ING-LC-IgGF primer

<400> SEQUENCE: 985
caaattgtga tgacgcaggc 20

<210> SEQ ID NO 986
<211> LENGTH: 33
<212> TYPE: DNA
<213> ORGANISM: Artificial sequence
<220> FEATURE:
<223> OTHER INFORMATION: Synthesized: ING-LC-IgGR primer

<400> SEQUENCE: 986
atatatcgta cgtttcatct ctagtttggt gcc 33

<210> SEQ ID NO 987
<211> LENGTH: 107
<212> TYPE: PRT
<213> ORGANISM: Artificial sequence
<220> FEATURE:
<223> OTHER INFORMATION: Synthesized: XPA23 VKappa

<400> SEQUENCE: 987

```
Asp Ile Gln Met Thr Gln Ser Pro Ser Ser Val Ser Ala Ser Val Gly
1               5                   10                  15

Asp Arg Leu Thr Ile Ile Cys Arg Ala Ser Gln Asp Ile Asn Arg Trp
            20                  25                  30

Leu Ala Trp Tyr Gln Gln Thr Pro Gly Asn Ala Pro Lys Leu Leu Ile
        35                  40                  45

His Ser Ala Thr Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asp Ser Phe Pro Leu
                85                  90                  95
```

-continued

```
Thr Phe Gly Gly Gly Thr Lys Val Glu Ile Lys
            100                 105


<210> SEQ ID NO 988
<211> LENGTH: 97
<212> TYPE: PRT
<213> ORGANISM: Artificial sequence
<220> FEATURE:
<223> OTHER INFORMATION: Synthesized: ING-1 VH

<400> SEQUENCE: 988

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Trp Ile Asn
        35                  40                  45

Thr Tyr Thr Leu Glu Glu Thr Tyr Gly Asp Asp Phe Lys Gly Arg Phe
    50                  55                  60

Ala Phe Ser Leu Glu Thr Ser Ala Ser Thr Ala Asn Leu Gln Ile Asn
65                  70                  75                  80

Asn Leu Lys Ser Glu Asp Thr Ala Thr Tyr Phe Gly Ser Ala Val Asp
                85                  90                  95

Tyr


<210> SEQ ID NO 989
<211> LENGTH: 89
<212> TYPE: PRT
<213> ORGANISM: Artificial sequence
<220> FEATURE:
<223> OTHER INFORMATION: Synthesized: ING-1 Vkappa

<400> SEQUENCE: 989

Gln Ile Val Met Thr Gln Ala Ala Phe Ser Asn Pro Val Thr Leu Gly
1               5                   10                  15

Thr Ser Gly Ser Ile Ser Cys Arg Ser Ser Lys Ser Leu Leu Met Ser
            20                  25                  30

Asn Gly Ile Thr Tyr Leu Tyr Trp Tyr Leu Gln Lys Pro Leu Leu Ile
        35                  40                  45

Tyr Gln Met Ser Asn Leu Ala Ser Gly Val Pro Asp Arg Phe Ser Ser
    50                  55                  60

Ser Gly Ser Gly Thr Asp Phe Thr Leu Arg Ile Ser Arg Val Glu Ala
65                  70                  75                  80

Glu Asp Val Gly Val Tyr Cys Ala Gln
                85
```